(12) United States Patent
Ballentine et al.

(10) Patent No.: US 7,795,279 B2
(45) Date of Patent: Sep. 14, 2010

(54) METHOD OF INHIBITING FLT3 KINASE

(75) Inventors: Shelley K. Ballentine, Lansdale, PA (US); Christian Andrew Baumann, Exton, PA (US); Jinsheng Chen, Exton, PA (US); Carl R. Illig, Phoenixville, PA (US); Sanath K. Meegalla, Boothwyn, PA (US); M. Jonathan Rudolph, Doylestown, PA (US); Robert W. Tuman, Chalfont, PA (US); Mark J. Wall, Flourtown, PA (US); Kenneth Wilson, Media, PA (US); Dana L. Johnson, Upper Black Eddy, PA (US)

(73) Assignee: Janssen Pharmaceutica NV, Beerse (BE)

( * ) Notice: Subject to any disclaimer, the term of this patent is extended or adjusted under 35 U.S.C. 154(b) by 119 days.

(21) Appl. No.: 11/550,077

(22) Filed: Oct. 17, 2006

(65) Prior Publication Data
US 2007/0149572 A1    Jun. 28, 2007

Related U.S. Application Data

(60) Provisional application No. 60/727,687, filed on Oct. 18, 2005.

(51) Int. Cl.
*A61K 31/445* (2006.01)
*C07D 293/10* (2006.01)
(52) U.S. Cl. .............................. 514/326; 514/908; 544/1
(58) Field of Classification Search ........................ None
See application file for complete search history.

(56) References Cited

U.S. PATENT DOCUMENTS

| | | | |
|---|---|---|---|
| 5,474,765 A | 12/1995 | Thorpe | |
| 5,762,918 A | 6/1998 | Thorpe | |
| 5,855,866 A | 1/1999 | Thorpe et al. | |
| 6,342,219 B1 | 1/2002 | Thorpe et al. | |
| 6,987,119 B2 * | 1/2006 | Gaiba et al. | 514/341 |
| 7,157,456 B2 | 1/2007 | Straub et al. | |
| 2002/0119962 A1 * | 8/2002 | Jacobs et al. | 514/210.17 |
| 2003/0130280 A1 * | 7/2003 | O'Farrell et al. | 514/233.5 |
| 2003/0153610 A1 | 8/2003 | Straub et al. | |
| 2004/0049032 A1 | 3/2004 | Charrier et al. | |
| 2005/0004112 A1 * | 1/2005 | Player et al. | 514/227.5 |
| 2005/0113566 A1 | 5/2005 | Player et al. | |
| 2006/0258724 A1 | 11/2006 | Straub et al. | |
| 2006/0281771 A1 * | 12/2006 | Baumann et al. | 514/266.2 |
| 2007/0179125 A1 * | 8/2007 | Fraysse et al. | 514/210.2 |
| 2007/0259869 A1 * | 11/2007 | Binch et al. | 514/234.8 |

FOREIGN PATENT DOCUMENTS

| | | |
|---|---|---|
| EP | 1566379 A1 | 8/2005 |
| WO | WO 01/47919 A1 | 7/2001 |
| WO | WO 0232861 A2 | 4/2002 |
| WO | WO 02092599 A1 | 11/2002 |
| WO | WO 03024931 A1 | 3/2003 |
| WO | WO 03024969 A1 | 3/2003 |
| WO | WO 03035009 A2 | 5/2003 |
| WO | WO 03037347 A1 | 5/2003 |
| WO | WO 03057690 A1 | 7/2003 |
| WO | WO 03099771 A2 | 12/2003 |
| WO | WO 2004005281 A1 | 1/2004 |
| WO | WO 2004016597 A2 | 2/2004 |
| WO | WO 2004018419 A2 | 3/2004 |
| WO | WO 2004039782 A1 | 5/2004 |
| WO | WO 2004043389 A2 | 5/2004 |
| WO | WO 2004046120 A2 | 6/2004 |
| WO | WO 2004058749 A1 | 7/2004 |
| WO | WO 2006/047277 A2 | 5/2006 |
| WO | WO 2006/138155 A1 | 12/2006 |

OTHER PUBLICATIONS

Smith et al. Single-agent CEP-701, a novel FLT3 inhibitor, shows biological and clinical activity in patients with relapsed or refractory acute myeloid leukemia (Blood. May 15, 2004;103(10): 3669-3676.*
Vippagunta et al. Crystalline solids. Advanced Drug Delivery Reviews. 2001;48:3-26.*
International Search Report re: PCT/US2006/060028 dated Apr. 5, 2007.
Abdel-Magid, J Org. Chem. 61 pp. 3849-3862 (1996).
Ansari-Lari, A. et al., "FLT3 mutations in myeloid sarcoma" British Journal of Haematology. Sep. 2004 126(6):785-91.

(Continued)

*Primary Examiner*—David J Blanchard
*Assistant Examiner*—Kyle Purdy
(74) *Attorney, Agent, or Firm*—Mary A. Appollina

(57) ABSTRACT

A method of reducing or inhibiting kinase activity of FLT3 in a cell or a subject, and the use of such compounds for preventing or treating in a subject a cell proliferative disorder and/or disorders related to FLT3 using a compound of the present invention:

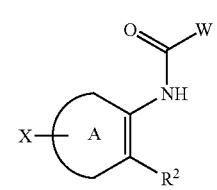

or a solvate, hydrate, tautomer or pharmaceutically acceptable salt thereof.

The present invention is further directed to methods for treating conditions such as cancers and other cell proliferative disorders.

2 Claims, 4 Drawing Sheets

OTHER PUBLICATIONS

Arnon et al., "Monoclonal Antibodies For Immunotargeting Of Drugs In Cancer Therapy", in Monoclonal Antibodies And Cancer Therapy, Reisfeld et al. (eds.), pp. 243-256 (Alan R. Liss, Inc. 1985).

Baumann CA, Zeng L, Donatelli RR, Maroney AC. Development of a quantitative, high-throughput cell-based enzyme-linked immunosorbent assay for detection of colony-stimulating factor-1 receptor tyrosine kinase inhibitors. J Biochem Biophys Methods. 2004; 60:69-79.

Berge, S., et al, "Pharmaceutical Salts", J. Pharm. Sci., Jan. 1977, 66(1): 1-19.

Bodansky, M. et al., "The Practice of Peptide Synthesis", Springer-Verlag, NY (1984).

British Journal of Haematology, "Flt3 mutations and leukaemia", 2003,122(4):523-38.

Buchwald, E.L. et al., Top. Curr. Chem., 219:131-209 (2001).

Canibano, V. et al., Synthesis 14, 2175 (2001).

Comprehensive Organic Transformations: Larock, R.S.; Wiley and Sons Inc., USA 1999.

Drexler, H. G. et al. (2004), "FLT3: receptor and ligand"; Growth Factors 22(2):71-3.

Drexler, H.G., "The Leukemia-Lymphoma Cell Line Factsbook", Academic Pres:SanDiego, CA, 2000.

Gilliand, G., et.al, "The roles of FLT3 in mematopoiesis and leukemia", Blood. 2002; 100:1532-42.

Gould, P., "Salt selection for basic drugs", Ref. International J. Pharm. 1986, 33, 201-217.

Gray, M. et al., Tetrahedron Lett., 41:6237-40 (2000).

Griswold, I. J. et al., "Effects of MLN518, A Dual FLT3 and KIT inhibitor, on Normal and Malignant Hematopoiesis" Blood, Jul. 2004 [Epub ahead of print].

Hartwig, J.F., "Organopalladium Chemistry for Organic Synthesis," Wiley Interscience, NY (2002).

Hellstrom et al., "Antibodies For Drug Delivery", in Controlled Drug Delivery (2nd Ed.), Robinson et al. (eds.), pp. 623-653 (Marcel Dekker, Inc. 1987).

Iddon. B. et al., J. Chem. Soc. Perkin Trans. 1., 1370, (1980).

Katritsky, A. et al., "*para*-Formylation of Nitroarenes via Vicarious Nucleophilic Substitution of Hydrogen with Tris(benzotriazol-1-yl)methane", Tetrahedron Lett., 37:347-50 (1996).

Kolder, C.R., et al, "Synthesis and Reactivity of 5-Chloro-2,4-Dihydrosypyridine", x Recl. Trav. Chim. Pays-Bas; 285 (1953).

Levis, M. et al. 2001, "A FLT3 tyrosine kinase inhibitor is selectively cytoxic to acute myeloid leukemia blasts harboring FLT3 internal tandem duplication mutations", Blood 98(3):885-7.

Levis, M. et al., "Novel FLT3 tyrosine kinase inhibitors" Expert Opin. Investing. Drugs (2003) 12 (12) 1951-1962.

Levis, M. et al., "Small Molecule FLT3 Tyrosine Kinase Inhibitors" Current Pharmaceutical Design, 2004, 10, 1183-1193.

Lyon, R. , et al., "Synthesis and Evaluation of Phenyl-and Benzoylpiperazines as Potential Serotonergic Agents", J. Med. Chem., 29: 630-4 (1986).

McKenna, H.J. et al., "Mice lacking flt3 ligand having deficient hematopoiesis affecting hematopoietic progenitor cells, dendritic cells and natural killer cells", Blood Jun. 2000; 95:3489-3497.

Miyaura, N. et al., "Palladium-Catalyzed Cross-Coupling Reactions of Organoboron Compounds", Chem. Rev. 95:2457 (1995).

Modern Amination Methods: Ricci, A., Ed., Wiley-VCH: Weinheim, 2000.

Murata, K. et al., "Selective cytotoxic mechanism of GTP-14564, a novel tyrosine kinase inhibitor in leukemia cells expressing a constitutively active Fms-like tyrosine kinase 3 (FLT3)" J Biol Chem. Aug. 29, 2003; 278(35):32892-8.

Nicolai, E., et al., "New Process for the Synthesis of Imidazo[4-5-b] pyridine Derivatives as Potent Orally Active Thromboxane $A_2$ Receptor Antagonists", J. Heterocyclic Chemistry, 31, (73) (1994).

O'Farrell, A.M. et al. "SU11248 is a novel FLT3 tyrosine kinase inhibitor with potent activity in vitro and in vivo" Blood, May 2003; 101:3597-3605.

Olah, G.A. et al., "Formylating Agents", Chemical Reviews, vol. 87, No. 4, 1987.

Protecting Groups, P, Kocienski Thieme Medical Publishers, 2000.

Quentmeier H, et al. FLT3 mutations in acute myeloid leukemia cell lines. Leukemia. Jan. 2003;17:120-124.

Regan, J., et al., Structure-Activity Relationships of the p38* MAP Kinsase Inhibitor 1-)5-*tert*-Butyl-2-*p*-tolyl-2h-pyrazol-3-yl)-3[4-(2-morpholin-4-yl-ethoxy)naph-thalen-1-yl-)urea (BIRB 796)J. Med. Chem., 46:4676-86 (2003).

Romeo, G., et al, "New Pyrimido [5,4-b_indoles as Ligands for *1-Adrenoceptor Subtypes", J. Med. Chem., 46: 2877-2894 (2003).

Sadick, M. et al., Analysis of Heregulin-Induced ErbB2 Phosphorylation with a High-Throughput Kinase Receptor Activation Enzyme-Linked Immunsorbent Assay, Analytical Biochemistry. 1996; 235:207-214.

Scheijen, B. et al. (2002), "Tyrosine kinase oncogenes innormal hematopoiesis and hematological disease", Oncogene 21(21):3314-33.

Simpson WG, The calcium channel blocker verapamil and cancer chemotherapy. Cell Calcium. Dec. 1985;6(6):449-67.

Smith, B. D. et al., "Single-agent CEP-701, a novel FLT3 inhibitor, shows biologic and clinical activity in patients with relapsed or refractory acute myeloid leukemia" Blood, May 2004; 103:3669-3676.

Smith, P, "The Curtius Reaction", Organic Reactions 3:337 (1947).

Stille, J.K., "The Palladium-Catalyzed Cross-Coupling Reactions of Organotin Reagents with Organic Electrophiles", Angew, Chem, Int. Ed. Engl., 25:508024 (1986).

Stirewalt, D.L. et al. (2003), "The role of FLT3 in haematopoietic malignancies", NatRev Cancer 3(9):650-65.

Stone, R.M. et al. "PKC 412 FLT3 inhibitor therapy in AML: results of a phase II trial" An Hematol 2004; 83 Suppl 1:S89-90.

Suzuki, A., "Metal-Catalyzed Coupling Reactions" F. Deiderich, P. Stang, Eds., Wiley-VCH, Weinheim (1998).

Thorpe, "Antibody Carriers of Cytotoxic Agents in Cancer Therapy: A Review", in Monoclonal Antibodies '84: Biological and Clinical Applications, Pinchera et al. (eds.), pp. 475-506 (1985).

Tse, K.F. et al., "Inhibition of FLT3-mediated transformation by use of a tyrosine kinase inhibitor" Leukemia, Jul. 2001 15(7):1001-10.

Wustrow, et al, "Coupling of Arylboronic Acids with a Partially Reduced Pyridine Derivative" Synthesis, 993 (1991).

Yee, K.W.H. et al., "SU5416 and SU5614 inhibit kinase activity of wild-type and mutant FLT3 receptor tyrosine kinase" Blood, Sep. 2002; 100:2941-294.

* cited by examiner

METHOD OF INHIBITING FLT3 KINASE

CROSS-REFERENCE TO RELATED APPLICATIONS

This application claims priority to U.S. Provisional Application Patent No. 60/727,687, filed Oct. 18, 2005, the entire disclosure of which is hereby incorporated in its entirely.

FIELD OF THE INVENTION

The present invention relates to methods of reducing or inhibiting kinase activity of FLT3 in a cell or a subject, and the use of such methods for preventing or treating in a subject a cell proliferative disorder and/or disorders related to FLT3.

BACKGROUND OF THE INVENTION

Protein kinases are enzymatic components of the signal transduction pathways which catalyze the transfer of the terminal phosphate from ATP to the hydroxy group of tyrosine, serine and/or threonine residues of proteins. Thus, compounds which inhibit protein kinase functions are valuable tools for assessing the physiological consequences of protein kinase activation. The overexpression or inappropriate expression of normal or mutant protein kinases in mammals has been a topic of extensive study and has been demonstrated to play a significant role in the development of many diseases, including diabetes, angiogenesis, psoriasis, restenosis, ocular diseases, schizophrenia, rheumatoid arthritis, atherosclerosis, cardiovascular disease and cancer. The cardiotonic benefits of kinase inhibition has also been studied. In sum, inhibitors of protein kinases have particular utility in the treatment of human and animal disease.

The fms-like tyrosine kinase 3 (FLT3) ligand (FLT3L) is one of the cytokines that affects the development of multiple hematopoietic lineages. These effects occur through the binding of FLT3L to the FLT3 receptor, also referred to as fetal liver kinase-2 (flk-2) and STK-1, a receptor tyrosine kinase (RTK) expressed on hematopoietic stem and progenitor cells. The FLT3 gene encodes a membrane-bound RTK that plays an important role in proliferation, differentiation and apoptosis of cells during normal hematopoiesis. The FLT3 gene is mainly expressed by early myeloid and lymphoid progenitor cells. See McKenna, Hilary J. et al. Mice lacking flt3 ligand have deficient hematopoiesis affecting hematopoietic progenitor cells, dendritic cells, and natural killer cells. Blood. June 2000; 95: 3489-3497; Drexler, H. G. and H. Quentmeier (2004). "FLT3: receptor and ligand." Growth Factors 22(2): 71-3.

The ligand for FLT3 is expressed by the marrow stromal cells and other cells and synergizes with other growth factors to stimulate proliferation of stem cells, progenitor cells, dendritic cells, and natural killer cells.

Hematopoietic disorders are pre-malignant disorders of these systems and include, for instance, the myeloproliferative disorders, such as thrombocythemia, essential thrombocytosis (ET), angiogenic myeloid metaplasia, myelofibrosis (MF), myelofibrosis with myeloid metaplasia (MMM), chronic idiopathic myelofibrosis (IMF), and polycythemia vera (PV), the cytopenias, and pre-malignant myelodysplastic syndromes. See Stirewalt, D. L. and J. P. Radich (2003). "The role of FLT3 in haematopoietic malignancies." Nat Rev Cancer 3(9): 650-65; Scheijen, B. and J. D. Griffin (2002). "Tyrosine kinase oncogenes in normal hematopoiesis and hematological disease." Oncogene 21(21): 3314-33.

Hematological malignancies are cancers of the body's blood forming and immune systems, the bone marrow and lymphatic tissues. Whereas in normal bone marrow, FLT3 expression is restricted to early progenitor cells, in hematological malignancies, FLT3 is expressed at high levels or FLT3 mutations cause an uncontrolled induction of the FLT3 receptor and downstream molecular pathway, possibly Ras activation. Hematological malignancies include leukemias, lymphomas (non-Hodgkin's lymphoma), Hodgkin's disease (also called Hodgkin's lymphoma), and myeloma—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM) and myeloid sarcoma. See Kottaridis, P. D., R. E. Gale, et al. (2003). "Flt3 mutations and leukaemia." Br J Haematol 122(4): 523-38. Myeloid sarcoma is also associated with FLT3 mutations. See Ansari-Lari, Ali et al. FLT3 mutations in myeloid sarcoma. British Journal of Haematology. 2004 September 126(6):785-91.

Mutations of FLT3 have been detected in about 30% of patients with acute myelogenous leukemia and a small number of patients with acute lymphomatic leukemia or myelodysplastic syndrome. Patients with FLT3 mutations tend to have a poor prognosis, with decreased remission times and disease free survival. There are two known types of activating mutations of FLT3. One is a duplication of 4-40 amino acids in the juxtamembrane region (ITD mutation) of the receptor (25-30% of patients) and the other is a point mutation in the kinase domain (5-7% of patients). The mutations most often involve small tandem duplications of amino acids within the juxtamembrane domain of the receptor and result in tyrosine kinase activity. Expression of a mutant FLT3 receptor in murine marrow cells results in a lethal myeloproliferative syndrome, and preliminary studies (Blood. 2002; 100: 1532-42) suggest that mutant FLT3 cooperates with other leukemia oncogenes to confer a more aggressive phenotype.

Specific inhibitors of FLT3 kinase present an attractive target for the treatment of hematopoietic disorders and hematological malignancies.

FLT3 kinase inhibitors known in the art include AG1295 and AG1296; Lestaurtinib (also known as CEP 701, formerly KT-5555, Kyowa Hakko, licensed to Cephalon); CEP-5214 and CEP-7055 (Cephalon); CHIR-258 (Chiron Corp.); EB-10 and IMC-EB10 (ImClone Systems Inc.); GTP 14564 (Merk Biosciences UK). Midostaurin (also known as PKC 412 Novartis AG); MLN 608 (Millennium USA); MLN-518 (formerly CT53518, COR Therapeutics Inc., licensed to Millennium Pharmaceuticals Inc.); MLN-608 (Millennium Pharmaceuticals Inc.); SU-11248 (Pfizer USA); SU-11657 (Pfizer USA); SU-5416 and SU 5614; THRX-165724 (Theravance Inc.); AMI-10706 (Theravance Inc.); VX-528 and VX-680 (Vertex Pharmaceuticals USA, licensed to Novartis (Switzerland), Merck & Co USA); and XL 999 (Exelixis USA). The following PCT International Applications and U.S. patent applications disclose additional kinase modulators, including modulators of FLT3: WO 2002032861, WO 2002092599, WO 2003035009, WO 2003024931, WO 2003037347, WO 2003057690, WO 2003099771, WO 2004005281, WO 2004016597, WO 2004018419, WO 2004039782, WO 2004043389, WO 2004046120, WO 2004058749, WO 2004058749, WO 2003024969 and U.S. Patent Application No. 20040049032.

See also Levis, M., K. F. Tse, et al. 2001 "A FLT3 tyrosine kinase inhibitor is selectively cytotoxic to acute myeloid leukemia blasts harboring FLT3 internal tandem duplication mutations." Blood 98(3): 885-7; Tse K F, et al. Inhibition of FLT3-mediated transformation by use of a tyrosine kinase inhibitor. Leukemia. 2001 July; 15(7): 1001-10; Smith, B. Douglas et al. Single-agent CEP-701, a novel FLT3 inhibitor, shows biologic and clinical activity in patients with relapsed or refractory acute myeloid leukemia Blood, May 2004; 103: 3669-3676; Griswold, Ian J. et al. Effects of MLN518, A Dual FLT3 and KIT Inhibitor, on Normal and Malignant Hematopoiesis. Blood, July 2004; [Epub ahead of print]; Yee, Kevin W. H. et al. SU5416 and SU5614 inhibit kinase activity of wild-type and mutant FLT3 receptor tyrosine kinase. Blood, September 2002; 100: 2941-294; O'Farrell, Anne-Marie et al. SU11248 is a novel FLT3 tyrosine kinase inhibitor with potent activity in vitro and in vivo. Blood, May 2003; 101: 3597-3605; Stone, R. M. et al. PKC 412 FLT3 inhibitor therapy in AML: results of a phase II trial. Ann Hematol. 2004; 83 Suppl 1:S89-90; and Murata, K. et al. Selective cytotoxic mechanism of GTP-14564, a novel tyrosine kinase inhibitor in leukemia cells expressing a constitutively active Fms-like tyrosine kinase 3 (FLT3). J Biol Chem. 2003 Aug. 29; 278(35):32892-8; Levis, Mark et al. Novel FLT3 tyrosine kinase inhibitors. Expert Opin. Investing. Drugs (2003) 12(12) 1951-1962; Levis, Mark et al. Small Molecule FLT3 Tyrosine Kinase Inhibitors. Current Pharmaceutical Design, 2004, 10, 1183-1193.

SUMMARY OF THE INVENTION

The present invention provides methods of reducing or inhibiting kinase activity of FLT3 in a cell or a subject, and the use of such methods for preventing or treating in a subject a cell proliferative disorder and/or disorders related to FLT3.

Other features and advantages of the invention will be apparent from the following detailed description of the invention and from the claims.

DETAILED DESCRIPTION OF THE INVENTION

Figure 1:
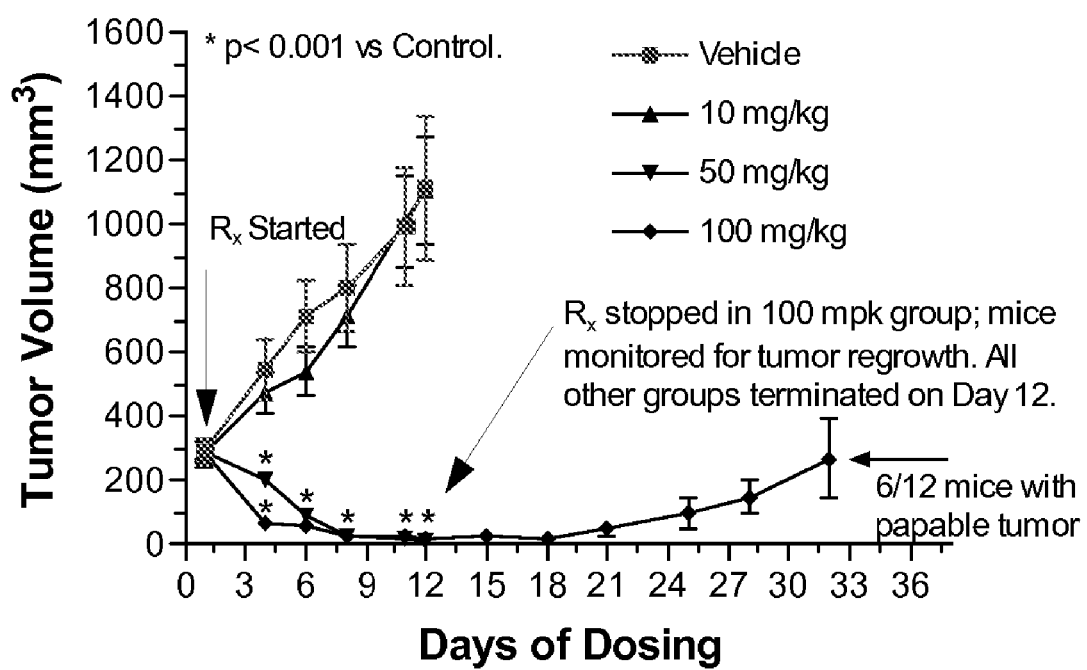
FIG. 1 shows the effects of oral administration of Example #38 of the present invention on the growth of MV4-11 tumor xenografts in nude mice.

The terms "comprising", "including", and "containing" are used herein in their open, non-limited sense.

Abbreviations

As used herein, the following abbreviations are intended to have the following meanings (additional abbreviations are provided where needed throughout the Specification):
ATP adenosine triphosphate
Boc or BOC tert-butoxycarbonyl
DCM dichloromethane
DMF dimethylformamide
DMSO dimethylsulfoxide
DIEA diisopropylethylamine
EDCI 1-(3-dimethylaminopropyl)-3-ethylcarbodiimide hydrochloride
EDTA ethylenediaminetetraaceticacid
EtOAc ethyl acetate
FBS fetal bovine serum
FP fluorescence polarization
GM-CSF granulocyte and macrophage colony stimulating factor
HOBT or HOBt 1-hydroxybenzotriazole hydrate
HPβCD hydroxypropyl β-cyclodextrin
HRP horse radish peroxidase
LC/MS (ESI) Liquid chromatography/mass spectrum (electrospray ionization)
MeOH Methyl alcohol
NMR nuclear magnetic resonance
PBS phosphatebufferedsaline
RPMI Rosewell Park Memorial Institute
RT room temperature
RTK receptor tyrosine kinase
SDS-PAGE sodium dodecyl sulfate polyacrylamide gel electrophoresis
TFA trifluoroacetic acid
THF tetrahydrofuran
TLC thin layer chromatography

DEFINITIONS

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "hydroxyalkyl" refers to both linear and branched chain radicals of up to 6 carbon atoms, in which one hydrogen atom has been replaced with an OH group.

The term "hydroxyalkylamino" refers to an hydroxyalkyl group in which one hydrogen atom from the carbon chain has been replaced with an amino group, wherein the nitrogen is the point of attachment to the rest of the molecule.

The term "cycloalkyl" refers to a saturated or partially unsaturated ring composed of from 3 to 8 carbon atoms. Up to four alkyl substituents may optionally be present on the ring. Examples include cyclopropyl, 1,1-dimethyl cyclobutyl, 1,2, 3-trimethylcyclopentyl, cyclohexyl, cyclopentenyl, cyclohexenyl, and 4,4-dimethyl cyclohexenyl.

The term "dihydrosulfonopyranyl" refers to the following radical:

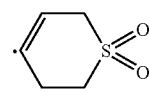

The term "hydroxyalkyl" refers to at least one hydroxyl group bonded to any carbon atom along an alkyl chain.

The term "aminoalkyl" refers to at least one primary or secondary amino group bonded to any carbon atom along an alkyl chain, wherein an alkyl group is the point of attachment to the rest of the molecule.

The term "alkylamino" refers to an amino with one alkyl substituent, wherein the amino group is the point of attachment to the rest of the molecule.

The term "dialkylamino" refers to an amino with two alkyl substituents, wherein the amino group is the point of attachment to the rest of the molecule.

The term "heteroaromatic" or "heteroaryl" refers to 5- to 7-membered mono- or 8- to 10-membered bicyclic aromatic ring systems, any ring of which may consist of from one to four heteroatoms selected from N, O, or S where the nitrogen and sulfur atoms can exist in any allowed oxidation state. Examples include benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "heteroatom" refers to a nitrogen atom, an oxygen atom or a sulfur atom wherein the nitrogen and sulfur atoms can exist in any allowed oxidation states.

The term "alkoxy" refers to straight or branched chain radicals of up to 12 carbon atoms, unless otherwise indicated, bonded to an oxygen atom. Examples include methoxy, ethoxy, propoxy, isopropoxy and butoxy.

The term "aryl" refers to monocyclic or bicyclic aromatic ring systems containing from 6 to 12 carbons in the ring. Alkyl substituents may optionally be present on the ring. Examples include benzene, biphenyl and napthalene.

The term "aralkyl" refers to a $C_{1-6}$ alkyl group containing an aryl substituent. Examples include benzyl, phenylethyl or 2-naphthylmethyl.

The term "sulfonyl" refers to the group $-S(O)_2R_a$, where $R_a$ is hydrogen, alkyl, cycloalkyl, haloalkyl, aryl, aralkyl, heteroaryl and heteroaralkyl. A "sulfonylating agent" adds the $-S(O)_2R_a$ group to a molecule.

Formula I

The present invention comprises methods of using the compounds of Formula I (referred to herein as "the compounds of the present invention"):

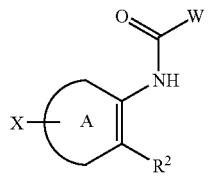

or a solvate, hydrate, tautomer or pharmaceutically acceptable salt thereof, wherein:

A is
  phenyl or pyridyl, either of which may be substituted with one of chloro, fluoro, methyl, $-N_3$, $-NH_2$, $-NH(alkyl)$, $-N(alkyl)_2$, $-S(alkyl)$, $-O(alkyl)$, or 4-aminophenyl;

W is
  pyrrolyl (including 1H-pyrrol-2-yl), imidazolyl, (including 1H-imidazol-2-yl), isoxazolyl, oxazolyl, 1,2,4 triazolyl, or furanyl (including furan-2-yl), any of which may be connected through any carbon atom, wherein the pyrrolyl, imidazolyl, isoxazolyl, oxazolyl, 1,2,4 triazolyl, or furanyl may contain one $-Cl$, $-CN$, $-NO_2$, $-OMe$, or $-CF_3$ substitution, connected to any other carbon;

$R^2$ is
  cycloalkyl (including cyclohexenyl, cyclopentenyl), thiophenyl, dihydrosulfonopyranyl, phenyl, furanyl, tetrahydropyridyl, or dihydropyranyl, any of which may be independently substituted with one or two of each of the following: chloro, fluoro, and $C_{(1-3)}$alkyl (including 4,4-dimethyl cyclohexenyl, 4-methyl cyclohexenyl, 2-methyl thiophenyl, 3-methyl thiophenyl), with the proviso that tetrahydropyridyl is connected to the ring A through a carbon-carbon bond;

X is

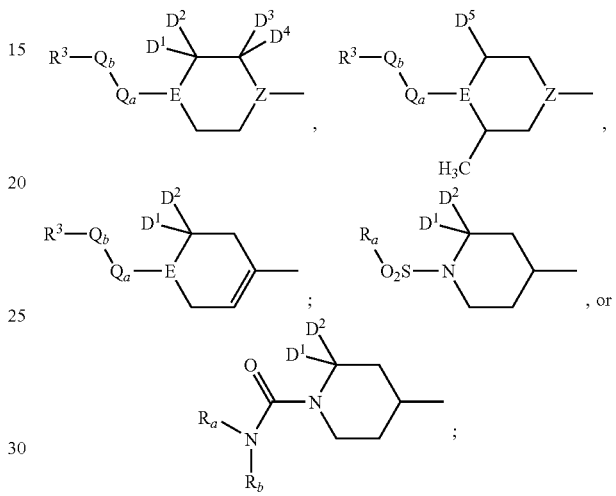

Z is
  CH or N;
$D^1$ and $D^2$ are
  each hydrogen or taken together form a double bond to an oxygen;
$D^3$ and $D^4$ are
  each hydrogen or taken together form a double bond to an oxygen;
$D^5$ is
  hydrogen or $-CH_3$, wherein said $-CH_3$ may be relatively oriented syn or anti;
$R_a$ and $R_b$ are independently
  hydrogen, cycloalkyl, haloalkyl, aryl, aralkyl, heteroaryl, or heteroaralkyl;
E is
  N, S, O, SO or $SO_2$, with the proviso that E may not be N if the following three conditions are simultaneously met: $Q_a$ is absent, $Q_b$ is absent, and $R^3$ is an amino group or cyclic amino radical wherein the point of attachment to E is N;
$Q_a$ is
  absent, $-CH_2-$, $-CH_2CH_2-$, or $C(O)$;
$Q_b$ is
  absent, $-NH-$, $-CH_2-$, $-CH_2CH_2-$, or $C(O)$, with the proviso that $Q_b$ may not be $C(O)$ if $Q_a$ is $C(O)$, and further provided that $Q_b$ may not be $-NH-$ if E is N and $Q_a$ is absent, further provided that $Q_b$ may not be $-NH-$ if $R^3$ is an amino group or cyclic amino radical wherein the point of attachment to $Q_b$ is N;
$R^3$ is
  hydrogen, phenyl, hydroxyalkylamino (including 2-hydroxy ethylamino), (hydroxyalkyl)$_2$amino, hydroxyalkyl(alkyl)amino (including 1-hydroxyeth-2-yl(methyl)amino), alkylamino (including methylamino), aminoalkyl (including 2-amino isopropyl), dihydroxyalkyl (including 1,3-dihydroxy isopropyl, 1,2-dihydroxy ethyl), alkoxy (including methoxy), dialkylamino (including dimethylamino), hydroxyalkyl (including 1-hydroxy eth-2-yl), —COOH, —CONH$_2$, —CN, —SO$_2$-alkyl-R$^4$ (including —SO$_2$CH$_3$), —NH$_2$, or a 5 or six membered ring which contains at least one heteroatom N and may optionally contain an additional heteromoiety selected from S, SO$_2$, N, and O, and the 5 or 6 membered ring may be saturated, partially unsaturated or aromatic (including piperidinyl, morpholinyl, imidazolyl, and pyridyl) wherein aromatic nitrogen in the 5 or 6 membered ring may be present as N-oxide (including pyridyl N-oxide), and the 5 or 6 membered ring may be optionally substituted with methyl, halogen, alkylamino, or alkoxy (including 1 methyl imidazolyl); R$^3$ may also be absent, with the proviso that R$^3$ is not absent when E is nitrogen; and R$^4$ is
  hydrogen, —OH, alkoxy, carboxy, carboxamido, or carbamoyl.

EMBODIMENTS

Embodiments of the present invention include a compound of Formula I wherein:

a) A is
  phenyl or pyridyl, either of which may be substituted with one of chloro, fluoro, methyl, —N$_3$, —NH$_2$, —NH(alkyl), —N(alkyl)$_2$, —S(alkyl), —O(alkyl), or 4-aminophenyl;

b) A is
  phenyl;

c) W is
  pyrrolyl (including 1H-pyrrol-2-yl), imidazolyl, (including 1H-imidazol-2-yl), isoxazolyl, oxazolyl, 1,2,4 triazolyl, or furanyl (including furan-2-yl), any of which may be connected through any carbon atom, wherein the pyrrolyl, imidazolyl, isoxazolyl, oxazolyl, 1,2,4 triazolyl, or furanyl may contain one —Cl, —CN, —NO$_2$, —OMe, or —CF$_3$ substitution, connected to any other carbon;

d) W is
  furan-2-yl, 1H-pyrrol-2-yl, or 1H-imidazol-2-yl, any of which may be substituted at the 4 or 5 carbons with —CN;

e) W is
  3H-2-imidazolyl-4-carbonitrile or 5-cyano-1H-pyrrol-2-yl;

f) W is
  3H-2-imidazolyl-4-carbonitrile;

g) R$^2$ is
  cycloalkyl (including cyclohexenyl, cyclopentenyl), thiophenyl, dihydrosulfonopyranyl, phenyl, furanyl, tetrahydropyridyl, or dihydropyranyl, any of which may be independently substituted with one or two of each of the following: chloro, fluoro, and C$_{(1-3)}$alkyl (including 4,4-dimethyl cyclohexenyl, 4-methyl cyclohexenyl, 2-methyl thiophenyl, 3-methyl thiophenyl), with the proviso that tetrahydropyridyl is connected to the ring A through a carbon-carbon bond;

h) R$^2$ is
  cycloalkyl (including cyclohexenyl, cyclopentenyl), which may substituted with one or two C$_{(1-3)}$alkyl (including 4,4-dimethyl cyclohexenyl, 4-methyl cyclohexenyl);

i) R$^2$ is
  cyclohexenyl, which may substituted with one or two C$_{(1-3)}$alkyl;

j) R$^2$ is
  cyclohexenyl, 4,4-dimethyl cyclohexenyl, or 4-methyl cyclohexenyl;

k) R$^2$ is
  cyclohexenyl;

l) X is

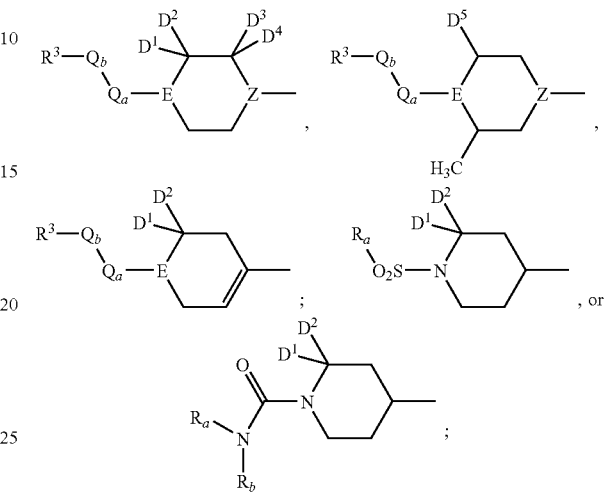

m) X is

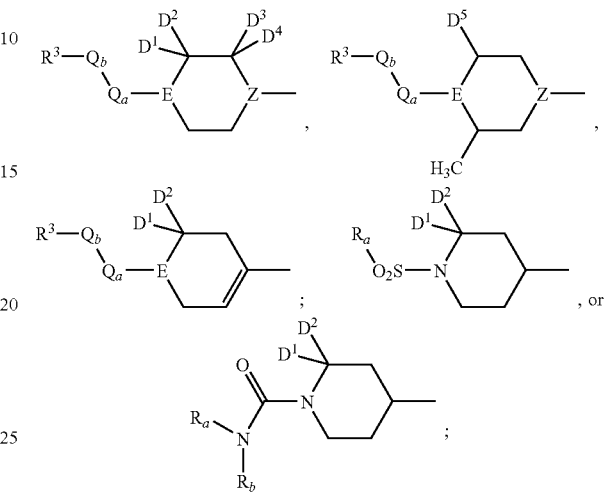

n) X is o) Z is
  CH or N;

p) Z is
  CH;

q) D$^1$ and D$^2$ are
  each hydrogen or taken together form a double bond to an oxygen;

r) D$^1$ and D$^2$ are
  each hydrogen;

s) D$^3$ and D$^4$ are
  each hydrogen or taken together form a double bond to an oxygen;

t) $D^3$ and $D^4$ are
  each hydrogen;
u) $D^5$ is
  hydrogen or —$CH_3$, wherein said —$CH_3$ may be relatively oriented syn or anti;
v) $R_a$ and $R_b$ are independently
  hydrogen, cycloalkyl, haloalkyl, aryl, aralkyl, heteroaryl, or heteroaralkyl;
w) E is
  N, S, O, SO or $SO_2$, with the proviso that E may not be N if the following three conditions are simultaneously met: $Q_a$ is absent, $Q_b$ is absent, and $R^3$ is an amino group or cyclic amino radical wherein the point of attachment to E is N;
x) E is
  N, with the proviso that E may not be N if the following three conditions are simultaneously met: $Q_a$ is absent, $Q_b$ is absent, and $R^3$ is an amino group or cyclic amino radical wherein the point of attachment to E is N;
y) $Q_a$ is
  absent, —$CH_2$—, —$CH_2CH_2$—, or C(O);
z) $Q_a$ is
  absent, —$CH_2CH_2$—, or C(O);
aa) $Q_a$ is
  absent, or C(O);
bb) $Q_a$ is
  C(O);
cc) $Q_b$ is
  absent, —NH—, —$CH_2$—, —$CH_2CH_2$—, or C(O), with the proviso that $Q_b$ may not be C(O) if $Q_a$ is C(O), and further provided that $Q_b$ may not be —NH— if E is N and $Q_a$ is absent, further provided that $Q_b$ may not be —NH— if $R^3$ is an amino group or cyclic amino radical wherein the point of attachment to $Q_b$ is N;
dd) $Q_b$ is
  absent, —$CH_2CH_2$—, or C(O), with the proviso that $Q_b$ may not be C(O) if $Q_a$ is C(O);
ee) $Q_b$ is
  absent, or C(O), with the proviso that $Q_b$ may not be C(O) if $Q_a$ is C(O);
ff) $R^3$ is
  hydrogen, phenyl, hydroxyalkylamino (including 2-hydroxy ethylamino), (hydroxyalkyl)$_2$amino, hydroxyalkyl(alkyl)amino (including 1-hydroxyeth-2-yl(methyl)amino), alkylamino (including methylamino), aminoalkyl (including 2-amino isopropyl), dihydroxyalkyl (including 1,3-dihydroxy isopropyl, 1,2-dihydroxy ethyl), alkoxy (including methoxy), dialkylamino (including dimethylamino), hydroxyalkyl (including 1-hydroxyeth-2-yl), —COOH, —$CONH_2$, —CN, —$SO_2$-alkyl-$R^4$ (including —$SO_2CH_3$), —$NH_2$, or a 5 or six membered ring which contains at least one heteroatom N and may optionally contain an additional heteromoiety selected from S, $SO_2$, N, and O, and the 5 or 6 membered ring may be saturated, partially unsaturated or aromatic (including piperidinyl, morpholinyl, imidazolyl, and pyridyl) wherein aromatic nitrogen in the 5 or 6 membered ring may be present as N-oxide (including pyridyl N-oxide), and the 5 or 6 membered ring may be optionally substituted with methyl, halogen, alkylamino, or alkoxy (including 1 methyl imidazolyl); $R^3$ may also be absent, with the proviso that $R^3$ is not absent when E is nitrogen;
gg) $R^3$ is
  hydrogen, phenyl, 2-hydroxy ethylamino, 1-hydroxyeth-2-yl(methyl)amino, methylamino, 2-amino isopropyl, 1,3-dihydroxy isopropyl, 1,2-dihydroxy ethyl, methoxy, dimethylamino, 1-hydroxyeth-2-yl, —COOH, —$CONH_2$, —CN, —$SO_2$—, —$SO_2CH_3$), —$NH_2$, piperidinyl, morpholinyl, imidazolyl, pyridyl, pyridyl N-oxide), or 1 methyl imidazolyl;
hh) $R^3$ is
  alkylamino (including methylamino), dialkylamino (including dimethylamino), or —$SO_2$-alkyl-$R^4$ (including —$SO_2CH_3$);
ii) $R^3$ is
  methylamino, dimethylamino, or —$SO_2CH_3$;
jj) $R^3$ is
  dimethylamino;
kk) $R^4$ is
  hydrogen, —OH, alkoxy, carboxy, carboxamido, or carbamoyl; and
ll) $R^4$ is
  hydrogen;

and all combinations of a) to ll), inclusive, herein above.

Preferred compounds of Formula I are those wherein W is substituted with one —CN.

Still other preferred compounds of Formula I are those wherein:

A is
  phenyl which may be substituted with one of chloro, fluoro, and methyl;
W is
  pyrrolyl, imidazolyl, isoxazolyl, oxazolyl, 1,2,4 triazolyl, or furanyl any of which may be connected through any carbon atom, wherein the pyrrolyl, imidazolyl, isoxazolyl, oxazolyl, 1,2,4 triazolyl, or furanyl may contain one —Cl, —CN, —$NO_2$, —OMe, or —$CF_3$ substitution, connected to any other carbon;
$R^2$ is
  cycloalkyl, thiophenyl, dihydrosulfonopyranyl, phenyl, furanyl, tetrahydropyridyl, or dihydropyranyl, any of which may be independently substituted with one or two of each of the following: chloro, fluoro, and $C_{(1-3)}$ alkyl, with the proviso that tetrahydropyridyl is connected to the ring A through a carbon-carbon bond;
X is and is attached to the phenyl A ring para to the nitrogen substituent, as depicted in formula II;

II

Z is
  CH or N;
$D^1$ and $D^2$ are
  each hydrogen or taken together form a double bond to an oxygen;

$D^3$ and $D^4$ are hydrogen;

E is
  N or $SO_2$; with the proviso that E may not be N if the following three conditions are simultaneously met: $Q_a$ is absent, $Q_b$ is absent, and $R^3$ is an amino group or cyclic amino radical wherein the point of attachment to E is N;

$Q_a$ is
  absent, —$CH_2$—, —$CH_2CH_2$—, or C(O);

$Q_b$ is
  absent, —NH—, —$CH_2$—, —$CH_2CH_2$—, or C(O), with the proviso that $Q_b$ may not be C(O) if $Q_a$ is C(O), and further provided that $Q_b$ may not be —NH— if E is N and $Q_a$ is absent, further provided that $Q_b$ may not be —NH— if $R^3$ is an amino group or cyclic amino radical wherein the point of attachment to $Q_b$ is N; and $R^3$ is
  hydrogen, piperidinyl, alkylamino, dialkylamino, hydroxyalkylamino, (hydroxyalkyl)$_2$amino, imidazolyl, 1-methyl imidazolyl, pyridyl, pyridyl N-oxide, hydroxyalkyl, —COOH, —$CONH_2$, —CN, —$SO_2CH_3$, —$NH_2$, morpholinyl; $R^3$ may also be absent, with the proviso that $R^3$ is not absent when E is nitrogen.

More preferred compounds of Formula I are those wherein:

A is
  phenyl;

W is
  pyrrolyl, imidazolyl, isoxazolyl, oxazolyl, or 1,2,4 triazolyl, any of which may be connected through any carbon atom, wherein the pyrrolyl, imidazolyl, isoxazolyl, oxazolyl, or 1,2,4 triazolyl, may contain one —Cl, —CN, —$NO_2$, —OMe, or —$CF_3$ substitution, connected to any other carbon;

$R^2$ is
  cycloalkyl, furanyl, or tetrahydropyridyl, any of which may be independently substituted with one or two of each of the substituents selected from the group consisting of chloro, fluoro, and $C_{(1-3)}$alkyl, with the proviso that tetrahydropyridyl must be connected to the ring A through a carbon-carbon bond.

X is

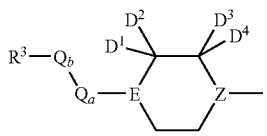

and is attached to the phenyl A ring para to the nitrogen substituent, as depicted in formula II;

II

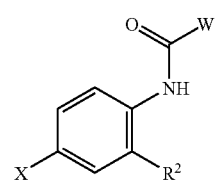

Z is
  CH or N;

$D^1$ and $D^2$ are
  each hydrogen or taken together form a double bond to an oxygen;

$D^3$ and $D^4$ are hydrogen;

E is
  N or $SO_2$; with the proviso that E may not be N if the following three conditions are simultaneously met: $Q_a$ is absent, $Q_b$ is absent, and $R^3$ is an amino group or cyclic amino radical wherein the point of attachment to E is N;

$Q_a$ is
  absent, —$CH_2$—, —$CH_2CH_2$—, or C(O);

$Q_b$ is
  absent, —NH—, —$CH_2$—, —$CH_2CH_2$—, or C(O), with the proviso that $Q_b$ may not be C(O) if $Q_a$ is C(O), and further provided that $Q_b$ may not be —NH— if E is N and $Q_a$ is absent, further provided that $Q_b$ may not be —NH— if $R^3$ is an amino group or cyclic amino radical wherein the point of attachment to $Q_b$ is N; and $R^3$ is
  hydrogen, piperidinyl, alkylamino, dialkylamino, hydroxyalkylamino, (hydroxyalkyl)$_2$amino, imidazolyl, 1-methyl imidazolyl, pyridyl, pyridyl N-oxide, hydroxyalkyl, —COOH, —$CONH_2$, —CN, —$SO_2CH_3$, —$NH_2$, morpholinyl; $R^3$ may also be absent, with the proviso that $R^3$ is not absent when E is nitrogen.

Even more preferred compounds of Formula I are those wherein:

A is
  phenyl;

W is
  pyrrolyl, imidazolyl, isoxazolyl, oxazolyl, or 1,2,4 triazolyl, any of which may be connected through any carbon atom, wherein the pyrrolyl, imidazolyl, isoxazolyl, oxazolyl, or 1,2,4 triazolyl, may contain one —Cl, —CN, —$NO_2$, —OMe, or —$CF_3$ substitution, connected to any other carbon;

$R^2$ is
  cycloalkyl, furanyl, or tetrahydropyridyl, any of which may be independently substituted with one or two of each of the substituents selected from the group consisting of chloro, fluoro, and $C_{(1-3)}$alkyl, with the proviso that tetrahydropyridyl must be connected to the ring A through a carbon-carbon bond.

X is

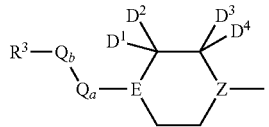

and is attached to the phenyl A ring para to the nitrogen substituent, as depicted in formula II;

II

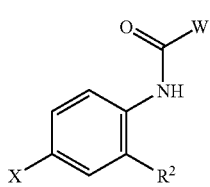

Z is
  CH or N;

D¹ and D² are
each hydrogen or taken together form a double bond to an oxygen;
D³ and D⁴ are hydrogen;
E is N; with the proviso that E may not be N if the following three conditions are simultaneously met: $Q_a$ is absent, $Q_b$ is absent, and R³ is an amino group or cyclic amino radical wherein the point of attachment to E is N;
$Q_a$ is
absent, —CH₂—, —CH₂CH₂—, or C(O);
$Q_b$ is
absent, —NH—, —CH₂—, —CH₂CH₂—, or C(O), with the proviso that $Q_b$ may not be C(O) if $Q_a$ is C(O), and further provided that $Q_b$ may not be —NH— if E is N and $Q_a$ is absent, further provided that $Q_b$ may not be —NH— if R³ is an amino group or cyclic amino radical wherein the point of attachment to $Q_b$ is N; and
R³ is
hydrogen, piperidinyl, alkylamino, dialkylamino, hydroxyalkylamino, (hydroxyalkyl)₂amino, imidazolyl, 1-methyl imidazolyl, hydroxyalkyl, —COOH, —CONH₂, —CN, —SO₂CH₃, —NH₂, or morpholinyl.

Especially preferred compounds of Formula I are those wherein:
A is
phenyl;
W is
pyrrolyl, or imidazolyl, wherein the pyrrolyl, or imidazolyl, may contain one —Cl, —CN, —NO₂, —OMe, or —CF₃ substitution, connected to any other carbon;
R² is
cycloalkyl, furanyl, or tetrahydropyridyl, any of which may be independently substituted with one or two of each of the substituents selected from the group consisting of chloro, fluoro, and $C_{(1-3)}$alkyl, with the proviso that tetrahydropyridyl must be connected to the ring A through a carbon-carbon bond.
X is

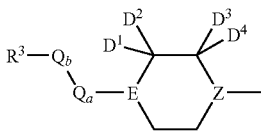

and is attached to the phenyl A ring para to the nitrogen substituent, as depicted in formula II;

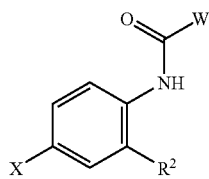

Z is
CH or N;
D¹ and D² are
each hydrogen or taken together form a double bond to an oxygen;
D³ and D⁴ are hydrogen;
E is N; with the proviso that E may not be N if the following three conditions are simultaneously met: $Q_a$ is absent, $Q_b$ is absent, and R³ is an amino group or cyclic amino radical wherein the point of attachment to E is N;
$Q_a$ is CO
$Q_b$ is
absent, —NH—, —CH₂—, —CH₂CH₂—, or C(O), with the proviso that $Q_b$ may not be C(O) if $Q_a$ is C(O), and further provided that $Q_b$ may not be —NH— if E is N and $Q_a$ is absent, further provided that $Q_b$ may not be —NH— if R³ is an amino group or cyclic amino radical wherein the point of attachment to $Q_b$ is N; and
R³ is
hydrogen, piperidinyl, hydroxyalkylamino, (hydroxyalkyl)₂amino, alkylamino, dialkylamino, imidazolyl, 1-methyl imidazolyl, pyridyl, pyridyl N-oxide, hydroxyalkyl, —COOH, —CONH₂, —CN, —SO₂CH₃, —NH₂, or morpholinyl.

Examples of compounds of Formula I include:
5-cyano-furan-2-carboxylic acid [4-(4-methyl-piperazin-1-yl)-2-(3-methyl-thiophen-2-yl)-phenyl]-amide, and
5-cyano-furan-2-carboxylic acid [4-(4-methyl-piperazin-1-yl)-2-(2-methyl-thiophen-3-yl)-phenyl]-amide, and solvates, hydrates, tautomers and pharmaceutically acceptable salts thereof.

Additional examples of compounds of Formula I include:
4-cyano-1H-imidazole-2-carboxylic acid [4-(1-acetyl-piperidin-4-yl)-2-(1,2,5,6-tetrahydro-pyridin-3-yl)-phenyl]-amide,
4-cyano-1H-imidazole-2-carboxylic acid [2-cyclohex-1-enyl-4-(1,1-dioxo-hexahydro-1λ⁶-thiopyran-4-yl)-phenyl]-amide,
5-cyano-furan-2-carboxylic acid [2-cyclohex-1-enyl-4-(4-methyl-piperazin-1-yl)-phenyl]-amide,
5-cyano-furan-2-carboxylic acid [2-(3,6-dihydro-2H-pyran-4-yl)-4-(4-methyl-piperazin-1-yl)-phenyl]-amide,
4-cyano-1H-imidazole-2-carboxylic acid [2-(1,1-dioxo-1,2,3,6-tetrahydro-1λ⁶-thiopyran-4-yl)-4-piperidin-4-yl-phenyl]-amide,
4-cyano-1H-imidazole-2-carboxylic acid [4-(1-acetyl-piperidin-4-yl)-2-(1,1-dioxo-1,2,3,6-tetrahydro-1λ⁶-thiopyran-4-yl)-phenyl]-amide,
5-cyano-furan-2-carboxylic acid [2'-methyl-5-(4-methyl-piperazin-1-yl)-biphenyl-2-yl]-amide, and
5-cyano-furan-2-carboxylic acid [2'-fluoro-5-(4-methyl-piperazin-1-yl)-biphenyl-2-yl]-amide, and solvates, hydrates, tautomers and pharmaceutically acceptable salts thereof.

Further examples of compounds of Formula I are:
(4-{4-[(4-cyano-1H-imidazole-2-carbonyl)-amino]-3-cyclohex-1-enyl-phenyl}-piperidin-1-yl)-acetic acid,
4-cyano-1H-imidazole-2-carboxylic acid [4-(1-carbamoylmethyl-piperidin-4-yl)-2-cyclohex-1-enyl-phenyl]-amide,
4-cyano-1H-imidazole-2-carboxylic acid [2-(4-methyl-cyclohex-1-enyl)-4-piperidin-4-yl-phenyl]-amide,
4-cyano-1H-imidazole-2-carboxylic acid {2-cyclohex-1-enyl-4-[1-(2-hydroxy-ethyl)-piperidin-4-yl]-phenyl}-amide,
4-cyano-1H-imidazole-2-carboxylic acid [2-(4-methyl-cyclohex-1-enyl)-4-(1-pyridin-2-ylmethyl-piperidin-4-yl)-phenyl]-amide,
4-cyano-1H-imidazole-2-carboxylic acid {2-cyclohex-1-enyl-4-[1-(2-hydroxy-1-hydroxymethyl-ethyl)-piperidin-4-yl]-phenyl}-amide,
4-cyano-1H-imidazole-2-carboxylic acid {4-[1-(2-cyano-ethyl)-piperidin-4-yl]-2-cyclohex-1-enyl-phenyl}-amide, 4-cyano-1H-imidazole-2-carboxylic acid {2-cyclohex-1-enyl-4-[1-(2-morpholin-4-yl-ethyl)-piperidin-4-yl]-phenyl}-amide,
4-cyano-1H-imidazole-2-carboxylic acid (2-cyclohex-1-enyl-4-piperidin-4-yl-phenyl)-amide,
4-cyano-1H-imidazole-2-carboxylic acid {2-cyclohex-1-enyl-4-[1-(2-methanesulfonyl-ethyl)-piperidin-4-yl]-phenyl}-amide,
4-cyano-1H-imidazole-2-carboxylic acid [2-cyclohex-1-enyl-4-(1-pyridin-2-ylmethyl-piperidin-4-yl)-phenyl]-amide,
4-cyano-1H-imidazole-2-carboxylic acid {2-cyclopent-1-enyl-4-[1-(1-methyl-1 H-imidazol-2-ylmethyl)-piperidin-4-yl]-phenyl}-amide,
4-cyano-1H-imidazole-2-carboxylic acid (2-cyclopent-1-enyl-4-piperidin-4-yl-phenyl)-amide,
4-cyano-1H-pyrrole-2-carboxylic acid (2-cyclohex-1-enyl-4-piperidin-4-yl-phenyl)-amide,
4-cyano-1H-imidazole-2-carboxylic acid [2-cyclohex-1-enyl-4-(3,4,5,6-tetrahydro-2H-[1,2']bipyridinyl-4-yl)-phenyl]-amide, and
4-cyano-1H-pyrrole-2-carboxylic acid [4-(1-acetyl-piperidin-4-yl)-2-cyclohex-1-enyl-phenyl]-amide, and solvates, hydrates, tautomers and pharmaceutically acceptable salts thereof.

Other examples of compounds of Formula I are:
4-cyano-1H-imidazole-2-carboxylic acid {2-cyclohex-1-enyl-4-[1-(1-oxy-pyridine-3-carbonyl)-piperidin-4-yl]-phenyl}-amide,
4-cyano-1H-imidazole-2-carboxylic acid {2-cyclohex-1-enyl-4-[1-(1-oxy-pyridine-4-carbonyl)-piperidin-4-yl]-phenyl}-amide,
4-cyano-1H-imidazole-2-carboxylic acid {2-cyclohex-1-enyl-4-[1-(3-morpholin-4-yl-propionyl)-piperidin-4-yl]-phenyl}-amide,
4-{4-[(4-cyano-1H-imidazole-2-carbonyl)-amino]-3-cyclohex-1-enyl-phenyl}-piperidine-1-carboxylic acid amide,
4-cyano-1H-imidazole-2-carboxylic acid {2-cyclohex-1-enyl-4-[1-(pyridine-3-carbonyl)-piperidin-4-yl]-phenyl}-amide,
4-{4-[(4-cyano-1H-imidazole-2-carbonyl)-amino]-3-cyclohex-1-enyl-phenyl}-piperidine-1-carboxylic acid (2-hydroxy-ethyl)-amide,
4-cyano-1H-imidazole-2-carboxylic acid {2-cyclohex-1-enyl-4-[1-(2-3 H-imidazol-4-yl-acetyl)-piperidin-4-yl]-phenyl}-amide,
4-cyano-1H-imidazole-2-carboxylic acid {2-cyclohex-1-enyl-4-[1-(2-pyridin-4-yl-acetyl)-piperidin-4-yl]-phenyl}-amide,
4-cyano-1H-imidazole-2-carboxylic acid (2-cyclohex-1-enyl-4-{1-[2-(1-methyl-1H-imidazol-4-yl)-acetyl]-piperidin-4-yl}-phenyl)-amide,
4-cyano-1H-imidazole-2-carboxylic acid {2-cyclohex-1-enyl-4-[1-(2-pyridin-3-yl-acetyl)-piperidin-4-yl]-phenyl}-amide,
4-cyano-1H-imidazole-2-carboxylic acid {2-cyclohex-1-enyl-4-[1-(2-methanesulfonyl-acetyl)-piperidin-4-yl]-phenyl}-amide,
4-cyano-1H-imidazole-2-carboxylic acid {2-cyclohex-1-enyl-4-[1-(2-pyridin-2-yl-acetyl)-piperidin-4-yl]-phenyl}-amide, and
4-cyano-1H-imidazole-2-carboxylic acid [4-(1-acetyl-piperidin-4-yl)-2-cyclohex-1-enyl-phenyl]-amide, and solvates, hydrates, tautomers and pharmaceutically acceptable salts thereof.

Another example compound of Formula I is:
4-cyano-1H-imidazole-2-carboxylic acid [2-cyclohex-1-enyl-4-(1-{2-[(2-hydroxy-ethyl)-methyl-amino]-acetyl}-piperidin-4-yl)-phenyl]-amide, and solvates, hydrates, tautomers and pharmaceutically acceptable salts thereof.

Another example compound of Formula I is:
4-cyano-1H-imidazole-2-carboxylic acid {2-cyclohex-1-enyl-4-[1-(2-dimethylamino-acetyl)-piperidin-4-yl]-phenyl}-amide, and solvates, hydrates, tautomers and pharmaceutically acceptable salts thereof.

Another example compound of Formula I is:
4-cyano-1H-imidazole-2-carboxylic acid {2-cyclohex-1-enyl-4-[1-(2-morpholin-4-yl-acetyl)-piperidin-4-yl]-phenyl}-amide, and solvates, hydrates, tautomers and pharmaceutically acceptable salts thereof.

Still other example compounds of formula I are:
4-Cyano-1H-imidazole-2-carboxylic acid {4-[1-(3-amino-3-methyl-butyryl)-piperidin-4-yl]-2-cyclohex-1-enyl-phenyl}-amide trifluoroacetic acid salt,
4H-[1,2,4]-triazole-3-carboxylic acid (2-cyclohex-1-enyl-4-piperidin-4-yl-phenyl)-amide bis trifluoroacetic acid salt,
5-Chloro-4H-[1,2,4]-triazole-3-carboxylic acid (2-cyclohex-1-enyl-4-piperidin-4-yl-phenyl)-amide trifluoroacetic acid salt,
5-Cyano-1H-imidazole-2-carboxylic acid [2-cyclohex-1-enyl-4-(cis-2,6-dimethyl-piperidin-4-yl)-phenyl]-amide bis trifluoroacetic acid salt,
5-cyano-1H-imidazole-2-carboxylic acid [2-cyclohex-1-enyl-4-(trans-2,6-dimethyl-piperidin-4-yl)-phenyl]-amide bis trifluoroacetic acid salt,
5-Cyano-1H-imidazole-2-carboxylic acid {2-cyclohex-1-enyl-4-[1-(R)-(+)-(2,3-dihydroxy-propionyl)-piperidin-4-yl]-phenyl}-amide,
5-Cyano-1H-imidazole-2-carboxylic acid [2-cyclohex-1-enyl-4-(1-methoxy-piperidin-4-yl)-phenyl]-amide trifluoroacetic acid salt,
4-Cyano-1H-imidazole-2-carboxylic acid [6-(4,4-dimethyl-cyclohex-1-enyl)-1',2',3',4',5',6'-hexahydro-[2,4']bipyridinyl-5-yl]-amide trifluoroacetic acid salt,
5-Cyano-1H-imidazole-2-carboxylic acid {4-[1-(2-amino-2-methyl-propionyl)-piperidin-4-yl]-2-cyclohex-1-enyl-phenyl}-amide trifluoroacetic acid salt, and
5-Cyano-1H-imidazole-2-carboxylic acid [6-cyclohex-1-enyl-1'-(2-methanesulfonyl-ethyl)-1',2',3',4',5',6'-hexahydro-[2,4']bipyridinyl-5-yl]-amide, and solvates, hydrates, tautomers and pharmaceutically acceptable salts thereof.

Additional example compounds of Formula I are:
4-Cyano-1H-imidazole-2-carboxylic acid {2-cyclohex-1-enyl-4-[1-(2-methylamino-acetyl)-piperidin-4-yl]-phenyl}-amide,
4-Cyano-1H-imidazole-2-carboxylic acid [1'-(2-dimethylamino-acetyl)-6-(4,4-dimethyl-cyclohex-1-enyl)-1',2',3',4',5',6'-hexahydro-[2,4']bipyridinyl-5-yl]-amide trifluoroacetic acid salt, and
4-Cyano-1H-imidazole-2-carboxylic acid [6-(4,4-dimethyl-cyclohex-1-enyl)-1'-(2-methanesulfonyl-ethyl)-1',2',3',4',5',6'-hexhydro-[2,4']bipyridinyl-5-yl]-amide trifluoroacetic acid salt, and solvates, hydrates, tautomers and pharmaceutically acceptable salts thereof.

As used herein, the term "the compounds of the present invention" shall also include solvates, hydrates, tautomers or pharmaceutically acceptable salts thereof.

Pharmaceutically Acceptable Salts

As stated, the compounds of the present invention may also be present in the form of pharmaceutically acceptable salts.

For use in medicines, the salts of the compounds of the present invention refer to non-toxic "pharmaceutically acceptable salts." FDA approved pharmaceutically acceptable salt forms (Ref. International J. Pharm. 1986, 33, 201-217; J. Pharm. Sci., 1977, January, 66(1), p1) include pharmaceutically acceptable acidic/anionic or basic/cationic salts.

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate (SEH), sodium hydroxide, or zinc.

Prodrugs

The present invention also includes within its scope, prodrugs of the compounds of the present invention. In general, such prodrugs will be functional derivatives of the compounds which are readily convertible in vivo into an active compound. Thus, in the methods of treatment of the present invention, the term "administering" shall encompass the means for treating, ameliorating or preventing a syndrome, disorder or disease described herein with the compounds of the present invention or a prodrug thereof, which would obviously be included within the scope of the invention albeit not specifically disclosed any given compound. Conventional procedures for the selection and preparation of suitable prodrug derivatives are described in, for example, "Design of Prodrugs", ed. H. Bundgaard, Elsevier, 1985.

Stereochemical Isomers

One skilled in the art will recognize that some compounds of the present invention have one or more asymmetric carbon atoms in their structure. It is intended that the present invention include within its scope single enantiomer forms of the compounds of the present invention, racemic mixtures, and mixtures of enantiomers in which an enantiomeric excess is present.

The term "single enantiomer" as used herein defines all the possible homochiral forms which the compounds of the present invention and their N-oxides, addition salts, quaternary amines, and physiologically functional derivatives may possess.

Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (enantiomers).

The term "stereoisomer" refers to isomers of identical constitution that differ in the arrangement of their atoms in space. Enantiomers and diastereomers are examples of stereoisomers.

The term "chiral" refers to the structural characteristic of a molecule that makes it impossible to superimpose it on its mirror image.

The term "enantiomer" refers to one of a pair of molecular species that are mirror images of each other and are not superimposable.

The term "diastereomer" refers to stereoisomers that are not mirror images.

The symbols "R" and "S" represent the configuration of substituents around a chiral carbon atom(s).

The term "racemate" or "racemic mixture" refers to a composition composed of equimolar quantities of two enantiomeric species, wherein the composition is devoid of optical activity.

The term "homochiral" refers to a state of enantiomeric purity.

The term "optical activity" refers to the degree to which a homochiral molecule or nonracemic mixture of chiral molecules rotates a plane of polarized light.

It is to be understood that the various substituent stereoisomers, geometric isomers and mixtures thereof used to prepare the compounds of the present invention are either commercially available, can be prepared synthetically from commercially available starting materials or can be prepared as isomeric mixtures and then obtained as resolvedisomers using techniques well-known to those of ordinary skill in the art.

The isomeric descriptors "R," and "S" are used as described herein for indicating atom configuration(s) relative to a core molecule and are intended to be used as defined in the literature (IUPAC Recommendations for Fundamental Stereochemistry (Section E), Pure Appl. Chem., 1976, 45:13-30).

The compounds of the present invention may be prepared as an individual isomer by either isomer-specific synthesis is or resolved from an isomeric mixture. Conventional resolution techniques include forming the free base of each isomer of an isomeric pair using an optically active salt (followed by fractional crystallization and regeneration of the free base), forming an ester or amide of each of the isomers of an isomeric pair (followed by chromatographic separation and removal of the chiral auxiliary) or resolving an isomeric mixture of either a starting material or a final product using preparative TLC (thin layer chromatography) or a chiral HPLC column.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope solvates of the compounds of the present invention. Thus, in the methods of treatment of the present invention, the term "administering" shall encompass the means for treating, ameliorating or preventing a syndrome, disorder or disease described herein with the compounds of the present invention or a solvate thereof, which would obviously be included within the scope of the invention albeit not specifically disclosed.

N-oxides

The compounds of the present invention may be converted to the corresponding N-oxide form following art-known procedures for converting a trivalent nitrogen into its N-oxide form. Said N-oxidation reaction may generally be carried out by reacting the starting material with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tbutyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Tautomeric Forms

The compounds of the present invention may also exist in their tautomeric forms. Such forms although not explicitly indicated in the present application are intended to be included within the scope of the present invention.

Preparation of the Compounds of the Present Invention

During any of the processes for preparation of the compounds of the present invention, it may be necessary and/or desirable to protect sensitive or reactive groups on any of the molecules concerned. This may be achieved by means of conventional protecting groups, such as those described in *Protecting Groups*, P. Kocienski, Thieme Medical Publishers, 2000; and T. W. Greene & P. G. M. Wuts, *Protective Groups in Organic Synthesis*, $3^{rd}$ ed. Wiley Interscience, 1999. The protecting groups may be removed at a convenient subsequent stage using methods known in the art.

Methods of Preparation

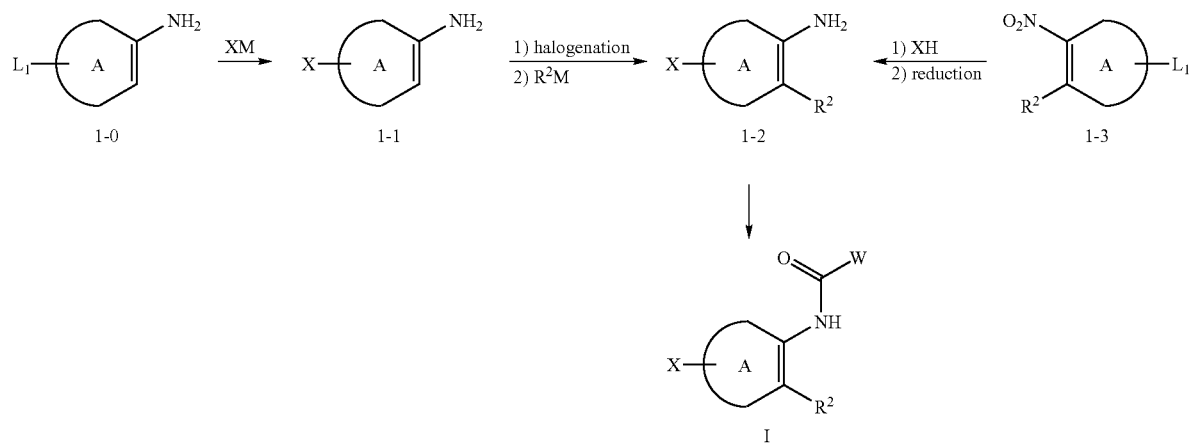

Scheme 1

Scheme 1 illustrates general methodology for the preparation of compounds of Formula I. Compounds of Formula 1-2 can be obtained by ortho-halogenation, preferably bromination, of amino compounds of Formula 1-1 followed by metal-catalyzed coupling reactions with boronic acids or boronate esters (Suzuki reactions, where $R^2M$ is $R^2B(OH)_2$ or a boronic ester) or tin reagents (Stille reactions, where $R^2M$ is $R^2Sn(alkyl)_3$) (for reviews, see N. Miyaura, A. Suzuki, *Chem. Rev.*, 95:2457 (1995), J. K. Stille, *Angew. Chem, Int. Ed. Engl.*, 25: 508024 (1986) and A. Suzuki in Metal-Catalyzed Coupling Reactions, F. Deiderich, P. Stang, Eds., Wiley-VCH, Weinheim (1988)). Compounds of formula 1-1 may be commercially available, or the above palladium mediated cross-coupling reactions described above may be used to generate compounds of Formula 1-1 from starting material 1-0.

Preferred conditions for the bromination of 1-1 are N-bromosuccinimide (NBS) in a suitable solvent such as N,N-dimethylformamide (DMF), dichloromethane (DCM) or acetonitrile. Metal-catalyzed couplings, preferably Suzuki reactions, can be performed according to standard methodology, preferably in the presence of a palladium catalyst such as tetrakis(triphenylphosphine)palladium(0) (Pd(PPh$_3$)$_4$), an aqueous base such aq. Na$_2$CO$_3$, and a suitable solvent such as toluene, ethanol, dimethoxyethane (DME), or DMF.

Compounds of Formula I can be prepared by reaction of compounds of Formula 1-2 with carboxylic acids WCOOH according to standard procedures for amide bond formation (for a review, see: M. Bodansky and A. Bodansky, The Practice of Peptide Synthesis, Springer-Verlag, NY (1984)) or by reaction with acid chlorides WCOCl or activated esters WCO$_2$Rq (where Rq is a leaving group such as pentafluorophenyl or N-succinimide). The preferred reaction conditions for coupling with WCOOH are: when W is a furan, oxalyl chloride in DCM with DMF as a catalyst to form the acid chloride WCOCl and then coupling in the presence of a trialkylamine such as DIEA; when W is a pyrrole, 1-(3-dimethylaminopropyl)-3-ethylcarbodiimide hydrochloride (EDCI) and 1-hydroxybenzotriazole-6-sulfonamidomethyl hydrochloride (HOBt); and when W is an imidazole, the preferred conditions are bromotripyrrolidinophosphonium hexafluorophosphate (PyBrOP) and diisopropylethylamine (DIEA) in DCM.

It is understood that the optional substitution present on ring A in Formula I may be present in the starting materials 1-1 or 1-3 and, in such cases, would be carried through the synthesis outlined in Scheme 1. Alternatively various substituents on compounds of Formula I may be introduced in a number of ways described below to provide the optional substitution listed for Formula I. The leaving group "$L_1$" present on ring A in Formula 1-0 or 1-3, can be substituted before or at any step during Scheme 1. When such leaving groups (preferably fluoro or chloro) are activated by the nitro group of Formula 1-3 for nucleophilic attack, they can undergo direct nucleophilic aromatic substitution by ammonia and azide anion or by amines, alcohols, thiols and other nucleophiles in the presence of a suitable base such as K$_2$CO$_3$, N,N-diisopropylethylamine (DIEA) or NEt$_3$. When the leaving group is suitable for metal-catalyzed couplings (preferably bromo or trifluoromethane-sulfonyloxy), a number of cross-coupling reactions (such as Suzuki or Stille reactions as discussed above for the introduction of R$^2$) may be performed. Other metal-catalyzed coupling reactions that can be employed include aromatic and heteroaromatic amination and amidation (for reviews, see: S. L. Buchwald, et al, *Top. Curr. Chem.*, 219:131-209 (2001) and J. F. Hartwig in "*Organopalladium Chemistry for Organic Synthesis*," Wiley Interscience, NY (2002). Additional metal catalyzed cross coupling reactions with 2,4,6-trimethyl-cyclotriboroxane may be employed if L$_1$ is bromo, iodo, or chloro activated by nitro to generate optional methyl substitution (see M. Gray, et al, Tetrahedron Lett., 41: 6237-40 (2000)).

In some cases, the initial substituents can be further derivatized as described below to provide the final substitution of Formula I.

An alternative method for the introduction of nitrogen-containing heterocyclic substituents onto ring A is to form the heterocycle from an amino group on ring A. The amino group may be originally present in the starting material in a protected or unprotected form or may result from the reduction of a nitro group which also can be either originally present in the starting material or attached by a nitration reaction. In addition, the amino group may be formed by reduction of an azide group which can be present in the starting material or may result from nucleophilic aromatic substitution of an activated halide by azide anion as mentioned above. The amino group may also result from nucleophilic aromatic substitution of an activated halide (in, for example a nitrohalo compound) by ammonia or by the anion of a protected ammonia equivalent, for example, t-butyl carbamate. If introduced in protected form, the amine can be deprotected according to standard literature methods. (For examples of amine protecting groups and deprotection methods see: Theodora W. Greene and Peter G. M. Wuts, John Wiley and Sons, Inc., NY (1991).) The ring-forming reaction involves treatment of the aniline amino group with a suitable optionally substituted di-electrophile, preferably a dihalide or dicarbonyl compound, which results in two substitutions on the amino group to form an optionally substituted heterocycle. In the case of dihalides, any of a number of suitable bases can be added as an acid scavenger such as potassium carbonate, sodium hydroxide, or, a trialkylamine such as triethylamine. Thus, treatment with a bis(2-haloethyl)amine such as bis(2-chloroethyl)amine or bis(2-bromoethyl)amine would afford a piperazine ring (see, for example, *J. Med. Chem.*, 29: 640-4 (1986) and *J. Med. Chem.*, 46: 2837 (2003)). Optional substitution on the amine nitrogen of the reagent would incorporate optional substitution on the terminal amine of the piperazine. For example, treatment with N,N-bis(2-chloroethyl)aniline would give an N-phenylpiperazino group. Treatment with a bis(2-haloethyl)ether or bis(2-haloethyl)thioether would afford a morpholine or thiomorpholine ring, respectively.

Another alternative method to direct substitution to introduce heterocyclic substituents onto ring A is to form the heterocycle from an aldehyde (i.e. from a formyl group on ring A). The formyl group may be originally present in the starting material in a protected or unprotected form or may result from or any of a number of formylation reactions known in the literature including a Vilsmeier-Haack reaction (for a review of formylation chemistry, see: G. A. Olah, et al, Chem Rev., 87: (1987)) or by para-formylation of nitroaromatics (see: A. Katritsky and L. Xie, *Tetrahedron Lett.*, 37:347-50 (1996)).

Finally it is understood that compounds of Formula I may be further derivatized. Protecting groups on compounds of Formula I can be removed according to standard synthetic methodologies (Theodora W. Greene and Peter G. M. Wuts, John Wiley and Sons, Inc., NY (1991)) and can be then subjected to further derivatization. Examples of further derivatization of compounds of I include, but are not limited to: when compounds of Formula I contain a primary or secondary amine, the amine may be reacted with aldehydes or ketones in the presence of a reducing agent such as sodium triacetoxyborohydride (see Abdel-Magid *J. Org. Chem.* 61, pp. 3849-3862, (1996)) to reductively alkylate; with acid chlorides or carboxylic acids and an amide bond forming reagent as described above to form amides; with sulfonyl chlorides to form sulfonamides; with isocyanates to form ureas; with aryl- or heteroaryl-halides in the presence of a palladium catalyst as described above (see Buchwald and Hartwig references above) to form aryl and heteroarylamines. In addition, when compounds of Formulae I contain an aryl halide or heteroaryl halide, these compounds may be subjected to metal-catalyzed reactions with boronic acids (for example, Suzuki or Stille couplings as described above), or, amines or alcohols (Buchwald- or Hartwig-type couplings, see Buchwald and Hartwig references above). When compounds of Formulae I contain a cyano group, this group may be hydrolyzed to amides or acids under acid or basic conditions. Basic amines may be oxidized to N-oxides and conversely N-oxides may be reduced to basic amines. When compounds of Formula I contain a sulfide, either acyclic or cyclic, the sulfide can be further oxidized to the corresponding sulfoxides or sulfones. Sulfoxides can be obtained by oxidation using an appropriate oxidant such as one equivalent of (meta-chloroperbenzoicacid) MCPBA or by treatment with $NaIO_4$ (see, for example, J. Regan, et al, *J. Med. Chem.*, 46: 4676-86 (2003)) and sulfones can be obtained using two equivalents of MCPBA or by treatment with 4-methylmorpholine N-oxide and catalytic osmium tetroxide (see, for example, PCT application WO 01/47919).

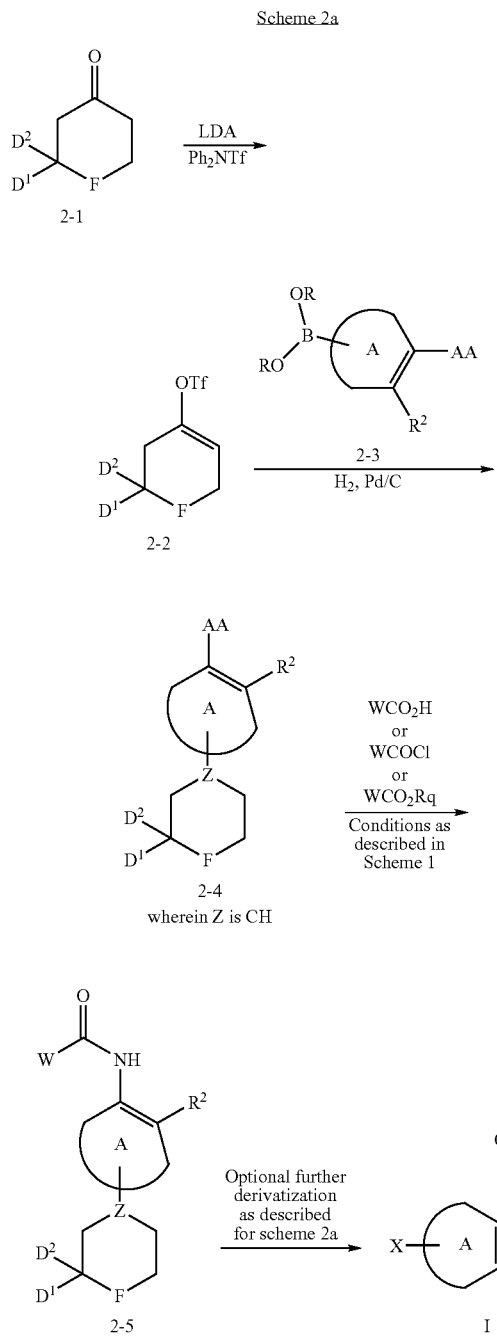

Scheme 2a illustrates a route to compounds of Formula I. F represents $—NQ_aQ_bR^3—$, —O—, S, SO, or $SO_2$, and AA represents $—NH_2$ or $—NO_2$. $D^1$ and $D^2$ are shown for illustrative purposes only; it is recognized by those skilled in art that $D^5 D^6 D^7 D^8$ may also be present. Ketones of formula 2-1 can be converted to a vinyl triflate of formula 2-2 by treatment with a non-nucleophilic base such as LDA and then trapping of the resulting enolate with a triflating reagent such as trifluoromethanesulfonic anhydride or preferably N-phenyltrifluoromethanesulfonimide. Suzuki coupling of boronic acids or boronate esters of formula 2-3 to vinyl triflates of formula 2-2 can provide compounds of formula 2-4 where Z is C (*Synthesis*, 993 (1991)).

For compounds of formula 2-4 treatment with Pd/C can reduce both the olefin (and the nitro if AA is $NO_2$) to give Z is CH, AA is $NH_2$. Compounds of formula 2-4 where F represents $—SO_2$ can be prepared from compounds of formula 2-4 where AA is $—NO_2$ and F is a sulfide (F is —S—) by oxidation with MCPBA or other methods described in Scheme 1. The nitro group may then be reduced with Pd/C to reduce both the nitro and the olefin.

Compounds of formula 2-4 (AA is $NH_2$) are then converted to compounds of Formula 2-5 (which also represent compounds of Formulae I if no further modifications are required) as described in Scheme 1.

Compounds of formula 2-5 may be further modified to provide additional compounds of Formula I. For example, in cases where F is $—NQ_aQ_bR^3—$, $Q_aQ_b$ is a direct bond, and $R_3$ represents a BOC protecting group ($CO_2tBu$), the BOC group may be removed according to standard methodology such as trifluoroactic acid (TFA) in DCM (Greene and Wuts, ibid.) to provide a secondary amine that can then be further derivatized to provide compounds of Formula I. Further derivatization includes, but is not limited to: reactions with aldehydes or ketones in the presence of a reducing agent such as sodium triacetoxyborohydride to provide compounds of Formula II where F is $—NCH_2R^3$ (A. F. Abdel-Magid, ibid.); with acid chlorides or with carboxylic acids and an amide bond forming reagent (as described in Scheme 1) to provide compounds of formula II where F is $—NCOR^3$; with sulfonyl chlorides (as described in Scheme 1) to provide compounds of Formula I where F is $—NSO_2R_a$; with isocyanates (as described in Scheme 1) to provide compounds of Formula II where F is $—NCONR_aR_b$; or subjected to metal-catalyzed substitution reactions as outlined in Scheme 1 to provide compounds of Formula I where F is $—NR^3$. (S. L. Buchwald, et al, ibid.; J. H. Hartwig, ibid.) For the above example, $R_a$ and $R_b$ are independently hydrogen, alkyl, cycloalkyl, haloalkyl, aryl, aralkyl, heteroaryl and heteroaralkyl.

Scheme 2b

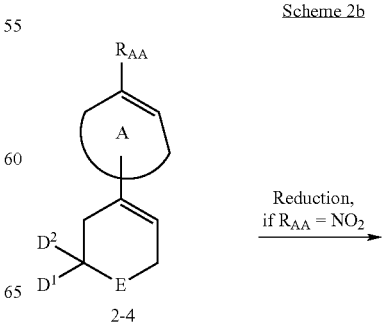

-continued

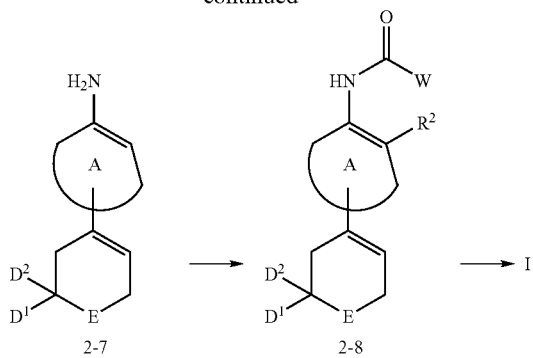

Scheme 2b illustrates a modification of Scheme 2a to synthesize partially unsaturated compounds of Formula I. E represents —$NQ_aQ_bR^3$—, —O-($D^1$ and $D^2$ are H), —S-($D^1$ and $D^2$ are H), -($D^1$ and $D^2$ are H), or —$SO_2$-($D^1$ and $D^2$ are H), and $R_{AA}$ represents —$NH_2$ or —$NO_2$. Compounds of formula 2-4 are prepared as shown in Scheme 2. If $R_{AA}$ is —$NO_2$, the nitro group must be reduced by a method that does not reduce olefins, such as iron and ammonium chloride. If $R_{AA}$ of formula 2-4 is an amino group then no step is necessary and compounds of formula 2-4 are also compounds of formula 2-7. To prepared compounds of formula 2-7 where E is —$SO_2$— or —SO—, the oxidation of the sulfide must be performed on compound 2-4 where $R_{AA}$ is —$NO_2$ as described above, followed by nitro reduction.

Scheme 3

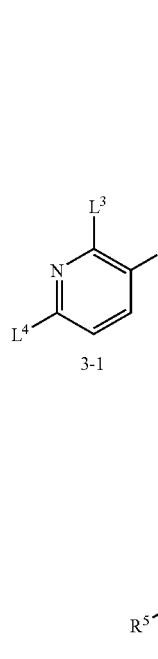

Scheme 3 illustrates the preparation of intermediates for the synthesis of compounds of Formula I, where ring A is pyridyl, and $R^5$ is the optional substitution on ring A or one of the heterocyclic substituents as defined in Formula I. K is $NH_2$ or other functional groups such as $NO_2$, COOH or COOR which can eventually be converted to amino group by known literature methods such as reductions for $NO_2$ (as discussed for Scheme 1) or Curtius rearrangement for COOH (for a review, see *Organic Reactions,* 3: 337 (1947)). $L^3$ and $L^4$ are halogens. (K is COOH can also be formed from K is COOR by simple base- or acid-catalyzed hydrolysis.)

In general, the selectivity and order in introducing $R^2$ and $R^5$ can be achieved by the relative reactivity of the halogens $L^3$ and $L^4$ chosen in compound (3-1), the intrinsic selectivity of the heterocycle and/or the reaction conditions employed. An example of using the relative reactivity of the halogens $L^3$ and $L^4$ in selectively introducing $R^2$ and $R^5$ would include the situation where, in compounds of Formula 3-1 where $L^3$ is a fluoro group and $L^4$ is a bromo group, selective displacement of the fluoro group by a nucleophile can be achieved followed by substitution of the remaining bromo group by metal-catalyzed substitution chemistry (such as Suzuki or Stille cross-coupling reactions as further outlined below). Similarly in compounds of Formula 3-1 where one of $L^3$ and $L^4$ is an iodo group and the other is a bromo or chloro group, selective metal-catalyzed substitution chemistry (such as Suzuki or Stille cross-coupling reactions or Buchwald/Hartwig aminations as further discussed below) on the iodo group can be achieved followed by replacement of the remaining bromo or chloro group by another metal-catalyzed substitution reaction.

As illustrated in Scheme 3, leaving group $L^3$ in Formula 3-1 can be first substituted to obtain compounds of Formula 3-3 or leaving group $L^4$ can be first substituted to obtain compound of Formula 3-2. Compounds 3-2 or 3-3 can then be reacted to displace $L^3$ or $L^4$ to furnish the compound of Formula 3-4.

Thus, a direct nucleophilic displacement or metal-catalyzed amination of compound of Formula 3-1 with a secondary amine, ammonia or a protected amine such as tert-butyl carbamate (for review, see Modern Amination Methods: Ricci, A., Ed.; Wiley-VCH: Weinheim, 2000), can be used to introduce $R^5$ in Formulae 3-2 or 3-3 where $R^5$ is a primary or secondary amine, amino group ($NH_2$), and amine equivalent or a protected amino group. Metal-catalyzed coupling of compound 3-1 with boronic acids or boronates esters (Suzuki reaction, M is boronic acid group or boronate ester group) or with organotin compounds (Stille reaction, M is $SnR_3$, where R is alkyl and the other substituents as defined above, as described in Scheme 1 can provide compounds of Formulae 3-2 or 3-3.

Compound 3-2 can be further converted to compound 3-4 by a metal-catalyzed Suzuki or Stille coupling as described above. $L^4$ in compound 3-3 also subsequently can be substituted with $R^5$ to obtain compounds of Formula 3-4, again, by a direct nucleophilic substitution or metal-catalyzed reaction with a nucleophile or by the same metal-catalyzed cross-coupling reaction as described above. When $R^5$ in the formulae (3-2, 3-3 or 3-4) is a protected amine and K not an amino group, it can be deprotected to unmask the amino functionality. This amino functionality can then be further derivatized as described in Scheme 1. When the K group in Formula 3-4 is not an amino group (such as functionality described above), it can be converted to an amino group according to known literature methods (see, for example Comprehensive Organic Transformations: Larock, R. S.; Wiley and Sons Inc., USA, 1999) and the resulting amine 3-5 can be employed in amide bond formation reactions as described in Scheme (1) to obtain the compounds in Formula I. When K in Formula 3-4 is an amino group it can be directly used in amide coupling as described above.

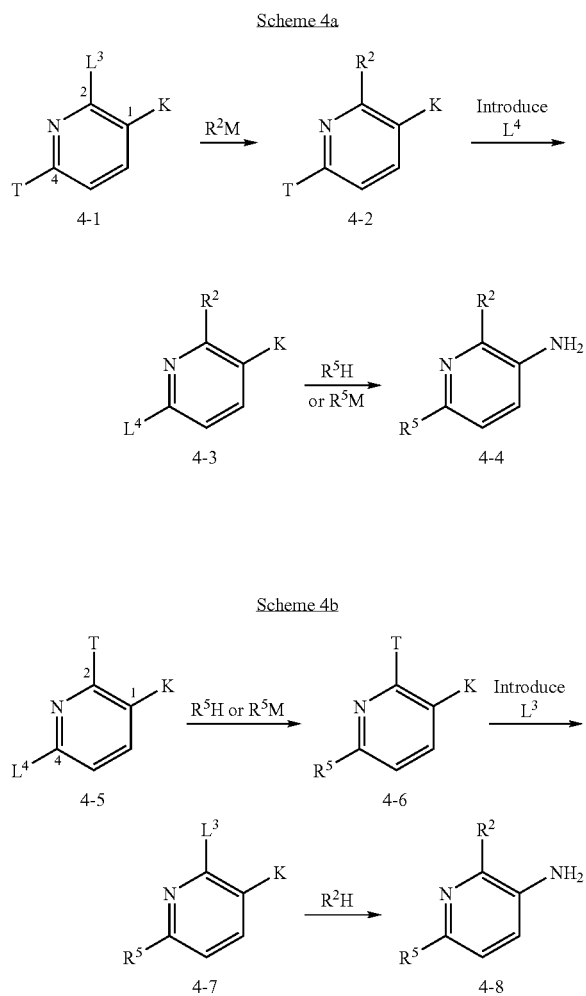

Scheme 4a

Scheme 4b

Schemes 4a and 4b illustrate the preparation of intermediates to be further modified according to Scheme 3 starting from a monohalo-substituted compound of Formulae 4-1 and 4-5 by introducing the second leaving group after the replacement of the first one has been completed. These can also be used for the synthesis of compounds of Formula I where ring A is a pyridine and $R^5$ is either the optional substitution on Ring A or one of the heterocyclic substituents. As in Scheme 3, the remaining positions on the pyridine ring can be substituted as described in Formula I. K is $NH_2$ or other functional groups such as $NO_2$, COOH or COOR which can eventually be converted to amino group by known literature methods such as reductions or Curtius rearrangement as described in Scheme 3. $L^3$ and $L^4$ are halogens. In these compounds, T is either H or is a functional group such as OH that can be converted to leaving groups $L^3$ or $L^4$ such as halogen, triflate or mesylate by known literature methods (see, for example, Nicolai, E., et al., *J. Heterocyclic Chemistry*, 31, (73), (1994)). Displacement of $L^3$ in compound of Formula 4-1 or $L^4$ in Formula 4-5 by methods described in Scheme 3, can yield compounds of Formulae 4-2 and 4-6. At this point, the substituent T of compounds 4-2 or 4-6 can be converted to a leaving group $L^4$ or $L^3$ (preferably a halogen) by standard methods to provide compounds of Formulae 4-3 and 4-5. For example, when T is OH, the preferred reagents to effect this transformation are thionyl chloride, $PCl_5$, $POCl_3$ or $PBr_3$ (see, for examples, Kolder, den Hertog., *Recl. Trav. Chim.* Pays-Bas; 285, (1953), and Iddon, B, et. al., *J. Chem. Soc. Perkin Trans.* 1., 1370, (1980)). When T is H, it can be directly halogenated (preferably brominated) to provide compounds of Formulae 4-3 or 4-7 (see, for example, Canibano, V. et al., *Synthesis*, 14, 2175, (2001)). The preferred conditions for bromination are NBS in a suitable solvent such as DCM or acetonitrile. The compounds of Formulae 4-3 or 4-7 can be converted to compounds of Formulae 4-4 or 4-8 by introduction of the remaining groups $R^2$ or $R^5$, respectively, by the methods described above and then on to compounds of Formula I, by the methods described in Scheme 3 for conversion of compounds of Formulae 3-4 and 3-5 to compounds of Formula I.

Representative compounds of the present invention and their synthesis are presented in the following chart and examples thereafter. The following are for exemplary purposes only and are in no way meant to limit the invention.

| | Name | Structure |
|---|---|---|
| 4 | 5-Cyano-furan-2-carboxylic acid [4-(4-methyl-piperazin-1-yl)-2-(3-methyl-thiophen-2-yl)-phenyl]-amide | 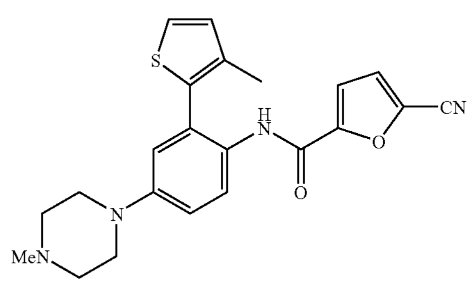 |

| Name | Structure |
|---|---|
| 5 5-Cyano-furan-2-carboxylic acid [4-(4-methyl-piperazin-1-yl)-2-(4-methyl-thiophen-3-yl)-phenyl]-amide | |
| 6 4-Cyano-1H-imidazole-2-carboxylic acid {2-cyclohex-1-enyl-4-[1-(2-hydroxy-1-hydroxymethyl-ethyl)-piperidin-4-yl]-phenyl}-amide trifluoroacetic acid salt | |
| 7 4-Cyano-1H-imidazole-2-carboxylic acid {2-cyclohex-1-enyl-4-[1-(2-morpholin-4-yl-acetyl)-piperidin-4-yl]-phenyl}-amide | |

-continued

| Name | Structure |
|---|---|
| 8 4-Cyano-1H-imidazole-2-carboxylic acid {2-cyclohex-1-enyl-4-[1-(3-morpholin-4-yl-propionyl)-piperidin-4-yl]-phenyl}-amide | |
| 9 5-Cyano-furan-2-carboxylic acid [2'-methyl-5-(4-methyl-piperazin-1-yl)-biphenyl-2-yl]-amide | |
| 10 5-Cyano-furan-2-carboxylic acid [2'-fluoro-5-(4-methyl-piperazin-1-yl)-biphenyl-2-yl]-amide | |
| 11 5-Cyano-furan-2-carboxylic acid [2-cyclohex-1-enyl-4-(4-methyl-piperazin-1-yl)-phenyl]-amide | |

-continued

| | Name | Structure |
|---|---|---|
| 12 | 5-Cyano-furan-2-carboxylic acid[2-(3,6-dihydro-2H-pyran-4-yl)-4-(4-methyl-piperazin-1-yl)-phenyl-amide] | 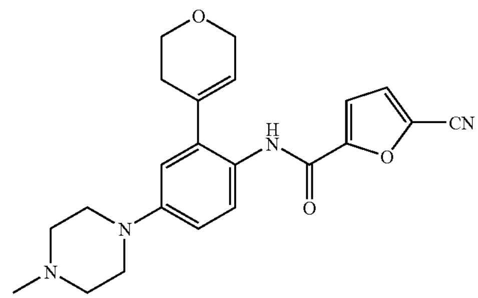 |
| 13 | 4-Cyano-1H-pyrrole-2-carboxylic acid (2-cyclohex-1-enyl-4-piperidin-4-yl-phenyl)-amide trifluoroacetic acid salt | 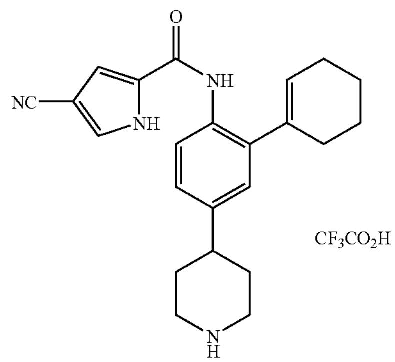 |
| 14 | 4-Cyano-1H-imidazole-2-carboxylic acid (2-cyclohex-1-enyl-4-piperidin-4-yl-phenyl)-amide trifluoroacetic acid salt | 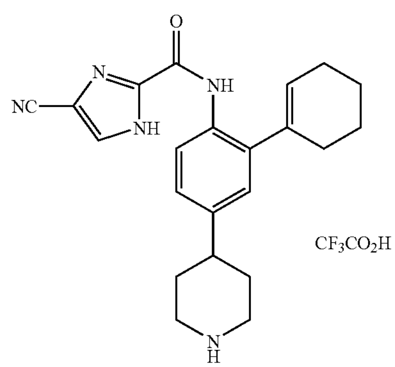 |
| 15 | 4-Cyano-1H-pyrrole-2-carboxylic acid [4-(1-acetyl-piperidin-4-yl)-2-cyclohex-1-enyl-phenyl]-amide | 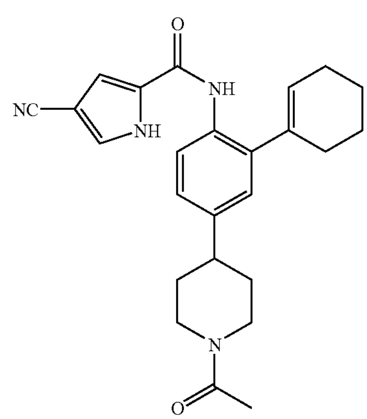 |

-continued

| | Name | Structure |
|---|---|---|
| 16 | 4-Cyano-1H-imidazole-2-carboxylic acid [4-(1-acetyl-piperidin-4-yl)-2-cyclohex-1-enyl-phenyl]-amide | 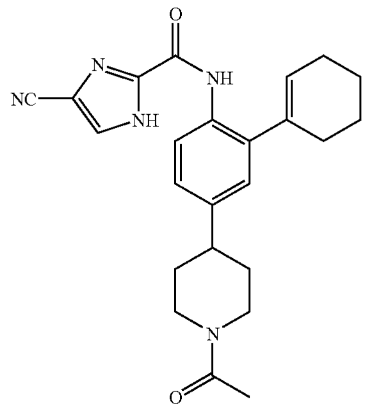 |
| 17 | 4-Cyano-1H-imidazole-2-carboxylic acid [2-(4-methyl-cyclohex-1-enyl)-4-piperidin-4-yl-phenyl]-amide trifluoroacetic acid salt | $CF_3CO_2H$ |
| 18 | 4-Cyano-1H-imidazole-2-carboxylic acid (2-cyclopent-1-enyl-4-piperidin-4-yl-phenyl)-amide trifluoroacetic acid salt | $CF_3CO_2H$ |
| 20 | 4-Cyano-1H-imidazole-2-carboxylic acid {2-cyclohex-1-enyl-4-[1-(2-methanesulfonyl-acetyl)-piperidin-4-yl]-phenyl}-amide | 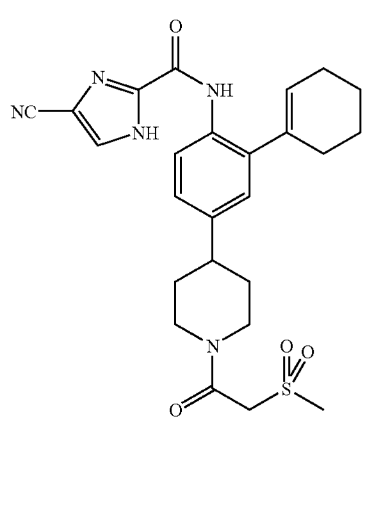 |

-continued

| Name | Structure |
|---|---|
| 21 4-Cyano-1H-imidazole-2-carboxylic acid [2-cyclohex-1-enyl-4-(1-pyridin-2-ylmethyl-piperidin-4-yl)-phenyl]-amide trifluoroacetic acid salt | 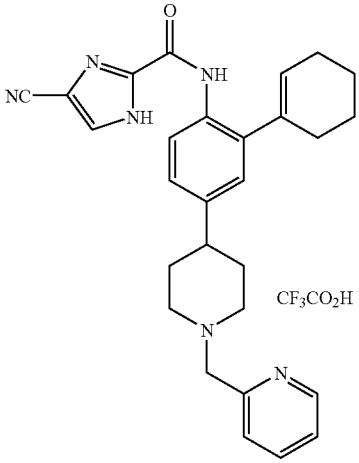 |
| 22 4-Cyano-1H-imidazole-2-carboxylic acid [2-(4-methyl-cyclohex-1-enyl)-4-(1-pyridin-2-ylmethyl-piperidin-4-yl)-phenyl]-amide trifluoroacetic acid salt | 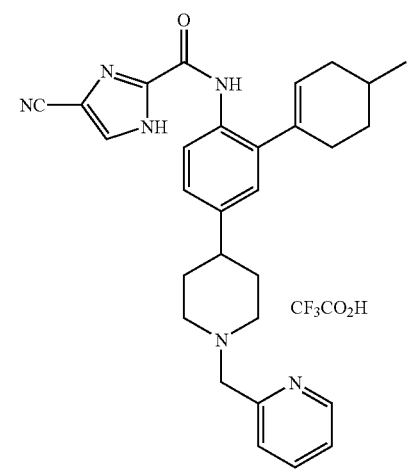 |
| 23 4-Cyano-1H-imidazole-2-carboxylic acid {2-cyclopent-1-enyl-4-[1-(1-methyl-1H-imidazol-2-ylmethyl)-piperidin-4-yl]-phenyl}-amide trifluoroacetic acid salt | 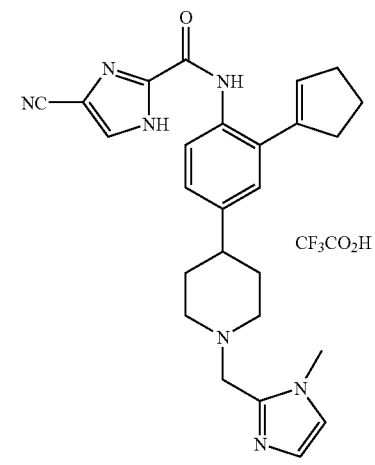 |

| Name | Structure |
|---|---|
| 24 4-{4-[(4-Cyano-1H-imidazole-2-carbonyl)-amino]-3-cyclohex-1-enyl-phenyl}-piperidine-1-carboxylic acid amide | |
| 25 4-Cyano-1H-imidazole-2-carboxylic acid [2-cyclohex-1-enyl-4-(3,4,5,6-tetrahydro-2H-[1,2']bipyridinyl-4-yl)-phenyl]-amide trifluoroacetic acid salt | |
| 26 4-Cyano-1H-imidazole-2-carboxylic acid {2-cyclohex-1-enyl-4-[1-(2-hydroxy-ethyl)-piperidin-4-yl]-phenyl}-amide trifluoroacetic acid salt | |

-continued

| | Name | Structure |
|---|---|---|
| 27 | 4-Cyano-1H-imidazole-2-carboxylic acid {4-[1-(2-cyano-ethyl)-piperidin-4-yl]-2-cyclohex-1-enyl-phenyl}-amide trifluoroacetic acid salt | 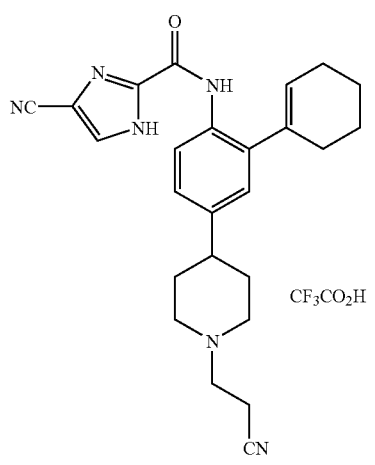 |
| 28 | 4-Cyano-1H-imidazole-2-carboxylic acid [4-(1-carbamoylmethyl-piperidin-4-yl)-2-cyclohex-1-enyl-phenyl]-amide trifluoroacetic acid salt | 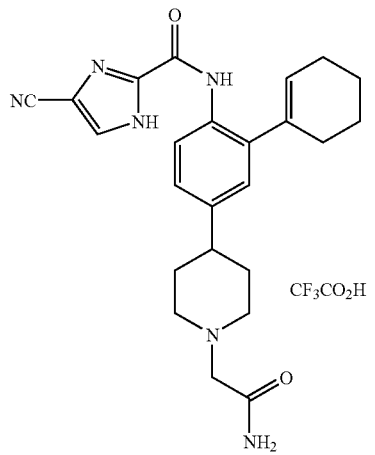 |
| 29 | 4-Cyano-1H-imidazole-2-carboxylic acid {2-cyclohex-1-enyl-4-[1-(2-pyridin-2-yl-acetyl)-piperidin-4-yl]-phenyl}-amide trifluoroacetic acid salt | 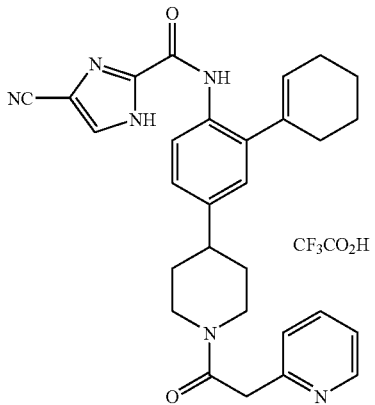 |

| Name | Structure |
|---|---|
| 30 4-Cyano-1H-imidazole-2-carboxylic acid {2-cyclohex-1-enyl-4-[1-(2-pyridin-3-yl-acetyl)-piperidin-4-yl]-phenyl}-amide trifluoroacetic acid salt | |
| 31 4-Cyano-1H-imidazole-2-carboxylic acid {2-cyclohex-1-enyl-4-[1-(2-pyridin-4-yl-acetyl)-piperidin-4-yl]-phenyl}-amide trifluoroacetic acid salt | |
| 32 4-Cyano-1H-imidazole-2-carboxylic acid (2-cyclohex-1-enyl-4-{1-[2-(1-methyl-1H-imidazol-4-yl)-acetyl]-piperidin-4-yl}-phenyl)-amide trifluoroacetic acid salt | |

-continued

| | Name | Structure |
|---|---|---|
| 33 | 4-Cyano-1H-imidazole-2-carboxylic acid {2-cyclohex-1-enyl-4-[1-(2-1H-imidazol-4-yl-acetyl)-piperidin-4-yl]-phenyl}-amide trifluoroacetic acid salt | 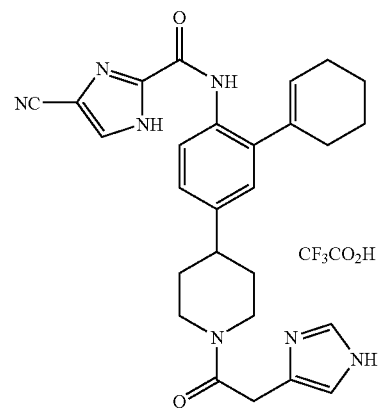 |
| 34 | 4-Cyano-1H-imidazole-2-carboxylic acid {2-cyclohex-1-enyl-4-[1-(2-morpholin-4-yl-ethyl)-piperidin-4-yl]-phenyl}-amide di-trifluoroacetic acid salt | 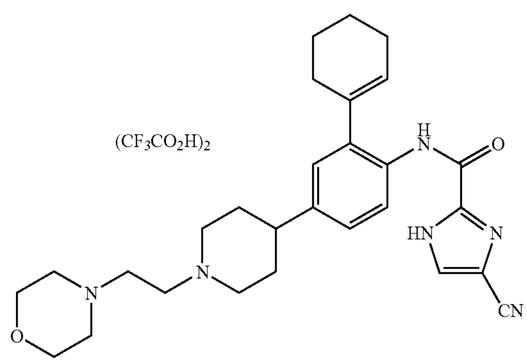 |
| 35 | 4-Cyano-1H-imidazole-2-carboxylic acid [2-(1,1-dioxo-1,2,3,6-tetrahydro-1$\lambda^6$-thiopyran-4-yl)-4-piperidin-4-yl-phenyl]-amide | 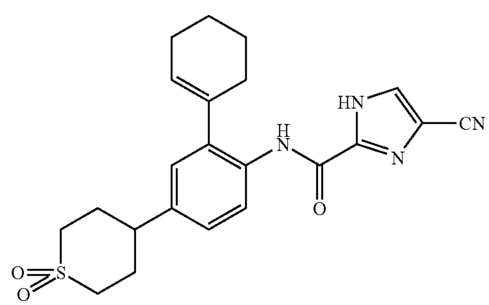 |
| 36 | 4-Cyano-1H-imidazole-2-carboxylic acid [2-(1,1-dioxo-1,2,3,6-tetrahydro-1$\lambda^6$-thiopyran-4-yl)-4-piperidin-4-yl-phenyl]-amide trifluoroacetic acid salt | 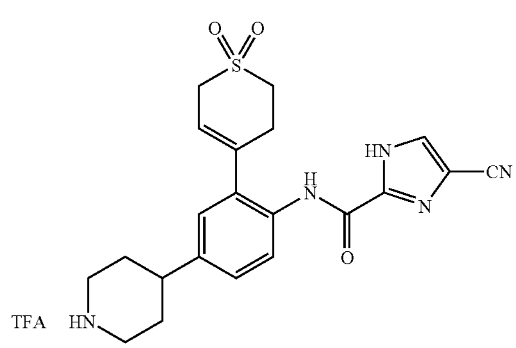 |

-continued

| Name | Structure |
|---|---|
| 37 | 4-Cyano-1H-imidazole-2-carboxylic acid [4-(1-acetyl-piperidin-4-yl)-2-(1,1-dioxo-1,2,3,6-tetrahydro-1$\lambda^6$-thiopyran-4-yl)-phenyl]-amide |
| 38 | 4-Cyano-1H-imidazole-2-carboxylic acid {2-cyclohex-1-enyl-4-[1-(2-dimethylamino-acetyl)-piperidin-4-yl]-phenyl}-amide |
| 38b | 4-Cyano-1H-imidazole-2-carboxylic acid {2-cyclohex-1-enyl-4-[1-(2-methylamino-acetyl)-piperidin-4-yl]-phenyl}-amide |
| 39 | 4-{4-[(4-Cyano-1H-imidazole-2-carbonyl)-amino]-3-cyclohex-1-enyl-phenyl}-piperidine-1-carboxylic acid (2-hydroxy-ethyl)-amide |

-continued

| | Name | Structure |
|---|---|---|
| 40 | 4-Cyano-1H-imidazole-2-carboxylic acid {2-cyclohex-1-enyl-4-[1-(2-methanesulfonyl-ethyl)-piperidin-4-yl]-phenyl}-amide | 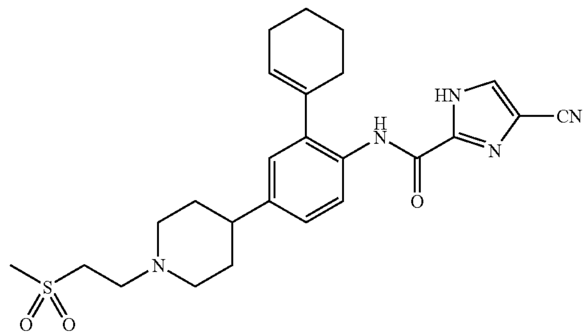 |
| 41 | 4-Cyano-1H-imidazole-2-carboxylic acid {2-cyclohex-1-enyl-4-[1-(1-oxy-pyridine-4-carbonyl)-piperidin-4-yl]-phenyl}-amide | 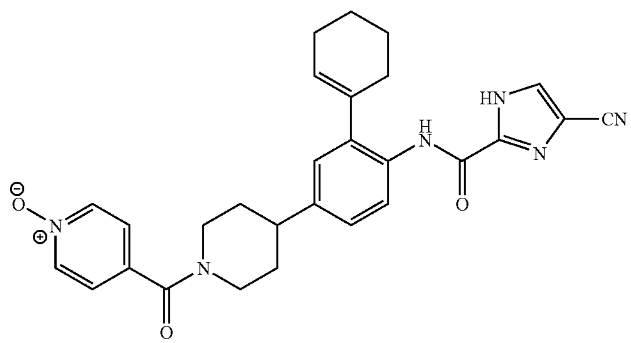 |
| 42 | 4-Cyano-1H-imidazole-2-carboxylic acid {2-cyclohex-1-enyl-4-[1-(1-oxy-pyridine-3-carbonyl)-piperidin-4-yl]-phenyl}-amide | 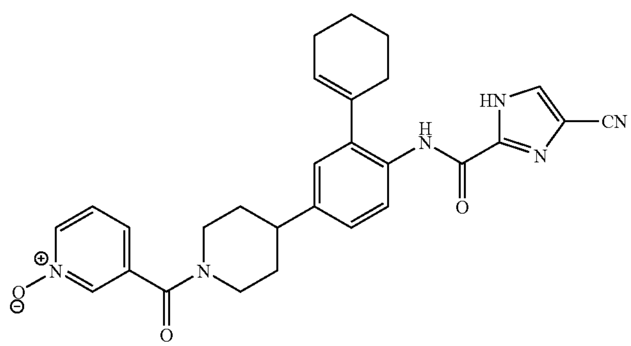 |
| 43 | 4-Cyano-1H-imidazole-2-carboxylic acid {2-cyclohex-1-enyl-4-[1-(pyridine-3-carbonyl)-piperidin-4-yl]-phenyl}-amide | 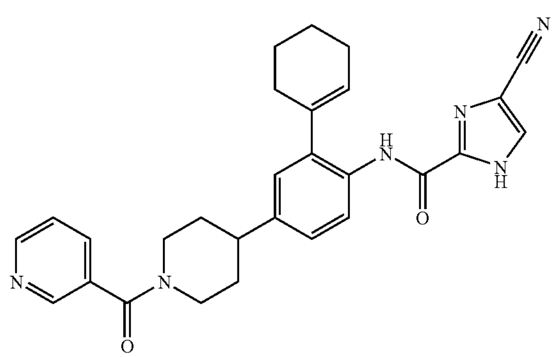 |

-continued

| Name | | Structure |
|---|---|---|
| 44 | 4-Cyano-1H-imidazole-2-carboxylic acid (2-cyclohex-1-enyl-4-{1-[2-(2-hydroxy-ethylamino)-acetyl]-piperidin-4-yl}-phenyl)-amide trifluoroacetic acid salt | 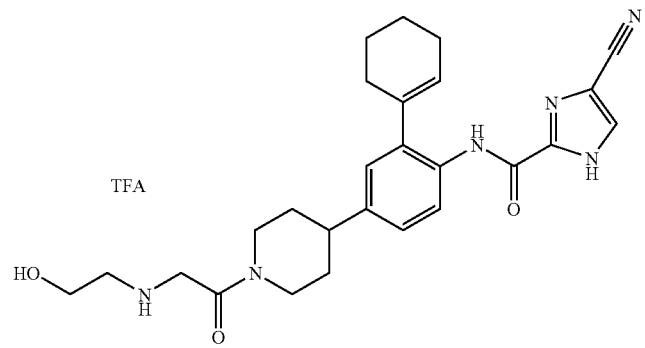 |
| 45 | 4-Cyano-1H-imidazole-2-carboxylic acid (2-cyclohex-1-enyl-4-{1-[2-(2-hydroxy-ethyl)-methyl-amino-acetyl]-piperidin-4-yl}-phenyl)-amide trifluoroacetic acid salt | 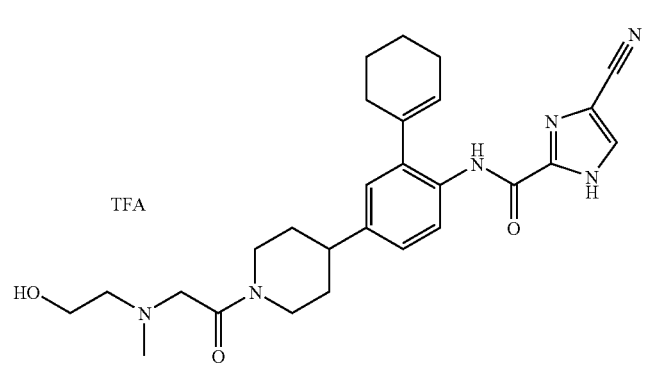 |
| 46 | 4-Cyano-1H-imidazole-2-carboxylic acid [4-(1-acetyl-piperidin-4-yl)-2-(1,2,5,6-tetrahydro-pyridin-3-yl)-phenyl]-amide trifluoroacetic acid salt | 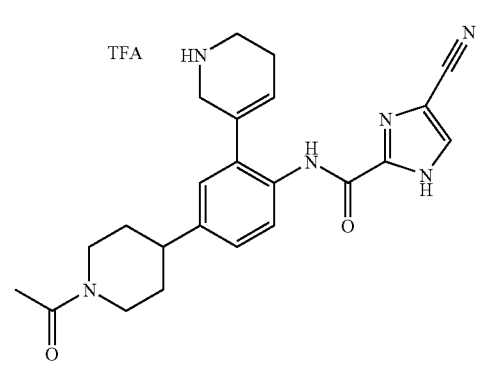 |
| 47 | (4-{4-[(4-Cyano-1H-imidazole-2-carbonyl)-amino]-3-cyclohex-1-enyl-phenyl}-piperidin-1-yl)-acetic acid trifluoroacetic acid salt | 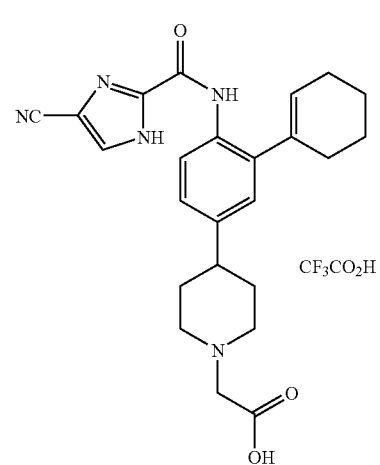 |

-continued

| Name | Structure |
|---|---|
| 48 | 4-Cyano-1H-imidazole-2-carboxylic acid 1-(3-amino-3-methyl-butyryl)-piperidin-4-yl]-2-cyclohex-1-enyl-phenyl}-amide trifluoroacetic acid salt |
| 49 | 4H-[1,2,4]-triazole-3-carboxylic acid (2-cyclohex-1-enyl-4-piperidin-4-yl-phenyl)-amide bis trifluoroacetic acid salt |
| 50 | 5-Chloro-4H-[1,2,4]-triazole-3-carboxylic acid (2-cyclohex-1-enyl-4-piperidin-4-yl-phenyl)-amide trifluoroacetic acid salt |
| 51a | 5-Cyano-1H-imidazole-2-carboxylic acid [2-cyclohex-1-enyl-4-(cis-2,6-dimethyl-piperidin-4-yl)-phenyl]-amide bis trifluoroacetic acid salt |

| Name | Structure |
|---|---|
| 51b 5-cyano-1H-imidazole-2-carboxylic acid [2-cyclohex-1-enyl-4-(trans-2,6-dimethyl-piperidin-4-yl)-phenyl]-amide bis trifluoroacetic acid salt | 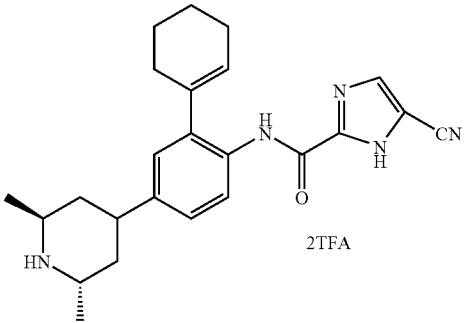 2TFA |
| 52 5-Cyano-1H-imidazole-2-carboxylic acid {2-cyclohex-1-enyl-4-[1-(R)-(+)-(2,3-dihydroxy-propionyl)-piperidin-4-yl]-phenyl}-amide | 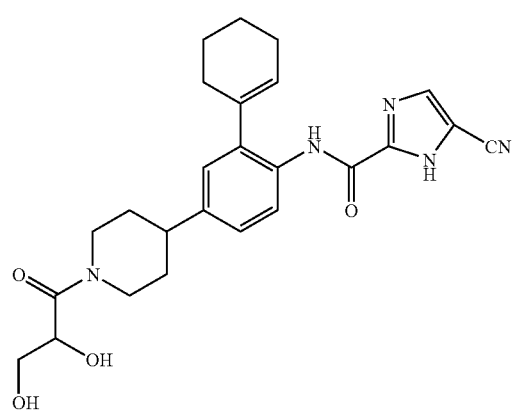 |
| 53 5-Cyano-1H-imidazole-2-carboxylic acid [2-cyclohex-1-enyl-4-(1-methoxy-piperidin-4-yl)-phenyl]-amide trifluoroacetic acid salt | 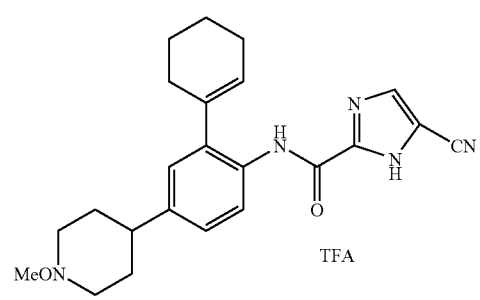 TFA |
| 54 4-Cyano-1H-imidazole-2-carboxylic acid [6-(4,4-dimethyl-cyclohex-1-enyl)-1',2',3',4',5',6'-hexahydro-[2,4']bipyridinyl-5-yl]-amide trifluoroacetic acid salt | 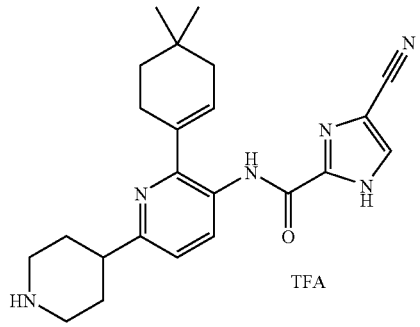 TFA |

-continued

| Name | Structure |
|---|---|
| 55 | 4-Cyano-1H-imidazole-2-carboxylic acid [1'-(2-dimethylamino-acetyl)-6-(4,4-dimethyl-cyclohex-1-enyl)-1',2',3',4',5',6'-hexahydro-[2,4']bipyridinyl-5-yl]-amide trifluoroacetic acid salt | 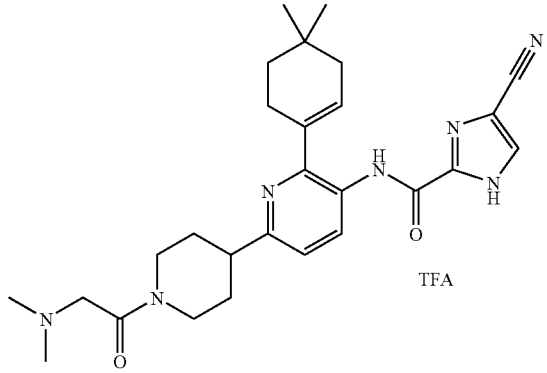 TFA |
| 56 | 4-Cyano-1H-imidazole-2-carboxylic acid [6-(4,4-dimethyl-cyclohex-1-enyl)-1'-(2-methanesulfonyl-ethyl)-1',2',3',4',5',6'-hexhydro-[2,4']bipyridinyl-5-yl]-amide trifluoroacetic acid salt | 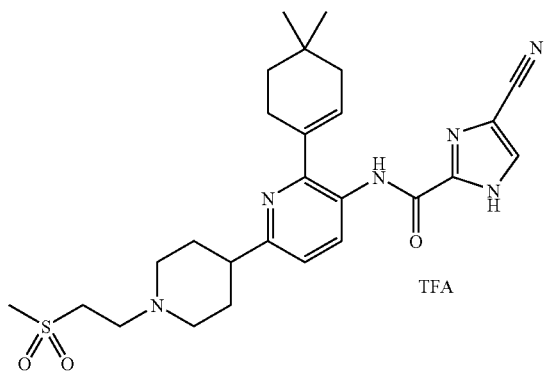 TFA |
| 57 | 5-Cyano-1H-imidazole-2-carboxylic acid {4-[1-(2-amino-2-methyl-propionyl)-piperidin-4-yl]-2-cyclohex-1-enyl-phenyl}-amide trifluoroacetic acid salt | 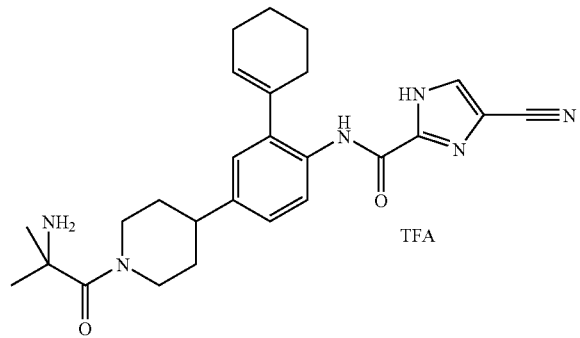 TFA |
| 58 | 5-Cyano-1H-imidazole-2-carboxylic acid [6-cyclohex-1-enyl-1'-(2-methanesulfonyl-ethyl)-1',2',3',4',5',6'-hexhydro-[2,4']bipyridinyl-5-yl]-amide | 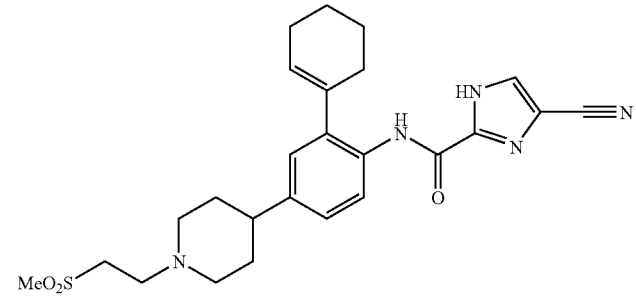 |

Example 1

5-Cyano-furan-2-carboxylic acid

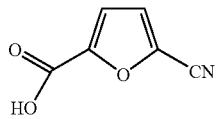

To a flask with a stir bar and Vigreaux column under Ar was added 2-formyl-5-furancarboxylic acid (2.8 g, 20 mmol), hydroxylamine hydrochloride (2.7 g, 40 mmol), and dry pyridine (50 mL). The mixture was heated to 85° C., acetic anhydride (40 mL) was added and the mixture was stirred for 3 h. After cooling to 60° C., water (250 mL) was added and the mixture was stirred at RT for 70 h. The mixture was acidified to pH 2 with concentrated hydrochloric acid and extracted with 3:1 dichloromethane-isopropanol (8×100 mL). The combined organic layers were washed with water (100 mL), brine (100 mL), dried over anh sodium sulfate and concentrated in vacuo to afford the title compound as a tan solid (1.26 g, 46%). $^1$H-NMR NMR (CD$_3$OD; 400 MHz): δ 14.05 (br s, 1H), 7.74 (d, 1H, J=3.8 Hz), 7.42 (d, 1H, J=3.8 Hz).

Example 2

4-Cyano-1H-pyrrole-2-carboxylic acid

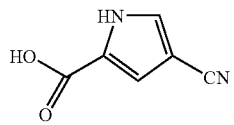

The title compound was prepared by the literature procedure (Loader and Anderson, *Canadian J. Chem.* 59: 2673 (1981)). $^1$H-NMR (CDCl$_3$; 400 MHz): δ 12.70 (br s, 1H), 7.78 (s, 1H), 7.13 (s, 1H).

Example 3

4-Cyano-1-(2-trimethylsilanyl-ethoxymethyl)-1H-imidazole-2-carboxylate potassium salt

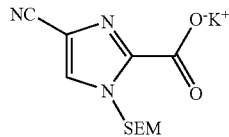

a) 1-(2-Trimethylsilanyl-ethoxymethyl)-1H-imidazole-4-carbonitrile

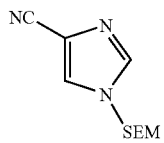

A flask charged with imidazole-4-carbonitrile (0.5 g, 5.2 mmol) (Synthesis, 677, 2003), 2-(trimethylsilyl)ethoxymethyl chloride (SEMCl) (0.95 mL, 5.3 mmol), K$_2$CO$_3$ (1.40 g, 10.4 mmol), and acetone (5 mL) was stirred for 10 h at RT. The mixture was diluted with EtOAc (20 mL) and washed with water (20 mL) and brine (20 mL) and the organic layer dried over MgSO$_4$. The crude product was eluted from a 20-g SPE cartridge (silica) with 30% EtOAc/hexane to give 0.80 g (70%) of the title compound as a colorless oil. Mass spectrum (CI(CH$_4$), m/z) Calcd. for C$_{10}$H$_{17}$N$_3$OSi, 224.1 (M+H), found 224.1.

b) 2-Bromo-1-(2-trimethylsilanyl-ethoxymethyl)-1H-imidazole-4-carbonitrile

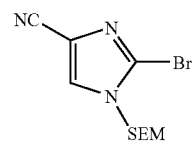

To a solution of 1-(2-trimethylsilanyl-ethoxymethyl)-1H-imidazole-4-carbonitrile (0.70 g, 3.1 mmol) (as prepared in the previous step) in CCl$_4$ (10 mL) was added NBS (0.61 g, 3.4 mmol) and AIBN (cat), and the mixture heated at 60° C. for 4 h. The reaction was diluted with EtOAc (30 mL) and washed with NaHCO$_3$ (2×30 mL) and brine (30 mL) and the organic layer was dried over Na$_2$SO$_4$ and then concentrated. The title compound was eluted from a 20-g SPE cartridge (silica) with 30% EtOAc/hexane to give 0.73 g (77%) of a yellow solid. Mass spectrum (CI(CH$_4$), m/z) Calcd. for C$_{10}$H$_{16}$BrN$_3$OSi, 302.0/304.0 (M+H), found 302.1/304.1.

c) 4-Cyano-1-(2-trimethylsilanyl-ethoxymethyl)-1H-imidazole-2-carboxylic acid ethyl ester

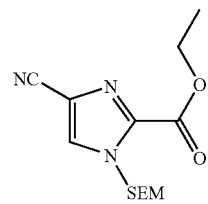

To a solution of 2-bromo-1-(2-trimethylsilanyl-ethoxymethyl)-1H-imidazole-4-carbonitrile (0.55 g, 1.8 mmol) (as prepared in the previous step) in THF (6 mL) at −40° C. was added drop wise a solution of 2M i-PrMgCl in THF (1 mL). The reaction was allowed to stir for 10 min at −40° C. and then cooled to −78° C., and ethyl cyanoformate (0.3 g, 3.0 mmol) was added. The reaction allowed to attain RT and stirred for 1 h. The reaction was quenched with satd aq NH$_4$Cl, diluted with EtOAc (20 mL) and washed with brine (2×20 mL), and the organic layer was dried over Na$_2$SO$_4$ and then concentrated. The title compound was eluted from a 20-g SPE cartridge (silica) with 30% EtOAc/hexane to give 0.4 g (74%) of a colorless oil. Mass spectrum (ESI, m/z): Calcd. for C$_{13}$H$_{21}$N$_3$O$_3$Si, 296.1 (M+H), found 296.1.

d) 4-Cyano-1-(2-trimethylsilanyl-ethoxymethyl)-1H-imidazole-2-carboxylate potassium salt b) 4,4,5,5-Tetramethyl-2-(3-methyl-thiophen-2-yl)-[1,3,2]dioxaborolane

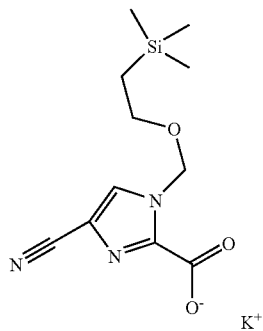

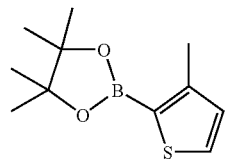

To a solution of 4-cyano-1-(2-trimethylsilanyl-ethoxymethyl)-1H-imidazole-2-carboxylic acid ethyl ester (0.4 g, 1.3 mmol) (as prepared in the previous step) in ethanol (3 mL) was added a solution of 6M KOH (0.2 mL) and the reaction was stirred for 10 min and then concentrated to give 0.40 g (100%) of the title compound as a yellow solid. $^1$H-NMR (400 MHz, CD$_3$OD) δ 7.98 (s, 1H), 5.92 (s, 2H), 3.62 (m, 2H), 0.94 (m, 2H), 0.00 (s, 9H). Mass spectrum (ESI-neg, m/z) Calcd. for C$_{11}$H$_{17}$N$_3$O$_3$Si, 266.1 (M−H), found 266.0.

To a stirred solution of 2-bromo-3-methythiophene (337 mg, 1.9 mmol) in 8 mL of THF at −40° C. was added n-BuLi (0.8 mL, 2.5 M/hexanes), and the reaction was allowed to stir for 30 min. At this time 2-isopropoxy-4,4,5,5-tetramethyl-[1,3,2]dioxaborolane (775 µL, 3.8 mmol) was added, and the reaction was allowed to warm to ambient temperature, and stirring was continued for 1 h. The reaction was then cooled to 0° C. and quenched with satd aq NaHCO$_3$ (10 mL). The mixture was poured into EtOAc (100 mL), washed with H$_2$O (2×50 mL), dried (Na$_2$SO$_4$) and concentrated in vacuo. Purification of the residue by silica gel preparative thin layer chromatography (20% EtOAc-hexanes) afforded 224 mg (53%) of the title compound as an oil. $^1$H-NMR (CDCl$_3$; 400 MHz): δ 1.36 (s, 12H), 2.5 (s, 3H), 6.99 (d, 1H, J=4.8 Hz), 7.50 (d, 1H, J=4.8 Hz).

Example 4

5-Cyano-furan-2-carboxylic acid [4-(4-methyl-piperazin-1-yl)-2-(3-methyl-thiophen-2-yl)-phenyl]-amide c) 1-Methyl-4-[3-(3-methyl-thiophen-2-yl)-4-nitro-phenyl]-piperazine

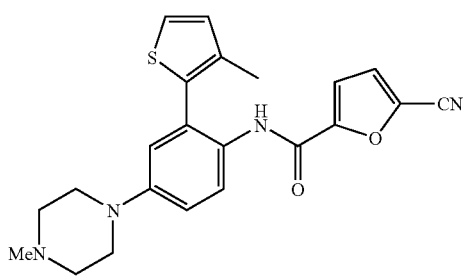

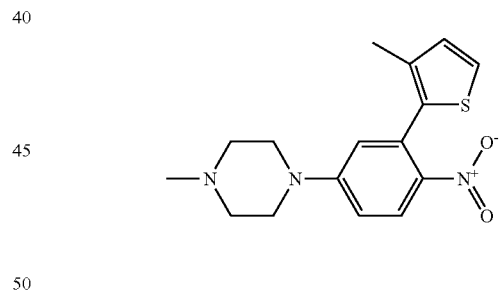

a) 1-(3-Bromo-4-nitro-phenyl)-4-methyl-piperazine

2-Bromo-4-fluoronitrobenzene (949 mg, 4.31 mmol) was added in two portions to neat N-methypiperazine (8 mL) at 0° C. and allowed to warm to room temperature. The reaction was heated to 60° C. for 1 h, and then it was diluted with 50 mL of EtOAc and poured into H$_2$O (50 mL). The layers were separated and the organic layer was washed with satd aq NaHCO$_3$, dried (Na$_2$SO$_4$), and concentrated in vacuo to afford 580 mg (45%) of the title compound as a yellow solid: Mass spectrum (ESI, m/z): Calcd. for C$_{11}$H$_{14}$BrN$_3$O$_2$, 300.0 (M+H), found 300.1.

To a flask containing 1-(3-bromo-4-nitro-phenyl)-4-methyl-piperazine (68 mg, 0.2 mmol, as prepared in Example 4, step (a)), 4,4,5,5-tetramethyl-2-(3-methyl-thiophen-2-yl)-[1,3,2]dioxaborolane (61 mg, 0.27 mmol, as prepared in the previous step) and Pd(PPh$_3$)$_4$ (14 mg, 6 mol %) was charged toluene (3 mL), ethanol (3 mL) and 2M Na$_2$CO$_3$ (4 mL). The resultant mixture was heated at 80° C. for 2 h and then poured into EtOAc (25 mL). The organic layer was separated, dried (Na$_2$SO$_4$) and concentrated in vacuo. Purification by silica gel preparative thin layer chromatography (EtOAc) afforded 40 mg (63%) of the title compound as a light yellow solid. Mass spectrum (ESI, m/z): Calcd. for C$_{16}$H$_{19}$N$_3$O$_2$S, 318.1 (M+H), found 318.2.

d) 5-Cyano-furan-2-carboxylic acid [4-(4-methyl-piperazin-1-yl)-2-(3-methyl-thiophen-2-yl)-phenyl]-amide

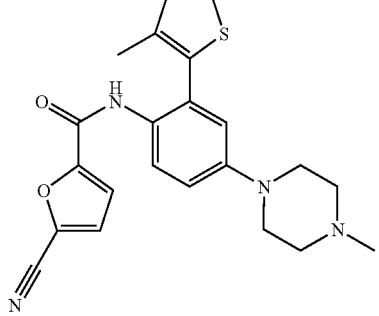

1-Methyl-4-[3-(3-methyl-thiophen-2-yl)-4-nitro-phenyl]-piperazine (60 mg, 0.18 mmol, as prepared in the previous step) was stirred with 40 mg 5% Pd—C in MeOH (5 mL) under $H_2$ (1 atm) for 2 h. The reaction was filtered through Celite and concentrated in vacuo to afford 40 mg (72%) of 4-(4-methyl-piperazin-1-yl)-2-(3-methyl-thiophen-2-yl)-phenylamine as a brown solid, which was used immediately without further purification. Using a procedure similar to Example 9, step (c), 4-(4-methyl-piperazin-1-yl)-2-(3-methyl-thiophen-2-yl)-phenylamine (40 mg, 0.13 mmol) was allowed to react with 5-cyano-furan-2-carbonyl chloride (30 mg, 0.19 mmol, as prepared in Example 9, step (c)) in the presence of DIEA (61 μL, 0.34 mmol) to afford 18.9 mg (36%) of the title compound as a yellow solid. $^1$H-NMR (CDCl$_3$; 400 MHz): δ 2.13 (s, 3H), 2.38 (s, 3H), 2.59-2.62 (m, 4H), 3.24-3.27 (m, 4H), 6.92 (d, 1H, J=2.8 Hz), 7.06 (d, 1H, J=5.1 Hz), 7.15 (d, 1H, J=3.7 Hz), 7.19 (d, 1H, J=3.7 Hz), 7.02 (dd, 1H, J=2.8, 9.0 Hz), 7.42 (d, 1H, J=5.1 Hz), 8.11 (s, 1H), 8.34 (d, 1H, J=9.0 Hz); Mass spectrum (ESI, m/z): Calcd. for $C_{22}H_{22}N_4O_2S$, 407.1 (M+H), found 407.1.

Example 5

5-Cyano-furan-2-carboxylic acid [4-(4-methyl-piperazin-1-yl)-2-(4-methyl-thiophen-3-yl)-phenyl]-amide

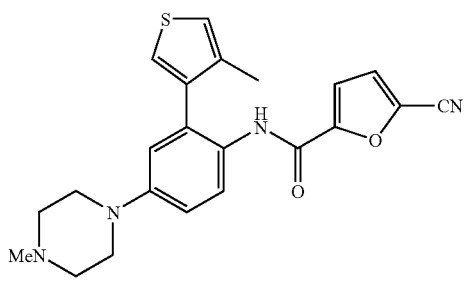

a) 4,4,5,5-Tetramethyl-2-(2-methyl-thiophen-3-yl)-[1,3,2]dioxaborolane

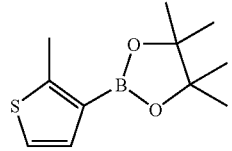

Using a procedure similar to Example 4, step (b), 3-bromo-4-methylthiophene (571 mg, 3.2 mmol) was treated with n-BuLi (1.41 mL, 2.5M/hexanes) and then allowed to react with 2-isopropoxy-4,4,5,5-tetramethyl-[1,3,2]dioxaborolane (775 μL, 3.8 mmol) to afford 189 mg (26%) of the title compound as a colorless oil. $^1$H-NMR (CDCl$_3$; 400 MHz): δ 1.32 (s, 12H), 2.42 (s, 3H), 6.90-6.91 (m, 1H), 7.84 (d, 1H, J=2.9 Hz).

b) 1-Methyl-4-[3-(4-methyl-thiophen-3-yl)-4-nitro-phenyl]-piperazine

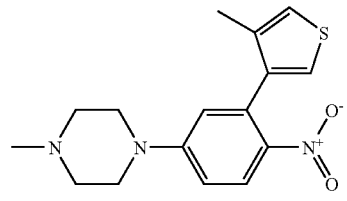

Using a procedure similar to Example 4, step (c), 1-(3-bromo-4-nitro-phenyl)-4-methyl-piperazine (162 mg, 0.54 mmol), 4,4,5,5-tetramethyl-2-(2-methyl-thiophen-3-yl)-[1,3,2]dioxaborolane (145 mg, 0.64 mmol) and Pd(PPh$_3$)$_4$ (37 mg, 6 mol %) were allowed to react to afford 108 mg (71%) of the title compound as a yellow solid. $^1$H-NMR (CDCl$_3$; 400 MHz): δ 2.02 (s, 3H), 2.37 (s, 3H), 2.55-2.57 (m, 4H), 3.42-3.45 (m, 4H), 6.66 (d, 1H, J=2.8 Hz), 6.87 (s, 1H), 6.99-7.00 (m, 1H), 7.09 (d, 1H, J=3.2 Hz), 8.13 (d, 1H, J=9.2 Hz).

c) 4-(4-Methyl-piperazin-1-yl)-2-(4-methyl-thiophen-3-yl)-phenylamine

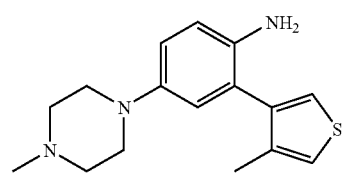

Using a procedure similar to Example 4, step (d), 1-methyl-4-[3-(4-methyl-thiophen-3-yl)-4-nitro-phenyl]-piperazine (100 mg, 0.32 mmol) was stirred with 80 mg 5% Pd—C under $H_2$ to afford 82 mg (89%) of the title compound as a dark oil, which was used immediately without further purification spectrum (ESI, m/z): Calcd. for $C_{16}H_{21}N_3S$, 288.15 (M+H), found 288.1.

d) 5-Cyano-furan-2-carboxylic acid [4-(4-methyl-piperazin-1-yl)-2-(4-methyl-thiophen-3-yl)-phenyl]-amide

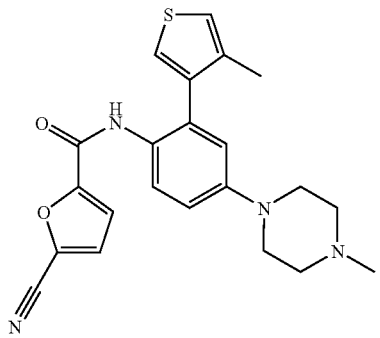

Using a procedure similar to Example 9, step (c), 5-cyano-furan-2-carbonyl chloride (64 mg, 0.41 mmol, as prepared in Example 9, step (c)) was allowed to react with 4-(4-methyl-piperazin-1-yl)-2-(4-methyl-thiophen-3-yl)-phenylamine (80 mg, 0.27 mmol, as prepared in the previous step) in the presence of DIEA (0.10 mL, 0.59 mmol) to afford 25.8 mg (24%) of the title compound as a yellow solid. $^1$H-NMR (CDCl$_3$; 400 MHz): δ 2.09 (s, 3H), 2.37 (s, 3H), 2.59-2.60 (m, 4H), 3.24-3.26 (m, 4H), 6.83 (d, 1H, J=2.9 Hz), 6.98-7.06 (m, 2H), 7.14-7.21 (m, 3H), 7.96 (s, 1H), 8.32 (d, 1H, J=9.0 Hz). Mass spectrum (ESI, m/z): Calcd. for $C_{22}H_{22}N_4O_2S$, 407.1 (M+H), found 407.1.

Example 6

4-Cyano-1H-imidazole-2-carboxylic acid {2-cyclohex-1-enyl-4-[1-(2-hydroxy-1-hydroxymethyl-ethyl)-piperidin-4-yl]-phenyl}-amide trifluoroacetic acid salt

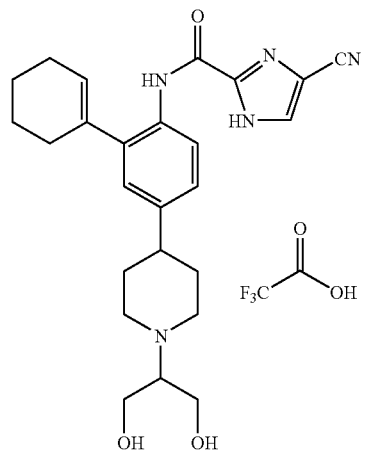

a) 4-Cyano-1H-imidazole-2-carboxylic acid {2-cyclohex-1-enyl-4-[1-(2,2-dimethyl-[1,3]dioxan-5-yl)-piperidin-4-yl]-phenyl}-amide To a slurry of 4-cyano-1H-imidazole-2-carboxylic acid (2-cyclohex-1-enyl-4-piperidin-4-yl-phenyl)-amide trifluoroacetic acid salt (81 mg, 0.16 mmol, as prepared in Example 14, step (b)) in CH$_2$Cl$_2$ (3 mL) was added NEt$_3$ (33 μL, 0.24 mmol). The solution was then treated with 2,2-dimethyl-[1,3]dioxan-5-one (31 mg, 0.24 mmol) and the reaction was allowed to stir for 3 h. At this time NaBH(OAc)$_3$ (51 mg, 0.24 mmol) was added in one portion, and the reaction was allowed to stir for an additional 4 h. The reaction was diluted with H$_2$O (10 mL) and extracted with EtOAc (2×25 mL). The organic extracts were dried (Na$_2$SO$_4$) and concentrated in vacuo. Purification by silica gel preparative thin layer chromatography (10% MeOH—CHCl$_3$) afforded 22 mg (28%) of the title compound as an off-white semi-solid. Mass spectrum (ESI, m/z): Calcd. for $C_{28}H_{35}N_5O_3$, 490.2 (M+H), found 490.6.

b) 4-Cyano-1H-imidazole-2-carboxylic acid {2-cyclohex-1-enyl-4-[1-(2-hydroxy-1-hydroxymethyl-ethyl)-piperidin-4-yl]-phenyl}-amide trifluoro-acetic acid To a solution of 4-cyano-1H-imidazole-2-carboxylic acid {2-cyclohex-1-enyl-4-[1-(2,2-dimethyl-[1,3]dioxan-5-yl)-piperidin-4-yl]-phenyl}-amide (22 mg, 0.04 mmol, as prepared in the previous step) in THF—H$_2$O (1 mL, 4:1 v/v) was added TFA (0.4 mL), and the reaction was allowed to stir for 1 h. Removal of the solvent under vacuum afforded 14 mg (60%) of the title compound as an amber foam. $^1$H-NMR (CD$_3$OD, 400 MHz): δ 1.78-1.90 (m, 4H), 2.03-2.16 (m, 3H), 2.29 (br s, 4H), 2.88-2.96 (m, 1H), 3.37-3.40 (m, 1H), 3.46-3.53 (m, 2H), 3.74-3.78 (m, 3H), 5.83 (s, 1H), 7.13 (d, 1H, J=2.0 Hz), 7.22 (dd, 1H, J=2.0, 8.4 Hz), 8.03 (s, 1H), 8.17 (d, 1H, J=8.4 Hz); Mass spectrum (ESI, m/z): Calcd. for $C_{25}H_{31}N_5O_3$, 450.2 (M+H), found 450.2.

Example 7

4-Cyano-1H-imidazole-2-carboxylic acid {2-cyclohex-1-enyl-4-[1-(2-morpholin-4-yl-acetyl)-piperidin-4-yl]-phenyl}-amide

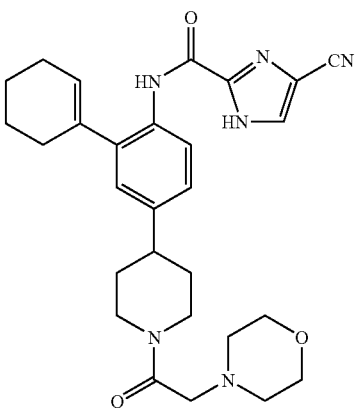

To a solution of morpholin-4-yl-acetic acid ethyl ester (117 mg, 0.67 mmol) in ethanol (4 mL) was added 6N KOH (110 μL, 0.67 mmol) via syringe and stirring was continued for 3 h. Concentration in vacuo afforded 122 mg (100%) of morpholin-4-yl-acetic acid potassium salt. To a mixture of morpholin-4-yl-acetic acid potassium salt (29 mg, 0.15 mmol), 4-cyano-1H-imidazole-2-carboxylic acid (2-cyclohex-1-enyl-4-piperidin-4-yl-phenyl)-amide trifluoroacetic acid salt (65.1 mg, 0.13 mmol, as prepared in Example 14, step (b)) and PyBroP (93 mg, 0.19 mmol) in CH$_2$Cl$_2$ (4 mL) was added DIEA (51 µL, 0.29 mmol) and the reaction was allowed to stir overnight. The reaction was diluted with CH$_2$Cl$_2$ (50 mL), washed with H$_2$O (2×25 mL), dried (Na$_2$SO$_4$) and concentrated in vacuo. Purification of the crude product by silica gel preparative TLC afforded 8.1 mg (12%) of the title compound as a white solid. $^1$H-NMR (CDCl$_3$; 400 MHz): δ 1.68-2.04 (m, 5H), 2.20-2.29 (m, 4H), 2.53-2.78 (m, 5H), 3.09-3.23 (m, 6H), 3.35-3.40 (m, 1H), 3.72 (br s, 4H), 4.16-4.22 (m, 1H), 4.73-4.77 (m, 1H), 5.82 (s, 1H), 7.00 (s, 1H), 7.12 (dd, 1H, J=0.6, 8.0 Hz), 7.73 (s, 1 H), 8.27 (d, 1H, J=8.1 Hz), 9.48 (s, 1H); Mass spectrum (ESI, m/z): Calcd. for C$_{28}$H$_{34}$N$_6$O$_3$, 503.27 (M+H), found 503.1.

Example 8

4-Cyano-1H-imidazole-2-carboxylic acid {2-cyclohex-1-enyl-4-[1-(3-morpholin-4-yl-propionyl)-piperidin-4-yl]-phenyl}-amide

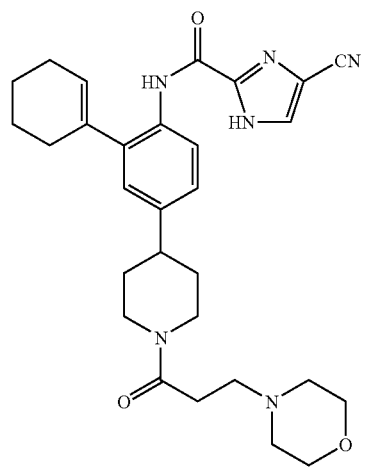

To a flask containing 3-morpholin-4-yl-propionic acid potassium salt (94 mg, 0.47 mmol, prepared from 3-morpholin-4-yl-propionic acid ethyl ester exactly as described in Example 7, 4-cyano-1H-imidazole-2-carboxylic acid (2-cyclohex-1-enyl-4-piperidin-4-yl-phenyl)-amide trifluoroacetic acid salt (179 mg, 0.36 mmol, as prepared in Example 14 (b)), EDCI (83 mg, 0.43 mmol), and HOBT (68 mg, 0.5 mmol) was added DMF (4 mL). To the stirred slurry was added DIEA (157 µL, 0.9 mmol) and the reaction was allowed to stir overnight. The reaction was diluted with H$_2$O (10 mL) and extracted with EtOAc (2×25 mL). The combined organic extracts were dried (Na$_2$SO$_4$), concentrated in vacuo and the crude product was purified by silica gel preparative TLC to afford 10.4 mg (6%) of the title compound as a white solid. $^1$H-NMR (CDCl$_3$; 400 MHz): δ 1.49-1.93 (m, 5H), 2.22-2.31 (m, 3H), 2.52 (br s, 4H), 2.58-2.63 (m, 3H), 2.74-2.76 (m, 4H), 3.10-3.17 (m, 2H), 3.72 (br s, 4H), 3.97-4.02 (m, 2H), 4.76-4.81 (m, 2H), 5.81-5.82 (m, 1H), 6.81-6.82 (m, 1H), 6.99-7.00 (m, 1H), 7.09-7.13 (m, 1H), 7.70 (s, 1H), 8.26 (d, 1H, J=8.2 Hz), 9.51 (s, 1H); Mass spectrum (ESI, m/z): Calcd. for C$_{29}$H$_{36}$N$_6$O$_3$, 517.28 M+H), found 517.3.

Example 9

5-Cyano-furan-2-carboxylic acid [2'-methyl-5-(4-methyl-piperazin-1-yl)-biphenyl-2-yl]-amide

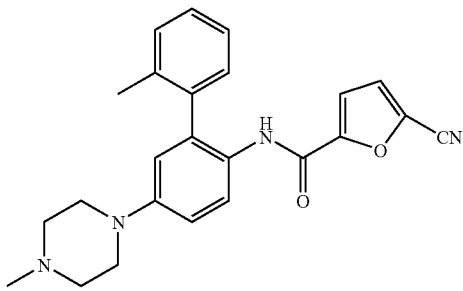

a) 1-(3-Bromo-4-nitro-phenyl)-4-methyl-piperazine

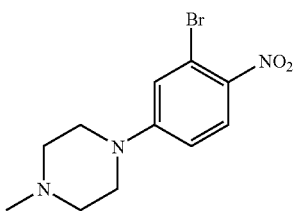

To a cooled (0° C.) solution of 1.00 g (4.55 mmol) of 2-bromo-4-fluoronitrobenzene (Oakwood) in 12 mL of EtOH was added 1.52 mL (13.7 mmol) of piperidine. The solution was stirred at 0° C. for 0.5 h and then at 60° C. for 4 h. The mixture was concentrated in vacuo, dissolved in EtOAc (60 mL), washed with water (3×100 mL) and brine (100 mL), and dried (Na$_2$SO$_4$). Concentration in vacuo and chromatography on a 50-g silica SPE column with 1-3% MeOH-dichloromethane afforded 1.06 g (77%) of the title compound as a tannish yellow solid. Mass spectrum (ESI, m/z): Calcd. for C$_{11}$H$_{14}$BrN$_3$O$_2$, 300.0 (M+H, $^{79}$Br), found 300.1.

b) 1-Methyl-4-(2'-methyl-6-nitro-biphenyl-3-yl)-piperazine

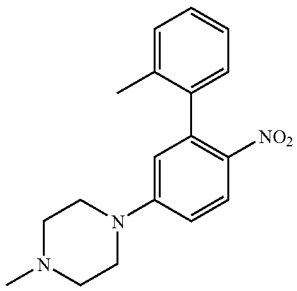

A mixture of 200 mg (0.666 mmol) 1-(3-bromo-4-nitrophenyl)-4-methyl-piperazine (as prepared in the previous step), 136 mg (0.999 mmol) and 77.0 mg (0.0666 mmol) of tetrakis(triphenylphosphine)palladium (0) under Ar was added 4.0 mL of degassed dimethoxyethane (DME) and 400 µL (0.799 mmol) of 2.0 M aq $Na_2CO_3$. The mixture was heated with stirring under Ar at 80° C. for 14 h. The cooled (RT) mixture was concentrated and chromatographed on a 10-g silica SPE column with 1-5% MeOH in dichloromethane-hexane (1:1). The product fractions were treated with 80 mg of decolorizing carbon, filtered, concentrated, and then rechromatographed on a similar column with 1-3% EtOH-dichloromethane to afford 265 mg of the title compound as a yellow resin (75% purity by $^1$H-NMR as a mixture with triphenylphosphine) that was used in the following reaction without further purification: Mass spectrum (ESI, m/z): Calcd. for $C_{11}H_{21}N_3O_3$, 312.2 (M+H), found 312.2.

c) 5-Cyano-furan-2-carboxylic acid [2'-methyl-5-(4-methyl-piperazin-1-yl)-biphenyl-2-yl]-amide

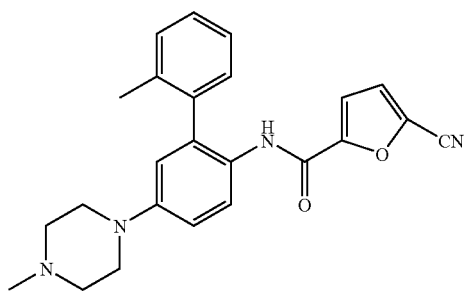

A mixture of 140 mg (0.337 mmol based on 75% purity) of 1-methyl-4-(2'-methyl-6-nitro-biphenyl-3-yl)-piperazine (as prepared in the previous step) and 70 mg of 10% palladium on carbon (Degussa type E101-NE/W, Aldrich, 50% by weight water) in 5 mL of THF was stirred vigorously under a balloon of hydrogen for 1 h. The mixture was filtered (Celite), washed with dichloromethane (2×2 mL), and the solution of the resulting aniline was placed under Ar and used immediately in the following reaction.

Simultaneously to the above reduction, 55.4 mg (0.404 mmol) of 5-cyanofuran-2-carboxylic acid (as prepared in Example 1) in 2.5 mL of anh dichloromethane under a $CaSO_4$ drying tube was treated with 52.9 µL (0.606 mmol) of oxalyl chloride followed by 10 µL of anh DMF. The solution was stirred for 25 min and quickly concentrated in vacuo at 20-25° C. The resulting 5-cyano-furan-2-carbonyl chloride was placed under high vacuum for 2-3 min and then immediately placed under Ar, cooled to 0° C. in an ice bath, and treated with the aniline solution produced above followed by 141 µL (0.808 mmol) of N,N-diisopropylethylamine (DIEA). After stirring for 30 min at RT, the mixture was concentrated in vacuo, and the resulting residue was chromatographed on a 20-g silica SPE column with 2-10% EtOH-dichloromethane to give a yellow resin (which was crystallized from EtOAc-hexane) to afford 17.2 mg (13%) of the pure title compound as a yellow solid along with 70.3 mg of impure title compound. The impure fraction was dissolved in 50 mL of EtOAc, washed with satd aq $NaHCO_3$-1M $K_2CO_3$ (1:1, 2×20 mL) and brine (20 mL), dried ($Na_2SO_4$) and concentrated to afford 43.4 mg (32%) additional title compound as a crystalline yellow solid (total yield 45%). $^1$H-NMR ($CDCl_3$; 400 MHz): δ 8.32 (d, 1H, J=9.0 Hz), 7.73 (br s, 1H), 7.34-7.54 (m, 3H), 7.25 (d, 1H, J=7.7 Hz), 7.12, 7.14 (AB q, 2H, J=3.7 Hz), 7.01 (dd, 1H, J=9.0, 2.8 Hz), 3.25-3.27 (m, 4H), 2.59-2.62 (m, 4H), 2.38 (s, 3H), and 2.15 (s, 3H). Mass spectrum (ESI, m/z): Calcd. for $C_{21}H_{24}N_4O_3$, 401.2 (M+H), found 401.1.

Example 10

5-Cyano-furan-2-carboxylic acid [2'-fluoro-5-(4-methyl-piperazin-1-yl)-biphenyl-2-yl]-amide

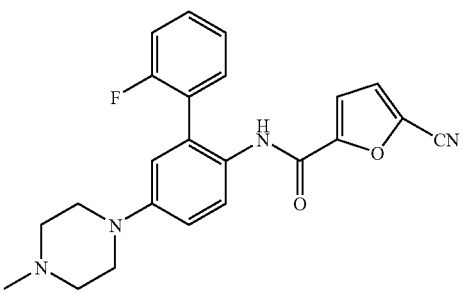

a) 1-(2'-Fluoro-6-nitro-biphenyl-3-yl)-4-methyl-piperazine

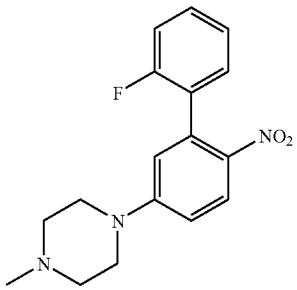

The procedure of Example 9, step (b) was followed using 75.0 mg (0.250 mmol) 1-(3-bromo-4-nitro-phenyl)-4-methyl-piperazine (as prepared in Example 9, step (a)), 136 mg (0.999 mmol) 2-fluorophenylboronic acid, 26.8 mg (0.0232 mmol) of tetrakis(triphenylphosphine)palladium (0) and 400 µL (0.799 mmol) of 2.0 M aq $Na_2CO_3$ in DME except the mixture was heated for 22 h. Chromatography on a 5-g silica SPE column with 1-5% MeOH in dichloromethane-hexane (1:1) afforded 95.0 mg of the title compound (76% purity by $^1$H-NMR as a mixture with triphenylphosphine) as a yellow resin that was used in the following reaction without further purification. Mass spectrum (ESI, m/z): Calcd. for $C_{17}H_{18}FN_3O_3$, 316.1 (M+H), found 316.2.

b) 5-Cyano-furan-2-carboxylic acid [2'-fluoro-5-(4-methyl-piperazin-1-yl)-biphenyl-2-yl]-amide

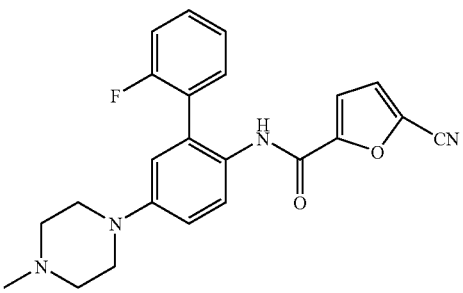

The procedure of Example 9, step (c) was followed using 93.2 mg (0.225 mmol based on 76% purity) of 1-(2'-fluoro-6-nitro-biphenyl-3-yl)-4-methyl-piperazine (as prepared in the previous step), 46 mg of 10% palladium on carbon, 37.0 mg (0.270 mmol) of 5-cyanofuran-2-carboxylic acid (as prepared in Example 1), 35.3 µL (0.405 mmol) of oxalyl chloride, 5.0 µL of anh DMF, and 94.1 µL (0.540 mmol) of DIEA. Chromatography on a 5-g silica SPE column with 1-4% MeOH-dichloromethane afforded 69.8 mg (77%) of the title compound as a yellow resin. $^1$H-NMR (CDCl$_3$; 400 MHz): δ 8.04 (d, 1H, J=9.0 Hz), 7.93 (br s, 1H), 7.434-7.48 (m, 1H), 7.37 (td, 1H, J=7.5, 1.8 Hz), 7.22-7.31 (m, 2H), 7.13, 7.18 (AB q, 2H, J=3.7 Hz), 7.02 (dd, 1H, J=9.0, 2.9 Hz), 6.88 (d, 1H, J=2.9 Hz), 3.24-3.27 (m, 4H), 2.57-2.60 (m, 4H), and 2.36 (s, 3H). Mass spectrum (ESI, m/z): Calcd. for C$_{23}$H$_{21}$FN$_4$O$_2$, 405.2 (M+H), found 405.2.

Example 11

5-Cyano-furan-2-carboxylic acid [2-cyclohex-1-enyl-4-(4-methyl-piperazin-1-yl)-phenyl]-amide

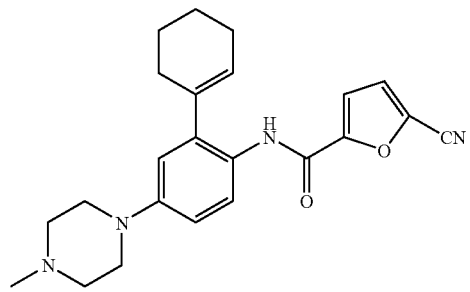

a) 1-(3-Cyclohex-1-enyl-4-nitro-phenyl)-4-methyl-piperazine

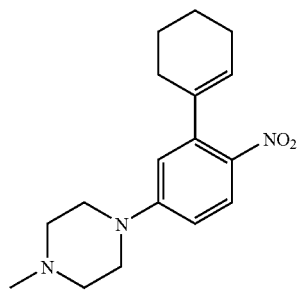

A mixture of 102 mg (0.340 mmol) 1-(3-bromo-4-nitro-phenyl)-4-methyl-piperazine (as prepared in Example 9, step (a)), 59.7 mg (0.474 mmol) cyclohexen-1-ylboronic acid, 43.8 mg (0.0379 mmol) of tetrakis(triphenylphosphine)palladium (0) under Ar was treated with 206 µL (0.412 mmol) of 2.0 M degassed aq Na$_2$CO$_3$, 0.6 mL degassed anh toluene and 0.2 mL degassed anh EtOH and the mixture was heated at 100° C. for 21 h. After cooling to RT, the mixture was poured into EtOAc (10 mL), washed with brine (10 mL), dried (Na$_2$SO$_4$) and concentrated in vacuo. Chromatography on a 5-g silica SPE column with 1-3% EtOH in dichloromethane afforded 126 mg of the title compound (74% purity by RP-HPLC (C18 column) as a mixture with triphenylphosphine) as a yellow oil that was used in the following reaction without further purification. Mass spectrum (ESI, m/z): Calcd. for C$_{17}$H$_{23}$N$_3$O$_3$, 302.2 (M+H), found 302.2.

b) 5-Cyano-furan-2-carboxylic acid [2-cyclohex-1-enyl-4-(4-methyl-piperazin-1-yl)-phenyl]-amide

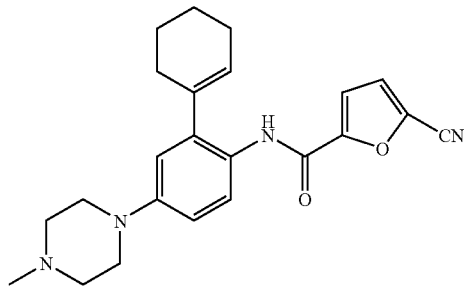

To 122 mg (0.299 mmol based on 74% purity) of 1-(3-cyclohex-1-enyl-4-nitro-phenyl)-4-methyl-piperazine (as prepared in the previous step) in 5.0 mL of EtOH-water (2:1) was added 83.8 mg (1.50 mmol) of iron powder and 160 mg (2.99 mmol) of NH$_4$Cl and the mixture refluxed under Ar for 12 h. An additional 83.8 mg (1.50 mmol) of iron powder was added, and the mixture was refluxed for 1 h. The mixture was poured into EtOAc (12 mL), filtered (Celite), washed with EtOAc (2×4 mL), concentrated in vacuo and dissolved in anh THF (4.0 mL). The resulting aniline solution was placed under Ar and used immediately in the following reaction. 61.6 mg (0.449 mmol) of 5-cyanofuran-2-carboxylic acid (as prepared in Example 1) in 2.5 mL of anh dichloromethane under a CaSO$_4$ drying tube was treated with 60.0 µL (0.688 mmol) of oxalyl chloride followed by 10 µL of anh DMF. The solution was stirred for 25 min and quickly concentrated in vacuo at 20-25° C. The residue was placed under high vacuum for 2-3 min and then immediately placed under Ar, cooled to 0° C. in an ice bath and treated with the aniline solution produced above followed by 104 µL (0.598 mmol) of DIEA. After stirring 30 min at RT, the mixture was concentrated in vacuo, dissolved in EtOAc (20 mL), washed with 1M K$_2$CO$_3$ (2×10 mL) and brine (10 mL), dried (Na$_2$SO$_4$) and concentrated in vacuo. The resulting residue was chromatographed on a 10-g silica SPE column with 1-4% MeOH-dichloromethane to give a yellow resin which was then crystallized from Et$_2$O-hexane to afford 84.7 mg (72%) of the title compound as a crystalline yellow solid. $^1$H-NMR (CDCl$_3$; 400 MHz): δ 8.57 (br s, 1H), 8.26 (d, 1H, J=9.0 Hz), 7.20, 7.23 (AB q, 2H, J=3.7 Hz), 6.86 (dd, 1H, J=9.0, 2.9 Hz), 6.74 (d, 1H, J=2.9 Hz), 5.84-5.85 (m, 1H), 3.20-3.22 (m, 4H), 2.57-2.59 (m, 4H), 2.36 (s, 3H), 2.23-2.30 (m, 4H) and 1.79-1.84 (m, 4H). Mass spectrum (ESI, m/z): Calcd. for C$_{23}$H$_{26}$N$_4$O$_2$, 391.2 (M+H), found 391.2.

Example 12

5-Cyano-furan-2-carboxylic acid [2-(3,6-dihydro-2H-pyran-4-yl)-4-(4-methyl-piperazin-1-yl)-phenyl]-amide

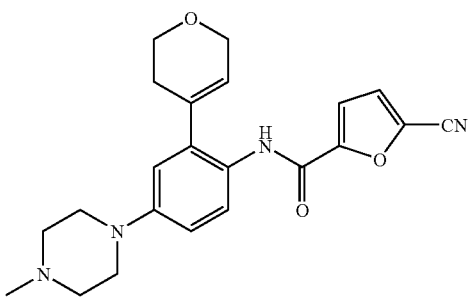

a) 1-[3-(3,6-Dihydro-2H-pyran-4-yl)-4-nitro-phenyl]-4-methyl-piperazine

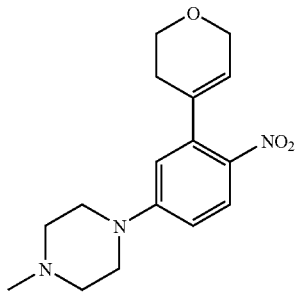

1-(3-Bromo-4-nitro-phenyl)-4-methyl-piperazine (as prepared in Example 9, step (a)) (225.1 mg, 0.79 mmol), K$_2$CO$_3$ (310.9 mg, 2.25 mmol) and 4-(4,4,5,5-tetramethyl-[1,3,2] dioxaborolan-2-yl)-3,6-dihydro-2H-pyran (Murata, M., et al, Synthesis, 778, (2000)) (157 mg, 0.75 mmol) in dioxane (5 mL) was heated at 80° C. overnight under Ar. The reaction mixture was allowed to cool to RT, concentrated, and the resulting residue was chromatographed on silica (10% EtOAc/hexane—20% MeOH/EtOAc) to obtain the title compound (82 mg, 36%). $^1$H-NMR (CDCl$_3$; 400 MHz): δ 8.04 (d, 1H, J=9.4 Hz), 6.78 (dd, 1H, J=9.4, 2.6 Hz), 6.58 (m, 1H, J=2.6 Hz), 5.58 (m, 1H), 4.34 (m, 2H), 3.95 (t, 2H, J=5.3 Hz), 3.46 (m, 4H), 2.57 (m, 4H), 2.38 (s, 3H), 2.30 (m, 2H).

b) 5-Cyano-furan-2-carboxylic acid [2-(3,6-dihydro-2H-pyran-4-yl)-4-(4-methyl-piperazin-1-yl)-phenyl-amide

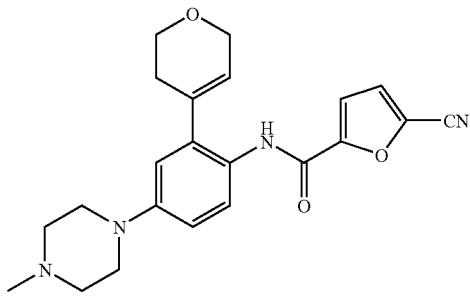

1-[3-(3,6-Dihydro-2H-pyran-4-yl)-4-nitro-phenyl]-4-methyl-piperazine (as prepared in previous step) (80 mg, 0.26 mmol) was converted to the corresponding amine using a procedure similar to Example 4, step (d), and coupled with 5-cyano-furan-2-carbonyl chloride as prepared in Example 9, step (c) (obtained from 137 mg, 1.00 mmol of 5-cyano-furan-2-carboxylic acid as prepared in Example 1) in CH$_2$Cl$_2$ (2 mL) at 0° C. The product was isolated by flash chromatography on silica (50% EtOAc/hexane—10% MeOH/EtOAc) to obtain the title compound (62.2 mg, 60%). $^1$H-NMR (CDCl$_3$; 400 MHz): δ 8.35 (br s, 1H), 8.12 (d, 1H each, J=8.76 Hz), 7.24 (d, 1H, J=5.08 Hz), 7.19 (d, 1H, J=5.08 Hz), 6.88 (dd, 1H, J=8.76, 2.7 Hz), 6.73 (d, 1H, J=2.7 Hz), 5.88 (br s, 1H), 4.34 (m, 2H), 3.94 (t, 2H, J=5.3 Hz), 3.23 (m, 4H), 2.59 (m, 4H), 2.38 (br s, 5H). LC-MS (ESI, m/z): Calcd. for C$_{22}$H$_{24}$N$_4$O$_3$, 393.1 (M+H), found 393.2.

Example 13

4-Cyano-1H-pyrrole-2-carboxylic acid (2-cyclohex-1-enyl-4-piperidin-4-yl-phenyl)-amide trifluoroacetic acid salt

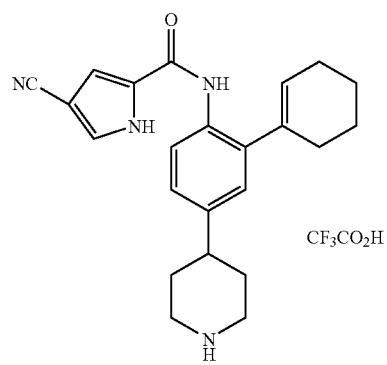

a) 4-(4-Amino-phenyl)-3,6-dihydro-2H-pyridine-1-carboxylic acid tert-butyl ester

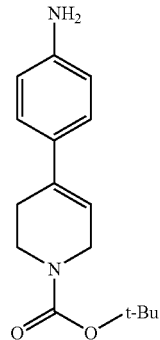

The title compound was prepared by Suzuki coupling of 4-(4,4,5,5-tetramethyl-[1,3,2]dioxaborolan-2-yl)-phenylamine with 4-trifluoromethanesulfonyloxy-3,6-dihydro-2H-pyridine-1-carboxylic acid tert-butyl ester (Synthesis, 993, (1991)) according to the procedure in Example 35, step (b). Mass spectrum (ESI, m/z): Calcd. for C$_{16}$H$_{22}$N$_2$O$_2$, 275.2 (M+H), found 275.1.

b) 4-(4-Amino-phenyl)-piperidine-1-carboxylic acid tert-butyl ester

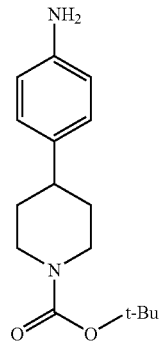

A solution of 4-(4-amino-phenyl)-3,6-dihydro-2H-pyridine-1-carboxylic acid tert-butyl ester (0.35 g, 1.2 mmol) (as prepared in the previous step) in methanol was hydrogenated over 10% Pd/C at 20 psi for 1 h. The solution was filtered and concentrated to give 0.35 g (100%) of the title compound as a yellow solid: Mass spectrum (ESI, m/z): Calcd. for $C_{16}H_{24}N_2O_2$, 277.2 (M+H), found 277.1.

c) 4-(4-Amino-3-bromo-phenyl)-piperidine-1-carboxylic acid tert-butyl ester

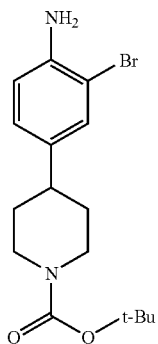

To a solution of 4-(4-amino-phenyl)-piperidine-1-carboxylic acid tert-butyl ester (0.20 g, 0.71 mmol) (as prepared in the previous step) in DCM (3 mL) was added N-bromosuccinimide (NBS) (0.13 g, 0.71 mmol), and the reaction stirred at RT for 10 h. The reaction was diluted with EtOAc (10 mL) and washed with NaHCO$_3$ (2×10 mL) and brine (10 mL). Concentration of the organic layer gave 0.26 g (100%) of the title compound as a yellow foam. Mass spectrum (ESI, m/z): Calcd. for $C_{16}H_{23}BrN_2O_2$, 355.1 (M+H), found 355.1.

d) 4-(4-Amino-3-cyclohex-1-enyl-phenyl)-piperidine-1-carboxylic acid tert-butyl ester

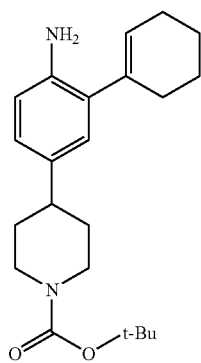

A flask was charged with 4-(4-amino-3-bromo-phenyl)-piperidine-1-carboxylic acid tert-butyl ester (0.13 g, 0.36 mmol) (as prepared in the previous step), cyclohex-1-enyl boronic acid (0.060 g, 0.48 mmol), Pd(PPh$_3$)$_4$ (0.04 g, 10 mol %), aqueous 2M Na$_2$CO$_3$ (1.5 mL), ethanol (1.5 mL), and toluene (3 mL), and heated at 80° C. for 3 h. The reaction was diluted EtOAc (10 mL), washed with NaHCO$_3$ (2×10 mL) and brine (10 mL), and the organic layer was dried over Na$_2$SO$_4$ and then concentrated. The title compound was eluted from a 20-g SPE cartridge (silica) with 30% EtOAc/hexane to give 0.10 g (85%) of the title compound as a yellow oil. Mass spectrum (ESI, m/z): Calcd. for $C_{22}H_{32}N_2O_2$, 357.2 (M+H), found 357.1.

e) 4-Cyano-1H-pyrrole-2-carboxylic acid (2-cyclohex-1-enyl-4-piperidin-4-yl-phenyl)-amide trifluoroacetic acid salt A flask was charged with 4-(4-amino-3-cyclohex-1-enyl-phenyl)-piperidine-1-carboxylic acid tert-butyl ester (0.050 g, 0.14 mmol) (as prepared in the previous step), 4-cyano-1H-pyrrole-2-carboxylic acid (0.019 g, 0.14 mmol) (as prepared in Example 2), EDCI (0.040 g, 0.21 mmol), HOBt (0.019 g, 0.14 mmol), DIEA (0.073 mL, 0.42 mmol), and DCM (0.5 mL) and stirred at 25° C. for 10 h. The reaction was loaded directly on a 10-g solid phase extraction (SPE) cartridge (silica) and the resulting intermediate was eluted with 30% EtOAc/hexane. This compound was stirred at RT for 1 h in 50% TFA/DCM (2 mL) and then concentrated and purified by RP-HPLC (C18), eluting with 30-50% CH$_3$CN in 0.1% TFA/H$_2$O over 12 min to give the title compound (0.052 g, 77%). $^1$H-NMR (400 MHz, CD$_3$OD): δ 7.59 (s, 1H), 7.50 (d, 1H), 7.22 (d, 1H), 7.16 (m, 2H), 5.74 (m, 1H), 3.54. (m, 2H), 3.16 (m, 2H), 2.94 (m, 1H), 2.29 (m, 2H), 2.15 (m, 4H), 1.92 (m, 2H), 1.72 (m, 4H). Mass spectrum (ESI, m/z): Calcd. for $C_{23}H_{26}N_4O$, 375.2 (M+H), found 375.1.

Example 14

4-Cyano-1H-imidazole-2-carboxylic acid (2-cyclohex-1-enyl-4-piperidin-4-yl-phenyl)-amide trifluoroacetic acid salt

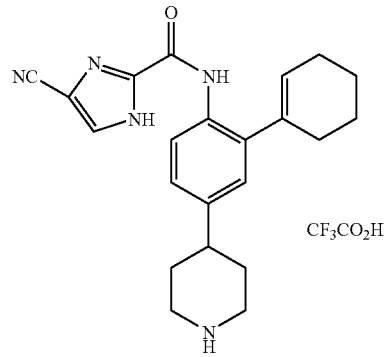

a) 4-(4-{[4-Cyano-1-(2-trimethylsilanyl-ethoxymethyl)-1H-imidazole-2-carbonyl]-amino}-3-cyclohex-1-enyl-phenyl)-piperidine-1-carboxylic acid tert-butyl ester

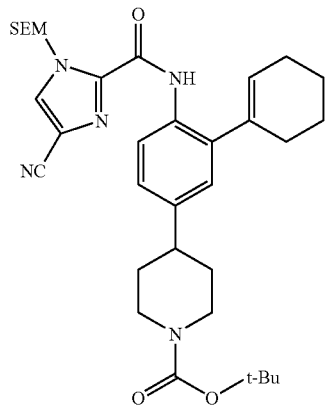

To a solution of 4-cyano-1-(2-trimethylsilanyl-ethoxymethyl)-1H-imidazole-2-carboxylate potassium salt (3.34 g, 10.9 mmol) (as prepared in Example 3, step (d)) in 20 mL DCM was added DIEA (3.8 mL, 21.8 mmol) and PyBroP (5.6 g, 12.0 mmol), and the reaction stirred at 25° C. for 15 min. A solution of 4-(4-amino-3-cyclohex-1-enyl-phenyl)-piperidine-1-carboxylic acid tert-butyl ester (3.9 g, 10.9 mmol) (as prepared in Example 13, step (d)) in 10 mL DCM was added and the reaction stirred for 8 h at 25° C. The reaction was diluted EtOAc (60 mL) and washed with NaHCO$_3$ (2×60 mL) and brine (100 mL) and the organic layer was dried over Na$_2$SO$_4$ and then concentrated. The title compound was purified by flash chromatography (silica gel, 2% EtOAc/DCM) to give 5.5 g (85%) of the title compound as a yellow oil. Mass spectrum (ESI, m/z): Calcd. for $C_{33}H_{47}N_5O_4Si$, 606.2 (M+H), found 606.2.

b) 4-Cyano-1H-imidazole-2-carboxylic acid (2-cyclohex-1-enyl-4-piperidin-4-yl-phenyl)-amide trifluoroacetic acid salt To a solution of 4-(4-{[4-cyano-1-(2-trimethylsilanyl-ethoxymethyl)-1H-imidazole-2-carbonyl]-amino}-3-cyclohex-1-enyl-phenyl)-piperidine-1-carboxylic acid tert-butyl ester (1.5 g, 2.5 mmol) (as prepared in the previous step) in 10 mL of DCM and 0.3 mL EtOH was added 3 mL of TFA and the solution stirred for 3 h at 25° C. The reaction was diluted with 5 mL of EtOH and then concentrated. The residue was crystallized from methanol and ethyl ether to give 0.85 g (70%) of the title compound as a white solid. $^1$H-NMR (400 MHz, CD$_3$OD) δ 8.18 (d, 1H), 8.04 (s, 1H), 7.22 (dd, 1H), 7.12 (d, 1H), 5.76 (m, 1H), 3.54. (m, 2H), 3.16 (m, 2H), 2.92 (m, 1H), 2.30 (m, 4H), 2.10 (m, 2H), 1.75 (m, 6H). Mass spectrum (ESI, m/z): Calcd. for $C_{22}H_{25}N_5O$, 376.2 (M+H), found 376.2.

Example 15

4-Cyano-1H-pyrrole-2-carboxylic acid [4-(1-acetyl-piperidin-4-yl)-2-cyclohex-1-enyl-phenyl]-amide

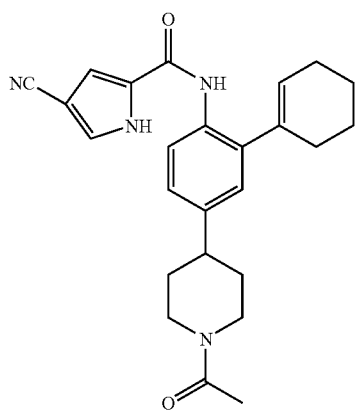

The title compound was prepared from 4-cyano-1H-pyrrole-2-carboxylic acid (2-cyclohex-1-enyl-4-piperidin-4-yl-phenyl)-amide trifluoroacetic acid salt (as prepared in Example 13, step (e)) according to the procedure in Example 37. $^1$H-NMR (400 MHz, CDCl$_3$) δ 10.82 (s, 1H), 8.28 (d, 1H), 8.18 (s, 1H), 7.48 (d, 1H), 7.16 (dd, 1H), 7.02 (s, 1H), 6.72 (s, 1H), 5.88 (m, 1H), 4.82 (m, 1H), 3.98. (m, 1H), 3.20 (m, 1H), 2.70 (m, 2H), 2.29 (m, 4H), 2.18 (s, 3H), 1.80 (m, 8H). Mass spectrum (ESI, m/z): Calcd. for $C_{25}H_{28}N_4O_2$, 417.2 (M+H), found 417.1.

Example 16

4-Cyano-1H-imidazole-2-carboxylic acid [4-(1-acetyl-piperidin-4-yl)-2-cyclohex-1-enyl-phenyl]-amide

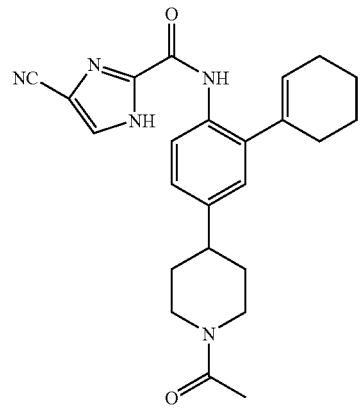

The title compound was prepared from 4-cyano-1H-imidazole-2-carboxylic acid (2-cyclohex-1-enyl-4-piperidin-4-yl-phenyl)-amide trifluoroacetic acid salt (as prepared in Example 13, step (b)) according to the procedure in Example 37: $^1$H-NMR (400 MHz, CDCl$_3$) δ 13.12 (br s, 1H), 9.58 (s, 1H), 8.34 (d, 1H), 7.76 (s, 1H), 7.21 (dd, 1H), 7.05 (d, 1H), 5.86 (s, 1H), 4.84 (m, 2H), 4.00 (m, 1H), 3.22 (m, 1H), 2.72 (m, 2H), 2.30 (m, 4H), 2.21 (s, 3H), 1.80 (m, 8H). Mass spectrum (ESI, m/z): Calcd. for $C_{24}H_{27}N_5O_2$, 418.2 (M+H), found 418.1.

Example 17

4-Cyano-1H-imidazole-2-carboxylic acid [2-(4-methyl-cyclohex-1-enyl)-4-piperidin-4-yl-phenyl]-amide trifluoroacetic acid salt

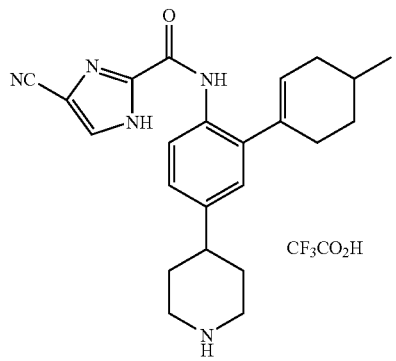

The title compound was prepared from 4-cyano-1-(2-trimethylsilanyl-ethoxymethyl)-1H-imidazole-2-carboxylate potassium salt (as prepared in Example 3, step (d)) and 4-[4-amino-3-(4-methyl-cyclohex-1-enyl)-phenyl]-piperidine-1-carboxylic acid tert-butyl ester (prepared according to the procedure in Example 13, step (d), substituting 4-methyl-1-cyclohex-1-enyl boronic acid for cyclohex-1-enyl boronic acid) according to the procedure for Example 14: $^1$H-NMR (400 MHz, CD$_3$OD): δ 8.18 (d, 1H), 8.04 (s, 1H), 7.22 (dd, 1H), 7.12 (d, 1H), 5.80 (m, 1H), 3.54. (m, 2H), 3.18 (m, 2H), 2.94 (m, 1H), 2.30 (m, 3H), 2.12 (m, 2H), 1.92 (m, 5H), 1.54 (m, 1H), 1.12 (d, 3 H). Mass spectrum (ESI, m/z): Calcd. for C$_{23}$H$_{27}$N$_5$O, 390.2 (M+H), found 390.2.

Example 18

4-Cyano-1H-imidazole-2-carboxylic acid (2-cyclopent-1-enyl-4-piperidin-4-yl-phenyl)-amide trifluoroacetic acid salt

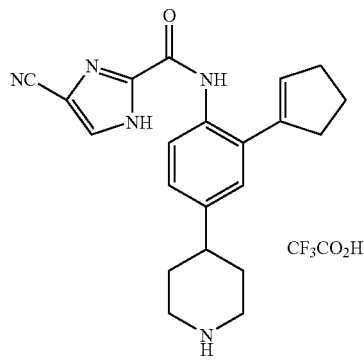

The title compound was prepared from 4-cyano-1-(2-trimethylsilanyl-ethoxymethyl)-1H-imidazole-2-carboxylate potassium salt (as prepared in Example 3, step (d)) and 4-(4-amino-3-cyclopent-1-enyl-phenyl)-piperidine-1-carboxylic acid tert-butyl ester (prepared according to the procedure in Example 13, step (d), substituting cyclopenten-1-yl boronic acid for cyclohex-1-enyl boronic acid) according to the procedure for Example 14. $^1$H-NMR (400 MHz, DMSO-d$_6$) δ 14.25 (br s, 1H), 10.00 (s, 1H), 8.36 (s, 1H), 7.72 (d, 1H), 7.18 (m, 2H), 6.06 (s, 1H), 4.12 (m, 1 H), 3.42 (m, 2H), 3.18 (m, 2H), 3.00 (m, 3H), 2.80 (m, 2H), 1.92 (m, 5H). Mass spectrum (ESI, m/z): Calcd. for C$_{21}$H$_{23}$N$_5$O, 362.2 (M+H), found 362.2.

Example 19

An alternate method for the synthesis of the intermediate described in Example 1 is described below.

5-Cyano-furan-2-carboxylic acid

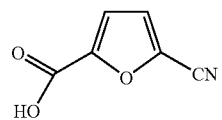

A 250-mL, three-neck, round-bottom flask equipped with a mechanical stirrer, a heating mantle, and a condenser was charged with 5-formyl-2-furancarboxylic acid (9.18 g, 65.6 mmol) and pyridine (60 mL). Hydroxylamine hydrochloride (5.01 g, 72.2 mmol) was added and the mixture was heated to 85° C. Acetic anhydride (40 mL) was added and the reaction was stirred at 85° C. for 3 h, after which time the solvent was evaporated at 40° C. under reduced pressure. The residue was dissolved in water, basified with 2.0 N NaOH solution to pH 9, and extracted with 4:1 dichloromethane/2-propanol until the pyridine was completely removed (5×200 mL). The aqueous solution was then acidified with 2.0 N HCl solution to pH 2, saturated with solid NaCl, and extracted with 4:1 dichloromethane/2-propanol (5×200 mL). The combined organic extracts were dried over Na$_2$SO$_4$ and concentrated in vacuo to dryness. The residue was crystallized from dichloromethane to give 6.80 g of the title compound as a white solid (76%). Mass spectrum (ESI-neg, m/z) Calcd. for C$_6$H$_3$NO$_3$, 136.0 (M−H), found 136.1. The $^1$H NMR spectrum was consistent with the assigned structure.

Example 20

4-Cyano-1H-imidazole-2-carboxylic acid {2-cyclohex-1-enyl-4-[1-(2-methanesulfonyl-acetyl)-piperidin-4-yl]-phenyl}-amide

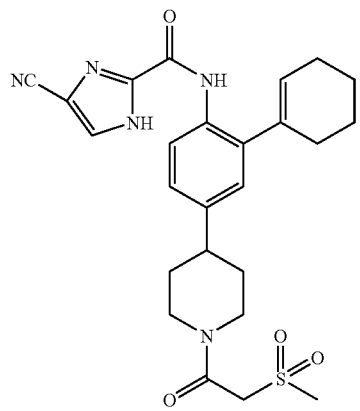

A flask was charged with methanesulfonyl-acetic acid (14 mg, 0.10 mmol), EDCI (30 mg, 0.15 mmol), HOBt (14 mg, 0.10 mmol), DIEA (36 μL, 0.20 mmol) and 0.5 mL DCM and stirred at 25° C. After 10 min, a solution containing 4-cyano-1H-imidazole-2-carboxylic acid (2-cyclohex-1-enyl-4-piperidin-4-yl-phenyl)-amide TFA salt (40 mg, 0.08 mmol) (as prepared in Example 20, step (b)) and NEt$_3$ (14 μL, 0.09 mmol) in 0.5 mL DCM was added and the reaction allowed to proceed for 10 h at 25° C. The reaction mixture was loaded on a 5-g SPE cartridge (silica) and the title compound was eluted with 10% EtOH/EtOAc to give 10 mg (25%) of a white solid. 1H-NMR (400 MHz, CDCl$_3$): δ 11.60 (br s, 1H), 9.52 (s, 1H), 8.30 (d, 1H), 7.74 (s, 1H), 7.60 (dd, 1H), 7.03 (d, 1H), 5.86 (m, 1H), 4.84 (m, 1H), 4.18 (s, 2H), 4.12 (m, 1H), 3.32 (m, 1H), 3.20 (s, 3H), 2.82 (m, 2H), 2.30 (m, 4H), 1.98 (m, 2H), 1.84 (m, 5H), 1.72 (m, 1H). Mass spectrum (ESI, m/z): Calcd. for C$_{25}$H$_{29}$N$_5$O$_4$S, 496.2 (M+H), found 496.2.

Example 21

4-Cyano-1H-imidazole-2-carboxylic acid [2-cyclohex-1-enyl-4-(1-pyridin-2-ylmethyl-piperidin-4-yl)-phenyl]-amide trifluoroacetic acid salt

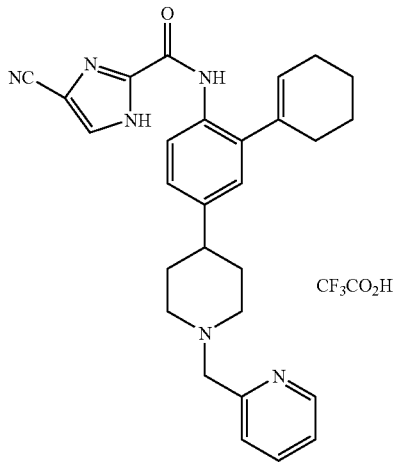

A flask was charged with 4-cyano-1H-imidazole-2-carboxylic acid (2-cyclohex-1-enyl-4-piperidin-4-yl-phenyl)-amide TFA salt (88 mg, 0.18 mmol) (as prepared in Example 14, step (b)), pyridine-2-carbaldehyde (17 μL, 0.21 mmol), $NEt_3$ (30 μL, 0.21 mmol), sodium triacetoxyborohydride (56 mg, 0.25 mmol) and 0.8 mL of 1,2-dichloroethane and stirred for 10 h at 25° C. The solvent was evaporated, and the title compound was purified by RP-HPLC (C18), eluting with 30-50% $CH_3CN$ in 0.1% $TFA/H_2O$ over 20 min to give 81 mg (78%) of a white solid. $^1$H-NMR (400 MHz, DMSO-$d_6$): δ 14.25 (br s, 1H), 9.90 (br s, 1H), 9.79 (s, 1H), 8.72 (s, 1H), 8.36 (s, 1H), 7.98 (m, 1H), 7.88 (dd, 1H), 7.58 (d, 1H), 7.52 (m, 1H), 7.20 (m, 1H), 7.12 (d, 1H), 5.76 (m, 1H), 4.56 (s, 2H), 3.40 (m, 2H), 3.18 (m, 2H), 2.88 (m, 1H), 2.20 (m, 4H), 2.00 (m, 4H), 1.72 (m, 4H). Mass spectrum (ESI, m/z): Calcd. for $C_{28}H_{30}N_6O$, 467.2 (M+H), found 467.2.

Example 22

4-Cyano-1H-imidazole-2-carboxylic acid [2-(4-methyl-cyclohex-1-enyl)-4-(1-pyridin-2-ylmethyl-piperidin-4-yl)-phenyl]-amide trifluoroacetic acid salt

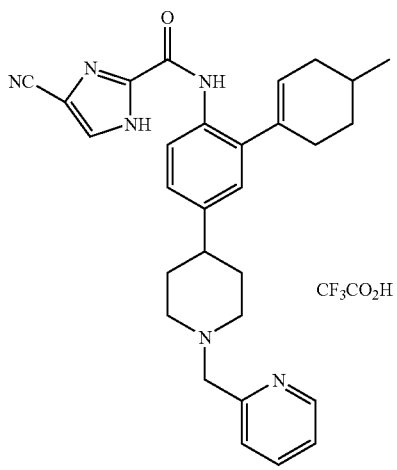

This compound was prepared according to the procedure in Example 21 from 4-cyano-1H-imidazole-2-carboxylic acid [2-(4-methyl-cyclohex-1-enyl)-4-piperidin-4-yl-phenyl]-amide (as prepared in Example 17) and pyridine-2-carbaldehyde. $^1$H-NMR (400 MHz, DMSO-$d_6$): δ 14.25 (br s, 1H), 9.90 (br s, 1H), 9.79 (s, 1H), 8.72 (s, 1H), 8.36 (s, 1H), 7.98 (m, 1H), 7.86 (dd, 1H), 7.54 (d, 1H), 7.52 (m, 1H), 7.20 (m, 1H), 7.12 (d, 1H), 5.74 (m, 1H), 4.56 (s, 2H), 3.40 (m, 2H), 3.18 (m, 2H), 2.88 (m, 1H), 2.48-2.22 (m, 3H), 2.18-2.06 (m, 4H), 1.98-1.82 (m, 3H), 1.52 (m, 1H), 1.02 (s, 3H). Mass spectrum (ESI, m/z): Calcd. for $C_{28}H_{32}N_6O$, 481.2 (M+H), found 481.2.

Example 23

4-Cyano-1H-imidazole-2-carboxylic acid {2-cyclopent-1-enyl-4-[1-(1-methyl-1H-imidazol-2-ylmethyl)-piperidin-4-yl]-phenyl}-amide trifluoroacetic acid salt

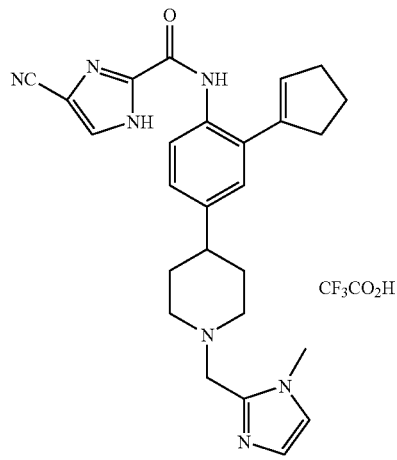

This compound was prepared from 4-cyano-1H-imidazole-2-carboxylic acid (2-cyclopent-1-enyl-4-piperidin-4-yl-phenyl)-amide TFA salt (as prepared in Example 18) and 1-methyl-1H-imidazole-2-carbaldehyde according to the procedure in Example 21. $^1$H-NMR (400 MHz, $CD_3OD$): δ 8.03 (m, 2H), 7.50 (d, 1H), 7.42 (s, 1H), 7.20 (m, 2H), 6.02 (m, 1H), 4.22 (s, 2H), 3.96 (s, 3H), 3.30 (m, 2H), 2.82-2.40 (m, 7H), 2.13-1.84 (m, 6H). Mass spectrum (ESI, m/z): Calcd. for $C_{26}H_{29}N_7O$, 456.2 (M+H), found 456.2.

Example 24

4-{4-[(4-Cyano-1H-imidazole-2-carbonyl)-amino]-3-cyclohex-1-enyl-phenyl}-piperidine-1-carboxylic acid amide

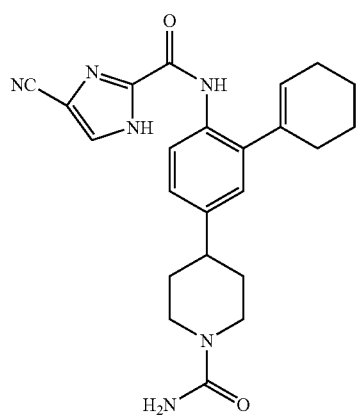

A flask was charged with 4-cyano-1H-imidazole-2-carboxylic acid (2-cyclohex-1-enyl-4-piperidin-4-yl-phenyl)-amide TFA salt (51 mg, 0.10 mmol) (as prepared in Example 14, step (b)), NEt$_3$ (22 µL, 0.15 mmol), trimethylsilyl isocyanate (16 µL, 0.11 mmol) and 1.0 mL of DCM and stirred for 10 h at 25° C. The solvent was evaporated and the title compound was purified by RP-HPLC (C18), eluting with 35-60% CH$_3$CN in 0.1% TFA/H$_2$O over 11 min to give 30 mg (70%) of a white solid. $^1$H-NMR (400 MHz, DMSO-d$_6$): δ 14.28 (br s, 1H), 9.76 (s, 1H), 8.34 (s, 1H), 7.84 (d, 1H), 7.18 (dd, 1H), 7.08 (d, 1H), 6.00 (br s, 2H), 5.72 (m, 1H), 4.18 (m, 2H), 2.80-2.60 (m, 3H), 2.24-2.10 (m, 4H), 1.80-1.60 (m, 6H), 1.50 (m, 2H). Mass spectrum (ESI, m/z): Calcd. for C$_{23}$H$_{26}$N$_6$O, 419.2 (M+H), found 419.0.

Example 25

4-Cyano-1H-imidazole-2-carboxylic acid [2-cyclohex-1-enyl-4-(3,4,5,6-tetrahydro-2H-[1,2']bipyridinyl-4-yl)-phenyl]-amide trifluoroacetic acid salt

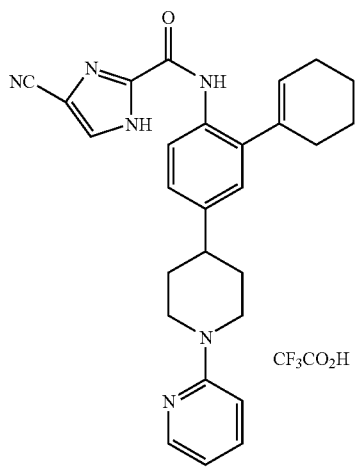

A flask was charged with 4-cyano-1H-imidazole-2-carboxylic acid (2-cyclohex-1-enyl-4-piperidin-4-yl-phenyl)-amide TFA salt (75 mg, 0.15 mmol) (as prepared in Example 14, step (b)), K$_2$CO$_3$ (84 mg, 0.60 mmol), 2-fluoropyridine (27 µL, 0.30 mmol) and 0.3 mL of N,N-dimethylacetamide and stirred for 8 h at 120° C. The reaction was diluted with 3 mL of H$_2$O and the title compound was purified by RP-HPLC (C18), eluting with 30-50% CH$_3$CN in 0.1% TFA/H$_2$O over 9 min to give 50 mg (75%) of a white solid. $^1$H-NMR (400 MHz, CD$_3$OD): δ 8.18 (d, 1H), 8.06 (m, 1H), 8.02 (s, 1H), 7.94 (dd, 1H), 7.48 (d, 2H), 7.22 (dd, 1H), 7.12 (d, 1 H), 6.98 (t, 1H), 5.82 (m, 1H), 4.32 (m, 2H), 3.46 (m, 2H), 3.00 (m, 1H), 2.30 (m, 4H), 2.18 (m, 2H), 1.96-1.74 (m, 6H). Mass spectrum (ESI, m/z): Calcd. for C$_{27}$H$_{28}$N$_6$O, 453.2 (M+H), found 453.2.

Example 26

4-Cyano-1H-imidazole-2-carboxylic acid {2-cyclohex-1-enyl-4-[1-(2-hydroxy-ethyl)-piperidin-4-yl]-phenyl}-amide trifluoroacetic acid salt

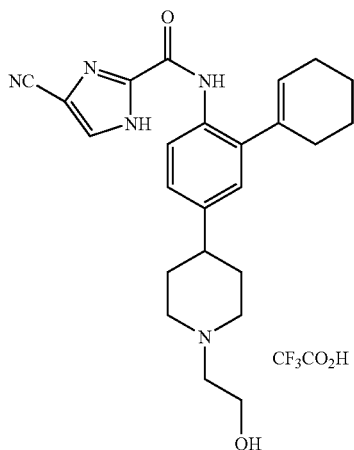

The title compound was prepared from 4-cyano-1H-imidazole-2-carboxylic acid (2-cyclohex-1-enyl-4-piperidin-4-yl-phenyl)-amide TFA salt (as prepared in Example 14, step (b)), and hydroxy-acetaldehyde according to the procedure in Example 21. $^1$H-NMR (400 MHz, CD$_3$OD): δ 8.18 (d, 1H), 8.02 (s, 1H), 7.22 (dd, 1H), 7.14 (d, 2H), 5.82 (m, 1H), 3.94 (m, 2H), 3.74 (m, 2H), 3.30 (m, 2H), 3.18 (t, 2H), 2.92 (m, 1H), 2.30 (m, 4H), 2.20-1.98 (m, 4H), 1.96-1.74 (m, 4H). Mass spectrum (ESI, m/z): Calcd. for C$_{24}$H$_{29}$N$_5$O$_2$, 420.2 (M+H), found 420.2.

Example 27

4-Cyano-1H-imidazole-2-carboxylic acid {4-[1-(2-cyano-ethyl)-piperidin-4-yl]-2-cyclohex-1-enyl-phenyl}-amide trifluoroacetic acid salt

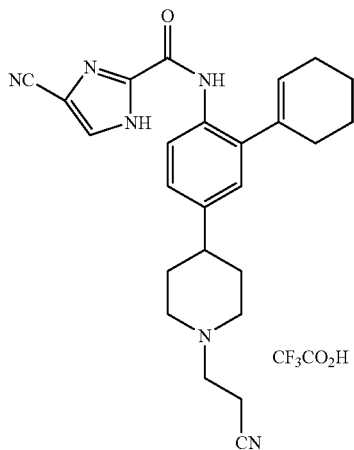

A flask was charged with 4-cyano-1H-imidazole-2-carboxylic acid (2-cyclohex-1-enyl-4-piperidin-4-yl-phenyl)-amide TFA salt (77 mg, 0.16 mmol) (as prepared in Example 14, step (b)), NEt$_3$ (24 µL, 0.16 mmol), acrylonitrile (12 µL, 0.18 mmol), 0.1 mL MeOH and 1.0 mL of 1,2-dichloroethane and stirred for 1 h at 80° C. The reaction was concentrated and the title compound was purified by RP-HPLC (C18), eluting with 30-50% CH$_3$CN in 0.1% TFA/H$_2$O over 12 min to give 83 mg (95%) of a white solid. $^1$H-NMR (400 MHz, CD$_3$OD): δ 8.18 (d, 1H), 8.06 (m, 1H), 7.22 (dd, 1H), 7.12 (d, 1H), 5.82 (m, 1H), 3.76 (m, 2H), 3.60 (m, 2H), 3.28 (t, 2H), 3.12 (t, 2H), 2.92 (m, 1H), 2.30 (m, 4H), 2.18-1.98 (m, 4H), 1.92-1.74 (m, 4H). Mass spectrum (ESI, m/z): Calcd. for C$_{25}$H$_{28}$N$_6$O, 429.2 (M+H), found 429.2.

Example 28

4-Cyano-1H-imidazole-2-carboxylic acid [4-(1-carbamoylmethyl-piperidin-4-yl)-2-cyclohex-1-enyl-phenyl]-amide trifluoroacetic acid salt

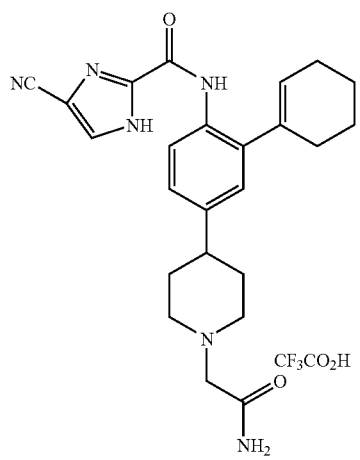

A flask was charged with 4-cyano-1H-imidazole-2-carboxylic acid (2-cyclohex-1-enyl-4-piperidin-4-yl-phenyl)-amide TFA salt (50 mg, 0.10 mmol) (as prepared in Example 14, step (b)), NEt$_3$ (32 µL, 0.23 mmol), 2-bromoacetamide (16 mg, 0.12 mmol), and 0.5 mL of DCM and stirred for 4 h at 25° C. The reaction was concentrated and the title compound was purified by RP-HPLC (C18), eluting with 30-50% CH$_3$CN in 0.1% TFA/H$_2$O over 12 min to give 42 mg (75%) of a white solid. $^1$H-NMR (400 MHz, DMSO-d$_6$): δ 14.28 (br s, 1H), 9.78 (s, 1H), 9.50 (br s, 1H), 8.34 (s, 1H), 8.00 (s, 1H), 7.88 (d, 1H), 7.72 (s, 1H), 7.18 (dd, 1H), 7.10 (d, 1H), 5.76 (m, 1H), 3.94 (s, 2H), 3.58 (m, 2H), 3.12 (m, 2H), 2.80 (m, 1H), 2.20 (m, 4H), 1.98 (m, 4H), 1.80 (m, 4H). Mass spectrum (ESI, m/z): Calcd. for C$_{24}$H$_{28}$N$_6$O$_2$, 433.2 (M+H), found 433.2.

Example 29

4-Cyano-1H-imidazole-2-carboxylic acid {2-cyclohex-1-enyl-4-[1-(2-pyridin-2-yl-acetyl)-piperidin-4-yl]-phenyl}-amide trifluoroacetic acid salt

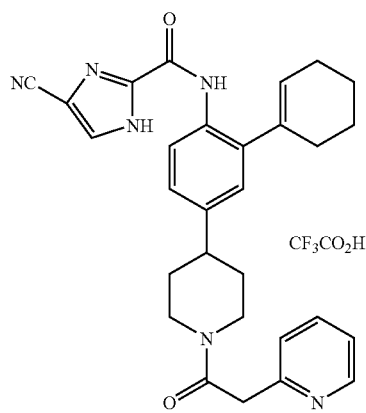

A flask was charged with 4-cyano-1H-imidazole-2-carboxylic acid (2-cyclohex-1-enyl-4-piperidin-4-yl-phenyl)-amide TFA salt (25 mg, 0.05 mmol) (as prepared in Example 14, step (b)), pyridin-2-yl-acetic acid hydrochloride (10 mg, 0.06 mmol), EDCI (12 mg, 0.06 mmol), HOBt (8.0 mg, 0.06 mmol), DIEA (36 µL, 0.20 mmol) and 0.2 mL DMF and stirred at 25° C. for 10 h. The reaction was diluted with 2 mL of H$_2$O and the title compound was purified by RP-HPLC (C18), eluting with 30-50% CH$_3$CN in 0.1% TFA/H$_2$O over 9 min to give 22 mg (70%) of a white solid. $^1$H-NMR (400 MHz, CD$_3$OD): δ 8.82 (d, 1H), 8.52 (t, 1H), 8.14 (d, 1H), 8.04 (s, 1H), 7.96 (m, 3H), 7.20 (dd, 1H), 7.10 (d, 1H), 5.82 (m, 1H), 4.68 (m, 1H), 4.32 (m, 2H), 4.18 (m, 1H), 3.40 (m, 1H), 2.88 (m, 2H), 2.30 (m, 4H), 2.06-1.60 (m, 8H). Mass spectrum (ESI, m/z): Calcd. for C$_{29}$H$_{30}$N$_6$O$_2$, 495.2.2 (M+H), found 495.2.

Example 30

4-Cyano-1H-imidazole-2-carboxylic acid {2-cyclohex-1-enyl-4-[1-(2-pyridin-3-yl-acetyl)-piperidin-4-yl]-phenyl}-amide trifluoroacetic acid salt

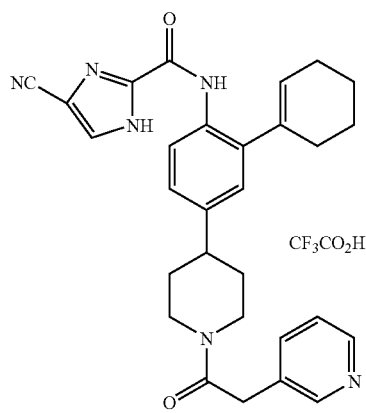

The title compound was prepared from 4-cyano-1H-imidazole-2-carboxylic acid (2-cyclohex-1-enyl-4-piperidin-4-yl-phenyl)-amide TFA salt (as prepared in Example 14, step (b)), according to the procedure in Example 29 using pyridin-3-yl-acetic acid. $^1$H-NMR (400 MHz, CD$_3$OD): δ 8.80 (m, 2H), 8.54 (d, 1H), 8.10 (d, 1H), 8.06 (t, 1H), 7.98 (s, 1H), 7.18 (dd, 1H), 7.08 (d, 1H), 5.78 (m, 1H), 4.68 (m, 1H), 4.20 (m, 1H), 4.18 (s, 2H), 3.36 (m, 1H), 2.84 (m, 2H), 2.28 (m, 4H), 2.06-1.70 (m, 7H), 1.62 (m, 1H). Mass spectrum (ESI, m/z): Calcd. for C$_{29}$H$_{30}$N$_6$O$_2$, 495.2 (M+H), found 495.2.

Example 31

4-Cyano-1H-imidazole-2-carboxylic acid {2-cyclohex-1-enyl-4-[1-(2-pyridin-4-yl-acetyl)-piperidin-4-yl]-phenyl}-amide trifluoroacetic acid salt

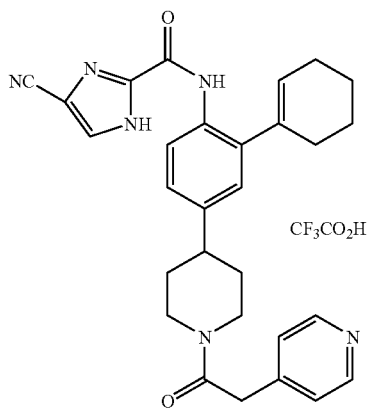

The title compound was prepared from 4-cyano-1H-imidazole-2-carboxylic acid (2-cyclohex-1-enyl-4-piperidin-4-yl-phenyl)-amide TFA salt (as prepared in Example 14, step (b)), according to the procedure in Example 29 using pyridin-4-yl-acetic acid. $^1$H-NMR (400 MHz, CD$_3$OD): δ 8.78 (d, 2H), 8.12 (d, 1H), 8.00 (m, 3H), 7.18 (dd, 1H), 7.08 (d, 1H), 5.80 (m, 1H), 4.66 (m, 1H), 4.22 (s, 2H), 4.18 (m, 1H), 3.34 (m, 1H), 2.84 (m, 2H), 2.24 (m, 4H), 2.00-1.70 (m, 7H), 1.64 (m, 1H). Mass spectrum (ESI, m/z): Calcd. for C$_{29}$H$_{30}$N$_6$O$_2$, 495.2 (M+H), found 495.2.

Example 32

4-Cyano-1H-imidazole-2-carboxylic acid (2-cyclohex-1-enyl-4-{1-[2-(1-methyl-1H-imidazol-4-yl)-acetyl]-piperidin-4-yl}-phenyl)-amide trifluoroacetic acid salt

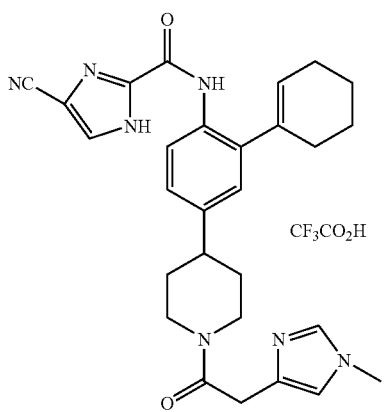

The title compound was prepared from 4-cyano-1H-imidazole-2-carboxylic acid (2-cyclohex-1-enyl-4-piperidin-4-yl-phenyl)-amide TFA salt (as prepared in Example 14, step (b)), according to the procedure in Example 29 using (1-methyl-1H-imidazol-4-yl)-acetic acid. $^1$H-NMR (400 MHz, CD$_3$OD): δ 8.82 (s, 1H), 8.10 (d, 1H), 8.00 (s, 1H), 7.42 (s, 1H), 7.16 (dd, 1H), 7.06 (d, 1H), 5.80 (m, 1H), 4.66 (m, 1H), 4.12 (m, 1H), 4.04 (m, 2H), 3.92 (s, 3H), 3.28 (m, 1H), 2.82 (m, 2H), 2.26 (m, 4H), 2.00-1.70 (m, 7H), 1.64 (m, 1H). Mass spectrum (ESI, m/z): Calcd. for C$_{28}$H$_{31}$N$_7$O$_2$, 498.2 (M+H), found 498.2.

Example 33

4-Cyano-1H-imidazole-2-carboxylic acid {2-cyclohex-1-enyl-4-[1-(2-1H-imidazol-4-yl-acetyl)-piperidin-4-yl]-phenyl}-amide trifluoroacetic acid salt

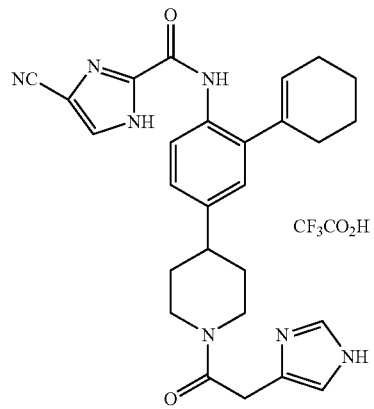

The title compound was prepared from 4-cyano-1H-imidazole-2-carboxylic acid (2-cyclohex-1-enyl-4-piperidin-4-yl-phenyl)-amide TFA salt (as prepared in Example 14, step (b)), according to the procedure in Example 29 using (1-methyl-1H-imidazol-4-yl)-acetic acid. $^1$H-NMR (400 MHz, CD$_3$OD): δ 8.88 (s, 1H), 8.12 (d, 1H), 8.02 (s, 1H), 7.44 (s, 1H), 7.20 (dd, 1H), 7.10 (d, 1H), 5.82 (m, 1H), 4.70 (m, 1H), 4.18 (m, 1H), 4.06 (m, 2H), 3.36 (m, 1H), 2.84 (m, 2H), 2.30 (m, 4H), 2.00-1.70 (m, 7H), 1.64 (m, 1H). Mass spectrum (ESI, m/z): Calcd. for C$_{27}$H$_{29}$N$_7$O$_2$, 484.2 (M+H), found 484.2.

Example 34

4-Cyano-1H-imidazole-2-carboxylic acid {2-cyclohex-1-enyl-4-[1-(2-morpholin-4-yl-ethyl)-piperidin-4-yl]-phenyl}-amide di-trifluoroacetic acid salt

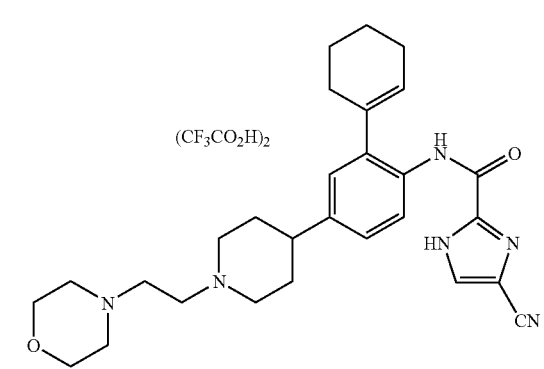

89 a) 4-Cyano-1-(2-trimethylsilanyl-ethoxymethyl)-1H-imidazole-2-carboxylic acid {2-cyclohex-1-enyl-4-[1-(2-morpholin-4-yl-ethyl)-piperidin-4-yl]-phenyl}-amide

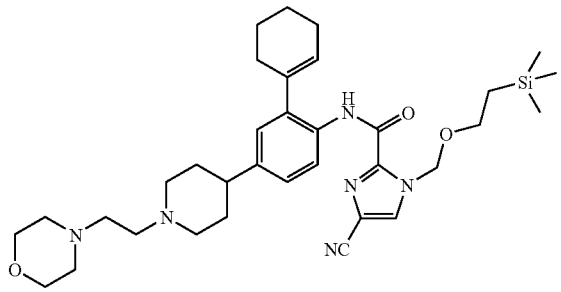

A flask was charged with 4-cyano-1-(2-trimethylsilanyl-ethoxymethyl)-1H-imidazole-2-carboxylic acid (2-cyclohex-1-enyl-4-piperidin-4-yl-phenyl)-amide TFA salt (830 mg, 1.34 mmol) (as prepared in Example 39, step (a)), $K_2CO_3$ (600 mg, 4.34 mmol), sodium iodide (40 mg, 0.27 mmol), 4-(2-chloro-ethyl)-morpholine hydrochloride (260 mg, 1.40 mmol), and 5.0 mL of N,N-dimethylacetamide and stirred for 8 h at 80° C. The reaction was diluted with EtOAc (50 mL) and washed with $NaHCO_3$ (2×50 mL), brine (50 mL) and concentrated. The title compound was purified by flash chromatography (silica gel, 5% MeOH/DCM) to give 650 mg (78%) of a white solid. Mass spectrum (ESI, m/z): Calcd. for $C_{34}H_{50}N_6O_3Si$, 619.4 (M+H), found 619.3.

b) 4-Cyano-1H-imidazole-2-carboxylic acid {2-cyclohex-1-enyl-4-[1-(2-morpholin-4-yl-ethyl)-piperidin-4-yl]-phenyl}-amide trifluoroacetic acid salt To a solution of 4-cyano-1-(2-trimethylsilanyl-ethoxymethyl)-1H-imidazole-2-carboxylic acid {2-cyclohex-1-enyl-4-[1-(2-morpholin-4-yl-ethyl)-piperidin-4-yl]-phenyl}-amide (650 mg, 1.05 mmol) (as prepared in the previous step) in 10 mL of DCM was added 0.3 mL of EtOH and 3.0 mL of TFA, and the reaction was allowed to proceed for 2 h at 25° C. The reaction was diluted with 10 mL of EtOH and concentrated. The title compound was purified by RP-HPLC (C18), eluting with 30-50% $CH_3CN$ in 0.1% $TFA/H_2O$ over 9 min to give 600 mg (80%) of a white solid. $^1$H-NMR (400 MHz, $CD_3OD$): δ 8.18 (d, 1H), 8.04 (s, 1H), 7.24 (dd, 1H), 7.14 (d, 1H), 5.84 (m, 1H), 3.84 (m, 4H), 3.76 (m, 2H), 3.50 (m, 2H), 3.30-3.10 (m, 4H), 2.92 (m, 5H), 2.30 (m, 4H), 2.20-2.00 (m, 4H), 1.90-1.74 (m, 4H). Mass spectrum (ESI, m/z): Calcd. for $C_{28}H_{36}N_6O_2$, 489.2, found 489.2.

Example 35

4-Cyano-1H-imidazole-2-carboxylic acid [2-(1,1-dioxo-1,2,3,6-tetrahydro-1λ$^6$-thiopyran-4-yl)-4-piperidin-4-yl-phenyl]-amide

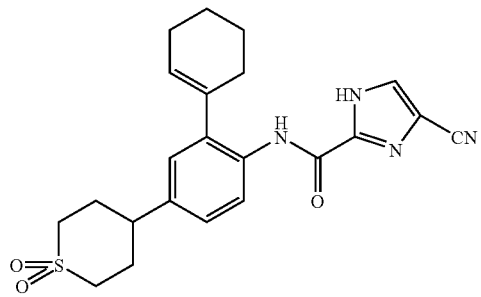

90 a) Trifluoromethanesulfonic acid 3,6-dihydro-2H-thiopyran-4-yl ester

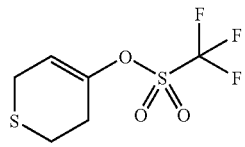

A solution of tetrahydro-thiopyran-4-one (1.00 g, 8.61 mmol) in 10 ml of THF was added to a solution of LDA (2.0 M, 4.52 ml, 9.04 mmol) in 20 ml of THF at −78° C. under Ar. The mixture was warmed to RT and stirred for 0.5 h, then cooled to −78° C. again. A solution of N-phenyltrifluoromethanesulfonimide (3.42 g, 9.47 mmol) in 10 ml of THF was added. The resulting mixture was warmed to RT and stirred for 0.5 h under Ar. Treated with 200 ml of EtOAc, the mixture was washed with $H_2O$ (3×50 mL), brine (50 mL) and dried ($Na_2SO_4$). Removal of the solvent under reduced pressure followed by flash chromatography of the residue on silica gel (hexane-3% EtOAc/hexane) gave 810 mg (38%) of the title compound as a colorless oil. $^1$H-NMR ($CDCl_3$; 400 MHz): δ 6.01 (m, 1H), 3.30 (m, 2H), 2.86 (dd, 2H, J=5.7, 5.7 Hz), 2.58-2.64 (m, 2H). Mass spectrum (ESI, m/z): Calcd. for $C_6H_7F_3O_3S_2$, 249.0 (M+H), found 249.3.

b) 4-(4-Nitro-phenyl)-3,6-dihydro-2H-thiopyran

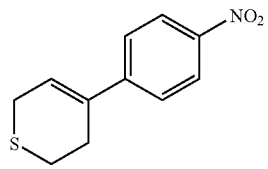

To a mixture of 4-nitrophenylboronic acid (418 mg, 2.50 mmol), trifluoromethanesulfonic acid 3,6-dihydro-2H-thiopyran-4-yl ester (as prepared in the previous step, 931 mg, 3.75 mmol), $Pd(PPh_3)_4$ (433 mg, 0.375 mmol) and lithium chloride (LiCl) (212 mg, 5.0 mmol) in 20 mL of 1,4-dioxane was added 2.0 M aq $Na_2CO_3$ solution (3.13 mL, 6.25 mmol). The resulting mixture was stirred at 80° C. for 2 h and then cooled to RT. Treated with 200 mL of EtOAc, the mixture was washed with $H_2O$ (2×30 mL), brine (30 mL) and dried ($Na_2SO_4$). Removal of the solvent under reduced pressure followed by flash chromatography of the residue on silica gel (1-3% EtOAc/hexane) gave 470 mg (85%) of the title compound as a light brown oil. $^1$H-NMR ($CDCl_3$; 400 MHz): δ 8.19 (d, 2H, J=9.1 Hz), 7.48 (d, 2H, J=9.1 Hz), 6.36 (m, 1H), 3.39 (m, 2H), 2.91 (t, 2H, J=5.7 Hz), 2.72 (m, 2H). Mass spectrum (ESI, m/z): Calcd. for $C_{11}H_{11}NO_2S$, 222.1 (M+H), found 222.3.

c) 4-(4-Nitro-phenyl)-3,6-dihydro-2H-thiopyran 1,1-dioxide

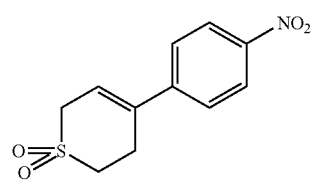

A solution of 3-chloroperoxybenzoic acid (1.04 g, 4.62 mmol, 77%) in 15 mL of dichloromethane (DCM) was added slowly to a solution of 4-(4-nitro-phenyl)-3,6-dihydro-2H-thiopyran (as prepared in the previous step, 465 mg, 2.10 mmol) in 15 mL of DCM at −78° C. under Ar. The mixture was stirred at −78° C. for 0.5 h, and then warmed to RT. Treated with 100 mL of EtOAc, the mixture was washed with 10% $Na_2SO_3$ (2×15 mL), satd aq $NaHCO_3$ solution (20 mL), $H_2O$ (20 mL), brine (20 mL) and dried ($Na_2SO_4$). Removal of the solvent under reduced pressure followed by flash chromatography of the residue on silica gel (2-5% EtOAc/DCM) gave 518 mg (97%) of the title compound as a white solid. $^1$H-NMR ($CDCl_3$; 400 MHz): δ 8.23 (d, 2H, J=9.0 Hz), 7.52 (d, 2H, J=9.0 Hz), 6.04 (m, 1H), 3.86 (m, 2H), 3.26-3.31 (m, 2H), 3.18-3.23 (m, 2H).

d) 4-(1,1-Dioxo-hexahydro-1λ$^6$-thiopyran-4-yl)-phenylamine

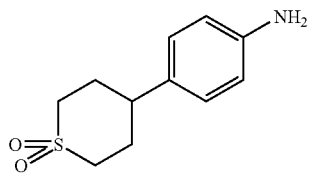

A mixture of 4-(4-nitro-phenyl)-3,6-dihydro-2H-thiopyran 1,1-dioxide (as prepared in the previous step, 502 mg, 1.98 mmol) and 10% Pd/C (250 mg, 50 wt %) in 15 mL of MeOH was stirred at RT under $H_2$ (balloon pressure) for 2 h. The Pd catalyst was removed by filtration on Celite, and the filtrate was concentrated to give 314 mg (70%) of the title compound as a slightly yellow solid. $^1$H-NMR ($CDCl_3$; 400 MHz): δ 7.03 (d, 2H, J=8.3 Hz), 6.67 (d, 2H, J=8.3 Hz), 3.51-3.79 (brs, 2H), 3.11-3.17 (m, 4H), 2.70 (dddd, 1H, J=12.3, 12.3, 2.9, 2.9 Hz), 2.31-2.43 (m, 2H), 2.15-2.23 (m, 2H).

e) 2-Bromo-4-(1,1-dioxo-hexahydro-1λ$^6$-thiopyran-4-yl)-phenylamine

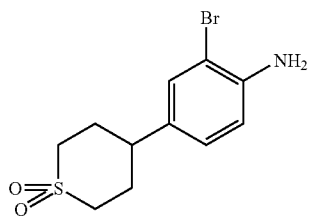

To a suspension of 4-(1,1-dioxo-hexahydro-1λ$^6$-thiopyran-4-yl)-phenylamine (as prepared in the previous step, 174 mg, 0.77 mmol) in 20 mL of 3:1 DCM/MeOH at 0° C. was added N-bromosuccinimide (NBS) (137 mg, 0.77 mmol) in 5 mL of DCM under Ar. The mixture was warmed to RT and stirred for 1 h under Ar. Treated with 100 mL of EtOAc, the mixture was washed with $H_2O$ (2×20 mL), brine (20 mL) and dried ($Na_2SO_4$). Removal of the solvent under reduced pressure followed by flash chromatography of the residue on silica gel (2-3% EtOAc/DCM) gave 155 mg (66%) of the title compound as a white solid. $^1$H-NMR ($CDCl_3$; 400 MHz): δ 7.28 (d, 1H, J=2.0 Hz), 6.97 (dd, 1H, J=8.3, 2.0 Hz), 6.73 (d, 1H, J=8.3 Hz), 4.07 (br s, 2H), 3.09-3.14 (m, 4H), 2.66 (dddd, 1H, J=12.1, 12.1, 3.3, 3.3 Hz), 2.26-2.39 (m, 2H), 2.12-2.21 (m, 2H). Mass spectrum (ESI, m/z): Calcd. for $C_{11}H_{14}BrNO_2S$, 304.0 (M+H), found 304.1.

f) 2-Cyclohex-1-enyl-4-(1,1-dioxo-hexahydro-1λ$^6$-thiopyran-4-yl)-phenylamine

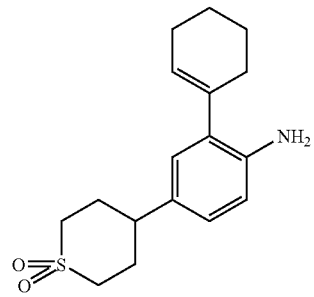

To a mixture of 2-bromo-4-(1,1-dioxo-hexahydro-1λ$^6$-thiopyran-4-yl)-phenylamine (as prepared in the previous step, 150 mg, 0.493 mmol), cyclohexen-1-yl boronic acid (70 mg, 0.542 mmol) and Pd(PPh$_3$)$_4$ (57 mg, 0.0493 mmol) in 5 mL of 1,4-dioxane was added 2.0 M aq $Na_2CO_3$ solution (2.0 mL, 4.0 mmol). The resulting mixture was stirred at 80° C. for 8 h under Ar, and then cooled to RT. Treated with 50 mL of EtOAc, the mixture was washed with $H_2O$ (3×15 mL), brine (20 mL) and dried ($Na_2SO_4$). Removal of the solvent under reduced pressure followed by flash chromatography of the residue on silica gel (2-5% EtOAc/DCM) gave 130 mg (86%) of the title compound as a brown solid. $^1$H-NMR ($CDCl_3$; 400 MHz): δ 6.89 (dd, 1H, J=8.4, 2.3 Hz), 6.84 (d, 1H, J=2.3 Hz), 6.65 (d, 1H, J=8.4 Hz), 5.74 (m, 1H), 3.74 (br s, 2H), 3.08-3.17 (m, 4H), 2.66 (dddd, 1H, J=12.1, 12.1, 3.1, 3.1 Hz), 2.29-2.42 (m, 2H), 2.13-2.25 (m, 6H), 1.73-1.81 (m, 2H), 1.65-1.73 (m, 2H). Mass spectrum (ESI, m/z): Calcd. for $C_{17}H_{23}NO_2S$, 306.1 (M+H), found 306.1.

g) 4-Cyano-1-(2-trimethylsilanyl-ethoxymethyl)-1H-imidazole-2-carboxylic acid [2-cyclohex-1-enyl-4-(1,1-dioxo-hexahydro-1λ$^6$-thiopyran-4-yl)-phenyl]-amide

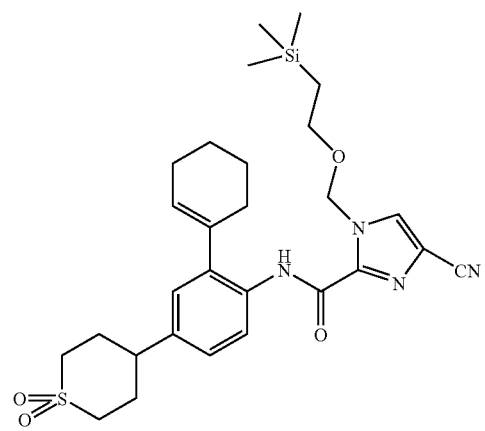

To a mixture of 2-cyclohex-1-enyl-4-(1,1-dioxo-hexahydro-1λ$^6$-thiopyran-4-yl)-phenylamine (as prepared in the previous step, 122 mg, 0.50 mmol), potassium 4-cyano-1-(2-trimethylsilanyl-ethoxymethyl)-1H-imidazole-2-carboxylate (as prepared in Example 3, step (d), 134 mg, 0.44 mmol) and bromotri(pyrrolidino)phosphonium hexafluorophosphate (PyBroP) (205 mg, 0.44 mmol) in 5 mL of DMF was added DIEA (209 µL, 1.20 mmol). The resulting mixture was stirred at RT for 18 h under Ar, cooled to RT. Treated with 50 mL of EtOAc, the mixture was washed with H$_2$O (3×10 mL), brine (10 mL) and dried (Na$_2$SO$_4$). Removal of the solvent under reduced pressure followed by flash chromatography of the residue on silica gel (1-3% EtOAc/DCM) gave 161 mg (73%) of the title compound as a colorless oil. $^1$H-NMR (CDCl$_3$; 400 MHz): δ 9.69 (s, 1H), 8.29 (d, 1H, J=8.4 Hz), 7.78 (s, 1H), 7.14 (dd, 1H, J=8.4, 2.2 Hz), 7.04 (d, 1H, J=2.2 Hz), 5.95 (s, 2H), 5.83 (m, 1H), 3.66 (t, 2H, J=8.2 Hz), 3.11-3.20 (m, 4H), 2.77 (dddd, 1H, J=12.1, 12.1, 3.2, 3.2 Hz), 2.35-2.47 (m, 2H), 2.17-2.33 (m, 6H), 1.74-1.89 (m, 4H), 0.97 (t, 2H, J=8.2 Hz), 0.00 (s, 9H). Mass spectrum (ESI, m/z): Calcd. for C$_{28}$H$_{38}$N$_4$O$_4$SSi, 555.2 (M+H), found 555.3.

h) 4-Cyano-1H-imidazole-2-carboxylic acid [2-cyclohex-1-enyl-4-(1,1-dioxo-hexahydro-1λ$^6$-thiopyran-4-yl)-phenyl]-amide

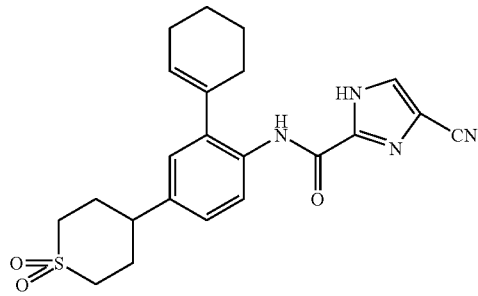

To a solution of 4-cyano-1-(2-trimethylsilanyl-ethoxymethyl)-1H-imidazole-2-carboxylic acid [2-cyclohex-1-enyl-4-(1,1-dioxo-hexahydro-1λ$^6$-thiopyran-4-yl)-phenyl]-amide (as prepared in the previous step, 145 mg, 0.261 mmol) in 6 mL of DCM was added 0.20 mL of EtOH followed by 2 mL of TFA. The resulting solution was stirred at RT for 3 h. Removal of the solvent under reduced pressure followed by flash chromatography of the residue on silica gel (20-25% EtOAc/DCM) gave 83 mg (90%) of the title compound as a white solid. $^1$H-NMR (CDCl$_3$; 400 MHz): δ 12.34 (s, 1H), 9.60 (s, 1H), 8.35 (d, 1H, J=8.4 Hz), 7.75 (s, 1H), 7.30 (dd, 1H, J=8.4, 2.2 Hz), 7.08 (d, 1H, J=2.2 Hz), 5.86 (m, 1H), 3.11-3.23 (m, 4H), 2.80 (dddd, 1H, J=12.2, 12.2, 2.8, 2.8 Hz), 2.40-2.57 (m, 2H), 2.17-2.35 (m, 6H), 1.74-1.91 (m, 4H). Mass spectrum (ESI, m/z): Calcd. for C$_{22}$H$_{24}$N$_4$O$_3$S, 425.2 (M+H), found 425.6.

Example 36

4-Cyano-1H-imidazole-2-carboxylic acid [2-(1,1-dioxo-1,2,3,6-tetrahydro-1λ$^6$-thiopyran-4-yl)-4-piperidin-4-yl-phenyl]-amide trifluoroacetic acid salt

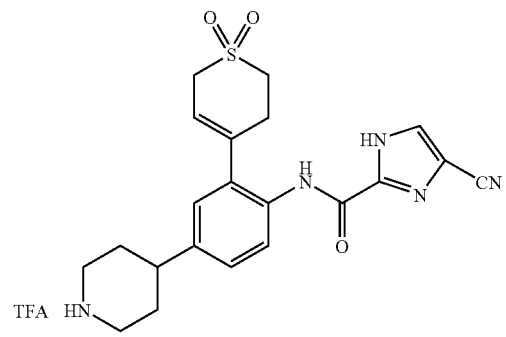

a) 2-(3,6-Dihydro-2H-thiopyran-4-yl)-5,5-dimethyl-[1,3,2]dioxaborinane

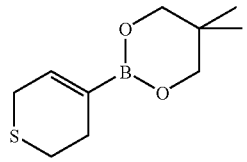

A mixture of trifluoromethanesulfonic acid 3,6-dihydro-2H-thiopyran-4-yl ester (as prepared in Example 35, step (a), 500 mg, 2.01 mmol), bis(neopentyl glycolato)diboron (478 mg, 2.11 mmol), Pd(dppf)Cl$_2$ (147 mg, 0.20 mmol) and KOAc (592 mg, 6.03 mmol) in 8 mL of 1,4-dioxane was stirred at 80° C. for 8 h under Ar, and then cooled to RT. Treated with 50 mL of EtOAc, the mixture was washed with H$_2$O (2×10 mL), brine (10 mL) and dried (Na$_2$SO$_4$). Removal of the solvent under reduced pressure followed by flash chromatography of the residue on silica gel (0-5% EtOAc/DCM) gave 351 mg (82%) of the title compound as a colorless oil. $^1$H-NMR (CDCl$_3$; 400 MHz): δ 6.62 (m, 1H), 3.63 (s, 4H), 3.21 (m, 2H), 2.68 (t, 2H, J=5.8 Hz), 2.37 (m, 2H), 0.96 (s, 6H). Mass spectrum (ESI, m/z): Calcd. for C$_{10}$H$_{17}$BO$_2$S, 213.1 (M+H), found 213.1.

b) 4-[4-Amino-3-(3,6-dihydro-2H-thiopyran-4-yl)-phenyl]-piperidine-1-carboxylic acid tert-butyl ester

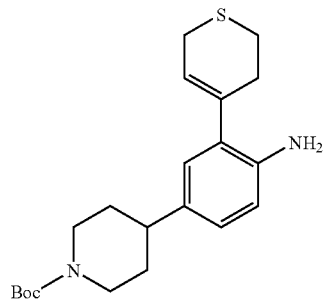

To a mixture of 4-(4-amino-3-bromo-phenyl)-piperidine-1-carboxylic acid tert-butyl ester (as prepared in Example 13, step (c), 200 mg, 0.563 mmol), 2-(3,6-dihydro-2H-thiopyran-4-yl)-5,5-dimethyl-[1,3,2]dioxaborinane (as prepared in the previous step, 131 mg, 0.619 mmol) and Pd(PPh$_3$)$_4$ (65 mg, 0.056 mmol) in 5 mL of 1,4-dioxane was added 2.0 M aq Na$_2$CO$_3$ solution (2.25 mL, 4.5 mmol). The resulting mixture was stirred at 80° C. for 7 h under Ar, and then cooled to RT. Treated with 50 mL of EtOAc, the mixture was washed with H$_2$O (3×15 mL), brine (20 mL) and dried (Na$_2$SO$_4$). Removal of the solvent under reduced pressure followed by flash chromatography of the residue on silica gel (15-30% EtOAc/hexane) gave 141 mg (67%) of the title compound as a colorless oil. $^1$H-NMR (CDCl$_3$; 400 MHz): δ 6.91 (dd, 1H, J=8.2, 2.2 Hz), 6.81 (d, 1H, J=2.2 Hz), 6.65 (d, 1H, J=8.2 Hz), 5.91 (m, 1H), 4.22 (br s, 2H), 3.66 (br s, 2H), 3.29-3.31 (m, 2H), 2.87 (dd, 2H, J=5.7, 5.7 Hz), 2.77 (m, 2H), 2.47-2.56 (m, 3H), 1.78 (d, 2H, J=12.6 Hz), 1.50-1.63 (m, 2 H), 1.48 (s, 9H). Mass spectrum (ESI, m/z): Calcd. for C$_{21}$H$_{30}$N$_2$O$_2$S, 375.2 (M+H), found 375.2.

c) 4-[4-{[4-Cyano-1-(2-trimethylsilanyl-ethoxymethyl)-1H-imidazole-2-carbonyl]-amino}-3-(3,6-dihydro-2H-thiopyran-4-yl)-phenyl]-piperidine-1-carboxylic acid tert-butyl ester

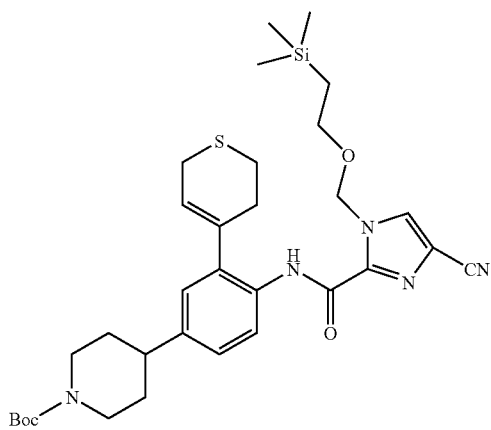

To a mixture of 4-[4-amino-3-(3,6-dihydro-2H-thiopyran-4-yl)-phenyl]-piperidine-1-carboxylic acid tert-butyl ester (as prepared in the previous step, 45 mg, 0.12 mmol), potassium 4-cyano-1-(2-trimethylsilanyl-ethoxymethyl)-1H-imidazole-2-carboxylate (as prepared in Example 3, step (d), 44 mg, 0.144 mmol) and PyBroP (67 mg, 0.144 mmol) in 2 mL of DMF was added DIEA (42 μL, 0.24 mmol). The resulting mixture was stirred at RT for 4 h under Ar. Treated with 30 mL of EtOAc, the mixture was washed with H$_2$O (3×10 mL), brine (10 mL) and dried (Na$_2$SO$_4$). Removal of the solvent under reduced pressure followed by flash chromatography of the residue on silica gel (1-2% EtOAc/DCM) gave 64 mg (85%) of the title compound as a light yellow oil. $^1$H-NMR (CDCl$_3$; 400 MHz): δ 9.51 (s, 1H), 8.21 (d, 1H, J=8.5 Hz), 7.78 (s, 1H), 7.16 (dd, 1H, J=8.5, 2.1 Hz), 7.02 (d, 1H, J=2.1 Hz), 6.00 (m, 1H), 5.92 (s, 2H), 4.25 (br s, 2H), 3.66 (t, 2H, J=8.2), 3.42 (m, 2H), 2.93 (dd, 2H, J=5.7, 5.7 Hz), 2.79 (m, 2H), 2.63 (dddd, 1H, J=12.3, 12.3, 3.3, 3.3 Hz), 2.49-2.56 (m, 2H), 1.82(d, 2H, J=12.8 Hz), 1.56-1.66 (m, 2H), 1.49 (s, 9H), 0.97 (t, 2H, J=8.2 Hz), 0.00 (s, 9H).

d) 4-[4-{[4-Cyano-1-(2-trimethylsilanyl-ethoxymethyl)-1H-imidazole-2-carbonyl]-amino}-3-(1,1-dioxo-1,2,3,6-tetrahydro-1λ$^6$-thiopyran-4-yl)-phenyl]-piperidine-1-carboxylic acid tert-butyl ester

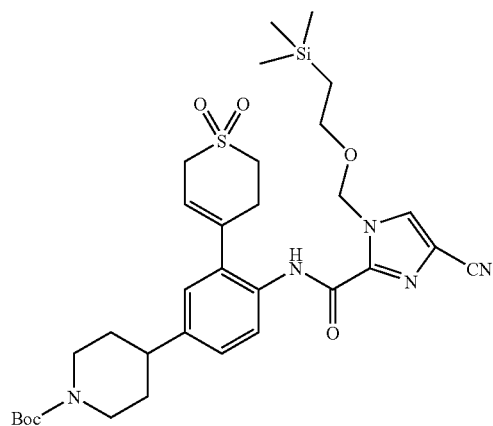

A solution of 3-chloroperoxybenzoic acid (91 mg, 0.404 mmol, 77%) in 1 mL of DCM was added slowly to 4-[4-{[4-cyano-1-(2-trimethylsilanyl-ethoxymethyl)-1H-imidazole-2-carbonyl]-amino}-3-(3,6-dihydro-2H-thiopyran-4-yl)-phenyl]-piperidine-1-carboxylic acid tert-butyl ester (as prepared in the previous step, 120 mg, 0.192 mmol) in 3 mL of DCM at −78° C. under Ar. The mixture was stirred at −78° C. for 15 min, and then warmed to RT. Treated with 40 mL of EtOAc, the mixture was washed with 15% Na$_2$SO$_3$ (5 mL), satd aq NaHCO$_3$ solution (2×10 mL), H$_2$O (10 mL), brine (10 mL) and dried (Na$_2$SO$_4$). Removal of the solvent under reduced pressure followed by flash chromatography of the residue on silica gel (2-10% EtOAc/DCM) gave 85 mg (67%) of the title compound as a colorless oil. $^1$H-NMR (CDCl$_3$; 400 MHz): δ 9.23 (s, 1H), 8.03 (d, 1H, J=8.3 Hz), 7.80 (s, 1H), 7.21 (dd, 1H, J=8.3, 2.0 Hz), 7.06 (d, 1H, J=2.0 Hz), 5.93 (s, 2H), 5.75 (t, 1H, J=4.1 Hz), 4.25 (br s, 2H), 3.86 (br s, 2H), 3.66 (t, 2H, J=8.2 Hz), 3.29 (t, 2H, J=6.3 Hz), 3.03 (t, 2H, J=5.4 Hz), 2.74-2.86 (m, 2H), 2.64 (dddd, 1H, J=12.3, 12.3, 3.3, 3.3 Hz), 1.82 (d, 2H, J=12.3 Hz), 1.55-1.65 (m, 2H), 1.49 (s, 9H), 0.98 (t, 2H, J=8.2 Hz), 0.01 (s, 9H). Mass spectrum (ESI, m/z): Calcd. for C$_{32}$H$_{45}$N$_5$O$_6$SSi, 656.3 (M+H), found 656.7.

e) 4-Cyano-1H-imidazole-2-carboxylic acid [2-(1,1-dioxo-1,2,3,6-tetrahydro-1λ$^6$-thiopyran-4-yl)-4-piperidin-4-yl-phenyl]-amide, trifluoroacetic acid salt

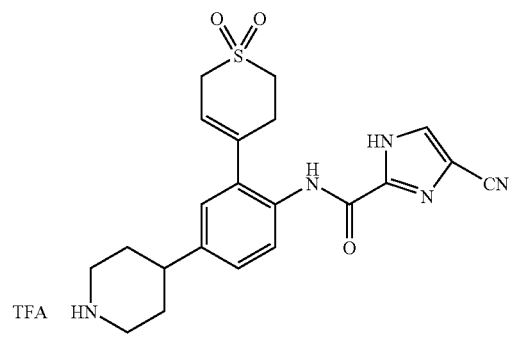

To a solution of 4-[4-{[4-cyano-1-(2-trimethylsilanyl-ethoxymethyl)-1H-imidazole-2-carbonyl]-amino}-3-(1,1-dioxo-1,2,3,6-tetrahydro-1λ⁶-thiopyran-4-yl)-phenyl]-piperidine-1-carboxylic acid tert-butyl ester (as prepared in the previous step, 81 mg, 0.123 mmol) in 6 mL of DCM was added 0.20 mL of EtOH followed by 2 mL of TFA. The resulting solution was stirred at RT for 3 h. Removal of the solvent under reduced pressure gave 64 mg (96%) of the title compound as a white solid. $^1$H-NMR (CD$_3$OD; 400 MHz): δ 8.02 (s, 1H), 7.78 (d, 1H, J=8.3 Hz), 7.29 (dd, 1H, J=8.3, 2.0 Hz), 7.21 (d, 1H, J=2.0 Hz), 5.71 (t, 1H, J=4.2 Hz), 3.83 (br s, 2H), 3.51 (d, 2H, J=12.4 Hz), 3.33 (t, 2H, J=6.0 Hz), 3.15 (td, 2H, J=13.1, 2.6 Hz), 3.01 (m, 2H), 2.94 (dddd, 1H, J=12.2, 12.2, 3.5, 3.5 Hz), 2.08 (d, 2H, J=12.9 Hz), 1.91 (m, 2H, J=13.3, 13.3, 13.3, 3.8 Hz). Mass spectrum (ESI, m/z): Calcd. for C$_{21}$H$_{23}$N$_5$O$_3$S, 426.2 (M+H), found 426.2.

Example 37

4-Cyano-1H-imidazole-2-carboxylic acid [4-(1-acetyl-piperidin-4-yl)-2-(1,1-dioxo-1,2,3,6-tetrahydro-1λ⁶-thiopyran-4-yl)-phenyl]-amide

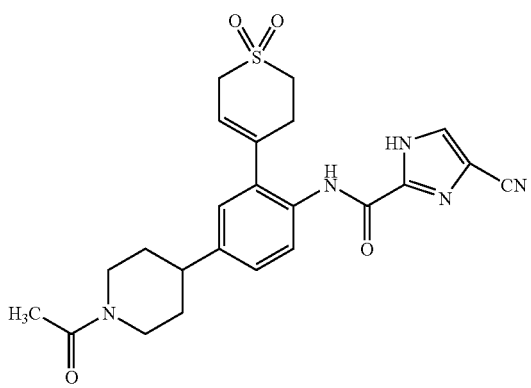

To a suspension of 4-cyano-1H-imidazole-2-carboxylic acid [2-(1,1-dioxo-1,2,3,6-tetrahydro-1λ⁶-thiopyran-4-yl)-4-piperidin-4-yl-phenyl]-amide trifluoroacetic acid salt (as prepared in Example 36, step (e), 62 mg, 0.115 mmol) in 4 mL of 1:1 DCM/DMF at RT was added DIEA (60 μL, 0.345 mmol). The mixture was stirred for 5 min, then acetic anhydride (11 μL, 0.121 mmol) was added slowly to the mixture, and the resulting mixture was stirred at RT for 0.5 h. Treated with 40 mL of EtOAc, the mixture was washed with H$_2$O (2×20 mL). The aqueous layers were extracted with EtOAc (4×10 mL). The combined organic layers were concentrated in vacuo. The residue was purified by flash chromatography on silica gel (1-4% MeOH/DCM) yielding 50.9 mg (95%) of the title compound as a white solid. $^1$H-NMR (CDCl$_3$; 400 MHz): δ 13.0 (s, 1H), 9.10 (s, 1H), 8.13 (d, 1H, J=8.4 Hz), 7.77 (d, 1H, J=2.3 Hz), 7.26 (dd, 1H, J=8.4, 2.0 Hz), 7.08 (d, 1H, J=2.0 Hz), 5.77 (t, 1H, J=4.3 Hz), 4.84 (dt, 1H, J=13.3, 2.1 Hz), 4.00 (dt, 1H, J=13.3, 2.1 Hz), 3.89 (br s, 2H), 3.31 (t, 2H, J=6.2 Hz), 3.23 (td, 1H, J=13.2, 2.5 Hz), 3.02 (m, 2H), 2.77 (dddd, 1H, J=11.9, 11.9, 3.4, 3.4 Hz), 2.68 (ddd, 1H, J=12.6, 12.6, 2.9 Hz), 2.18 (s, 3H), 1.70-1.97 (m, 4H). Mass spectrum (ESI, m/z): Calcd. for C$_{23}$H$_{25}$N$_5$O$_4$S, 468.2 (M+H), found 468.1.

Example 38

4-Cyano-1H-imidazole-2-carboxylic acid {2-cyclohex-1-enyl-4-[1-(2-dimethylamino-acetyl)-piperidin-4-yl]-phenyl}-amide

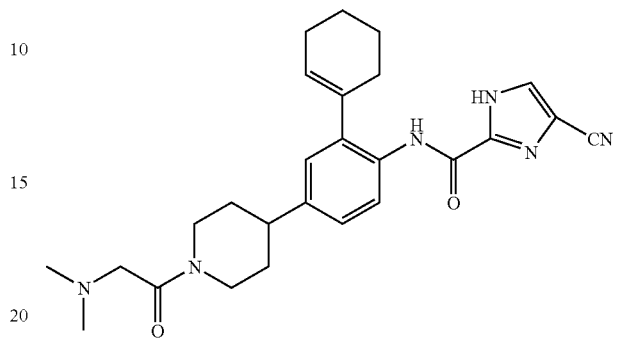

A mixture of 4-cyano-1H-imidazole-2-carboxylic acid (2-cyclohex-1-enyl-4-piperidin-4-yl-phenyl)-amide trifluoroacetic acid salt (as prepared in Example 14, step (b), 655 mg, 1.30 mmol) in DCM (15 mL) was cooled to 0° C. and DIEA (0.92 mL, 5.2 mmol) was added. Dimethylaminoacetyl chloride hydrochloride (211 mg, 1.3 mol) was then added portion wise over 10 min. The reaction mixture was stirred at 0° C. for 30 min and allowed to warm to RT and stirred for 2 h. Solvent was removed in vacuo and the resulting residue was partitioned between brine and DCM. The organic layer was separated, dried (Na$_2$SO$_4$) and concentrated. The residue obtained was purified on silica (5% MeOH: DCM) to obtain 432 mg (70%) of the title compound as a white solid. $^1$H-NMR (CDCl$_3$; 400 MHz): δ 9.49 (s, 1H), 8.24 (d, 1H, J=2.3 Hz), 7.70 (s, 1H), 7.12 (dd, 1H, J=8.4, 2.1 Hz), 7.01 (s, 1H), 5.82 (m, 1H), 4.75 (d, 1H, J=13.4 Hz), 4.13 (d, 1H, J=13.4 Hz), 3.57 (d, 1H, J=14.2 Hz), 3.18 (d, 1H, J=14.2 Hz), 3.12 (td, 1H, J=13.3, 2.4 Hz), 2.73 (dddd, 1H, J=11.9, 11.9, 3.8, 3.8 Hz), 2.65 (ddd, 1H, J=13.3, 13.3, 2.4 Hz), 2.40 (s, 6H), 2.18-2.32 (m, 4H), 1.60-1.98 (m, 8H). Mass spectrum (ESI, m/z): Calcd. for C$_{26}$H$_{32}$N$_6$O$_2$, 461.3 (M+H), found 461.2.

Example 38

4-Cyano-1H-imidazole-2-carboxylic acid {2-cyclohex-1-enyl-4-[1-(2-methylamino-acetyl)-piperidin-4-yl]-phenyl}-amide

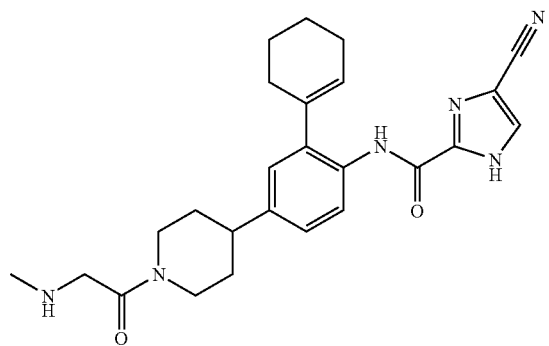

HPLC purification of Example 38a also afforded a small amount of 4-cyano-1H-imidazole-2-carboxylic acid {2-cyclohex-1-enyl-4-[1-(2-methylamino-acetyl)-piperidin-4-yl]-phenyl}-amide. ¹H-NMR (CD₃OD; 400 MHz): δ 8.02 (d, 1H, J=8.4 Hz), 7.92 (s, 1H), 7.07 (dd, 1H, J=8.4 Hz, J=2.4 Hz), 6.98 (d, 1H, J=2.4 Hz), 5.73-5.68 (m, 1H), 4.60-4.51 (m, 1H), 3.76-3.68 (m, 1H), 3.20-3.11 (m, 1H), 2.81-2.70 (m, 2H), 2.67 (s, 3H), 2.22-2.13 (m, 4H), 1.88-1.66 (m, 6H), 1.66-1.46 (m, 2H). Mass spectrum (ESI, m/z): Calcd. for C₂₅H₃₀N₆O₂, 447.2 (M+H), found 447.3.

Example 39

4-{4-[(4-Cyano-1H-imidazole-2-carbonyl)-amino]-3-cyclohex-1-enyl-phenyl}-piperidine-1-carboxylic acid (2-hydroxy-ethyl)-amide

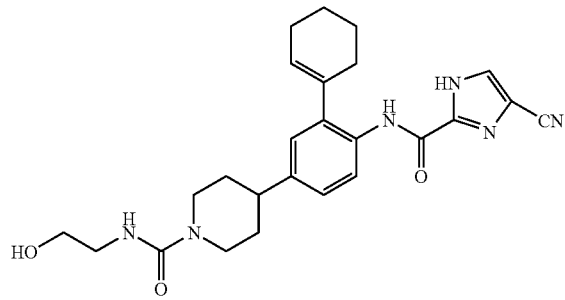

a) 4-Cyano-1-(2-trimethylsilanyl-ethoxymethyl)-1H-imidazole-2-carboxylic acid (2-cyclohex-1-enyl-4-piperidin-4-yl-phenyl)-amide, trifluoroacetic acid salt

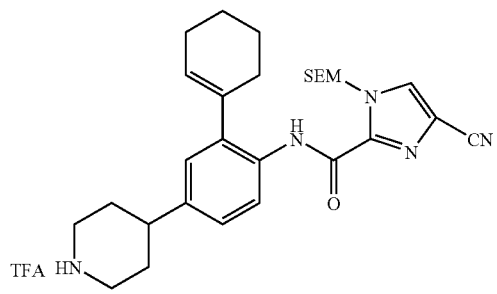

To a solution of 4-(4-{[4-cyano-1-(2-trimethylsilanyl-ethoxymethyl)-1H-imidazole-2-carbonyl]-amino}-3-cyclohex-1-enyl-phenyl)-piperidine-1-carboxylic acid tert-butyl ester (as prepared in Example 14, step (a), 81 mg, 0.123 mmol) in 18 mL of DCM was added 1 mL of EtOH followed by 5 mL of TFA at 0° C. The resulting solution was stirred at RT for 0.5 h, treated with 20 mL of EtOH followed by 20 mL of n-PrOH and 5 mL of H₂O, the mixture was then concentrated under reduced pressure to give a slightly yellow solid. Flash chromatography of the compound on silica gel (2-4% MeOH/DCM) gave 0.87 g (85%) of the title compound as a white solid. ¹H-NMR (CDCl₃; 400 MHz): δ 9.70 (s, 1H), 9.66 (br s, 1H), 9.15 (br s, 1H), 8.29 (d, 1H, J=8.3 Hz), 7.78 (s, 1H), 7.13 (dd, 1H, J=8.3, 2.2 Hz), 7.03 (d, 1H, J=2.2 Hz), 5.95 (s, 2H), 5.83 (m, 1H), 3.66 (t, 2H, J=8.4 Hz), 3.55 (d, 2H, J=12.3 Hz), 2.95-3.11 (m, 2H), 2.76 (m, 1H), 2.18-2.33 (m, 4H), 1.99-2.15 (m, 4H), 1.82 (m, 4H), 0.97 (t, 2H, J=8.3 Hz), 0.00 (s, 9H). Mass spectrum (ESI, m/z): Calcd. for C₂₈H₃₉N₅O₂Si, 506.3 (M+H), found 506.1.

b) 4-(4-{[4-Cyano-1-(2-trimethylsilanyl-ethoxymethyl)-1H-imidazole-2-carbonyl]-amino}-3-cyclohex-1-enyl-phenyl)-piperidine-1-carboxylic acid (2-hydroxy-ethyl)-amide

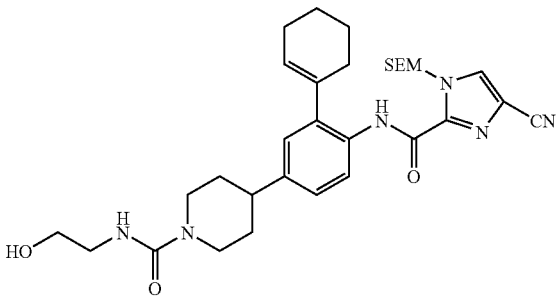

A solution of 4-cyano-1-(2-trimethylsilanyl-ethoxymethyl)-1H-imidazole-2-carboxylic acid (2-cyclohex-1-enyl-4-piperidin-4-yl-phenyl)-amide trifluoroacetic acid salt (as prepared in the previous step, 116 mg, 0.192 mmol) and DIEA (134 μL, 0.770 mmol) in 4 mL of DCM was added slowly to solution of triphosgene (23 mg, 0.0768 mmol) in 4 mL of DCM at −78° C. under Ar. The mixture was stirred at −78° C. for 15 min, warmed to RT and stirred for 15 min and cooled to −78° C. again. A suspension of 2-amino-ethanol (350 μL, 5.77 mmol) in 4 mL of THF was added and the resulting mixture was warmed to RT and stirred for 20 h under Ar. Treated with 100 mL of EtOAc, the mixture was washed with H₂O (3×20 mL), brine (20 mL) and dried (Na₂SO₄). Removal of the solvent in vacuo followed by flash chromatography of the residue on silica gel (10% EtOAc/DCM then 5% MeOH/DCM) gave 95 mg (83%) of the title compound as a colorless oil. ¹H-NMR (CDCl₃; 400 MHz): δ 9.68 (s, 1H), 8.25 (d, 1H, J=8.4 Hz), 7.77 (s, 1H), 7.12 (dd, 1H, J=8.4, 2.2 Hz), 7.01 (d, 1H, J=2.2 Hz), 5.94 (s, 2H), 5.83 (m, 1H), 4.96 (t, 1H, J=5.6 Hz), 4.11 (d, 2H, J=13.3 Hz), 3.75 (ddd, 2H, J=4.4 Hz), 3.66 (t, 2H, J=8.3 Hz), 3.44 (ddd, 2H, J=5.0 Hz), 3.36 (t, 1H, J=4.6 Hz), 2.91 (ddd, 2H, J=13.0, 2.2 Hz), 2.66 (dddd, 1H, J=12.2, 12.2, 3.3, 3.3 Hz), 2.18-2.33 (m, 4H), 1.75-1.91 (m, 6H), 1.67 (dddd, 2H, J=12.9, 12.9, 12.9, 4.0 Hz), 0.97 (t, 2H, J=8.3 Hz), 0.00 (s, 9H). Mass spectrum (ESI, m/z): Calcd. for C₃₁H₄₄N₆O₄Si, 593.3 (M+H), found 593.1.

c) 4-{4-[(4-Cyano-1H-imidazole-2-carbonyl)-amino]-3-cyclohex-1-enyl-phenyl}-piperidine-1-carboxylic acid (2-hydroxy-ethyl)-amide

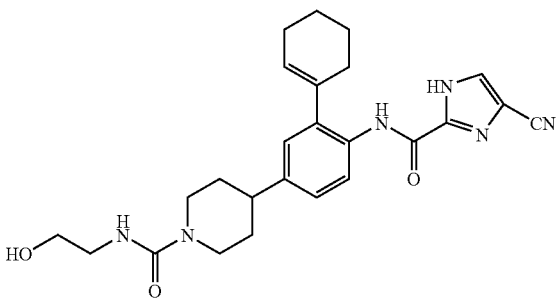

To a solution of 4-(4-{[4-cyano-1-(2-trimethylsilanyl-ethoxymethyl)-1H-imidazole-2-carbonyl]-amino}-3-cyclohex-1-enyl-phenyl)-piperidine-1-carboxylic acid (2-hydroxy-ethyl)-amide (as prepared in the previous step, 95 mg, 0.16 mmol) in 3 mL of DCM was added 0.10 mL of EtOH followed by 1.0 mL of TFA. The resulting solution was stirred at RT for 6 h. Removal of the solvent under reduced pressure followed by flash chromatography of the residue on silica gel (2-8% MeOH/DCM) gave 68 mg (92%) of the title compound as a white solid. ¹H-NMR (CD₃OD; 400 MHz): δ 8.09 (d, 1H, J=8.4 Hz), 8.00 (s, 1H), 7.15 (dd, 1H, J=8.4, 2.2 Hz), 5.79 (m, 1H), 4.15 (dd, 2H, J=13.3, 1.1 Hz), 3.61 (t, 2H, J=5.9 Hz), 3.27-3.32 (m, 2 H), 2.90 (ddd, 2H, J=13.0, 13.0, 2.5 Hz), 2.73 (dddd, 1H, J=12.1, 12.1, 2.6, 2.6 Hz), 2.26 (m, 4H), 1.73-1.88 (m, 6H), 1.62 (dddd, 2H, J=12.6, 12.6, 12.6, 4.0 Hz). Mass spectrum (ESI, m/z): Calcd. for C₂₅H₃₀N₆O₃, 463.2 (M+H), found 463.2.

Example 40

4-Cyano-1H-imidazole-2-carboxylic acid {2-cyclohex-1-enyl-4-[1-(2-methanesulfonyl-ethyl)-piperidin-4-yl]-phenyl}-amide

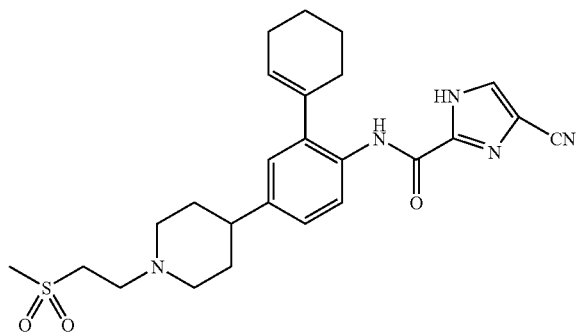

a) Methanesulfonic acid 2-methanesulfonyl-ethyl ester

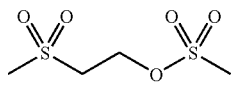

To a solution of methanesulfonyl chloride (484 mg, 4.23 mmol) in 15 mL of DCM at 0° C. was added 2-methanesulfonyl-ethanol (500 mg, 4.03 mmol) in 10 mL of DCM followed by DIEA (1.05 mL, 6.05 mmol) under Ar. The mixture was warmed to RT and stirred for 20 h under Ar. The mixture was treated with 100 mL of EtOAc and washed with H₂O (3×20 mL), brine (20 mL) and dried (Na₂SO₄). Removal of the solvent in vacuo gave 534 mg (66%) of the title compound as a brown oil. ¹H-NMR (CDCl₃; 400 MHz): δ 4.67 (d, 2H, J=5.5 Hz), 3.46 (d, 2H, J=5.5 Hz), 3.11 (s, 3H), 3.04 (s, 3H).

b) 4-Cyano-1H-imidazole-2-carboxylic acid {2-cyclohex-1-enyl-4-[1-(2-methanesulfonyl-ethyl)-piperidin-4-yl]-phenyl}-amide

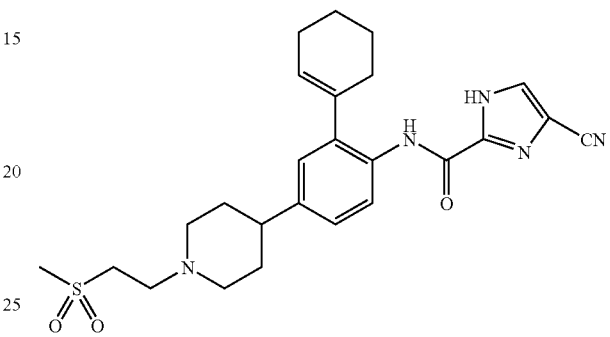

To a solution of 4-cyano-1H-imidazole-2-carboxylic acid (2-cyclohex-1-enyl-4-piperidin-4-yl-phenyl)-amide trifluoroacetic acid salt (as prepared in Example 14, step (b), 85 mg, 0.174 mmol) and DIEA (91 µL, 0.521 mmol) in 3 mL of DCM at RT was added 2-methanesulfonic acid 2-methanesulfonyl-ethyl ester (as prepared in the previous step, 42 mg, 0.208 mmol). The resulting mixture was stirred at RT for 3 h. Treated with 50 mL of EtOAc, the mixture was washed with H₂O (2×20 mL), brine (10 mL) and dried (Na₂SO₄). Removal of the solvent in vacuo followed by flash chromatography of the residue on silica gel (1-3% MeOH/DCM) gave 54 mg (65%) of the title compound as a white solid. ¹H-NMR (CDCl₃; 400 MHz): δ 9.54 (s, 1H), 8.25 (d, 1H, J=8.4 Hz), 7.72 (s, 1H), 7.15 (dd, 1H, J=8.4, 2.0 Hz), 7.04 (d, 1H, J=2.0 Hz), 5.85 (m, 1H), 3.21 (t, 1H, J=6.5 Hz), 3.09 (s, 3H), 3.02-3.11 (m, 2H), 2.92 (t, 2H, J=6.5 Hz), 2.52 (dddd, 1H, J=12.1, 12.1, 3.3, 3.3 Hz), 2.18-2.34 (m, 4H), 2.18 (t, 2H, J=10.8 Hz), 1.64-1.94 (m, 8H). Mass spectrum (ESI, m/z): Calcd. for C₂₅H₃₁N₅O₃S, 482.2 (M+H), found 482.2.

The following compounds have been prepared according to the examples as indicated:

| Example | Structure | Mass Spectrum [M + H]⁺ Calcd. | Found | Formula | Proc. Of Ex |
|---|---|---|---|---|---|
| 41 | 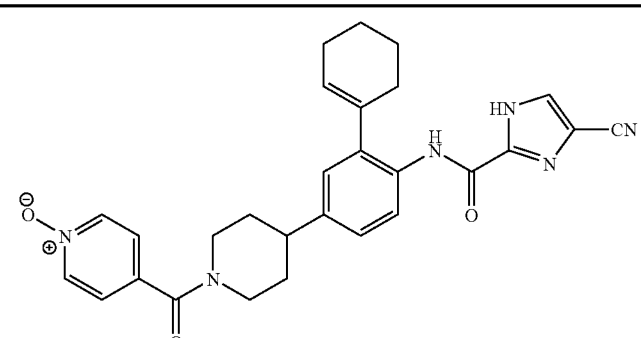 | 497.2 | 497.2 | C₂₈H₂₈N₆O₃ | 29 |

| Example | Structure | Mass Spectrum [M + H]+ Calcd. | Found | Formula | Proc. Of Ex |
|---|---|---|---|---|---|
| 42 | 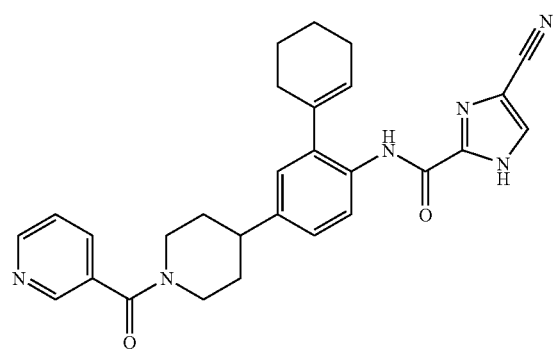 | 497.2 | 497.3 | C<sub>28</sub>H<sub>28</sub>N<sub>6</sub>O<sub>3</sub> | 29 |

Example 43

4-Cyano-1H-imidazole-2-carboxylic acid {2-cyclohex-1-enyl-4-[1-(pyridine-3-carbonyl)-piperidin-4-yl]-phenyl}-amide

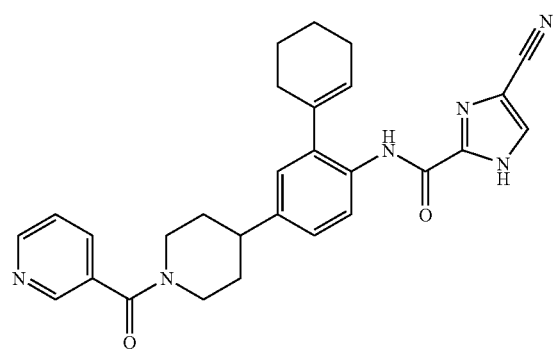

A solution of 4-cyano-1H-imidazole-2-carboxylic acid (2-cyclohex-1-enyl-4-piperidin-4-yl-phenyl)-amide trifluoroacetic acid salt (as prepared in Example 14, step (b), 75.0 mg, 0.15 mmol) in CH$_2$Cl$_2$ (10 mL) was treated with Et$_3$N (64.1 µL, 0.46 mmol) and cooled to 0° C. The mixture was treated with nicotinoyl chloride hydrochloride (0.030 g, 0.17 mmol) and stirred at 0° C. for 15 min then at room temperature for 17 h. The reaction mixture was adsorbed directly onto silica gel. Silica gel chromatography (10% MeOH in EtOAc) afforded the title compound (61.0 mg, 83%) as a white solid. $^1$H-NMR (CDCl$_3$; 400 MHz): δ 9.51 (br s, 1H), 8.77 (s, 1H), 8.70-8.66 (m, 1H), 8.32 (d, 1H, J=8.4 Hz), 7.86-7.81 (m, 1H), 7.70 (s, 1H), 7.42-7.37 (m, 1H), 7.17 (d, 1H, J=8.4 Hz), 7.06-7.04 (m, 1H), 5.87-5.82 (m, 1H), 4.98-4.87 (m, 1H), 3.94-3.84 (m, 1H), 3.29-3.18 (m, 1H), 2.98-2.86 (m, 1H), 2.86-2.76 (m, 1H), 2.34-2.20 (m, 4H), 1.94-1.72 (m, 9H). LC-MS (ESI, m/z): Calcd. for C$_{28}$H$_{28}$N$_6$O$_2$, 481.2 (M+H), found 481.3.

Example 44

4-Cyano-1H-imidazole-2-carboxylic acid (2-cyclohex-1-enyl-4-{1-[2-(2-hydroxy-ethylamino)-acetyl]-piperidin-4-yl}-phenyl)-amide trifluoroacetic acid salt

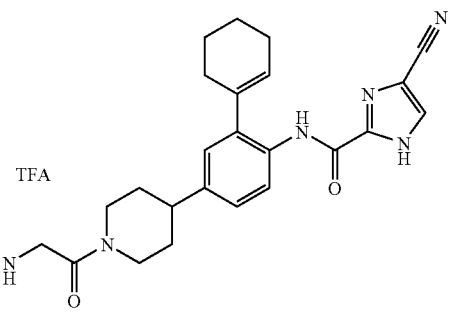

a) [2-(4-{4-[(4-Cyano-1H-imidazole-2-carbonyl)-amino]-3-cyclohex-1-enyl-phenyl}-piperidin-1-yl)-2-oxo-ethyl]-carbamic acid tert-butyl ester

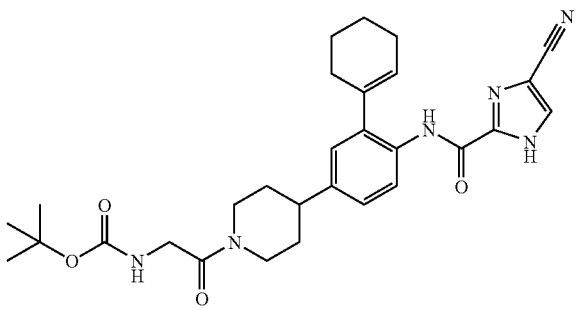

A solution of N—BOC-glycine (0.29 g, 1.63 mmol) in CH$_2$Cl$_2$ (10 mL) was treated with DIEA (0.85 mL, 4.90 mmol), HOBt (0.26 g, 1.96 mmol), and EDCI (0.38 g, 1.96 mmol). The mixture was stirred at room temperature for 10 min and added to a suspension of 4-cyano-1H-imidazole-2-carboxylic acid (2-cyclohex-1-enyl-4-piperidin-4-yl-phenyl)-amide trifluoroacetic acid salt (as prepared in Example 14, step (b), 0.80 g, 1.63 mmol) in $CH_2Cl_2$ (20 mL). The solution was stirred at room temperature for 17 h. Solvents were evaporated in vacuo. Silica gel chromatography (50% EtOAc in hexanes) afforded the title compound (0.41 g, 47%) as a white solid. 1H-NMR ($CDCl_3$; 400 MHz): δ 9.53 (s, 1H), 8.26 (d, 1H, J=8.4 Hz), 7.80-7.78 (m, 1H), 7.71 (s, 1H), 7.45-7.43 (m, 1H), 7.06 (d, 1H, J=8.4 Hz), 7.00 (s, 1 H), 5.83 (br s, 1H), 5.76 (br s, 1H), 4.78-4.68 (m, 1H), 3.96-3.85 (m, 2H), 3.17-3.03 (m, 1H), 2.78-2.63 (m, 2H), 2.29 (br s, 2H), 2.22 (br s, 2H), 1.95-1.87 (m, 2H), 1.86-1.72 (m, 4H), 1.70-1.55 (m, 2H), 1.44 (s, 9H). LC-MS (ESI, m/z): Calcd. for $C_{29}H_{36}N_6O_4$ 533.3 (M+H), found 532.9.

b) 4-Cyano-1H-imidazole-2-carboxylic acid {4-[1-(2-amino-acetyl)-piperidin-4-yl]-2-cyclohex-1-enyl-phenyl]-amide trifluoroacetic acid salt

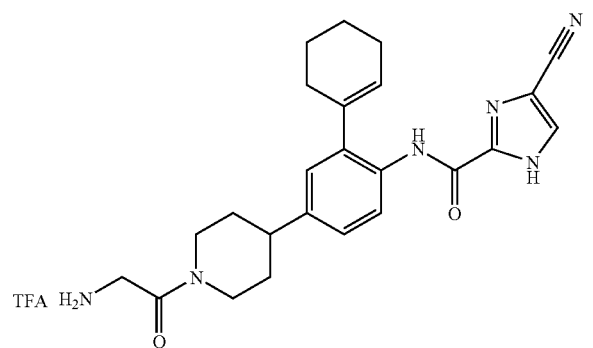

A solution of [2-(4-{4-[(4-cyano-1H-imidazole-2-carbonyl)-amino]-3-cyclohex-1-enyl-phenyl}-piperidin-1-yl)-2-oxo-ethyl]-carbamic acid tert-butyl ester (as prepared in the previous step, 0.41 g, 0.77 mmol) in $CH_2Cl_2$ (20 mL) was treated with EtOH (0.2 mL) and TFA (6 mL). The mixture stirred at room temperature for 45 min, and the solvents were evaporated in vacuo. The crude material was used directly in the next step. LC-MS (ESI, m/z): Calcd. for $C_{24}H_{28}N_6O_2$ 433.2 (M+H), found 433.2.

c) 4-Cyano-1H-imidazole-2-carboxylic acid (2-cyclohex-1-enyl-4-{1-[2-(2-hydroxy-ethylamino)-acetyl]-piperidin-4-yl}-phenyl)-amide trifluoroacetic acid salt

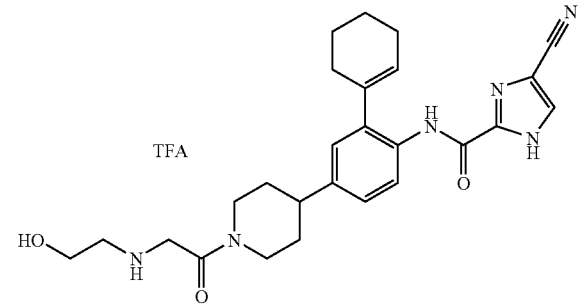

A suspension of 4-cyano-1H-imidazole-2-carboxylic acid {4-[1-(2-amino-acetyl)-piperidin-4-yl]-2-cyclohex-1-enyl-phenyl]-amide trifluoroacetic acid salt (as prepared in the previous step, 0.42 g, 0.77 mmol) in $CH_2Cl_2$ (20 mL) was treated with $Na(OAc)_3BH$ (0.33 g, 1.54 mmol) and solid glyoxal (44.6 mg, 0.77 mmol). The mixture stirred at room temperature for 1 h, and the solvent was evaporated in vacuo. The residue was taken up in MeOH and the solids filtered off, and the filtrate was concentrated in vacuo. Reverse phase HPLC (C-18 column) (20% to 60% acetonitrile in water with 0.1% TFA over 30 min) afforded the title compound (83 mg, 19% over two steps) as a white solid. $^1$H-NMR ($CD_3OD$; 400 MHz): δ 8.16-8.09 (m, 1H), 8.05-8.01 (m, 1H), 7.22-7.15 (m, 1H), 7.11-7.06 (m, 1H), 5.84-5.79 (m, 1H), 4.72-4.62 (m, 1H), 4.24-3.91 (m, 2H), 3.89-3.80 (m, 2H), 3.28-3.18 (m, 2H), 2.92-2.79 (m, 2H), 2.28 (br s, 4H), 1.98-1.89 (m, 2H), 1.89-1.76 (m, 4H), 1.76-1.57 (m, 2H). LC-MS (ESI, m/z): Calcd. for $C_{26}H_{32}N_6O_3$ 477.2 (M+H), found 477.2.

Example 45

4-Cyano-1H-imidazole-2-carboxylic acid (2-cyclohex-1-enyl-4-{1-[2-(2-hydroxy-ethyl)-methyl-amino-acetyl]-piperidin-4-yl}-phenyl)-amide trifluoroacetic acid salt

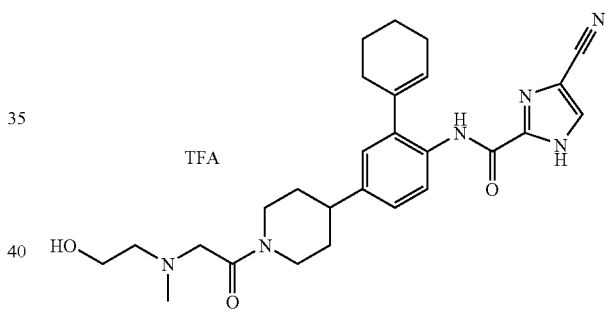

A solution of 4-cyano-1H-imidazole-2-carboxylic acid (2-cyclohex-1-enyl-4-{1-[2-(2-hydroxy-ethylamino)-acetyl]-piperidin-4-yl}-phenyl)-amide trifluoroacetic acid salt (as prepared in Example 44, step (c), 50.0 mg, 0.085 mmol) in MeOH (3 mL) was treated with $Na(OAc)_3BH$ (39.5 mg, 0.19 mmol) and 37% aqueous formaldehyde (8.2 μL, 0.10 mmol). The mixture was stirred at room temperature for 5.5 h, and the solvents were removed in vacuo. Reverse phase HPLC (C-18 column) (10% to 50% acetonitrile in water with 0.1% TFA over 30 min) afforded the title compound (19.5 mg, 47%) as a white solid. $^1$H-NMR ($CD_3OD$; 400 MHz): δ 8.12 (d, 1H, J=8.4 Hz), 8.02 (s, 1H), 7.19 (dd, 1H, J=8.4, 2.0 Hz), 7.09 (d, 1H, J=2.0 Hz), 5.84-5.79 (m, 1H), 4.72-4.64 (m, 1H), 4.39-4.23 (m, 2H), 3.84-3.79 (m, 1H), 3.31-3.21 (m, 1H), 3.03-2.94 (m, 6H), 2.92-2.80 (m, 2H), 2.32-2.24 (m, 4H), 2.00-1.90 (m, 2H), 1.90-1.76 (m, 5H), 1.78-1.59 (m, 2H). LC-MS (ESI, m/z): Calcd. for $C_{27}H_{34}N_6O_3$ 491.3 (M+H), found 491.2.

Example 46

4-Cyano-1H-imidazole-2-carboxylic acid [4-(1-acetyl-piperidin-4-yl)-2-(1,2,5,6-tetrahydro-pyridin-3-yl)-phenyl]-amide trifluoroacetic acid salt

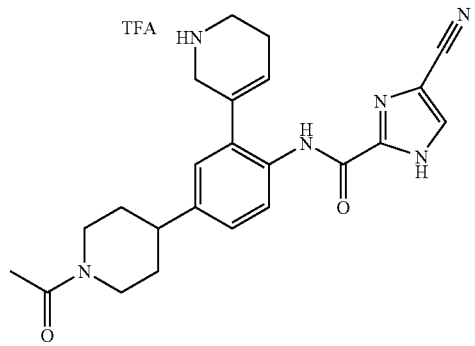

a) 5-Trifluoromethanesulfonyloxy-3,6-dihydro-2H-pyridine-1-carboxylic acid tert-butyl ester

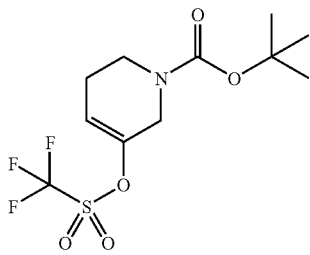

A solution of LDA (23.4 mL, 35.1 mmol, 1.5 M in cyclohex) in THF (50 mL) was cooled to −78° C. under Ar. The solution was treated with 3-oxo-piperidine-1-carboxylic acid tert-butyl ester (5.00 g, 25.1 mmol) as a solution in THF (15 mL) via drop wise addition and stirred for 15 min. The mixture was treated with 1,1,1-trifluoro-N-phenyl-N-[(trifluoromethyl)sulfonyl]methanesulfonimide (12.5 g, 35.1 mmol) as a solution in THF (40 mL). The mixture was allowed to warm to room temperature and stir 2.5 h. The reaction was quenched with saturated aqueous NaHCO$_3$, diluted with Et$_2$O, and washed with water. The organic layer was dried over MgSO$_4$ and concentrated in vacuo. Silica gel chromatography (5% EtOAc in hexanes) afforded the title compound (2.45 g, 30%) as a colorless oil. $^1$H-NMR (CDCl$_3$; 400 MHz): δ 5.97-5.89 (m, 1H), 4.09-4.01 (m, 2H), 3.54-3.45 (m, 2H), 2.36-2.26 (m, 2H), 1.48 (s, 9H). LC-MS (ESI, m/z): Calcd. for C$_{11}$H$_{16}$F$_3$NO$_5$S 332.1 (M+H), found 332.1.

b) 5-(4,4,5,5-Tetramethyl-[1,3,2]dioxaborolan-2-yl)-3,6-dihydro-2H-pyridine-1-carboxylic acid tert-butyl ester

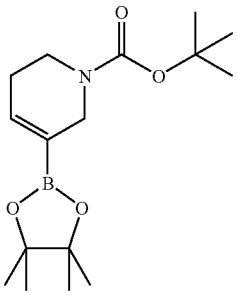

PdCl$_2$dppf (0.16 g, 0.22 mmol), KOAc (2.18 g, 22.2 mmol), 4,4,5,5,4',4',5',5'-octamethyl-[2,2']bi[[1,3,2]dioxaborolanyl] (2.07 g, 8.13 mmol), and dppf (0.12 g, 0.22 mmol) were placed in a round-bottomed flask, and the flask was flushed with Ar. A degassed solution of 5-trifluoromethanesulfonyloxy-3,6-dihydro-2H-pyridine-1-carboxylic acid tert-butyl ester (as prepared in the previous step, 2.45 g, 7.40 mmol) in dioxane (70 mL) was added to the flask and heated to 80° C. for 16 h. The mixture was filtered through a glass-fritted funnel to remove the solid KOAc, and the filtrate was concentrated in vacuo. Silica gel chromatography (5% EtOAc in hexanes) afforded the title compound (1.62 g, 71%) as a colorless oil. $^1$H-NMR (CDCl$_3$; 400 MHz): δ 6.69-6.60 (m, 1H), 3.98 (br s, 2H), 3.49-3.42 (m, 2H), 2.24-2.16 (m, 2H), 1.47 (s, 9H), 1.27 (s, 12H). LC-MS (ESI, m/z): Calcd. for C$_{18}$H$_{28}$BNO$_4$ 310.2 (M+H), found 311.0.

c) 4-(4-Nitro-phenyl)-3,6-dihydro-2H-pyridine-1-carboxylic acid tert-butyl ester

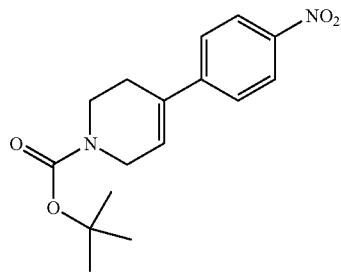

The title compound was prepared by the Suzuki coupling procedure of Example 35, step (b) using 4-nitrophenylboronic acid (167 mg, 1.00 mmol) and 4-trifluoromethanesulfonyloxy-3,6-dihydro-2H-pyridine-1-carboxylic acid tert-butyl ester (as prepared in Example 13, step (a), 295 mg, 1.00 mmol). Silica gel chromatography (10% EtOAc in hexanes) afforded the title compound (273 mg, 90%) as an oil. $^1$H-NMR (CDCl$_3$; 400 MHz): δ 8.19 (d, 2H, J=8.8 Hz), 7.50 (d, 2H, J=8.8 Hz), 6.23 (m, 1H), 4.12 (m, 2H), 3.66 (m, 2H), 2.54 (m, 2H), 1.49 (s, 9 H).

d) 1-[4-(4-Amino-phenyl)-piperidin-1-yl]-ethanone

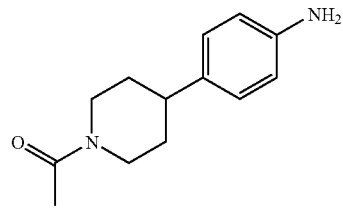

A solution of 4-(4-nitro-phenyl)-3,6-dihydro-2H-pyridine-1-carboxylic acid tert-butyl ester (as prepared in the previous step, 304 mg, 1.00 mmol) in a 1:1 mixture of DCM/TFA (10 mL) was stirred at room temperature for 3 h and concentrated. The residue was dried in vacuo overnight, was taken up in $CH_2Cl_2$ (10 mL) and was cooled to 0° C. To this solution, $Et_3N$ (280 µL, 2 mmol) was added drop wise, followed by acetic anhydride (102 µL, 1 mmol). The resulting mixture was stirred at 0° C. for 1 h and allowed to warm to room temperature. The reaction mixture was washed with brine, and the organic layer was separated, dried and concentrated. The resulting product was reduced to obtain the title compound (143 mg, 65%) using a procedure similar to Example 4, step (d). $^1$H-NMR ($CDCl_3$; 400 MHz): δ 6.97 (d, 2H, J=8.4 Hz), 6.64 (d, 2H, J=8.4 Hz), 4.75 (m, 1H), 3.93 (m, 1H), 3.13 (m, 3H), 2.66 (m, 2H), 2.12 (s, 3H), 1.84 (m, 2H), 1.57 (m, 2H).

e) 1-[4-(4-Amino-3-bromo-phenyl)-piperidin-1-yl]-ethanone

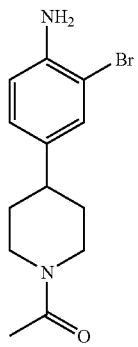

A solution of 1-[4-(4-amino-phenyl)-piperidin-1-yl]-ethanone (as prepared in the previous step, 0.36 g, 1.66 mmol) in $CH_2Cl_2$ (10 mL) was cooled to −78° C. and treated with NBS (0.28 g, 1.58 mmol) as a suspension in $CH_2Cl_2$ (4 mL). The reaction was allowed to warm to room temperature and stir for 30 min. The reaction was diluted with $CH_2Cl_2$ and washed with saturated aqueous $NaHCO_3$. The organic layer was dried over $MgSO_4$ and concentrated in vacuo. The crude material was used directly in the next reaction. LC-MS (ESI, m/z): Calcd. for $C_{13}H_{17}BrN_2O$ 297.1 (M+H), found 297.1.

f) 5-[5-(1-Acetyl-piperidin-4-yl)-2-amino-phenyl]-3,6-dihydro-2H-pyridine-1-carboxylic acid tert-butyl ester

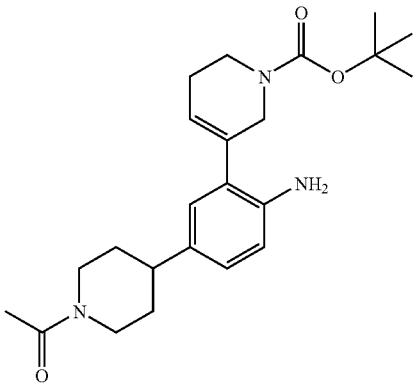

A solution of 5-(4,4,5,5-tetramethyl-[1,3,2]dioxaborolan-2-yl)-3,6-dihydro-2H-pyridine-1-carboxylic acid tert-butyl ester (as prepared in Example 46, step (b), 0.62 g, 2.02 mmol) and 1-[4-(4-amino-3-bromo-phenyl)-piperidin-1-yl]-ethanone (as prepared in the previous step, 0.20 g, 0.67 mmol) in toluene:EtOH (2:1, 9 mL) was treated with 2.0 M aqueous $Na_2CO_3$ (2.7 mL, 5.38 mmol) and was degassed with sonication under Ar. The mixture was heated to 80° C., treated with $Pd(PPh_3)_4$ (54 mg, 0.05 mmol), and stirred at 80° C. for 4.5 h. The reaction was cooled to room temperature, diluted with EtOAc, and washed with saturated aqueous $NaHCO_3$. The organic layer was dried over $MgSO_4$ and concentrated in vacuo to afford the title compound (0.25 g, 93%) as an off-white solid. LC-MS (ESI, m/z): Calcd. for $C_{23}H_{33}N_3O_3$ 422.2 (M+Na), found 422.0.

g) 5-(5-(1-Acetyl-piperidin-4-yl)-2-{[4-cyano-1-(2-trimethylsilanyl-ethoxymethyl)-1H-imidazole-2-carbonyl]-amino}-phenyl)-3,6-dihydro-2H-pyridine-1-carboxylic acid tert-butyl ester

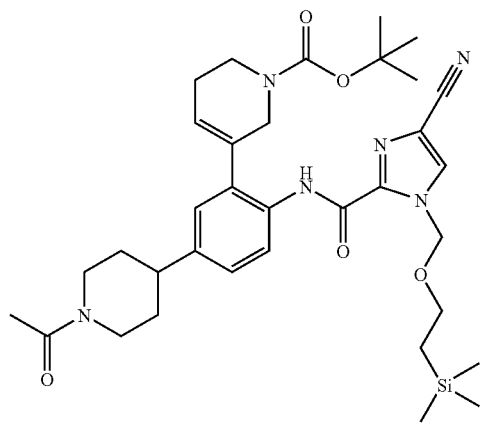

A solution of 5-[5-(1-acetyl-piperidin-4-yl)-2-amino-phenyl]-3,6-dihydro-2H-pyridine-1-carboxylic acid tert-butyl ester (as prepared in the previous step, 0.25 g, 0.63 mmol) in $CH_2Cl_2$ was treated with PyBroP (0.44 g, 0.94 mmol) and 4-cyano-1-(2-trimethylsilanyl-ethoxymethyl)-1H-imidazole-2-carboxylic acid, potassium salt (as prepared in Example 3, step (d), 0.21 g, 0.69 mmol). The resulting slurry was cooled to 0° C. and treated with DIEA (0.33 mL, 1.88 mmol). The ice bath was removed and the mixture stirred at room temperature for 18 h. The reaction was diluted with CH$_2$Cl$_2$ and washed with saturated aqueous NaHCO$_3$. The organic layer was dried over MgSO$_4$ and concentrated in vacuo. Silica gel chromatography (25-45% EtOAc in hexanes then 100% EtOAc) afforded the title compound (399 mg, 98%) as a white solid. LC-MS (ESI, m/z): Calcd. for C$_{34}$H$_{48}$N$_6$O$_5$Si 649.4 (M+H), found 649.9.

h) 4-Cyano-1H-imizazole-2-carboxylic acid [4-(1-acetyl-piperidin-4-yl)-2-(1,2,5,6-tetrahydro-pyridin-3-yl)-phenyl]-amide trifluoroacetic acid salt

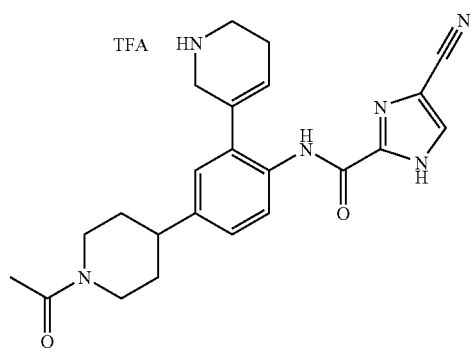

A solution of 5-(5-(1-acetyl-piperidin-4-yl)-2-{[4-cyano-1-(2-trimethylsilanyl-ethoxymethyl)-1H-imidazole-2-carbonyl]-amino}-phenyl)-3,6-dihydro-2H-pyridine-1-carboxylic acid tert-butyl ester (as prepared in the previous step, 0.40 g, 0.61 mmol) in CH$_2$Cl$_2$ (20 mL) and EtOH (0.4 mL) was treated with TFA (3 mL). The solution was stirred at room temperature for 0.5 h. The solvents were evaporated in vacuo, and the residue was immediately taken up in EtOH (25 mL) and stored at 5° C. for 11 h. The solution was concentrated in vacuo, and the residue was taken up in CH$_2$Cl$_2$ (20 mL) and EtOH (0.4 mL) then treated with TFA (6 mL). The reaction was stirred at room temperature for 2 h, and the solvents were evaporated in vacuo. Reverse phase HPLC (C-18 column) (10 to 80% acetonitrile in water with 0.1% TFA over 30 min) afforded the title compound (56.9 mg, 22%) as a white solid. $^1$H-NMR (CDCl$_3$; 400 MHz): δ 8.06 (s, 1H), 7.81 (d, 1H, J=8.4 Hz), 7.32 (d, 1H, J=8.4 Hz), 7.22 (s, 1H), 6.10-6.03 (m, 1H), 4.74-4.64 (m, 2H), 4.11-4.02 (m, 1H), 3.95 (s, 2H), 3.50-3.37 (m, 2H), 3.29-3.20 (m, 1H), 2.93-2.82 (m, 1H), 2.80-2.69 (m, 1H), 2.62-2.53 (m, 2H), 2.16 (s, 3H), 1.98-1.84 (m, 2H), 1.78-1.54 (m, 2H). LC-MS (ESI, m/z): Calcd. for C$_{23}$H$_{26}$N$_6$O$_2$ 419.2 (M+H), found 419.2.

Example 47

(4-{4-[(4-Cyano-1H-imidazole-2-carbonyl)-amino]-3-cyclohex-1-enyl-phenyl}-piperidin-1-yl)-acetic acid trifluoroacetic acid salt

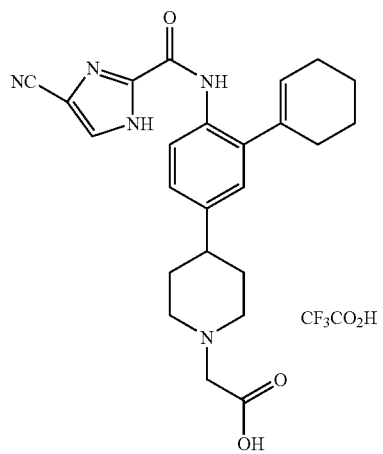

A flask was charged with 4-cyano-1H-imidazole-2-carboxylic acid (2-cyclohex-1-enyl-4-piperidin-4-yl-phenyl)-amide TFA salt (33 mg, 0.067 mmol) (as prepared in Example 14, step (b)), t-butyl bromoacetate (10 μL, 0.067 mmol), NEt$_3$ (20 μL, 0.135 mmol) and 0.25 mL of DCM and stirred for 10 h at 25° C. The reaction mixture was loaded on a 5 g SPE cartridge (silica) and 23 mg (70%) of (4-{4-[(4-cyano-1H-imidazole-2-carbonyl)-amino]-3-cyclohex-1-enyl-phenyl}-piperidin-1-yl)-acetic acid tert-butyl ester was eluted with 25% EtOAc/DCM. This compound was dissolved in 1 mL of DCM and 20 μL of EtOH and 1 mL of TFA were added and the reaction stirred for 3 h at 25° C. The title compound was purified by RP-HPLC (C18), eluting with 30-50% CH$_3$CN in 0.1% TFA/H$_2$O over 12 min to give 10 mg (40%) of a white solid. $^1$H-NMR (400 MHz, CD$_3$OD): δ 8.16 (d, 1H), 8.02 (s, 1H), 7.22 (dd, 1H), 7.10 (d, 1H), 5.72 (m, 1H), 4.04. (s, 2H), 3.76 (m, 2H), 3.22 (m, 2H), 2.90 (m, 1H), 2.29 (m, 4H), 2.10 (m, 4H), 1.82 (m, 4H). Mass spectrum (ESI, m/z): Calcd. for C$_{24}$H$_{27}$N$_5$O$_3$, 434.2 (M+H), found 434.2.

Example 48

4-Cyano-1H-imidazole-2-carboxylic acid {4-[1-(3-amino-3-methyl-butyryl)-piperidin-4-yl]-2-cyclohex-1-enyl-phenyl}-amide trifluoroacetic acid salt

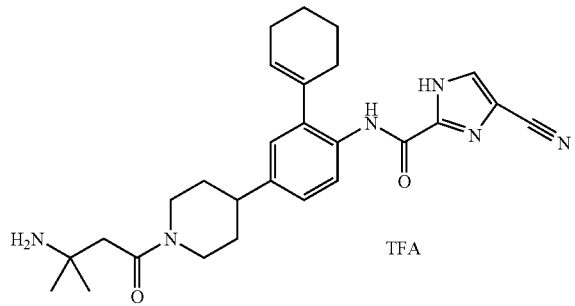

a) [3-(4-{4-[(4-Cyano-1H-imidazole-2-carbonyl)-amino]-3-cyclohex-1-enyl-phenyl}-piperidin-1-yl)-1,1-dimethyl-3-oxo-propyl]-carbamic acid tert-butyl ester

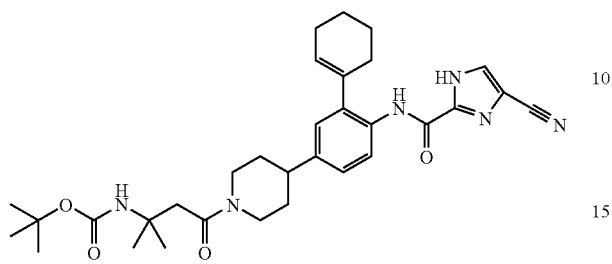

To a mixture of 4-cyano-1H-imidazole-2-carboxylic acid (2-cyclohex-1-enyl-4-piperidin-4-yl-phenyl)-amide trifluoroacetic acid salt (as prepared in Example 14, step (b), 40.0 mg, 0.0818 mmol), 3-tert-butoxycarbonylamino-3-methyl-butyric acid (*J. Med. Chem.*, 34(2), 633-642, (1991), 21.4 mg, 0.0981 mmol) and PyBroP (55.0 mg, 0.0981 mmol) in dichloroethane (2 mL) was added DIEA (43 µL, 0.25 mmol) and the resulting mixture was stirred at RT for 1 day under Ar. The mixture was diluted with EtOAc (30 mL) and washed with $H_2O$ (2×10 mL), brine (10 mL), dried over $Na_2SO_4$ and then concentrated in vacuo. The residue was purified by flash chomatography (silica gel, 10-40% EtOAc/hexane) to give 33.0 mg (70%) of the title compound as a colorless oil. Mass spectrum (ESI, m/z): Calcd. for $C_{32}H_{42}N_6O_4$, 575.3 (M+H), found 574.8.

b) 4-Cyano-1H-imidazole-2-carboxylic acid {4-[1-(3-amino-3-methyl-butyiyl)-piperidin-4-yl]-2-cyclohex-1-enyl-phenyl}-amide trifluoroacetic acid salt

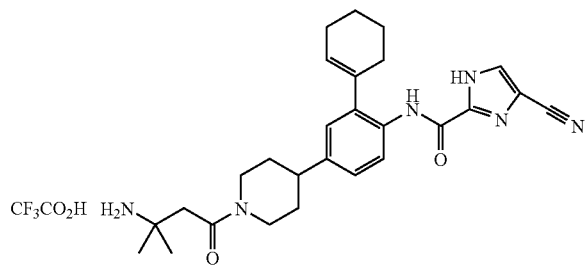

To a solution of [3-(4-{4-[(4-cyano-1H-imidazole-2-carbonyl)-amino]-3-cyclohex-1-enyl-phenyl}-piperidin-1-yl)-1,1-dimethyl-3-oxo-propyl]-carbamic acid tert-butyl ester (33.0 mg, 0.0574 mmol) (as prepared in the previous step) in 3 mL of DCM and 0.10 mL EtOH at 0° C. was added 1.0 mL of TFA, the mixture was warmed to RT and stirred for 3 h. The reaction was diluted with 3 mL of n-PrOH and then concentrated in vacuo. The residue was purified by flash chomatography (silica gel, 3-8% MeOH/DCM) to give 33.5 mg (99%) of the title compound as a white solid. $^1$H-NMR (400 MHz, $CDCl_3$): δ 13.3 (s, 1H), 9.52 (s, 1H), 8.57 (br s, 3H), 8.26 (d, 1H, J=8.6 Hz), 7.69 (s, 1H), 7.02 (dd, 1H, J=8.6, 1.7 Hz), 6.98 (d, 1H, J=1.7 Hz), 5.78 (m, 1H), 4.67 (br d, 1H, J=13.4 Hz), 3.88 (br d, 1H, J=13.4 Hz), 3.10 (m, 1H), 2.55-2.85 (m, 4H), 2.23 (m, 4H), 1.72-2.01 (m, 8H), 1.50 (s, 6H). Mass spectrum (ESI, m/z): Calcd. for $C_{27}H_{34}N_6O_2$, 475.3 (M+H), found 475.1.

Example 49

4H-[1,2,4]-triazole-3-carboxylic acid (2-cyclohex-1-enyl-4-piperidin-4-yl-phenyl)-amide bis trifluoroacetic acid salt

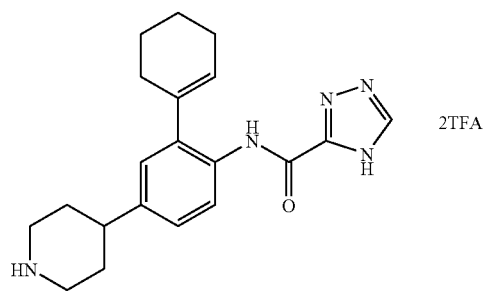

a) 1-(2-Trimethylsilanyl-ethoxymethyl)-1H-[1,2,4]-triazole-3-carboxylic acid methyl ester

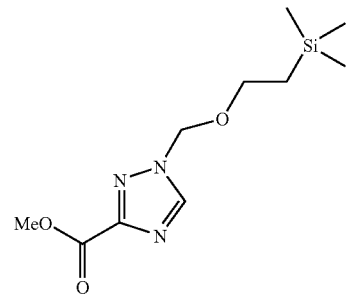

To a suspension of NaH (60% dispersion) (200 mg, 5.00 mmol) in DMF (5 mL) at 0° C., a solution of methyl-1H-1,2,4-triazolecarboxylate (635 mg, 5.00 mmol) in DMF (5 mL) was added dropwise. The resulting suspension was stirred at the same temperature for 30 min and treated with SEMCl (0.90 mL, 5.0 mmol). The resulting solution was stirred at RT for 30 min and poured onto ice. The product was extracted with ether (3×20 mL). The ether layers were combined, dried ($Na_2SO_4$) and concentrated in vacuo. The residue obtained was chromatographed on silica (10% EtOAc/hexane) to obtain the title compound (530 mg, 41%). Mass spectrum (ESI, m/z): Calcd. for $C_{10}H_{19}N_3O_3Si$, 258.1 (M+H), found 258.2.

b) 4-(3-Cyclohex-1-enyl-4-{[1-(2-trimethylsilanyl-ethoxymethyl)-1H-[1,2,4-]triazole-3-carbonyl]-amino}-phenyl)-piperidine-1-carboxylic acid tert-butyl ester

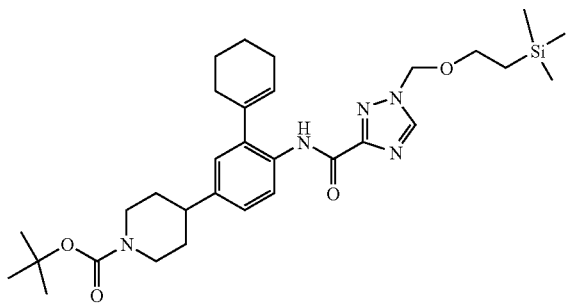

To a solution of 1-(2-trimethylsilanyl-ethoxymethyl)-1H-[1,2,4]-triazole-3-carboxylic acid methyl ester (as prepared in the previous step, 257 mg, 1.00 mmol) in EtOH (2 mL), 2 N KOH (0.5 mL, 1 mmol) was added. The resulting solution was stirred at RT for 20 min and concentrated in vacuo. The residue obtained was suspended in ether (10 mL) and sonicated for 5 min. The ether was then removed in vacuo and the resulting residue was dried for 4 hr to obtain 1-(2-trimethylsilanyl-ethoxymethyl)-1H-[1,2,4]-triazole-3-carboxylic acid potassium salt (273 mg, 97%) which was directly used in the next step without any further purification.

A mixture of 1-(2-trimethylsilanyl-ethoxymethyl)-1H-[1,2,4]-triazole-3-carboxylic acid potassium salt (as prepared above, 28 mg, 0.10 mmol), DIEA (34 µL, 0.20 mmol), 4-(4-amino-3-cyclohex-1-enyl-phenyl)-piperidine-1-carboxylic acid tert-butyl ester (as prepared in Example 14, step (b), 35.6 mg, 0.100 mmol) and PyBroP (69.9 mg, 0.150 mmol) in DCM (2 mL) was stirred at RT for 12 h. The reaction mixture was diluted with DCM (5 mL) and washed with saturated aqueous NaHCO$_3$ (10 mL) and water (10 mL). The organic layer was separated, dried (Na$_2$SO$_4$) and concentrated in vacuo. The product was chromatographed on silica (20-40% EtOAc/hexane) to obtain the title compound (31.9 mg, 55%). Mass spectrum (ESI, m/z): Calcd. for C$_{31}$H$_{47}$N$_5$O$_4$Si, 481.2 (M−BOC+2H), found. 481.2.

c) 4H-[1,2,4-]-triazole-3-carboxylic acid (2-cyclohex-1-enyl-4-piperidin-4-yl-phenyl)-amide bis trifluoroacetic acid salt

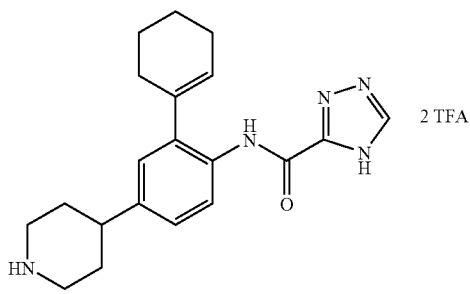

To a solution of 4-(3-cyclohex-1-enyl-4-{[1-(2-trimethylsilanyl-ethoxymethyl)-1H-[1,2,4]-triazole-3-carbonyl]-amino}-phenyl)-piperidine-1-carboxylic acid tert-butyl ester (as prepared in the previous step, 81.9 mg, 0.140 mmol) in DCM (0.4 mL) and EtOH (13 µL), was added TFA (0.13 mL). The resulting solution was stirred at RT for 3 h and concentrated in vacuo. The residue obtained was dried under vacuum for 1 h, suspended in ether (10 mL) and sonicated for 5 min. The solid formed was collected by suction filtration to obtain the title compound (56 mg, 68%). $^1$H-NMR (CD$_3$OD; 400 MHz): δ 8.53 (br s, 1H), 8.20 (d, 1H, J=8.4 Hz), 7.21 (dd, 1H, J=8.4, 2.1 Hz), 7.11 (d, 1H, J=2.1 Hz), 5.83 (br s, 1H), 3.45 (m, 2H), 3.19 (m, 2H), 2.98 (m, 1H), 2.28 (m, 4H), 2.14 (m, 2H), and 1.95-1.75 (m, 6H). Mass spectrum (ESI, m/z): Calcd. for C$_{20}$H$_{25}$N$_5$O, 352.4 (M+H), found 352.2.

Example 50

5-Chloro-4H-[1,2,4]-triazole-3-carboxylic acid (2-cyclohex-1-enyl-4-piperidin-4-yl-phenyl)-amide trifluoroacetic acid salt

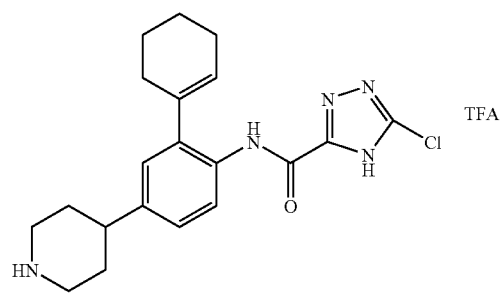

a) 5-Chloro-1-(2-trimethylsilanyl-ethoxymethyl)-1H-[1,2,4]-triazole-3-carboxylic acid methyl ester

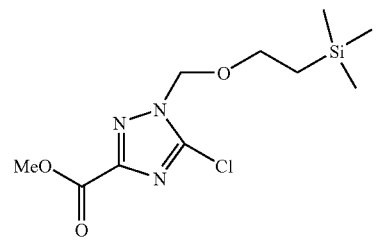

To a suspension of NaH (60% dispersion, 53.9 mg, 1.34 mmol) in DMF (5 mL) at 0° C., a solution of 5-chloro-1H-[1,2,4]-triazole-3-carboxylic acid methyl ester (Bull. Pharm. Sci., 20(1): 47-61, (1997), 218 mg, 1.35 mmol) in DMF (10 mL) was added dropwise. The resulting suspension was stirred at the same temperature for 30 min and then treated with SEMCl (0.24 mL, 1.4 mmol). The resulting solution was stirred at RT for 30 min and poured onto ice. The mixture was extracted with ether (3×20 mL) and the ether layers were combined, dried (Na$_2$SO$_4$) and concentrated in vacuo. The residue obtained was chromatographed on silica (10% EtOAc/hexane) to obtain the title compound (227 mg, 58%). Mass spectrum (ESI, m/z): Calcd. for C$_{10}$H$_{18}$ClN$_3$O$_3$Si, 292.0 and 294.0 (M+H), found 291.5 and 293.6.

b) 4-(4-{[5-Chloro-1-(2-trimethylsilanyl-ethoxymethyl)-1H-[1,2,4]-triazole-3-carbonyl]-amino}-3-cyclohex-1-enyl-phenyl)-piperidine-1-carboxylic acid tert-butyl ester

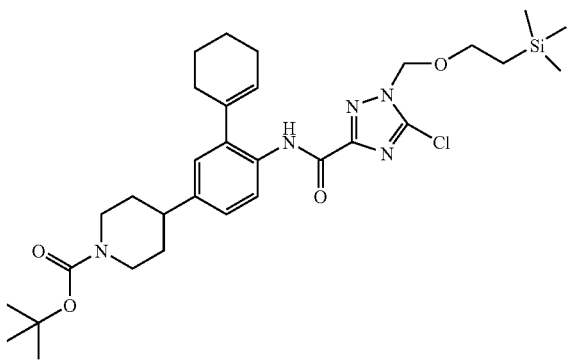

To a solution of 4-(4-{[5-chloro-1-(2-trimethylsilanyl-ethoxymethyl)-1H-[1,2,4]triazole-3-carboxylic acid methyl ester (as prepared in the previous step, 227 mg, 0.780 mmol) in EtOH (2 mL), 2 N KOH (0.4 mL, 0.8 mmol) was added. The resulting solution was stirred at RT for 20 min and concentrated in vacuo. The residue obtained was suspended in ether (10 mL) and sonicated for 5 min. The ether was then removed and the resulting residue was dried in vacuo for 4 h to obtain 4-(4-{[5-chloro-1-(2-trimethylsilanyl-ethoxymethyl)-1H-[1,2,4]triazole-3-carboxylic acid potassium salt (223 mg, 91%) which was directly used in the next step without any further purification.

A mixture of 4-(4-{[5-chloro-1-(2-trimethylsilanyl-ethoxymethyl)-1H-[1,2,4]-triazole-3-carboxylic acid potassium salt (as prepared above, 35 mg, 0.10 mmol), DIEA (34 µL, 0.10 mmol), 4-(4-amino-3-cyclohex-1-enyl-phenyl)-piperidine-1-carboxylic acid tert-butyl ester (as prepared in Example 14, step (b), 35.6 mg, 0.100 mmol) and PyBroP (69.9 mg, 0.150 mmol) in DCM (2 mL) was stirred at RT for 12 h. The reaction mixture was diluted with DCM (5 mL) and washed with saturated aqueous NaHCO$_3$ (10 mL) and water (10 mL). The organic layer was separated, dried (Na$_2$SO$_4$) and concentrated in vacuo. The product was chromatographed on silica (20-40% EtOAc/hexane) to obtain the title compound (52 mg, 85%). $^1$H-NMR (CDCl$_3$; 400 MHz): δ 9.60 (s, 1H), 8.29 (d, 1H, J=8.4 Hz), 7.18 (dd, 1H, J=8.4, 2.2 Hz), 7.13 (d, 1H, J=2.2 Hz), 5.99 (s, 2H), 5.84 (br s, 1H), 4.18-4.25 (m, 2 H), 3.72-3.76 (m, 2H), 2.58-2.67 (m, 2H), 2.51-2.64 (m, 1H), 2.18-2.33 (m, 4H), 1.78-1.92 (m, 6H), 1.55-1.65 (m, 2H), 1.49 (s, 9H), 0.93-0.98 (m, 2H), 0.10 (s, 9H).

c) 5-Chloro-1H-[1,2,4-]-triazole-3-carboxylic acid (2-cyclohex-1-enyl-4-piperidin-4-yl-phenyl)-amide trifluoroacetic acid salt

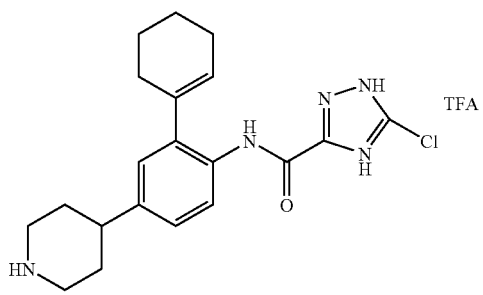

To a solution of 4-(4-{[5-chloro-1-(2-trimethylsilanyl-ethoxymethyl)-1H-[1,2,4]-triazole-3-carbonyl]-amino}-3-cyclohex-1-enyl-phenyl)-piperidine-1-carboxylic acid tert-butyl ester (as prepared in the previous step, 63.3 mg, 0.102 mmol) in DCM (0.5 mL) and EtOH (11 µL) was added TFA (0.1 mL). After stirring the resulting mixture at RT for 12 h, another 0.1 mL of TFA was added. The reaction mixture was stirred for an additional 5 h at RT, the solvents were evaporated, and the title compound was purified by RP-HPLC (C18) eluting with 20-70% CH$_3$CN in 0.1% TFA/H$_2$O over 20 min to obtain the title compound (30 mg, 58%). $^1$H-NMR (CD$_3$OD; 400 MHz): δ 8.14 (d, 1H, J=8.4 Hz), 7.20 (dd, 1H, J=8.4, 2.1 Hz), 7.13 (d, 1H, J=2.1 Hz), 5.82 (br s, 1H), 3.45 (m, 2H), 3.19 (m, 2H), 2.98 (m, 1H), 2.28 (m, 4H), 2.14 (m, 2H), and 1.95-1.75 (m, 6H). Mass spectrum (ESI, m/z): Calcd. for C$_{20}$H$_{24}$ClN$_5$O, 386.1 and 388.1 (M+H), found 386.2 and 388.1.

Example 51

5-Cyano-1H-imidazole-2-carboxylic acid [2-cyclohex-1-enyl-4-(cis-2,6-dimethyl-piperidin-4-yl)-phenyl]-amide bis trifluoroacetic acid salt, and 5-cyano-1H-imidazole-2-carboxylic acid [2-cyclohex-1-enyl-4-(trans-2,6-dimethyl-piperidin-4-yl)-phenyl]-amide bis trifluoroacetic acid salt

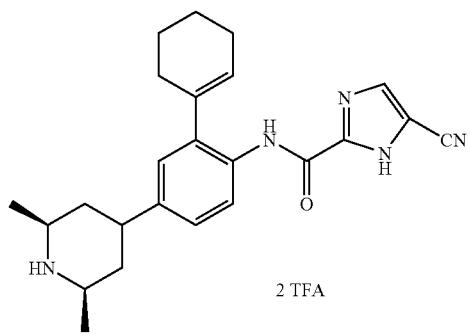

2 TFA

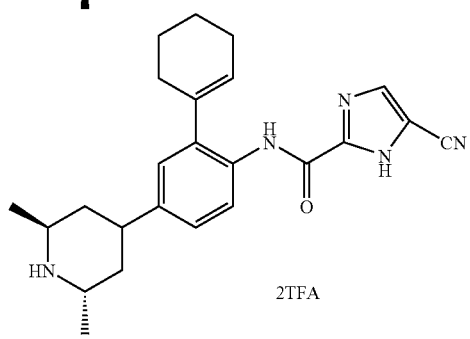

2TFA a) Cis/trans 2,6-Dimethyl-4-oxo-piperidine-1-carboxylic acid tert-butyl ester

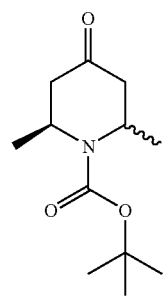

A solution of cis/trans-2,6-dimethylpiperidinone (*Coll. Czech. Chem. Commun.*: 31(11), 4432-41, (1966), 1.27 g, 10.0 mmol) in ether (100 mL) was treated with aq 1 N NaOH (11 mL, 11 mmol) and (BOC)$_2$O (2.18 g, 10.0 mmol). The resulting mixture as stirred at RT for 48 hr. The ether layer was separated, dried and concentrated. The residue was chromatographed on silica (10% EtOAc-hexane) to obtain the title compound (1.10 g, 50%): LC-MS (ESI, m/z): Calcd. for C$_{12}$H$_{21}$NO$_3$, 128.1 (M−BOC+2H), found 128.1.

b) 4-(4-Amino-phenyl)-cis/trans 2,6-dimethyl-piperidine-1-carboxylic acid tert-butyl ester

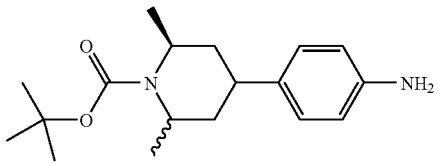

A solution of cis/trans N-Boc-2,6-dimethylpiperidinone (as prepared in the previous step, 1.14 g, 5.00 mmol) in THF (20 mL) was cooled to −78° C. and treated with LDA (1.5 M solution in cyclohex, THF and ethylbenzene, 4.4 mL, 6.5 mmol) under Ar. The resulting mixture was stirred at the same temperature for 30 min and treated with N-phenyltrifluoromethanesulfonimide (2.34 g, 6.55 mmol) in THF (20 mL). The reaction mixture was stirred for another 30 min and allowed to warm to RT. After 30 min. at RT the reaction mixture was concentrated in vacuo and the residue was taken up in ether (20 mL) and washed with cold water (2×10 mL). The ether layer was dried (Na$_2$SO$_4$) and concentrated to afforded cis/trans-2,6-dimethyl-4-trifluoromethanesulfonyloxy-3,6-dihydro-2H-pyridine-1-carboxylic acid tert-butyl ester (890 mg, 49%) which was directly used in next step.

The title compound was then prepared according to the Suzuki coupling procedure of Example 35, step (b) using 4-aminophenylboronic acid (219 mg, 1.00 mmol) and cis/trans-2,6-dimethyl-4-trifluoromethanesulfonyloxy-3,6-dihydro-2H-pyridine-1-carboxylic acid tert-butyl ester (as prepared above, 321 mg, 1.00 mmol). Silica gel chromatography (10-20% EtOAc/hexanes) afforded 4-(4-amino-phenyl)-2,6-dimethyl-3,6-dihydro-2H-pyridine-1-carboxylic acid tert-butyl ester (172 mg, 57%): Mass spectrum (ESI, m/z): Calcd. for $C_{18}H_{26}N_2O_2$, 303.2 (M+H) found 303.1. A solution of 4-(4-amino-phenyl)-2,6-dimethyl-3,6-dihydro-2H-pyridine-1-carboxylic acid tert-butyl ester (as prepared above, 380 mg, 1.25 mmol) in MeOH (10 mL) was hydrogenated over 10% Pd/C (190 mg) at 20 psi for 1 h. The solution was filtered through a pad of Celite and concentrated to give the title compound (360 mg, 94%). Mass spectrum (ESI, m/z): Calcd. for $C_{18}H_{28}N_2O_2$, 305.2 (M+H), found 305.6.

c) 4-(4-Amino-3-cyclohex-1-enyl-phenyl)-cis/trans 2,6-dimethyl-piperidine-1-carboxylic acid tert-butyl ester

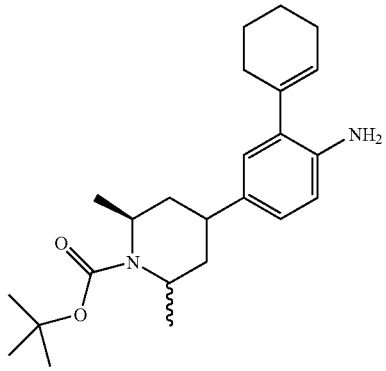

To a solution of 4-(4-amino-phenyl)-2,6-dimethyl-piperidine-1-carboxylic acid tert-butyl ester (as prepared in previous step, 334 mg, 1.09 mmol) in DCM (10 mL) was added NBS (195 mg, 1.09 mmol) and the reaction mixture was stirred at RT for 12 h. The reaction mixture was diluted with DCM (10 mL) and washed with saturated aqueous NaHCO$_3$ (10 mL) and water (10 mL). The organic layer was separated, dried (Na$_2$SO$_4$) and concentrated in vacuo to obtain 4-(4-amino-3-bromo-phenyl)-cis/trans-2,6-dimethyl-piperidine-1-carboxylic acid tert-butyl ester (367 mg, 87%). Mass spectrum (ESI, m/z): Calcd. for $C_{18}H_{27}BrN_2O_2$, 327.0 and 329.0 (M-t-Bu+H), found 327.0 and 328.9.

The title compound was then prepared according to the Suzuki coupling procedure of Example 12, step (d) using cyclohexan-1-enyl boronic acid (157 mg, 1.25 mmol) and 4-(4-amino-3-bromo-phenyl)-2,6-dimethyl-piperidine-1-carboxylic acid tert-butyl ester (as prepared above, 382 mg, 1.00 mmol) and chromatographed on silica (20% EtOAc/hexanes) to afford 254 mg (66%). Mass spectrum (ESI, m/z): Calcd. for $C_{24}H_{36}N_2O_2$, 384.2 (M+H), found 385.1.

d) 4-(4-{[4-Cyano-1-(2-trimethylsilanyl-ethoxymethyl)-1H-imidazole-2-carbonyl]-amino}-3-cyclohex-1-enyl-phenyl)-cis-2,6-dimethyl-piperidine-1-carboxylic acid tert-butyl ester and 4-(4-{[4-cyano-1-(2-trimethylsilanyl-ethoxymethyl)-1H-imidazole-2-carbonyl]-amino}-3-cyclohex-1-enyl-phenyl)-trans-2,6-dimethyl-piperidine-1-carboxylic acid tert-butyl ester

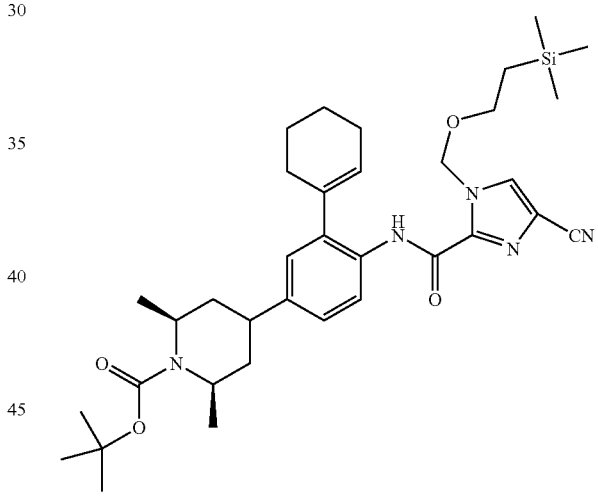

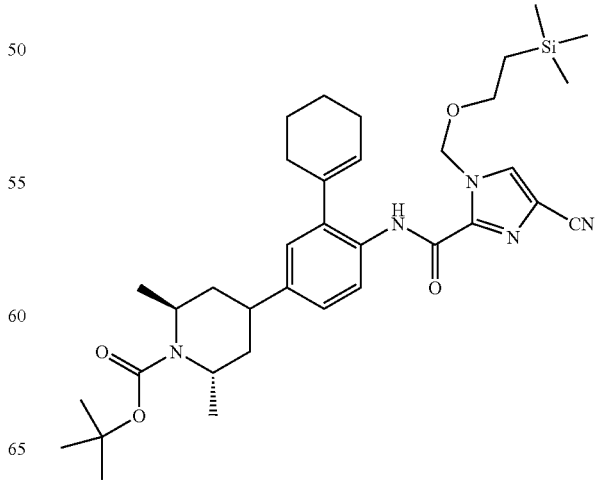

A mixture of 4-cyano-1-(2-trimethylsilanyl-ethoxymethyl)-1H-imidazole-2-carboxylic acid, potassium salt (as prepared in Example 3, step (d), 384 mg, 1.00 mmol), DIEA (0.34 μL, 2.0 mmol), 4-(4-amino-3-cyclohex-1-enyl-phenyl)-2,6-dimethyl-piperidine-1-carboxylic acid tert-butyl ester (as prepared in the previous step, 384 mg, 1.00 mmol) and PyBroP (699 mg, 1.50 mmol) in DCM (20 mL) was stirred at RT for 12 h. The reaction mixture was diluted with DCM (10 mL) and washed with saturated aqueous NaHCO₃ (10 mL) and water (10 mL). The organic layer was separated, dried (Na₂SO₄) and concentrated in vacuo to obtained a mixture of the above two title compounds (321 mg, 50.7%). The mixture was chromatographed on silica (10-20% EtOAc/hexane) to obtain the individual title compounds.

4-(4-{[4-cyano-1-(2-trimethylsilanyl-ethoxymethyl)-1H-imidazole-2-carbonyl]-amino}-3-cyclohex-1-enyl-phenyl)-trans-2,6-dimethyl-piperidine-1-carboxylic acid tert-butyl ester (31 mg). Mass spectrum (ESI, m/z): Calcd. for $C_{35}H_{51}N_5O_4Si$, 634.3 (M+H), found 634.1.

4-(4-{[4-cyano-1-(2-trimethylsilanyl-ethoxymethyl)-1H-imidazole-2-carbonyl]-amino}-3-cyclohex-1-enyl-phenyl)-cis-2,6-dimethyl-piperidine-1-carboxylic acid tert-butyl ester contaminated with 10% of 4-(4-{[4-cyano-1-(2-trimethylsilanyl-ethoxymethyl)-1H-imidazole-2-carbonyl]-amino}-3-cyclohex-1-enyl-phenyl)-trans-2,6-dimethyl-piperidine-1-carboxylic acid tert-butyl ester (290 mg). Mass spectrum (ESI, m/z): Calcd. for $C_{35}H_{51}N_5O_4Si$, 634.3 (M+H), found 634.1.

e) 5-Cyano-1H-imidazole-2-carboxylic acid [2-cyclohex-1-enyl-4-(cis-2,6-dimethyl-piperidin-4-yl)-phenyl]-amide bis trifluoroacetic acid salt and 5-cyano-1H-imidazole-2-carboxylic acid [2-cyclohex-1-enyl-4-(trans-2,6-dimethyl-piperidin-4-yl)-phenyl]-amide bis trifluoroacetic acid salt

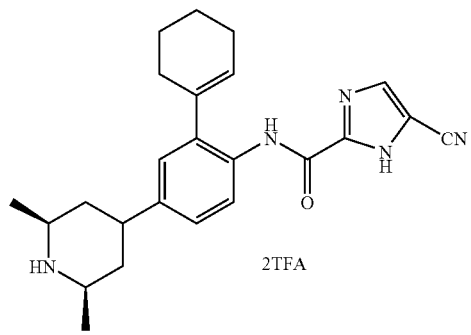

2TFA

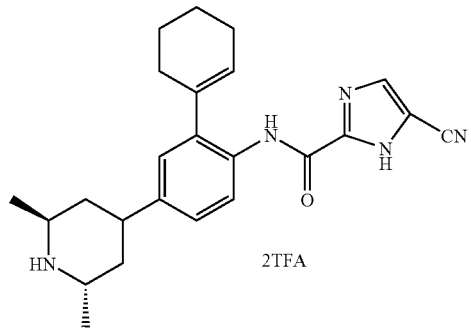

2TFA

The title compounds were prepared from 290 mg (0.457 mmol) of 4-(4-{[4-cyano-1-(2-trimethylsilanyl-ethoxymethyl)-1H-imidazole-2-carbonyl]-amino}-3-cyclohex-1-enyl-phenyl)-cis-2,6-dimethyl-piperidine-1-carboxylic acid tert-butyl ester and 31 mg (0.048 mmol) of 4-(4-{[4-cyano-1-(2-trimethylsilanyl-ethoxymethyl)-1H-imidazole-2-carbonyl]-amino}-3-cyclohex-1-enyl-phenyl)-trans-2,6-dimethyl-piperidine-1-carboxylic acid tert-butyl ester according to the procedure in Example 14, step (b).

5-Cyano-1H-imidazole-2-carboxylic acid [2-cyclohex-1-enyl-4-(cis-2,6-dimethyl-piperidin-4-yl)-phenyl]-amide bis trifluoroacetic acid salt (93 mg, 32%): ¹H-NMR (CD₃OD; 400 MHz): δ 8.17 (d, 1H, J=8.4 Hz), 8.03 (s, 1H), 7.22 (d, 1H, J=8.4 Hz), 7.11 (s, 1H), 5.72 (br s, 1H), 3.87 (m, 1H), 3.78 (m, 1H), 3.45 (m, 1H), 3.23 (m, 1H), 3.07 (m, 1H), 2.22 (m, 4H), 2.19 (m, 2H), 1.75-1.92 (m, 4H), 1.56 (m, 3H), 1.37 (m, 6H). Mass spectrum, ESI, m/z): Calcd. for $C_{24}H_{29}N_5O$, 404.2 (M+H), found 404.2.

5-Cyano-1H-imidazole-2-carboxylic acid [2-cyclohex-1-enyl-4-(trans-2,6-dimethyl-piperidin-4-yl)-phenyl]-amide bis trifluoroacetic acid salt (17.3 mg, 56%). ¹H-NMR (CDCl₃; 400 MHz): δ 13.9 (br s, 1H), 10.3 (br s, 1H), 9.98 (s, 1H), 8.41 (d, 1H, J=8.4 Hz), 7.75 (br s, 1H), 7.26 (dd, 1H, J=8.4, 2.0 Hz), 7.15 (d, 1H, J=2 Hz), 5.92 (br s, 1H), 4.12 (m, 1H), 3.59 (m, 1H), 3.1-3.3 (m, 4H), 2.25-2.42 (m, 6H), 2.05-1.78 (m, 6H), 1.62 (d, 3H, J=7.1 Hz), 1.43 (d, 3H, J=6.3 Hz). Mass spectrum (ESI, m/z): Calcd. for $C_{24}H_{29}N_5O$, 404.2 (M+H), found 404.2.

Example 52

5-Cyano-1H-imidazole-2-carboxylic acid {2-cyclohex-1-enyl-4-[1-(R)-(+)-(2,3-dihydroxy-propionyl)-piperidin-4-yl]-phenyl}-amide

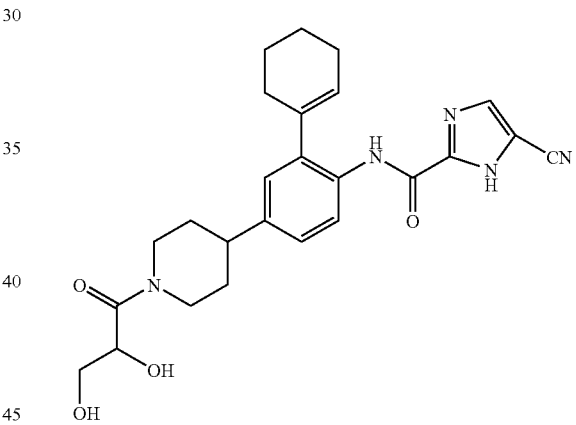

a) 5-Cyano-1H-imidazole-2-carboxylic acid {2-cyclohex-1-enyl-4-[1-(R)-(+)2,2-dimethyl-[1,3]dioxolane-4-carbonyl)-piperidin-4-yl]-phenyl}-amide

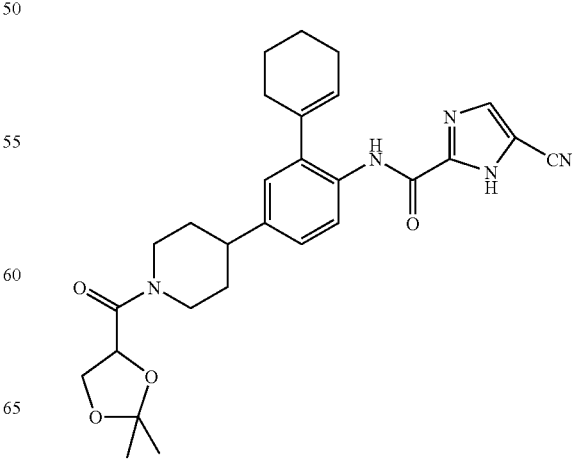

To a solution of methyl (R)-(+)-2,2-dimethyl-1,3-dioxolane-4-carboxylate (0.16 mL, 1.0 mmol) in MeOH (2 mL), 2 N KOH (0.5 mL, 1 mmol) was added. The resulting solution was stirred at RT for 20 min and concentrated in vacuo. The residue obtained was suspended in ether (10 mL) and sonicated for 5 min. The ether was then removed and the resulting residue was dried in vacuo for 4 h to obtain (R)-(+)-2,2-dimethyl-1,3-dioxolane-4-carboxylic acid potassium salt (173 mg, 94%) which was directly used in the next step without purification.

To a solution of 4-cyano-1H-imidazole-2-carboxylic acid (2-cyclohex-1-enyl-4-piperidin-4-yl-phenyl)-amide, trifluoroacetic acid salt (as prepared in Example 14, step (b), 40 mg, 0.08 mmol) in DCM (1.5 mL) was added to a mixture of (R)-(+)-2,2-dimethyl-1,3-dioxalane-4-carboxylic acid potassium salt (as prepared above, 18 mg, 0.090 mmol), EDCI (18.8 mg, 0.0900 mmol), HOBt (13.2 mg, 0.0900 mmol) and DIEA (42 µL, 0.24 mmol). The resulting mixture was stirred at RT for 6 h. Water (10 mL) was added and DCM layer was separated, dried ($Na_2SO_4$) and concentrated. The residue obtained was chromatographed on silica (2% MeOH/DCM) to obtain title compound (47 mg, 97%). Mass spectrum (ESI, m/z): Calcd. for $C_{28}H_{33}N_5O_4$, 504.2 (M+H), found 503.9.

b) 5-Cyano-1H-imidazole-2-carboxylic acid {2-cyclohex-1-enyl-4-[1-(R)-(+)-(2,3-dihydroxy-propionyl)-piperidin-4-yl]-phenyl}-amide

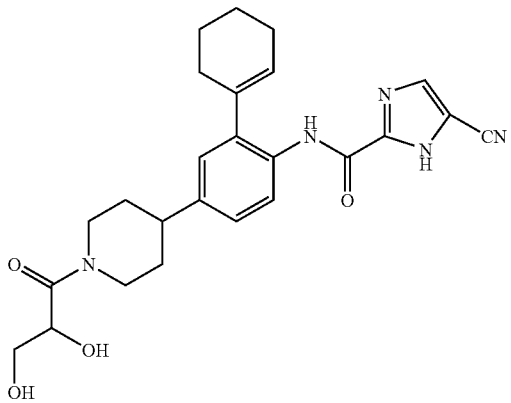

To a solution of 5-cyano-1H-imidazole-2-carboxylic acid {2-cyclohex-1-enyl-4-[1-(R)-(2,2-dimethyl-[1,3]dioxolane-4-carbonyl)-piperidin-4-yl]-phenyl}-amide (as prepared in the previous step, 45 mg, 0.090 mmol) in MeOH (1 mL) was added aq 2 N HCl (2 mL). The resulting mixture was stirred at RT for 12 hr. Solvents were removed in vacuo and the resulting residue was dried for 4 h. The ether (10 mL) was added and sonicated for 5 min. The ether was removed in vacuo and the residue was dried for 12 h to obtain the title compound (21.3 mg, 52%). $^1$H-NMR (DMSO; 400 MHz): δ 14.1 (br s, 1H), 9.85 (s, 1H), 8.32 (s, 1H), 7.92 (d, 1H, J=8.4 Hz), 7.18 (dd, 1H, J=8.4, 2.1 Hz), 7.13 (d, 1H, J=2.1 Hz), 5.72 (br s, 1H), 4.51 (m, 1H), 4.33 (m, 1H), 4.15 (m, 1H), 3.55 (m, 1H), 3.43 (m, 1H), 3.08 (m, 1H), 2.81 (m, 1H), 2.63 (m, 1H), 2.12-2.24 (m, 4H), 1.31-1.38 (m, 10H). mass spectrum (ESI, m/z): Calcd. for $C_{25}H_{29}N_5O_4$, 464.2 (M+H), found 464.1.

Example 53

5-Cyano-1H-imidazole-2-carboxylic acid [2-cyclohex-1-enyl-4-(1-methoxy-piperidin-4-yl)-phenyl]-amide trifluoroacetic acid salt

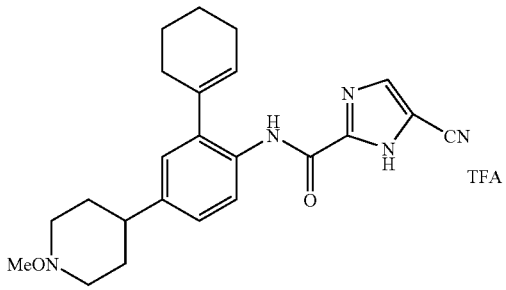

a) 4-(1-Methoxy-1,2,3,6-tetrahydro-pyridin-4-yl)-phenylamine

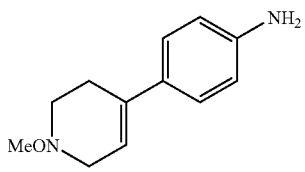

A solution of N-methoxypiperidinone (*J. Org. Chem.*, 26, 1867, (1961), 650 mg, 5.00 mmol) in THF (20 mL)) was cooled to −78° C. and treated with LDA (1.5 M solution in cyclohex, THF and ethylbenzene, 4.3 mL, 6.4 mmol) under Ar. The resulting mixture was stirred at same temperature for 30 min and treated with N-phenyltrifluoromethanesulfonimide (2.3 g, 6.4 mmol) in THF (20 mL). The reaction mixture was stirred for another 30 min and allowed to warm to RT. After 30 min at RT, the reaction mixture was concentrated in vacuo and the residue obtained was taken up in EtOAc (20 mL) and washed with cold water (2×10 mL). EtOAc layer was dried ($Na_2SO_4$) and concentrated to afforded trifluoromethanesulfonic acid 1-methoxy-1,2,3,6-tetrahydro-pyridin-4-yl ester (980 mg, 71%) as a white foam which was directly used in next step.

The title compound was then prepared according to Suzuki coupling procedure of Example 35, step (b) using 4-aminophenylboronic acid (219 mg, 1.00 mmol) and trifluoromethanesulfonic acid 1-methoxy-1,2,3,6-tetrahydro-pyridin-4-yl ester (as prepared above, 261 mg, 1.00 mmol). Silica gel chromatography (20-50% EtOAc/hexanes) afforded 60 mg (29%). Mass spectrum (ESI, m/z): Calcd. for $C_{12}H_{16}N_2O$, 205.1 (M+H), found 205.2.

b) 2-Cyclohex-1-enyl-4-(1-methoxy-piperidin-4-yl)-phenylamine

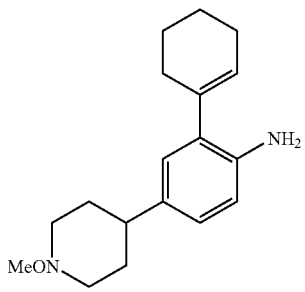

A solution of 4-(1-methoxy-1,2,3,6-tetrahydro-pyridin-4-yl)-phenylamine (as prepared in previous step) (40.8 mg, 0.200 mmol) in MeOH (5 mL) was hydrogenated over 10% Pd/C (20.4 mg) at 20 psi for 1 h. The solution was filtered through a pad of Celite and concentrated to give 4-(1-methoxy-piperidin-4-yl)-phenylamine (38 mg, 92%) which was directly used in the next step without purification.

To a solution of 4-(1-methoxy-piperidin-4-yl)-phenylamine (as prepared above, 42 mg, 0.20 mmol) in DCM (2 mL) was added NBS (36.2 mg, 0.20 mmol) and the reaction mixture was stirred at RT for 12 h. The reaction mixture was diluted with DCM (10 mL) and washed with saturated aqueous NaHCO$_3$ (10 mL) and water (10 mL). The organic layer was separated, dried (Na$_2$SO$_4$) and concentrated in vacuo to obtain 2-bromo-4-(1-methoxy-1,2,3,6-tetrahydro-pyridin-4-yl)-phenylamine (43 mg, 74.5%) which was used in the next step without purification.

The title compound was then prepared according to Suzuki coupling procedure of Example 12, step (d) using cyclohex-1-enyl boronic acid (27.9 mg, 1.00 mmol) and 2-bromo-4-(1-methoxy-1,2,3,6-tetrahydro-pyridin-4-yl)-phenylamine (as prepared above, 44 mg, 0.15 mmol) and chromatographed on silica (20-50% EtOAc/hexanes) afforded 2-cyclohex-1-enyl-4-(1-methoxy-piperidin-4-yl)-phenylamine (33 mg, 74%). Mass spectrum, (ESI, m/z): Calcd. for C$_{18}$H$_{26}$N$_2$O, 287.2 (M+H), found 286.8.

c) 4-Cyano-1-(2-trimethylsilanyl-ethoxymethyl)-1H-imidazole-2-carboxylic acid [2-cyclohex-1-enyl-4-(1-methoxy-piperidin-4-yl)-phenyl]-amide

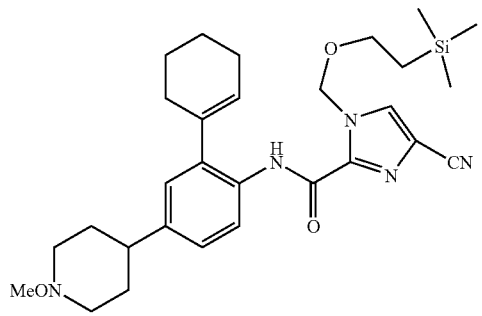

A mixture of 4-cyano-1-(2-trimethylsilanyl-ethoxymethyl)-1H-imidazole-2-carboxylic acid, potassium salt (as prepared in Example 3, step (d), 35.6 mg, 0.100 mmol), DIEA (0.34 µL, 0.20 mmol), 2-cyclohex-1-enyl-4-(1-methoxy-piperidin-4-yl)-phenylamine (as prepared in previous step, 28.6 mg, 0.1 mmol) and PyBroP (69.9 mg, 0.150 mmol) in DCM (2 mL) was stirred at RT for 12 h. The reaction mixture was diluted with DCM (10 mL) and washed with saturated aqueous NaHCO$_3$ (10 mL) and water (10 mL). The organic layer was separated, dried (Na$_2$SO$_4$) and concentrated in vacuo. The product was chromatographed on silica (20-40% EtOAc/hexane) to obtain the title compound (26 mg, 48%). Mass spectrum (ESI, m/z): Calcd. for C$_{29}$H$_{41}$N$_5$O$_3$Si, 536.3 (M+H), found 536.2.

d) 5-Cyano-1H-imidazole-2-carboxylic acid [2-cyclohex-1-enyl-4-(1-methoxy-piperidin-4-yl)-phenyl]-amide trifluoroacetic acid salt

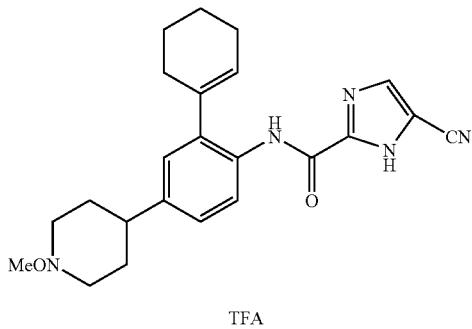

TFA

To a solution of 4-cyano-1-(2-trimethylsilanyl-ethoxymethyl)-1H-imidazole-2-carboxylic acid [2-cyclohex-1-enyl-4-(1-methoxy-piperidin-4-yl)-phenyl]-amide (as prepared in previous step, 31 mg, 0.020 mmol) in DCM (0.5 mL) and EtOH (11 µL) was added TFA (0.1 mL). The resulting solution was stirred at RT for 6 h. The reaction mixture was concentrated in vacuo and the resulting residue was dried for 1 h, suspended in ether (10 mL) and sonicated for 5 min. The solid formed was collected by suction filtration to obtain the title compound (17.3 mg, 58%). $^1$H-NMR (DMSO; 400 MHz): δ 9.70 (s, 1H), 8.30 (s, 1H), 7.83 (d, 1H, J=8.4 Hz), 7.14 (d, 1H, J=8.4 Hz), 7.05 (s, 1H), 5.71 (br s, 1H), 3.30-3.55 (m, 5H), 2.41-2.62 (m, 2H), 2.12-2.19 (m, 4H), 1.60-1.85 (m, 8H). Mass spectrum (ESI, m/z): Calcd. for C$_{23}$H$_{27}$N$_5$O$_2$, 406.2 (M+H), found 406.1.

Example 54

4-Cyano-1H-imidazole-2-carboxylic acid [6-(4,4-dimethyl-cyclohex-1-enyl)-1',2',3',4',5',6'-hexahydro-[2,4']bipyridinyl-5-yl]-amide trifluoroacetic acid salt

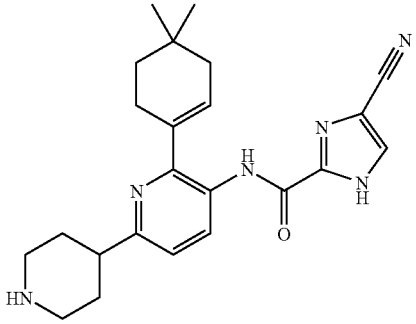

TFA a) 5-Nitro-3',6'-dihydro-2'H-[2,4']bipyridinyl-1'-carboxylic acid tert-butyl ester

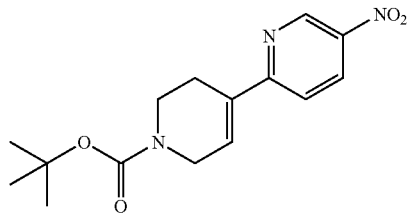

A solution of 202 mg (0.994 mmol) 2-bromo-5-nitropyridine in 4 mL of toluene and 2 mL of EtOH was treated with 338 mg (1.09 mmol) 4-trifluoromethane-sulfonyloxy-3,6-dihydro-2H-pyridine-1-carboxylic acid tert-butyl ester (Synthesis, 993, (1991)) and 1.49 mL (2.981 mmol) 2 M aqueous $Na_2CO_3$. The mixture was degassed via sonication, placed under argon, treated with 80.3 mg (0.00700 mmol) $Pd(PPh_3)_4$ and heated to 80° C. for 4 h. The mixture was diluted with EtOAc and washed with water. The organic layer was dried over $MgSO_4$ and concentrated in vacuo. The resulting residue was chromatographed on a 50-g silica Varian MegaBond Elut column with 10-25% EtOAc-hexane to afford 226 mg (75%) of the title compound as a light yellow solid: Mass spectrum (ESI, m/z): Calcd. for $C_{15}H_{19}N_3O_4$, 306.1 (M+H), found 305.7.

b) 5-Amino-3',4',5',6'-tetrahydro-2'H-[2,4']bipyridinyl-1'-carboxylic acid tert-butyl ester

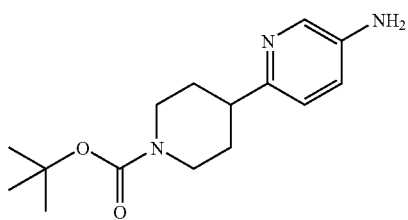

A solution of 226 mg (0.740 mmol) 5-nitro-3',6'-dihydro-2'H-[2,4']bipyridinyl-1'-carboxylic acid tert-butyl ester (as prepared in the previous step) in 15 mL MeOH was treated with 110 mg 10% Pd/C (Degussa type E101-NE/W, Aldrich, 50% by weight water) and 1 atm $H_2$ at room temperature for 18 h. The mixture was filtered through Celite, and the filter cake was washed with MeOH. Concentration afforded 220 mg (107%) of the title compound as a colorless glassy solid. Mass spectrum (ESI, m/z): Calcd. for $C_{15}H_{23}N_3O_2$, 278.2 (M+H), found 278.0.

c) 5-Amino-6-bromo-3',4',5',6'-tetrahydro-2'H-[2,4']bipyridinyl-1'-carboxylic acid tert-butyl ester

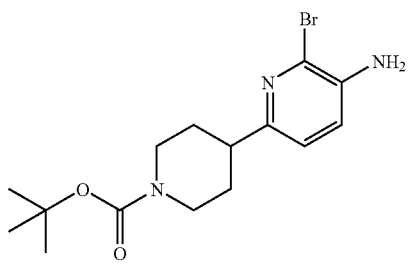

A solution of 220 mg (0.793 mmol) 5-amino-3',4',5',6'-tetrahydro-2'H-[2,4']bipyridinyl-1'-carboxylic acid tert-butyl ester (as prepared in the previous step) in 10 mL $CH_2Cl_2$ was treated with 134 mg (0.753 mmol) N-bromosuccinimide at room temperature for 20 min. The mixture was diluted with $CH_2Cl_2$ and washed with saturated aqueous $NaHCO_3$. The organic layer was dried over $MgSO_4$ and concentrated in vacuo. Chromatography of the residue on a 50-g silica Varian MegaBond Elut column with 10-35% EtOAc-hexanes afforded 209 mg (74%) of the title compound as a colorless glassy solid. $^1$H-NMR ($CDCl_3$; 400 MHz): δ 6.97 (d, 1H, J=8.0 Hz), 6.91 (d, 1H, J=8.0 Hz), 4.28-4.15 (br s, 2H), 4.06-3.90 (m, 2H), 2.85-2.75 (m, 2H), 2.77-2.68 (m, 1H), 1.92-1.83 (m, 2H), 1.68-1.54 (m, 2H), 1.47 (s, 9H).

d) 5-Amino-6-(4,4-dimethyl-cyclohex-1-enyl)-3',4',5',6'-tetrahydro-2'H-[2,4']bipyridinyl-1'-carboxylic acid tert-butyl ester

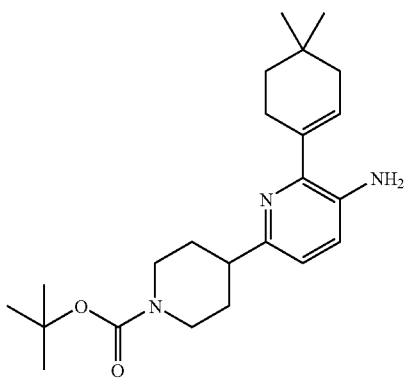

A solution of 209 mg (0.587 mmol) 5-amino-6-bromo-3',4',5',6'-tetrahydro-2'H-[2,4']bipyridinyl-1'-carboxylic acid tert-butyl ester (as prepared in the previous step) in 5 mL of toluene and 2.5 mL of EtOH was treated with 99.3 mg (0.645 mmol) 4,4-dicyclohex-1-enylboronic acid and 2.34 mL (4.69 mmol) 2 M aqueous $Na_2CO_3$. The mixture was degassed via sonication, placed under argon, treated with 47.4 mg (0.0410 mmol) $Pd(PPh_3)_4$, and heated to 80° C. for 16 h. The mixture was diluted with EtOAc and washed with water. The aqueous layer was extracted with additional EtOAc, and the combined organic layers were dried over $MgSO_4$ and concentrated in vacuo. Chromatography of the residue on a 50-g silica Varian MegaBond Elut column with 25% EtOAc-hexanes afforded 150 mg (66%) of the title compound as a white foamy solid. Mass spectrum (ESI, m/z): Calcd. for $C_{23}H_{35}N_3O_2$, 386.3 (M+H), found 386.3.

e) 5-{[4-Cyano-1-(2-trimethylsilanyl-ethoxymethyl)-1H-imidazole-2-carbonyl]-amino}-6-(4,4-dimethyl-cyclohex-1-enyl)-3',4',5',6'-tetrahydro-2'H-[2,4']bipyridinyl-1'-carboxylic acid tert-butyl ester

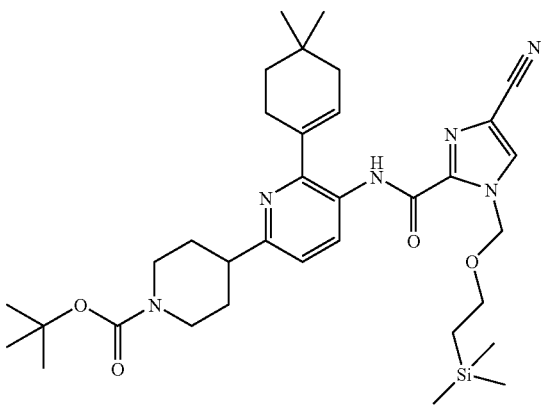

A solution of 150 mg (0.389 mmol) 5-amino-6-(4,4-dimethyl-cyclohex-1-enyl)-3',4',5',6'-tetrahydro-2'H-[2,4']bipyridinyl-1'-carboxylic acid tert-butyl ester (as prepared in the previous step) in 15 mL of $CH_2Cl_2$ was treated with 131 mg (0.428 mmol) of 4-cyano-1-(2-trimethylsilanyl-ethoxymethyl)-1H-imidazole-2-carboxylate potassium salt (as prepared in Example 3, step (b)), 272 mg (0.584 mmol) PyBroP, and 203 μL (1.17 mmol) DIEA at room temperature for 3 h. The mixture was diluted with $CH_2Cl_2$ and washed with saturated aqueous $NaHCO_3$. The organic layer was dried over $MgSO_4$ and concentrated in vacuo. Chromatography of the residue on a 50-g silica Varian MegaBond Elut column with 50% EtOAc-hexanes afforded 215 mg (87%) of the title compound as a white solid. Mass spectrum (ESI, m/z): Calcd. for $C_{34}H_{50}N_6O_4Si$, 635.4 (M+H), found 635.3.

f) 4-Cyano-1H-imidazole-2-carboxylic acid [6-(4,4-dimethyl-cyclohex-1-enyl)-1',2',3',4',5',6'-hexahydro-[2,4']bipyridinyl-5-yl]-amide trifluoroacetic acid salt

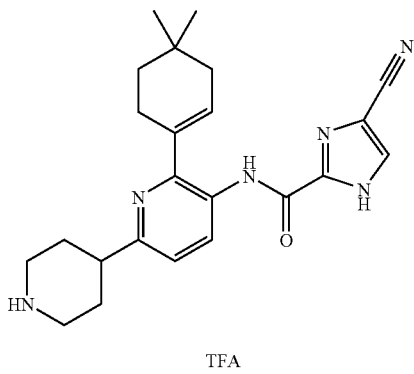

TFA

A solution of 215 mg (0.339 mmol) 5-{[4-cyano-1-(2-trimethylsilanyl-ethoxymethyl)-1H-imidazole-2-carbonyl]-amino}-6-(4,4-dimethyl-cyclohex-1-enyl)-3',4',5',6'-tetrahydro-2'H-[2,4']bipyridinyl-1'-carboxylic acid tert-butyl ester (as prepared in the previous step) in 10 mL of $CH_2Cl_2$ was treated with three drops MeOH and 3 mL TFA at room temperature for 4 h. MeOH (10 mL) was added and the solvents evaporated in vacuo. Chromatography of the residue on a 50-g silica Varian MegaBond Elut column with 10% MeOH—$CH_2Cl_2$ afforded 210 mg (97%) of the title compound as a white solid. $^1$H-NMR ($CD_3OD$; 400 MHz): δ 8.59 (d, 1H, J=8.4 Hz), 8.04 (s, 1H), 7.28 (d, 1H, J=8.4 Hz), 6.02-5.93 (m, 1H), 3.58-3.48 (m, 2 H), 3.32-3.03 (m, 3H), 2.54-2.42 (m, 2H), 2.23-2.02 (m, 6H), 1.11 (s, 6H). Mass spectrum (ESI, m/z): Calcd. for $C_{23}H_{28}N_6O$, 405.2 (M+H), found 405.2.

Example 55

4-Cyano-1H-imidazole-2-carboxylic acid [1'-(2-dimethylamino-acetyl)-6-(4,4-dimethyl-cyclohex-1-enyl)-1',2',3',4',5',6'-hexahydro-[2,4']bipyridinyl-5-yl]-amide trifluoroacetic acid salt

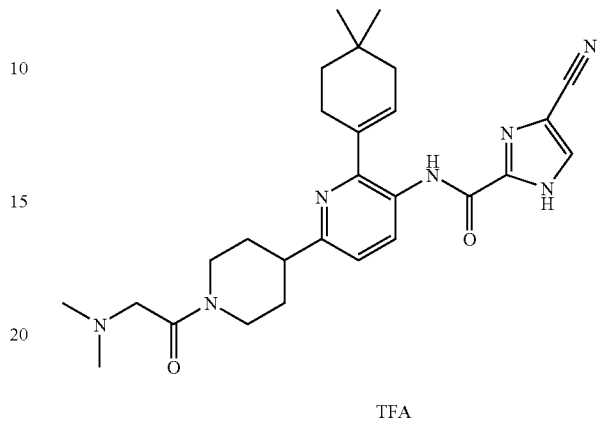

TFA

A suspension of 20.9 mg (0.203 mmol) N,N-dimethylglycine in 4 mL $CH_2Cl_2$ was treated with 49.8 mg (0.197 mmol) bis(2-oxo-3-oxazolidinyl)phosphinic chloride (BOP—Cl) and 75 μL (0.54 mmol) $Et_3N$ at room temperature for 1 h. The mixture was then treated with 70.0 mg (0.135 mmol) 4-cyano-1H-imidazole-2-carboxylic acid [6-(4,4-dimethyl-cyclohex-1-enyl)-1',2',3',4',5',6'-hexahydro-[2,4']bipyridinyl-5-yl]-amide trifluoroacetate (as prepared in Example 54, step (f)) at room temperature for 18 h. The mixture was diluted with $CH_2Cl_2$ and washed with water. The organic layer was dried over $MgSO_4$ and concentrated in vacuo. The residue was purified by RP-HPLC (C18) with 10-80% $CH_3CN$ in 0.1% TFA/$H_2O$ over 30 min to afford 34.9 mg (53%) of the title compound as a white solid. $^1$H-NMR ($CD_3OD$; 400 MHz): δ 8.38 (d, 1H, J=8.4 Hz), 8.05 (s, 1H), 7.33 (d, 1H, J=8.4 Hz), 6.05-5.98 (m, 1H), 4.68 (d, 1H, J=15.2 Hz), 3.82 (d, 1H, J=15.2 Hz), 3.16-3.05 (m, 1H), 3.01-2.94 (m, 6H), 2.52-2.40 (m, 2H), 2.39 (s, 6H), 2.17-2.10 (m, 2H), 2.09-1.87 (m, 2H), 1.67-1.59 (m, 2H), 1.12 (s, 6H). Mass spectrum (ESI, m/z): Calcd. for $C_{27}H_{35}N_7O_2$, 490.3 (M+H), found 490.4.

Example 56

4-Cyano-1H-imidazole-2-carboxylic acid [6-(4,4-dimethyl-cyclohex-1-enyl)-1'-(2-methanesulfonyl-ethyl)-1',2',3',4',5',6'-hexhydro-[2,4']bipyridinyl-5-yl]-amide trifluoroacetic acid salt

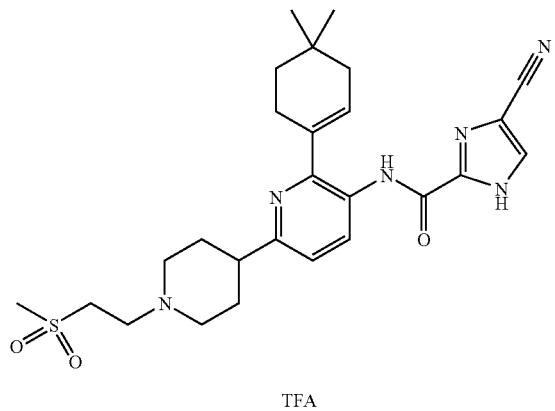

TFA

A solution of 70.0 mg (0.135 mmol) 4-cyano-1H-imidazole-2-carboxylic acid [6-(4,4-dimethyl-cyclohex-1-enyl)-1',2',3',4',5',6'-hexahydro-[2,4']bipyridinyl-5-yl]-amide (as prepared in Example 54, step (f)) in 10 mL of CH$_2$Cl$_2$ was treated with 32.7 mg (0.162 mmol) methanesulfonic acid 2-methanesulfonyl-ethyl ester (as prepared in Example 40, step (a)) and 70.5 µL (0.405 mmol) DIEA at room temperature for 6 h. The mixture was diluted with CH$_2$Cl$_2$ and washed with water. The organic layer was dried over MgSO$_4$ and concentrated in vacuo. The residue was purified by RP-HPLC (C18) with 20-60% CH$_3$CN in 0.1% TFA/H$_2$O over 30 min to afford 48 mg (85%) of the title compound as a white solid. $^1$H-NMR (CD$_3$OD; 400 MHz): δ 8.65 (d, 1H, J=8.4 Hz), 8.05 (s, 1H), 7.34 (d, 1H, J=8.4 Hz), 6.05-5.98 (m, 1H), 3.85-3.66 (m, 6H), 3.29-3.21 (m, 2H), 3.20-3.01 (m, 1H), 3.14 (s, 3H), 2.53-2.45 (m, 2H), 2.30-2.15 (m, 4H), 2.15-2.10 (m, 2H), 1.62 (t, 2H, J=6.4 Hz), 1.11 (s, 6H). Mass spectrum (ESI, m/z): Calcd. for C$_{26}$H$_{34}$N$_6$O$_3$S, 511.2 (M+H), found 511.3.

Example 57

5-Cyano-1H-imidazole-2-carboxylic acid {4-[1-(2-amino-2-methyl-propionyl)-piperidin-4-yl]-2-cyclohex-1-enyl-phenyl}-amide trifluoroacetic acid salt

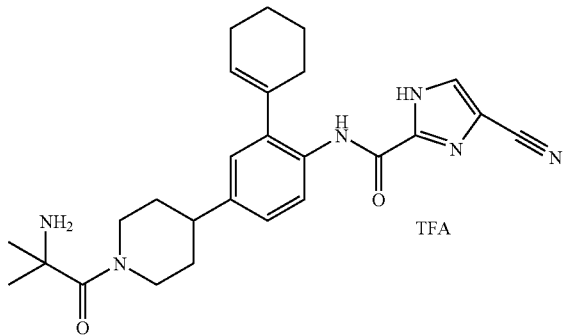

a) {2-[4-(4-{[4-Cyano-1-(2-trimethylsilanyl-ethoxymethyl)-1H-imidazole-2-carbonyl]-amino}-3-cyclohex-1-enyl-phenyl)-piperidin-1-yl]-1,1-dimethyl-2-oxo-ethyl}-carbamic acid tert-butyl ester

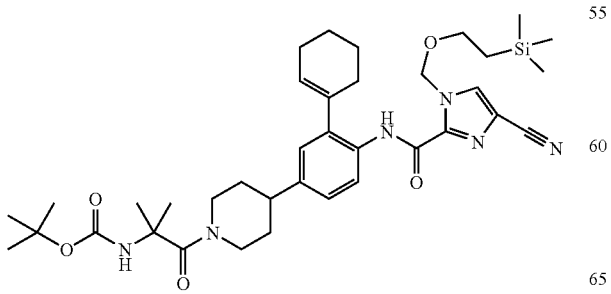

To a solution of 4-(4-{[4-cyano-1-(2-trimethylsilanyl-ethoxymethyl)-1H-imidazole-2-carbonyl]-amino}-3-cyclohex-1-enyl-phenyl)-piperidine-1-carboxylic acid tert-butyl ester (231 mg, 0.380 mmol) (as prepared in Example 14, step (a)) in 2.5 mL of DCM and 0.4 mL tOH was added 700 µL of TFA and the solution stirred for 3 h at 25° C. The reaction was diluted with 4 mL of EtOH and then concentrated to give ca. a 2:1 mixture of 5-cyano-1-(2-trimethylsilanyl-ethoxymethyl)-1H-imidazole-2-carboxylic acid (2-cyclohex-1-enyl-4-piperidin-4-yl-phenyl)-amide trifluoroacetic acid salt to starting material by $^1$H-NMR and LC/MS which was used in the following step without further purification. The mixture in 3 mL of DCM was added to a solution of 2-tert-butoxycarbonylamino-2-methyl-propionic acid (53 mg, 0.70 mmol), DIEA (122 µL, 0.700 mmol) and PyBroP (144 mg, 0.300 mmol) in 3 mL of DCM and the reaction was stirred at 25° C. overnight. The reaction was diluted with EtOAc (25 mL) and washed with satd aq NaHCO$_3$ (1×25 mL) and brine (25 mL) and the organic layer was dried over Na$_2$SO$_4$ and then concentrated. Purification of the residue by preparative TLC (50% EtOAc-hexanes) afforded 40 mg (15%) of the title compound as a white solid. Mass Spectrum (ESI, m/z): Calcd. for C$_{37}$H$_{55}$N$_6$O$_5$Si, 691.3 (M+H), found 691.1.

b) 5-Cyano-1H-imidazole-2-carboxylic acid {4-[1-(2-amino-2-methyl-propionyl)-piperidin-4-yl]-2-cyclohex-1-enyl-phenyl}-amide trifluoroacetic acid salt To a solution of {2-[4-(4-{[4-cyano-1-(2-trimethylsilanyl-ethoxymethyl)-1H-imidazole-2-carbonyl]-amino}-3-cyclohex-1-enyl-phenyl)-piperidin-1-yl]-1,1-dimethyl-2-oxo-ethyl}-carbamic acid tert-butyl ester (40 mg, 0.050 mmol) in 2 mL of DCM and 20 µL of EtOH was added 1.5 mL of TFA. The solution was stirred for 3 h at 25° C., diluted with 2 mL of EtOH and concentrated in vacuo. Trituration of the residue with ether afforded 8.4 mg (29%) of the title compound as a white solid. $^1$H-NMR (CD$_3$OD; 400 MHz): δ 8.10 (d, 1H, J=8.4 Hz), 8.00 (s, 1H), 7.16 (d, 1H, J=8.4 Hz), 7.07 (s, 1H), 5.79 (s, 1H), 4.55-4.48 (m, 1H), 3.30 (s, 6H), 2.89-2.87 (m, 2H), 2.40-2.25 (m, 4H), 1.96-1.93 (m, 2H), 1.86-1.83 (m, 6H), 1.64-1.61 (m, 2H). Mass Spectrum (ESI, m/z): Calcd. for C$_{26}$H$_{33}$N$_6$O$_2$, 461.2 (M+H), found 461.3.

Example 58

5-Cyano-1H-imidazole-2-carboxylic acid [6-cyclohex-1-enyl-1'-(2-methanesulfonyl-ethyl)-1',2',3',4',5',6'-hexahydro-[2,4']bipyridinyl-5-yl]-amide

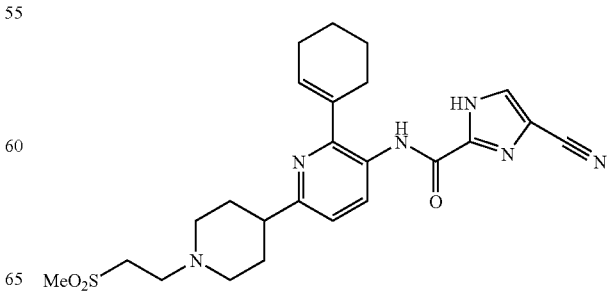

a) 5-Amino-6-cyclohex-1-enyl-3',4',5',6'-tetrahydro-2'H-[2,4']bipyridinyl-1'-carboxylic acid tert-butyl ester

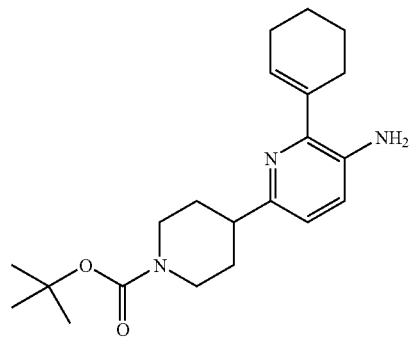

To a mixture of 5-amino-6-bromo-3',4',5',6'-tetrahydro-2'H-[2,4']bipyridinyl-1'-carboxylic acid tert-butyl ester (331 mg, 0.93 mmol) (as prepared in Example 54, step (c)) and cyclohexen-1-yl boronic acid (141 mg, 1.11 mmol) in 5 mL of EtOH, 10 mL of toluene and 5 mL of 2 M Na$_2$CO$_3$, was added Pd(PPh$_3$)$_4$ (107 mg, 0.0930 mmol) and the result was heated at 80° C. for 16 h. The reaction was diluted with 100 mL of ether and 100 mL of brine and the layers were separated. The organic layer was dried (Na$_2$SO$_4$) and concentrated in vacuo. Purification of the residue by column chromatography (silica gel, 30-60% ether-hexanes) afforded 248 mg (74%) the title compound as an light brown oil LC-MS (ESI, m/z): Calcd. for C$_{21}$H$_{32}$N$_3$O$_2$ (M+H), 358.2, found 358.1.

b) 5-{[4-Cyano-1-(2-trimethylsilanyl-ethoxymethyl)-1H-imidazole-2-carbonyl]-amino}-6-cyclohex-1-enyl-3',4',5',6'-tetrahydro-2'H-[2,4']bipyridinyl-1'-carboxylic acid tert-butyl ester

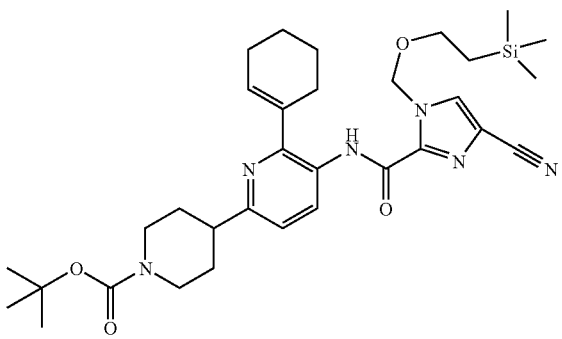

To a solution of 4-cyano-1-(2-trimethylsilanyl-ethoxymethyl)-1H-imidazole-2-carboxylate potassium salt (296 mg, 0.970 mmol) (as prepared in Example 3, step (d)) in 8 mL DCM was added DIEA (291 µL, 1.72 mmol) and PyBroP (512 mg, 1.10 mmol), and the reaction was stirred at 25° C. for 15 min. A solution of 5-amino-6-cyclohex-1-enyl-3',4',5',6'-tetrahydro-2'H-[2,4']bipyridinyl-1'-carboxylic acid tert-butyl ester (233 mg, 0.65 mmol) (as prepared in the previous step) in 4 mL DCM was added and the reaction stirred overnight at 25° C. The reaction was diluted with EtOAc (25 mL) and washed with NaHCO$_3$ (1×25 mL) and brine (25 mL) and the organic layer was dried over Na$_2$SO$_4$ and then concentrated. The residue was purified by flash chomatography (silica gel, 5% MeOH—CHCl$_3$) to afford 167 mg (40%) of the title compound as a white solid. Mass Spectrum (ESI, m/z): Calcd. for C$_{32}$H$_{46}$N$_6$O$_4$Si, 607.3 (M+H), found 607.3.

c) 5-Cyano-1H-imidazole-2-carboxylic acid (6-cyclohex-1-enyl-1',2',3',4',5',6'-hexahydro-[2,4']bipyridinyl-5-yl)-amide trifluoroacetic acid salt

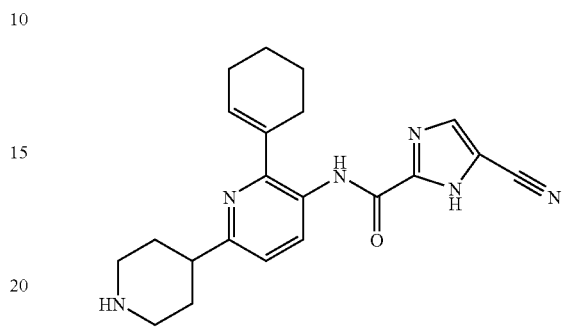

The title compound was prepared from 5-{[4-cyano-1-(2-trimethylsilanyl-ethoxymethyl)-1H-imidazole-2-carbonyl]-amino}-6-cyclohex-1-enyl-3',4',5',6'-tetrahydro-2'H-[2,4'] bipyridinyl-1'-carboxylic acid tert-butyl ester (167 mg, 0.27 mmol) using a procedure similar to Example 14, step (b) to afford 57 mg (43%) of the title compound as a white solid. LC-MS (ESI, m/z): Calcd. for C$_{21}$H$_{24}$N$_6$O, 377.2 (M+H), found 377.2.

d) 5-Cyano-1H-imidazole-2-carboxylic acid [6-cyclohex-1-enyl-1'-(2-methanesulfonyl-ethyl)-1',2',3',4',5',6'-hexahydro-[2,4']bipyridinyl-5-yl]-amide To a slurry of 5-cyano-1H-imidazole-2-carboxylic acid (6-cyclohex-1-enyl-1',2',3',4',5',6'-hexahydro-[2,4']bipyridinyl-5-yl)-amide trifluoroacetic acid salt (57 mg, 0.11 mmol) in 5 mL of DCM was added DIEA (50.4 µL, 0.290 mmol) followed by 30.5 mg (0.150 mmol) of methanesulfonic acid 2-methanesulfonyl-ethyl ester (as prepared in Example 40, step (a)). The reaction was allowed to stir overnight, diluted with 20 mL of DCM, washed with satd aq NaHCO$_3$ (1×20 mL) and dried over Na$_2$SO$_4$. Purification by preparative TLC (silica gel, 40% EtOAc-hexanes) afforded 22.3 mg (40%) of the title compound as a white solid. $^1$H-NMR (DMSO; 400 MHz): δ 10.02 (s, 1H), 8.24 (s, 1H), 8.11 (d, 1H, J=8.4 Hz), 7.18 (d, 1H, J=8.4 Hz), 5.96 (s, 1H), 3.04 (s, 3H), 3.02-2.99 (m, 3H), 2.73 (t, 2H, J=2.7 Hz), 2.39-2.37 (m, 2H), 2.11-2.05 (m, 4H), 1.85-1.64 (m, 10H). Mass Spectrum (ESI, m/z): Calcd. for C$_{24}$H$_{31}$N$_6$O$_3$S, 483.2 (M+H), found 483.3.

Example 59

An alternate method for the synthesis of the intermediate described in Example 3 is described below.

4-Cyano-1-(2-trimethylsilanyl-ethoxymethyl)-1H-imidazole-2-carboxylic acid potassium salt

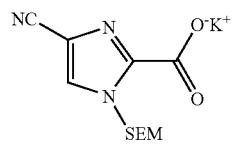

a) 1H-Imidazole-4-carbonitrile

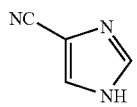

A 22-L, four-neck, round-bottom flask equipped with a mechanical stirrer, a temperature probe, a condenser, and an addition funnel with a nitrogen inlet was charged with 1H-imidazole-4-carboxaldehyde (Aldrich, 1.10 kg, 11.5 mol) and pyridine (3.0 L, 3.0 mol). The reaction flask was cooled to 8° C. with an ice bath and hydroxylamine hydrochloride (871 g, 12.5 mol) was added slowly in portions to maintain the internal temperature below 30° C. The reaction was allowed to cool to ambient temperature and stirred for 2 h at ambient temperature. The resulting thick yellow solution was heated to 80° C. with a heating mantle and acetic anhydride (2.04 L, 21.6 mol) was added dropwise over 200 min to maintain the temperature below 110° C. during the addition. The reaction mixture was heated at 100° C. for 30 min, after which time it was allowed to cool to ambient temperature and then further cooled in an ice bath. The pH was adjusted to 8.0 (pH meter) by the addition of 25 wt % NaOH (5.5 L) at such a rate that the internal temperature was maintained below 30° C. The reaction mixture was then transferred into a 22-L separatory funnel and extracted with ethyl acetate (6.0 L). The combined organic layer was washed with brine (2×4.0 L), dried over $MgSO_4$, filtered, and concentrated to dryness under reduced pressure at 35° C. to give the crude product as a yellow semisolid. The resulting semisolid was suspended in toluene (3.0 L) and stirred for 1 h, after which time it was filtered to give a light yellow solid, which was resuspended in toluene (3.0 L) and stirred for 1 h. The resulting slurry was filtered and the filter cake washed with toluene (2×500 mL) to give the title compound as a light yellow solid [870 g, 82%]. The $^1H$ and $^{13}C$ NMR spectra were consistent with the assigned structure.

b) 1-(2-Trimethylsilanyl-ethoxymethyl)-1H-imidazole-4-carbonitrile and 3-(2-trimethylsilanyl-ethoxymethyl)-3H-imidazole-4-carbonitrile

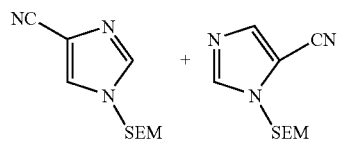

A 22-L, four-neck, round-bottom flask equipped with a mechanical stirrer, a temperature probe, and an addition funnel with a nitrogen inlet was charged with 1H-imidazole-4-carbonitrile (830 g, 8.91 mol, as prepared in the previous step), potassium carbonate (2.47 kg, 17.8 mol), and acetone (6.0 L). Agitation was initiated and the mixture was cooled to 10° C. with an ice bath. SEMCl (1.50 kg, 9.00 mol) was added through the addition funnel over 210 min to maintain the internal temperature below 15° C. The reaction was then allowed to warm to ambient temperature and stirred at ambient temperature overnight (20 h). The reaction mixture was then cooled in an ice bath to 10° C. and quenched by the slow addition of water (8.0 L) over 30 min to maintain the internal temperature below 30° C. The resulting mixture was transferred to a 22-L separatory funnel and extracted with ethyl acetate (2×7.0 L). The combined organics were concentrated under reduced pressure at 35° C. to give the crude product as a dark brown oil, which was purified through a plug of silica gel (16.5×20 cm, 2.4 kg silica gel) using 2:1 heptane/ethyl acetate (15 L) as eluent. The fractions containing the product were combined and concentrated under reduced pressure at 35° C. to afford a mixture of the title compounds as a light brown oil [1785 g, 90%]. The $^1H$ NMR spectrum was consistent with the assigned structure and indicated the presence of a 64:36 ratio of regioisomers.

c) 2-Bromo-1-(2-trimethylsilanyl-ethoxymethyl)-1H-imidazole-4-carbonitrile

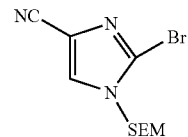

A 22-L, four-neck, round-bottom flask equipped with a mechanical stirrer, a temperature probe, and a condenser with a nitrogen inlet was charged with a mixture of 1-(2-trimethylsilanyl-ethoxymethyl)-1H-imidazole-4-carbonitrile and 3-(2-trimethylsilanyl-ethoxymethyl)-3H-imidazole-4-carbonitrile [600 g, 2.69 mol, as prepared in the previous step) and carbon tetrachloride (1.8 L). Agitation was initiated and the mixture was heated to 60° C. At this point N-bromosuccinimide (502 g, 2.82 mol) was added in several portions over 30 min, which resulted in an exotherm to 74° C. The reaction was allowed to cool to 60° C. and further stirred at 60° C. for 1 h. The reaction was allowed to cool slowly to ambient temperature and the resulting slurry was filtered and the filtrate washed with satd $NaHCO_3$ solution (4.0 L). The organics were passed through a plug of silica gel (8×15 cm, silica gel; 600 g) using 2:1 heptane/ethyl acetate (6.0 L) as eluent. The fractions containing the product (based on TLC analysis) were combined and concentrated under reduced pressure to give a crystalline light yellow solid, which was then filtered and washed with heptane (500 mL) to give the title compound as a crystalline white solid [593 g, 73%]. The $^1H$ and $^{13}C$ NMR spectra were consistent with the assigned structure and showed no evidence of the minor regioisomer.

d) 4-Cyano-1-(2-trimethylsilanyl-ethoxymethyl)-1H-imidazole-2-carboxylic acid ethyl ester

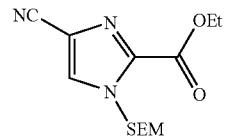

A 12-L, four-neck, round-bottom flask equipped with a mechanical stirrer, a temperature probe, and an addition funnel with a nitrogen inlet was charged with 2-bromo-1-(2-trimethylsilanyl-ethoxymethyl)-1H-imidazole-4-carbonitrile [390 g, 1.29 mol, as prepared in the previous step) and anhydrous tetrahydrofuran (4.0 L). Agitation was initiated and the reaction mixture was cooled to −50° C. using a dry ice/acetone bath. Isopropylmagnesium chloride (2.0 M in THF, 760 mL, 1.52 mol) was added through the addition funnel over 30 min to maintain the internal temperature below −40° C. The reaction was stirred for a further 30 min at −43° C., after which time it was cooled to −78° C. Ethyl chloroformate (210 mL, 2.20 mol) was added through the addition funnel over 10 min to maintain the internal temperature below −60° C. The reaction was stirred for a further 40 min at −70° C., at which point the dry ice/acetone bath was removed and the reaction was allowed to warm to ambient temperature over 1.5 h. The reaction mixture was cooled in an ice bath to 0° C. and quenched by the slow addition of satd ammonium chloride solution (1.8 L) at such a rate that the internal temperature was maintained below 10° C. The reaction mixture was transferred into a 12-L separatory funnel, diluted with ethyl acetate (4.0 L), and the layers were separated. The organic layer was washed with brine (2×2.0 L) and concentrated under reduced pressure at 35° C. to give a brown oil. The crude oil was dissolved in dichloromethane (300 mL) and purified by chromatography (15×22 cm, 1.5 kg of silica gel, 10:1 to 4:1 heptane/ethyl acetate) to give a yellow oil, which was dissolved in EtOAc (100 mL), diluted with heptane (2.0 L), and stored in a refrigerator for 5 h. The resulting slurry was filtered to give the title compound as a crystalline white solid (141 g, 37%). The $^1$H and $^{13}$C NMR spectra were consistent with the assigned structure.

e) 4-Cyano-1-(2-trimethylsilanyl-ethoxymethyl)-1H-imidazole-2-carboxylic acid potassium salt

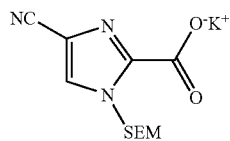

A 5-L, three-neck, round-bottom flask equipped with a mechanical stirrer, a temperature probe, and an addition funnel with a nitrogen inlet was charged with 5 [400 g, 1.35 mol) and ethanol (4.0 L). Agitation was initiated and a water bath was applied after all of the solid had dissolved. A solution of 6 N KOH (214.0 mL, 1.29 mol) was added through the addition funnel over 15 min to maintain the internal temperature below 25° C. and the reaction was stirred for 5 min at room temperature. The solution was then concentrated to dryness under reduced pressure at 20° C. to give a white solid. The resulting solid was suspended in methyl t-butyl ether (MTBE, 4.0 L) and stirred for 30 min, after which time the slurry was filtered and the filter cake washed with MTBE (1.0 L) to give the title compound as a white solid, which was further dried under vacuum at ambient temperature for 4 d [366 g, 89%). The $^1$H NMR, $^{13}$C NMR, and mass spectra were consistent with the assigned structure. Anal. Calcd for $C_{11}H_{16}KN_3O_3Si$: C, 43.25; H, 5.28; N, 13.76. Found: C, 42.77; H, 5.15; N, 13.37. Karl Fisher: 1.3% $H_2O$.

Biological Activity

In Vitro Assays

The following representative in vitro assays were performed in determining the FLT3 biological activity of the compounds of Formula I. They are given to illustrate the invention in a non-limiting fashion.

Inhibition of FLT3 enzyme activity, MV4-11 proliferation and Baf3-FLT3 phosphorylation exemplify the specific inhibition of the FLT3 enzyme and cellular processes that are dependent on FLT3 activity. Inhibition of Baf3 cell proliferation is used as a test of FLT3 independent cytotoxicity. All of the examples herein show significant and specific inhibition of the FLT3 kinase and FLT3-dependent cellular responses. The compounds of the present invention are also cell permeable.

FLT3 Fluorescence Polarization Kinase Assay

To determine the activity of the compounds of the present invention in an in vitro kinase assay, inhibition of the isolated kinase domain of the human FLT3 receptor (a.a. 571-993) was performed using the following fluorescence polarization (FP) protocol. The FLT3 FP assay utilizes the fluorescein-labeled phosphopeptide and the anti-phosphotyrosine antibody included in the Panvera Phospho-Tyrosine Kinase Kit (Green) supplied by Invitrogen. When FLT3 phosphorylates polyGlu$_4$Tyr, the fluorescein-labeled phosphopeptide is displaced from the anti-phosphotyrosine antibody by the phosphorylated poly Glu$_4$Tyr, thus decreasing the FP value. The FLT3 kinase reaction is incubated at room temperature for 30 minutes under the following conditions: 10 nM FLT3 571-993, 20 ug/mL poly Glu$_4$Tyr, 150 uM ATP, 5 mM MgCl$_2$, 1% compound in DMSO. The kinase reaction is stopped with the addition of EDTA. The fluorescein-labeled phosphopeptide and the anti-phosphotyrosine antibody are added and incubated for 30 minutes at room temperature.

Data points are an average of triplicate samples. Inhibition and IC$_{50}$ data analysis was done with GraphPad Prism using a non-linear regression fit with a multiparamater, sigmoidal dose-response (variable slope) equation. The IC$_{50}$ for kinase inhibition represents the dose of compound that results in a 50% inhibition of kinase activity compared to DMSO vehicle control.

Inhibition of MV4-11 Cell Proliferation

To assess the cellular potency of compounds of the present invention, FLT3 specific growth inhibition was measured in the leukemic cell line MV4-11 (ATCC Number: CRL-9591). MV4-11 cells are derived from a patient with childhood acute myelomonocytic leukemia with an 11q23 translocation resulting in a MLL gene rearrangement and containing an FLT3-ITD mutation (AML subtype M4)(1,2). MV4-11 cells cannot grow and survive without active FLT3ITD.

The IL-3 dependent, murine b-cell lymphoma cell line, Baf3, were used as a control to confirm the selectivity of compound inhibition of proliferation for representatives of the present invention by measuring non-specific growth inhibition by the compounds of the present invention (data not shown).

To measure proliferation inhibition by compounds of the present invention, the luciferase based CellTiterGlo reagent (Promega), which quantifies total cell number based on total cellular ATP concentration, was used. Cells are plated at 10,000 cells per well in 100 ul of in RPMI media containing penn/strep, 10% FBS and 1 ng/ml GM-CSF or 1 ng/ml IL-3 for MV4-11 and Baf3 cells respectively.

Compound dilutions or 0.1% DMSO (vehicle control) are added to cells and the cells are allowed to grow for 72 hours at standard cell growth conditions (37° C., 5% CO$_2$). For activity measurements in MV4-11 cells grown in 50% plasma, cells were plated at 10,000 cells per well in a 1:1 mixture of growth media and human plasma (final volume of 100 μL). To measure total cell growth an equal volume of CellTiterGlo reagent was added to each well, according to the manufacturer's instructions, and luminescence was quantified. Total cell growth was quantified as the difference in luminescent counts (relative light units, RLU) of cell number at Day 0 compared to total cell number at Day 3 (72 hours of growth and/or compound treatment). One hundred percent inhibition of growth is defined as an RLU equivalent to the Day 0 reading. Zero percent inhibition was defined as the RLU signal for the DMSO vehicle control at Day 3 of growth.

Data points are an average of triplicate samples. The $IC_{50}$ for growth inhibition represents the dose of a compound of the present invention that results in a 50% inhibition of total cell growth at day 3 of the DMSO vehicle control. Inhibition and $IC_{50}$ data analysis was done with GraphPad Prism using a non-linear regression fit with a multiparamater, sigmoidal dose-response (variable slope) equation.

MV4-11 cells express the FLT3 internal tandem duplication mutation, and thus are entirely dependent upon FLT3 activity for growth. Strong activity against the MV4-11 cells is anticipated to be a desirable quality of the invention. In contrast, the Baf3 cell proliferations is driven by the cytokine IL-3 and thus are used as a non-specific toxicity control. Example #38 of the present invention showed <50% inhibition at a 3 µM dose (data is not included), suggesting that it is not cytotoxic and has good selectivity for FLT3.

Cell-Based FLT3 Receptor Elisa

Specific cellular inhibition of FLT ligand-induced wild-type FLT3 phosphorylation was measured in the following manner: Baf3 FLT3 cells overexpressing the FLT3 receptor were obtained from Dr. Michael Heinrich (Oregon Health and Sciences University). The Baf3 FLT3 cell lines were created by stable transfection of parental Baf3 cells (a murine B cell lymphoma line dependent on the cytokine IL-3 for growth) with wild-type FLT3. Cells were selected for their ability to grow in the absence of IL-3 and in the presence of FLT3 ligand.

Baf3 cells were maintained in RPMI 1640 with 10% FBS, penn/strep and 10 ng/ml FLT ligand at 37° C., 5% $CO_2$. To measure direct inhibition of the wild-type FLT3 receptor activity and phosphorylation a sandwich ELISA method was developed similar to those developed for other RTKs (3,4). 200 µL of Baf3FLT3 cells ($1\times10^6$/mL) were plated in 96 well dishes in RPMI 1640 with 0.5% serum and 0.01 ng/mL IL-3 for 16 hours prior to 1 hour compound or DMSO vehicle incubation. Cells were treated with 100 ng/mL Flt ligand (R&D Systems Cat# 308-FK) for 10 min. at 37° C. Cells were pelleted, washed and lysed in 100 uL lysis buffer (50 mM Hepes, 150 mM NaCl, 10% Glycerol, 1% Triton-X-100, 10 mM NaF, 1 mM EDTA, 1.5 mM $MgCl_2$, 10 mM Na Pyrophosphate) supplemented with phosphatase (Sigma Cat# P2850) and protease inhibitors (Sigma Cat #P8340). Lysates were cleared by centrifugation at 1000×g for 5 minutes at 4° C. Cell lysates were transferred to white wall 96 well microtiter (Costar #9018) plates coated with 50 ng/well anti-FLT3 antibody (Santa Cruz Cat# sc-480) and blocked with SeaBlock reagent (Pierce Cat#37527). Lysates were incubated at 4° C. for 2 hours. Plates were washed 3× with 200 uL/well PBS/0.1% Triton-X-100. Plates were then incubated with 1:8000 dilution of HRP-conjugated anti-phosphotyrosine antibody (Clone 4G10, Upstate Biotechnology Cat#16-105) for 1 hour at room temperature. Plates were washed 3× with 200 uL/well PBS/0.1% Triton-X-100. Signal detection with Super Signal Pico reagent (Pierce Cat#37070) was done according to manufacturer's instruction with a Berthold microplate luminometer.

Data points are an average of triplicate samples. The total relative light units (RLU) of Flt ligand stimulated FLT3 phosphorylation in the presence of 0.1% DMSO control was defined as 0% inhibition and 100% inhibition was the total RLU of lysate in the basal state. Inhibition and $IC_{50}$ data analysis was done with GraphPad Prism using a non-linear regression fit with a multiparamater, sigmoidal dose-response (variable slope) equation.

BIOLOGICAL PROCEDURE REFERENCES

1. Drexler H G. *The Leukemia-Lymphoma Cell Line Factsbook*. Academic Pres: San Diego, Calif., 2000.
2. Quentmeier H, Reinhardt J, Zaborski M, Drexler H G. FLT3 mutations in acute myeloid leukemia cell lines. Leukemia. 2003 January; 17:120-124.
3. Sadick, M D, Sliwkowski, M X, Nuijens, A, Bald, L, Chiang, N, Lofgren, J A, Wong W L T. Analysis of Heregulin-Induced ErbB2 Phosphorylation with a High-Throughput Kinase Receptor Activation Enzyme-Linked Immunsorbent Assay, Analytical Biochemistry. 1996; 235:207-214.
4. Baumann C A, Zeng L, Donatelli R R, Maroney A C. Development of a quantitative, high-throughput cell-based enzyme-linked immunosorbent assay for detection of colony-stimulating factor-1 receptor tyrosine kinase inhibitors. J Biochem Biophys Methods. 2004; 60:69-79.

Biological Data

Biological Data for FLT3

The activity of selected compounds of the present invention is presented below. All activities are in µM and have the following uncertainties: FLT3 kinase: ±10%; MV4-11 and Baf3-FLT3: ±20%.

Preferred compounds of the present invention are Examples 5, 17, 23, 34, 38, and 51.

| | Structure | Flt-3 Kinase IC50 (µM) | MV4-11 IC50 (µM) | Baf3-FLT3 IC50 (µM) |
|---|---|---|---|---|
| 5 | 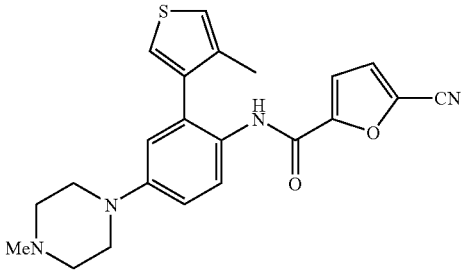 | 0.01 | 0.666 | N/A |

-continued
| | Structure | Flt-3 Kinase IC50 (μM) | MV4-11 IC50 (μM) | Baf3-FLT3 IC50 (μM) |
|---|---|---|---|---|
| 6 | 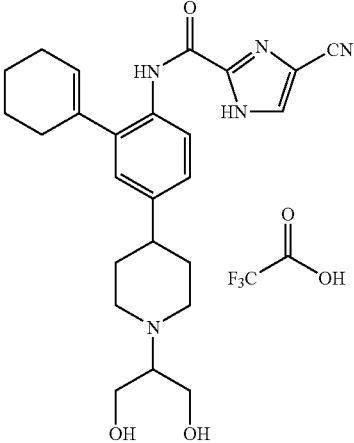 | 0.082 | N/A | N/A |
| 7 | 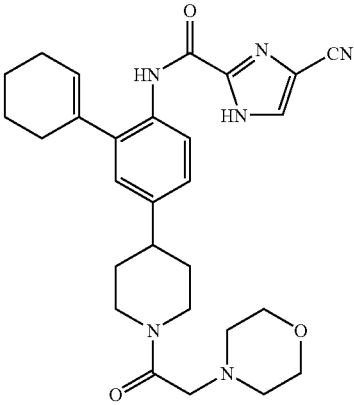 | 0.14 | N/A | N/A |
| 9 | 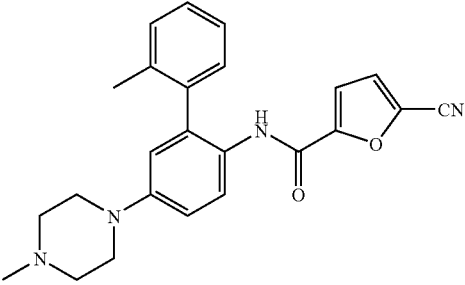 | 0.097 | 1.00 | N/A |
| 11 | 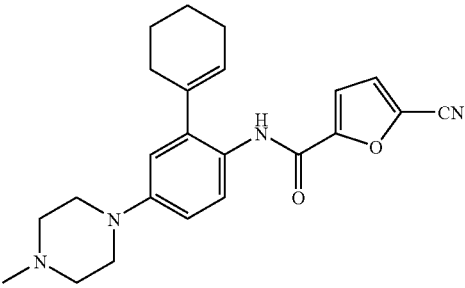 | 0.26 | 0.131 | 1.30 |

-continued
| | Structure | Flt-3 Kinase IC50 (μM) | MV4-11 IC50 (μM) | Baf3-FLT3 IC50 (μM) |
|---|---|---|---|---|
| 12 | 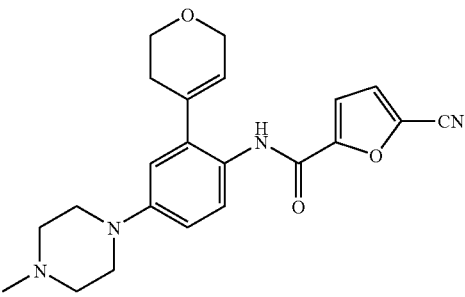 | 1.24 | >10 | N/A |
| 13 | 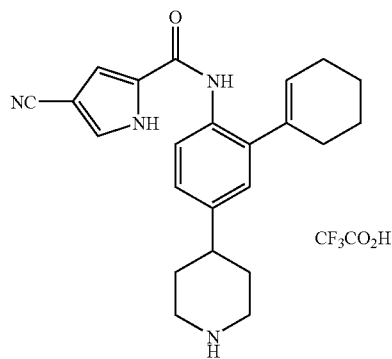 | 0.029 | N/A | N/A |
| 14 | 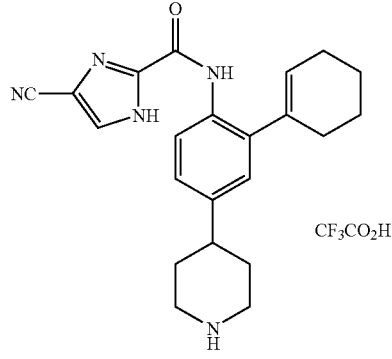 | 0.032 | N/A | 0.770 |
| 16 | 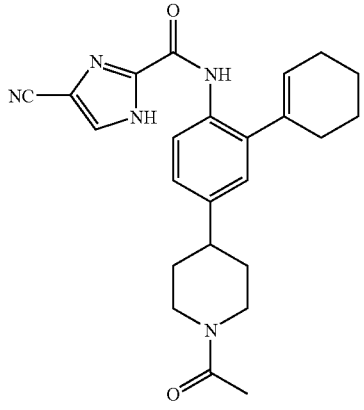 | 0.039 | N/A | N/A |

| | Structure | Flt-3 Kinase IC50 (μM) | MV4-11 IC50 (μM) | Baf3-FLT3 IC50 (μM) |
|---|---|---|---|---|
| 17 | 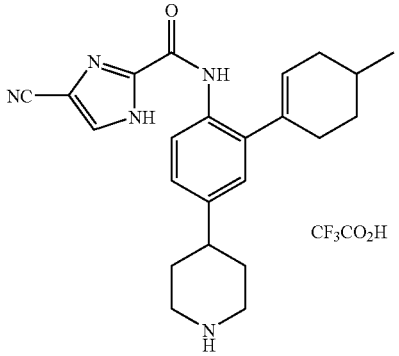 | 0.013 | N/A | N/A |
| 20 | 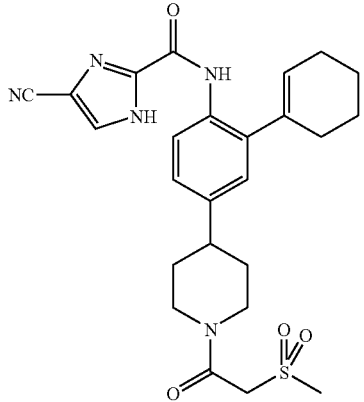 | 0.13 | N/A | N/A |
| 23 | 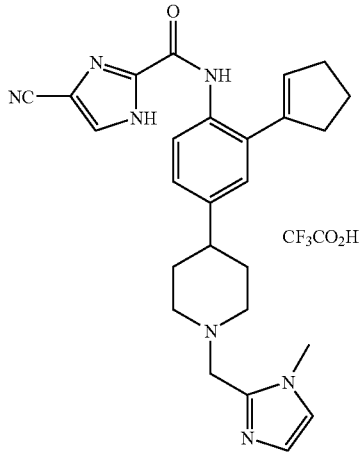 | 0.016 | 0.115 | N/A |

-continued
| | Structure | Flt-3 Kinase IC50 (μM) | MV4-11 IC50 (μM) | Baf3-FLT3 IC50 (μM) |
|---|---|---|---|---|
| 24 | 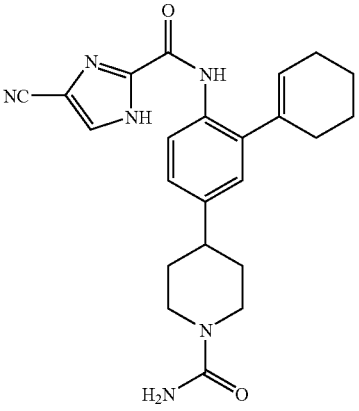 | 0.37 | N/A | N/A |
| 25 | 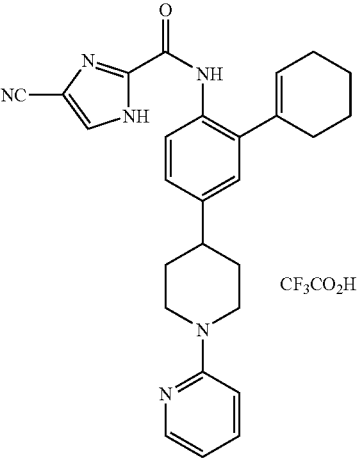 | 2.9 | N/A | N/A |
| 26 | 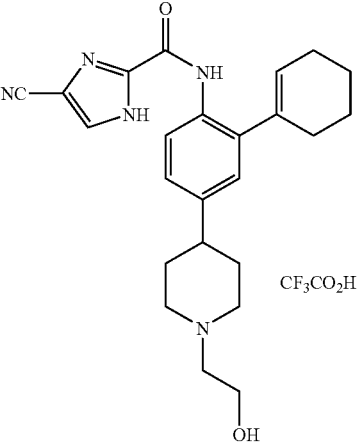 | 0.053 | N/A | N/A |

-continued
| | Structure | Flt-3 Kinase IC50 (μM) | MV4-11 IC50 (μM) | Baf3-FLT3 IC50 (μM) |
|---|---|---|---|---|
| 34 | 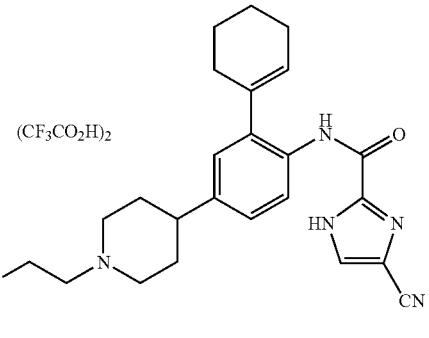 | 0.018 | 0.00800 | 0.205 |
| 35 | 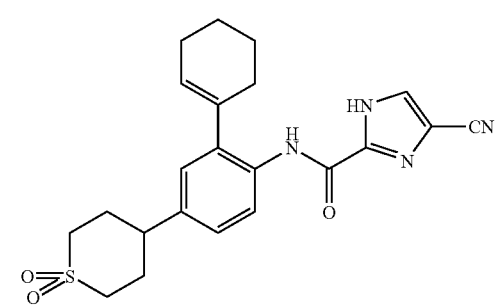 | 0.120 | 0.192 | N/A |
| 36 | 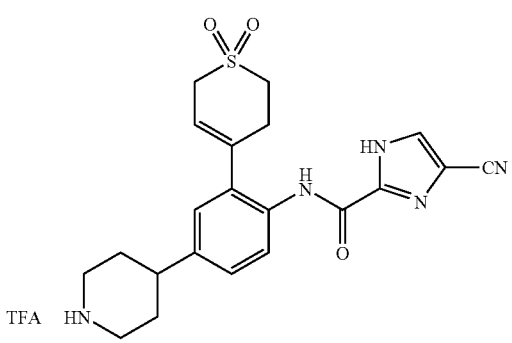 | 9.1 | 0.192 | N/A |
| 38 | 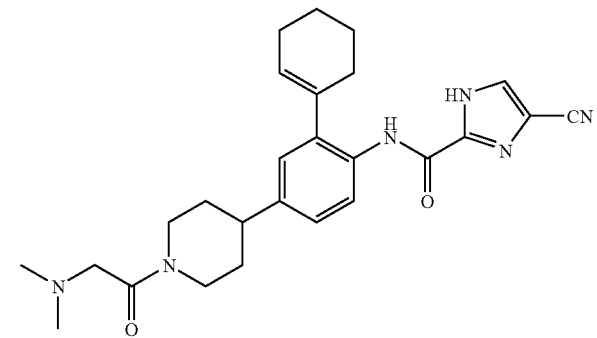 | 0.0142 | 0.0235 | 0.0760 |

-continued

| | Structure | Flt-3 Kinase IC50 (μM) | MV4-11 IC50 (μM) | Baf3-FLT3 IC50 (μM) |
|---|---|---|---|---|
| 40 | 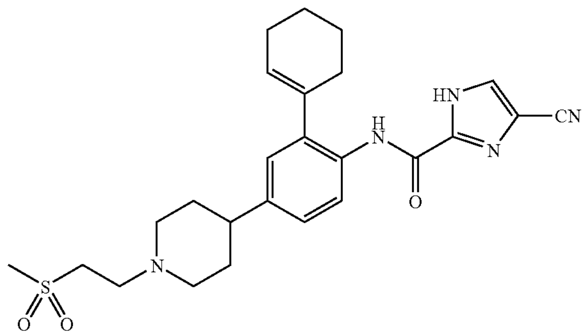 | 0.092 | 0.116 | 0.292 |
| 47 | | 0.11 | N/A | N/A |
| 46 | 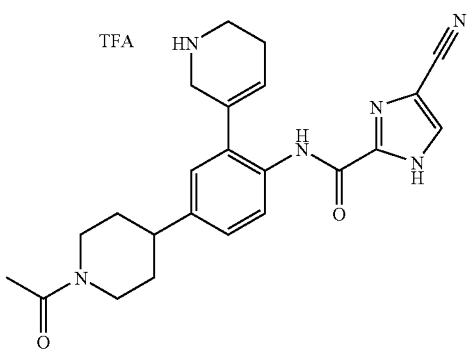 | 0.039 | N/A | N/A |
| 47 | | 0.083 | N/A | N/A |

| | Structure | Flt-3 Kinase IC50 (µM) | MV4-11 IC50 (µM) | Baf3-FLT3 IC50 (µM) |
|---|---|---|---|---|
| 51a | 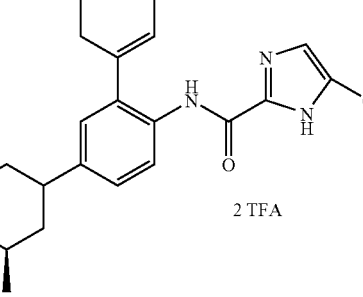 2 TFA | 0.0023 | 0.00472 | N/A |
| 55 | 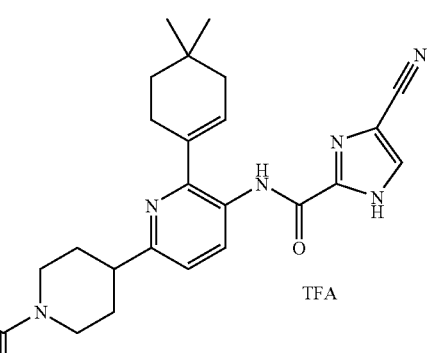 TFA | 0.034 | N/A | N/A |
| 56 | 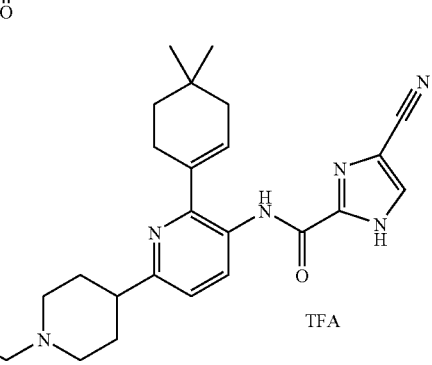 TFA | 0.14 | N/A | N/A |

In Vivo Assays

The following representative in vivo assay was performed in determining the biological activity of Example #38 of the present invention. They are given to illustrate the invention in a non-limiting fashion.

The oral anti-tumor efficacy of Example #38 of the present invention was evaluated in vivo using a nude mouse MV4-11 human tumor xenograft regression model.

Female athymic nude mice (CD-1, nu/nu, 9-10 weeks old) were obtained from Charles River Laboratories (Wilmington, Mass.) and were maintained according to NIH standards. All mice were group housed (5 mice/cage) under clean-room conditions in sterile micro-isolator cages on a 12-hour light/dark cycle in a room maintained at 21-22° C. and 40-50% humidity. Mice were fed irradiated standard rodent diet and water ad libitum. All animals were housed in a Laboratory Animal Medicine facility that is fully accredited by the American Association for Assessment and Accreditation of Laboratory Animal Care (AAALAC). All procedures involving animals were conducted in compliance with the NIH *Guide for the Care and Use of Laboratory Animals* and all protocols were approved by an Internal Animal Care and Use Committee (IACUC).

The human leukemic MV4-11 cell line was obtained from the American Type Culture Collection (ATCC Number: CRL-9591) and propagated in RPMI medium containing 10% FBS (fetal bovine serum) and 5 ng/mL GM-CSF (R&D Systems). MV4-11 cells are derived from a patient with childhood acute myelomonocytic leukemia with an 11q23 translocation resulting in a MLL gene rearrangement and containing an FLT3-ITD mutation (AML subtype M4)(1,2). MV4-11 cells express constitutively active phosphorylated FLT3 receptor as a result of this naturally occurring FLT3/ITD mutation.

Strong anti-tumor activity against MV4-11 tumor growth in the nude mouse tumor xenograft model is a desirable quality of the invention.

In pilot growth studies, the following conditions were identified as permitting MV4-11 cell growth in nude mice as subcutaneous solid tumor xenografts. Immediately prior to injection, cells were washed in PBS and counted, suspended 1:1 in a mixture of PBS:Matrigel (BD Biosciences) and then loaded into pre-chilled 1 cc syringes equipped with 25 gauge needles. Female athymic nude mice weighing no less than 20-21 grams were inoculated subcutaneously in the left inguinal region of the thigh with $5 \times 10^6$ tumor cells in a delivery volume of 0.2 mL. For regression studies, the tumors were allowed to grow to a pre-determined size prior to initiation of dosing. Approximately 3 weeks after tumor cell inoculation, mice bearing subcutaneous tumors ranging in size from 100 to 586 $mm^3$ (60 mice in this range; mean of 288±133 $mm^3$ (SD) were randomly assigned to treatment groups such that all treatment groups had statistically similar starting mean tumor volumes ($mm^3$). Mice were dosed orally by gavage with vehicle (control group) or compound at various doses twice-daily (b.i.d.) during the week and once-daily (qd) on weekends. Dosing was continued for 11 consecutive days, depending on the kinetics of tumor growth and size of tumors in vehicle-treated control mice. If tumors in the control mice reached ~10% of body weight (~2.0 grams), the study was to be terminated. Example #38 of the present invention was prepared fresh daily as a clear solution (@ 1, 5 and 10 mg/mL) in 20% HPβCD/D5W, pH 3-4 or other suitable vehicle and administered orally as described above. During the study, tumor growth was measured three times-a-week (M, W, F) using electronic Vernier calipers. Tumor volume ($mm^3$) was calculated using the formula $(L \times W)^2/2$, where L=length (mm) and W=width (shortest distance in mm) of the tumor. Body weight was measured three times-a-week and a loss of body weight >10% was used as an indication of lack of compound tolerability. Unacceptable toxicity was defined as body weight loss >20% during the study. Mice were closely examined daily at each dose for overt clinical signs of adverse, drug-related side effects.

On the day of study termination (Day 12), a final tumor volume and final body weight were obtained on each animal. Mice were euthanized using 100% $CO_2$ and tumors were immediately excised intact and weighed, with final tumor wet weight (grams) serving as a primary efficacy endpoint.

The time course of the inhibitory effects of Example #38 of the present invention on the growth of MV4-11 tumors is illustrated in FIG. 1. Values represent the mean±sem) of 15 mice per treatment group. Percent inhibition (% I) of tumor growth was calculated versus tumor growth in the vehicle-treated Control group on the last study day. Statistical significance versus Control was determined by Analysis of Variance (ANOVA) followed by Dunnett's t-test: * $p<0.05$; ** $p<0.01$.

As seen in FIG. 1, Example #38 of the present invention, administered orally by gavage at doses of 10, 50 and 100 mg/kg b.i.d. for 11 consecutive days, produced statistically significant, dose-dependent inhibition of growth of MV4-11 tumors grown subcutaneously in nude mice. On the last day of treatment (Day 11), mean tumor volume was dose-dependently decreased with nearly 100% inhibition ($p<0.001$) at doses of 50 and 100 mg/kg, compared to the mean tumor volume of the vehicle-treated group. Example #38 of the present invention produced tumor regression at doses of 50 mg/kg and 100 mg/kg, with statistically significant decreases of 98% and 93%, respectively, versus the starting mean tumor volumes on Day 1. At the lowest dose tested of 10 mg/kg, no significant growth delay was observed compared to the vehicle-treated control group. When dosing was stopped on Day 12 in the 100 mg/kg treated dose group and the tumor was allowed to re-grow, only 6/12 mice showed palpable, measurable tumor on study day 34.

Figure 2:
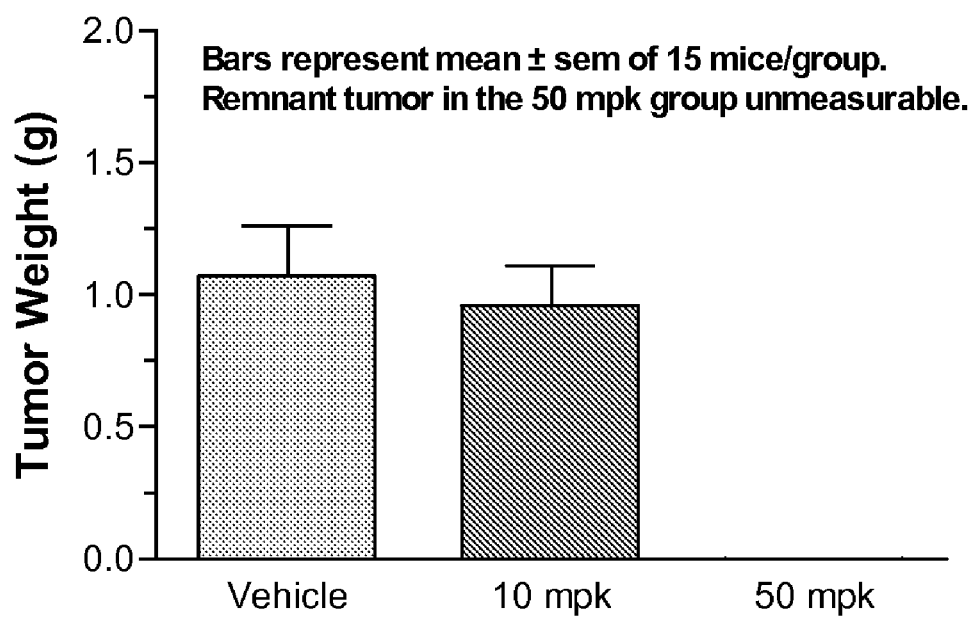
FIG. 2 shows shows the effects of oral administration of Example #38 of the present invention on the final weight of MV4-11 tumor xenografts in nude mice.

Example #38 of the present invention produced virtually complete regression of tumor mass as indicated by no measurable remnant tumor at study termination. (See FIG. 2). Bars on the graph of FIG. 2 represent the mean (±sem) of 15 mice per treatment group. As shown, there was no significant decrease in final tumor weight at the 10 mg/kg dose, consistent with the tumor volume data in FIG. 1. At the dose of 50 mg/kg, there is no bar represented on the graph since there was no measurable tumor mass detectable in these mice at termination, consistent with the complete regression of tumor volume noted in FIG. 1. The 100 mg/kg dose group is not represented on this graph since these mice were taken off drug and remnant tumor was allowed to regrow as stated above.

Following eleven consecutive days of oral dosing, Example #38 of the present invention produced dose-dependent reductions of final tumor weight compared to the mean tumor weight of the vehicle-treated group, with complete regression of tumor mass noted at the 50 mg/kg dose. (See FIG. 2).

Figure 3:
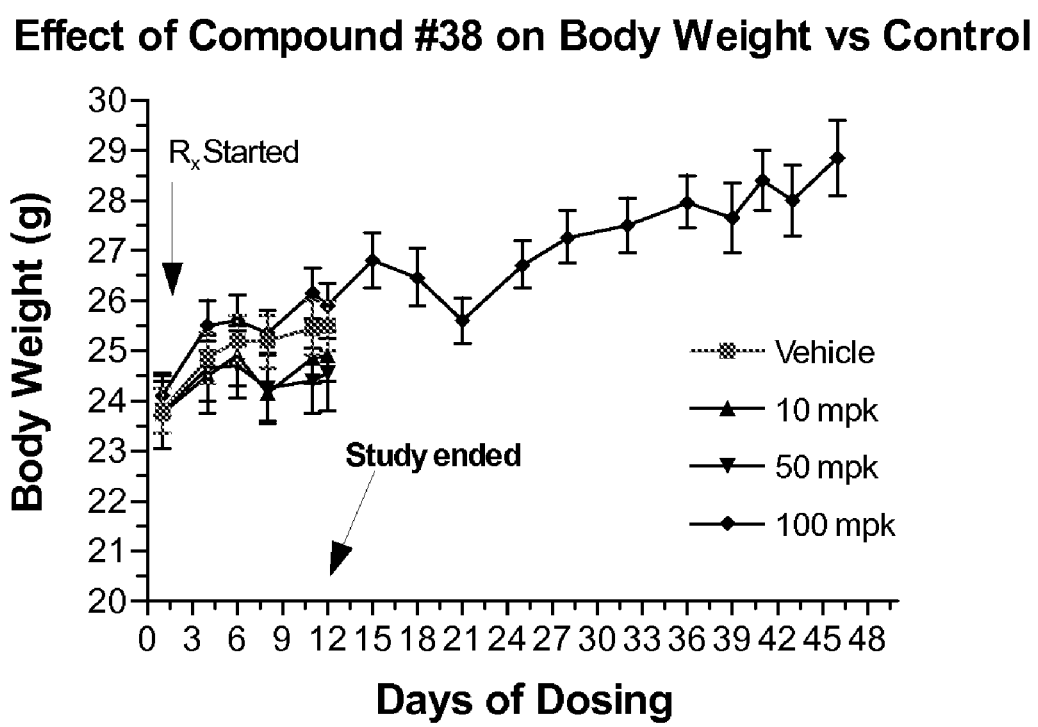
FIG. 3 shows the effects of oral administration of example #38 of the present invention on mouse body weight.

Mice were weighed three times each week (M, W, F) during the study and were examined daily at the time of dosing for overt clinical signs of any adverse, drug-related side effects. No overt toxicity was noted for Example #38 of the present invention and no significant adverse effects on body weight were observed during the 11-day treatment period at doses up to 200 mg/kg/day (See FIG. 3). Overall, across all dose groups, there was no significant loss of body weight compared to the starting body weight, indicating that Example #38 of the present invention was well-tolerated.

Figure 4:
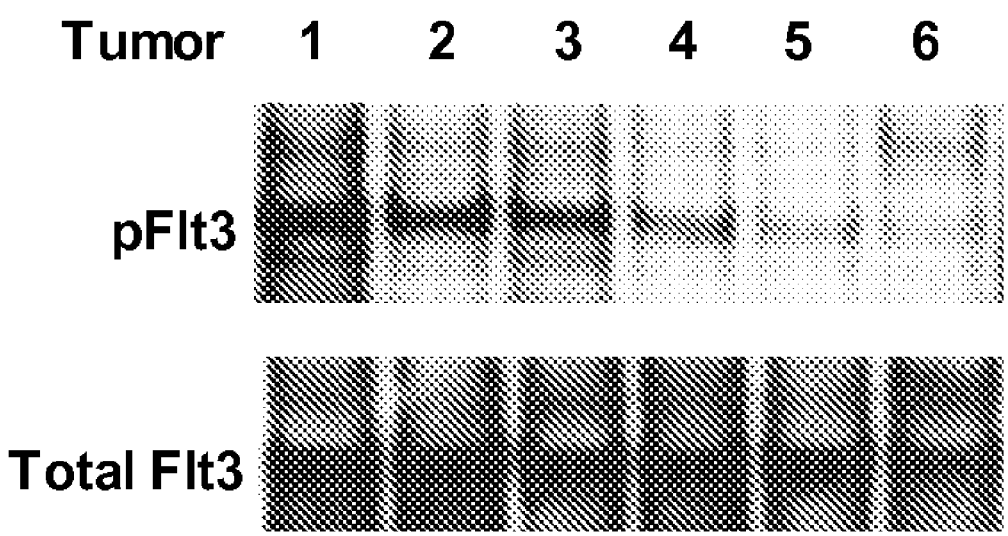
FIG. 4 shows FLT3 phosphorylation in MV4-11 tumors obtained from mice treated with Example #38 of the present invention.

To establish further that Example #38 of the present invention reached the expected target in tumor tissue, the level of FLT3 phosphorylation in tumor tissue obtained from vehicle- and compound-treated mice was measured. Results for Example #38 of the present invention is shown in FIG. 4. For this pharmacodynamic study, a sub-set of 6 mice from the vehicle-treated control group were randomized into three groups of 2 mice each and then treated with another dose of vehicle or compound (10 and 100 mg/kg, po). Tumors were harvested 6 hours later and snap frozen for assessment of FLT3 phosphorylation by western blots.

Harvested tumors were frozen and processed for immunoblot analysis of FLT3 phosphorylation in the following manner: 200 mg of tumor tissue was dounce homogenized in lysis buffer (50 mM Hepes, 150 mM NaCl, 10% Glycerol, 1% Triton-X-100, 10 mM NaF, 1 mM EDTA, 1.5 mM $MgCl_2$, 10 mM NaPyrophosphate) supplemented with phosphatase (Sigma Cat# P2850) and protease inhibitors (Sigma Cat #P8340). Insoluble debris was removed by centrifugation at 1000×g for 5 minutes at 4° C. Cleared lysates (15 mg of total potein at 10 mg/ml in lysis buffer) were incubated with 10 μg of agarose conjugated anti-FLT3 antibody, clone C-20 (Santa Cruz cat # sc-479ac), for 2 hours at 4° C. with gentle agitation. Immunoprecipitated FLT3 from tumor lysates were then washed four times with lysis buffer and separated by SDS-PAGE. The SDS-PAGE gel was transferred to nitrocellulose and immunoblotted with anti-phosphotyrosine antibody (clone-4G10, UBI cat. #05-777), followed by alkaline phosphatase-conjugated goat anti-mouse secondary antibody (Novagen cat. # 401212). Detection of protein was done by measuring the fluorescent product of the alkaline phosphatase reaction with the substrate 9H-(1,3-dichloro-9,9-dimethylacridin-2-one-7-yl) phosphate, diammonium salt (DDAO phosphate) (Molecular Probes cat. # D 6487) using a Molecular Dynamics Typhoon Imaging system (Molecular Dynamics, Sunnyvale, Calif.). Blots were then stripped and reprobed with anti-FLT3 antibody for normalization of phosphorylation signals.

As illustrated in FIG. 4, a single dose of Example #38 of the present invention at 100 mg/kg produced a biologically significant reduction in the level of FLT3 phosphorylation (top panel, tumor 5 and 6) in MV4-11 tumors compared to tumors from vehicle-treated mice (tumor 1 and 2). (Total FLT3 is shown in the bottom plot.) There was also a partial reduction of phosphorylation in animals treated with 10 mg/kg of the compound (tumor 3-4). These results further demonstrate that the compound of the present invention is in fact interacting with the expected FLT3 target in the tumor.

Methods of Treatment/Prevention

The present invention comprises the use of the compounds of the present invention to inhibit FLT3 kinase activity in a cell or a subject, or to treat disorders related to FLT3 kinase activity or expression in a subject.

In one embodiment to this aspect, the present invention provides a method for reducing or inhibiting the kinase activity of FLT3 in a cell comprising the step of contacting the cell with a compound of the present invention. The present invention also provides a method for reducing or inhibiting the kinase activity of FLT3 in a subject comprising the step of administering a compound of the present invention to the subject. The present invention further provides a method of inhibiting cell proliferation in a cell comprising the step of contacting the cell with a compound of the present invention.

The kinase activity of FLT3 in a cell or a subject can be determined by procedures well known in the art, such as the FLT3 kinase assay described herein.

The term "subject" as used herein, refers to an animal, preferably a mammal, most preferably a human, who has been the object of treatment, observation or experiment.

The term "contacting" as used herein, refers to the addition of compound to cells such that compound is taken up by the cell.

In other embodiments to this aspect, the present invention provides both prophylactic and therapeutic methods for treating a subject at risk of (or susceptible to) developing a cell proliferative disorder or a disorder related to FLT3.

In one example, the invention provides methods for preventing in a subject a cell proliferative disorder or a disorder related to FLT3, comprising administering to the subject a prophylactically effective amount of a pharmaceutical composition comprising a compound of the present invention and a pharmaceutically acceptable carrier. Administration of said prophylactic agent can occur prior to the manifestation of symptoms characteristic of the cell proliferative disorder or disorder related to FLT3, such that a disease or disorder is prevented or, alternatively, delayed in its progression.

In another example, the invention pertains to methods of treating in a subject a cell proliferative disorder or a disorder related to FLT3 comprising administering to the subject a therapeutically effective amount of a pharmaceutical composition comprising a compound of the present invention and a pharmaceutically acceptable carrier. Administration of said therapeutic agent can occur concurrently with the manifestation of symptoms characteristic of the disorder, such that said therapeutic agent serves as a therapy to compensate for the cell proliferative disorder or disorders related to FLT3.

The term "prophylactically effective amount" refers to an amount of active compound or pharmaceutical agent that inhibits or delays in a subject the onset of a disorder as being sought by a researcher, veterinarian, medical doctor or other clinician.

The term "therapeutically effective amount" as used herein, refers to an amount of active compound or pharmaceutical agent that elicits the biological or medicinal response in a subject that is being sought by a researcher, veterinarian, medical doctor or other clinician, which includes alleviation of the symptoms of the disease or disorder being treated.

Methods for determining therapeutically and prophylactically effective doses for pharmaceutical compositions comprising a compound of the present invention are disclosed herein and known in the art.

As used herein, the term "composition" is intended to encompass a product comprising the specified ingredients in the specified amounts, as well as any product which results, directly or indirectly, from combinations of the specified ingredients in the specified amounts.

As used herein, the terms "disorders related to FLT3", or "disorders related to FLT3 receptor", or "disorders related to FLT3 receptor tyrosine kinase" shall include diseases associated with or implicating FLT3 activity, for example, the overactivity of FLT3, and conditions that accompany with these diseases. The term "overactivity of FLT3" refers to either 1) FLT3 expression in cells which normally do not express FLT3; 2) FLT3 expression by cells which normally do not express FLT3; 3) increased FLT3 expression leading to unwanted cell proliferation; or 4) mutations leading to constitutive activation of FLT3. Examples of "disorders related to FLT3" include disorders resulting from over stimulation of FLT3 due to abnormally high amount of FLT3 or mutations in FLT3, or disorders resulting from abnormally high amount of FLT3 activity due to abnormally high amount of FLT3 or mutations in FLT3. It is known that overactivity of FLT3 has been implicated in the pathogenesis of a number of diseases, including the cell proliferative disorders, neoplastic disorders and cancers listed below.

The term "cell proliferative disorders" refers to unwanted cell proliferation of one or more subset of cells in a multicellular organism resulting in harm (i.e., discomfort or decreased life expectancy) to the multicellular organisms. Cell proliferative disorders can occur in different types of animals and humans. As used herein "cell proliferative disorders" include neoplastic disorders.

As used herein, a "neoplastic disorder" refers to a tumor resulting from abnormal or uncontrolled cellular growth. Examples of neoplastic disorders include, but are not limited to, hematopoietic disorders such as, for instance, the myeloproliferative disorders, such as thrombocythemia, essential thrombocytosis (ET), agnogenic myeloid metaplasia, myelofibrosis (MF), myelofibrosis with myeloid metaplasia (MMM), chronic idiopathic myelofibrosis (IMF), and polycythemia vera (PV), the cytopenias, and pre-malignant myelodysplastic syndromes; cancers such as glioma cancers, lung cancers, breast cancers, colorectal cancers, prostate cancers, gastric cancers, esophageal cancers, colon cancers, pancreatic cancers, ovarian cancers, and hematological malignancies, including myelodysplasia, multiple myeloma, leukemias and lymphomas. Examples of hematological malignancies include, for instance, leukemias, lymphomas (non-Hodgkin's lymphoma), Hodgkin's disease (also called Hodgkin's lymphoma), and myeloma—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma, (MM).

In a further embodiment to this aspect, the invention encompasses a combination therapy for treating or inhibiting the onset of a cell proliferative disorder or a disorder related to FLT3 in a subject. The combination therapy comprises administering to the subject a therapeutically or prophylactically effective amount of a compound of the present invention, and one or more other anti-cell proliferation therapy including chemotherapy, radiation therapy, gene therapy and immunotherapy.

In an embodiment of the present invention, a compound of the present invention may be administered in combination with chemotherapy. As used herein, chemotherapy refers to a therapy involving a chemotherapeutic agent. A variety of chemotherapeutic agents may be used in the combined treatment methods disclosed herein. Chemotherapeutic agents contemplated as exemplary, include, but are not limited to: platinum compounds (e.g., cisplatin, carboplatin, oxaliplatin); taxane compounds (e.g., paclitaxel, docetaxol); campothecin compounds (irinotecan, topotecan); vinca alkaloids (e.g., vincristine, vinblastine, vinorelbine); anti-tumor nucleoside derivatives (e.g., 5-fluorouracil, leucovorin, gemcitabine, capecitabine); alkylating agents (e.g., cyclophosphamide, carmustine, lomustine, thiotepa); epipodophyllotoxins/podophyllotoxins (e.g. etoposide, teniposide); aromatase inhibitors (e.g., anastrozole, letrozole, exemestane); anti-estrogen compounds (e.g., tamoxifen, fulvestrant), antifolates (e.g., premetrexed disodium); hypomethylating agents (e.g., azacitidine); biologics (e.g., gemtuzamab, cetuximab, rituximab, pertuzumab, trastuzumab, bevacizumab, erlotinib); antibiotics/anthracyclines (e.g. idarubicin, actinomycin D, bleomycin, daunorubicin, doxorubicin, mitomycin C, dactinomycin, carminomycin, daunomycin); anti-metabolites (e.g., aminopterin, clofarabine, cytosine arabinoside, methotrexate); tubulin-binding agents (e.g. combretastatin, colchicine, nocodazole); topoisomerase inhibitors (e.g., camptothecin). Further useful agents include verapamil, a calcium antagonist found to be useful in combination with antineoplastic agents to establish chemosensitivity in tumor cells resistant to accepted chemotherapeutic agents and to potentiate the efficacy of such compounds in drug-sensitive malignancies. See Simpson W G, The calcium channel blocker verapamil and cancer chemotherapy. Cell Calcium. 1985 December; 6(6):449-67. Additionally, yet to emerge chemotherapeutic agents are contemplated as being useful in combination with a compound of the present invention.

In another embodiment of the present invention, the compounds of the present invention may be administered in combination with radiation therapy. As used herein, "radiation therapy" refers to a therapy that comprises exposing the subject in need thereof to radiation. Such therapy is known to those skilled in the art. The appropriate scheme of radiation therapy will be similar to those already employed in clinical therapies wherein the radiation therapy is used alone or in combination with other chemotherapeutics.

In another embodiment of the present invention, the compounds of the present invention may be administered in combination with a gene therapy. As used herein, "gene therapy" refers to a therapy targeting on particular genes involved in tumor development. Possible gene therapy strategies include the restoration of defective cancer-inhibitory genes, cell transduction or transfection with antisense DNA corresponding to genes coding for growth factors and their receptors, RNA-based strategies such as ribozymes, RNA decoys, antisense messenger RNAs and small interfering RNA (siRNA) molecules and the so-called 'suicide genes'.

In other embodiments of this invention, the compounds of the present invention may be administered in combination with an immunotherapy. As used herein, "immunotherapy" refers to a therapy targeting particular protein involved in tumor development via antibodies specific to such protein. For example, monoclonal antibodies against vascular endothelial growth factor have been used in treating cancers.

Where a second pharmaceutical is used in addition to a compound of the present invention, the two pharmaceuticals may be administered simultaneously (e.g. in separate or unitary compositions) sequentially in either order, at approximately the same time, or on separate dosing schedules. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular chemotherapeutic agent being administered in conjunction with the compound of the present invention, their route of administration, the particular tumor being treated and the particular host being treated.

As will be understood by those of ordinary skill in the art, the appropriate doses of chemotherapeutic agents will be generally similar to or less than those already employed in clinical therapies wherein the chemotherapeutics are administered alone or in combination with other chemotherapeutics.

The optimum method and order of administration and the dosage amounts and regime can be readily determined by those skilled in the art using conventional methods and in view of the information set out herein.

By way of example only, platinum compounds are advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment. Cisplatin is not absorbed orally and must therefore be delivered via injection intravenously, subcutaneously, intratumorally or intraperitoneally.

By way of example only, taxane compounds are advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

By way of example only, camptothecin compounds are advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

By way of example only, vinca alkaloids may be advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

By way of example only, anti-tumor nucleoside derivatives may be advantageously administered in a dosage of 200 to 2500 mg per square meter ($mg/m^2$) of body surface area, for example 700 to 1500 $mg/m^2$. 5-fluorouracil (5-FU) is commonly used via intravenous administration with doses ranging from 200 to 500 $mg/m^2$ (preferably from 3 to 15 mg/kg/day). Gemcitabine is advantageously administered in a dosage of about 800 to 1200 $mg/m^2$ and capecitabine is advantageously administered in about 1000 to 2500 $mg/m^2$ per course of treatment.

By way of example only, alkylating agents may be advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg of body weight, for carmustine in a dosage of about 150 to 200 $mg/m^2$, and for lomustine in a dosage of about 100 to 150 $mg/m^2$ per course of treatment.

By way of example only, podophyllotoxin derivatives may be advantageously administered in a dosage of 30 to 300 mg per square meter (mg/m2) of body surface area, for example 50 to 250 $mg/m^2$, particularly for etoposide in a dosage of about 35 to 100 $mg/m^2$ and for teniposide in about 50 to 250 $mg/m^2$ per course of treatment.

By way of example only, anthracycline derivatives may be advantageously administered in a dosage of 10 to 75 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

By way of example only, anti-estrogen compounds may be advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

By way of example only, biologics may be advantageously administered in a dosage of about 1 to 5 mg per square meter ($mg/m^2$) of body surface area, or as known in the art, if different. For example, trastuzumab is advantageously administered in a dosage of 1 to 5 $mg/m^2$ particularly 2 to 4 $mg/m^2$ per course of treatment. Dosages may be administered, for example once, twice or more per course of treatment, which may be repeated for example every 7, 14, 21 or 28 days.

The compounds of the present invention can be administered to a subject systemically, for example, intravenously, orally, subcutaneously, intramuscular, intradermal, or parenterally. The compounds of the present invention can also be administered to a subject locally. Non-limiting examples of local delivery systems include the use of intraluminal medical devices that include intravascular drug delivery catheters, wires, pharmacological stents and endoluminal paving. A compound of the present invention can further be administered to a subject in combination with a targeting agent to achieve high local concentration of a compound at the target site. In addition, the compounds of the present invention may be formulated for fast-release or slow-release with the objective of maintaining the drugs or agents in contact with target tissues for a period ranging from hours to weeks.

The present invention also provides a pharmaceutical composition comprising a compound of the present invention in association with a pharmaceutically acceptable carrier. The pharmaceutical composition may contain between about 0.1 mg and 1000 mg, preferably about 100 to 500 mg, of the compound, and may be constituted into any form suitable for the mode of administration selected.

The phrase "pharmaceutically acceptable" refers to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

The pharmaceutical compositions of the present invention also include a pharmaceutical composition for slow release of the compounds of the present invention. The composition includes a slow release carrier (typically, a polymeric carrier) and a compound of the present invention.

Slow release biodegradable carriers are well known in the art. These are materials that may form particles that capture therein an active compound(s) and slowly degrade/dissolve under a suitable environment (e.g., aqueous, acidic, basic, etc) and thereby degrade/dissolve in body fluids and release the active compound(s) therein. The particles are preferably nanoparticles (i.e., in the range of about 1 to 500 nm in diameter, preferably about 50-200 nm in diameter, and most preferably about 100 nm in diameter).

The present invention also provides methods to prepare the pharmaceutical compositions of the invention. A compound of the present invention, as the active ingredient, is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. In preparation for slow release, a slow release carrier, typically a polymeric carrier, and a compound of the present invention are first dissolved or dispersed in an organic solvent. The obtained organic solution is then added into an aqueous solution to obtain an oil-in-water-type emulsion. Preferably, the aqueous solution includes surface-active agent(s). Subsequently, the organic solvent is evaporated from the oil-in-water-type emulsion to obtain a colloidal suspension of particles containing the slow release carrier and the compound of the present invention.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, from about 0.01 mg to 200 mg/kg of body weight per day. Preferably, the range is from about 0.03 to about 100 mg/kg of body weight per day, most preferably, from about 0.05 to about 10 mg/kg of body weight per day. The compound may be administered on a regimen of 1 to 5 times per day. The dosages, however, may be varied depending upon the requirement of the patients, the severity of the condition being treated and the compound(s) being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the composition of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, acetyl alcohol and cellulose acetate.

The liquid forms in which a compound of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Advantageously, the compounds of the present invention may be administered in a single daily dose, or the total daily dosage may be administered in divided doses of two, three or four times daily. Furthermore, compounds of the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The daily dosage of the products of the present invention may be varied over a wide range from 1 to 5000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of a compound of the present invention is ordinarily supplied at a dosage level of from about 0.01 mg/kg to about 200 mg/kg of body weight per day. Particularly, the range is from about 0.03 to about 15 mg/kg of body weight per day, and more particularly, from about 0.05 to about 10 mg/kg of body weight per day. The compounds of the present invention may be administered on a regimen up to four or more times per day, preferably of 1 to 2 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The compounds of the present invention can also be administered in the form of liposome delivery systems, such as small unilamellar vesicles, large unilamellar vesicles, and multilamellar vesicles. Liposomes can be formed from a variety of lipids, including but not limited to amphipathic lipids such as phosphatidylcholines, sphingomyelins, phosphatidylethanolamines, phophatidylcholines, cardiolipins, phosphatidylserines, phosphatidylglycerols, phosphatidic acids, phosphatidylinositols, diacyl trimethylammonium propanes, diacyl dimethylammonium propanes, and stearylamine, neutral lipids such as triglycerides, and combinations thereof. They may either contain cholesterol or may be cholesterol-free.

Another alternative method for administering the compounds of the invention may be by conjugating a compound to a targeting agent which directs the conjugate to its intended site of action, i.e., to vascular endothelial cells, or to tumor cells. Both antibody and non-antibody targeting agents may be used. Because of the specific interaction between the targeting agent and its corresponding binding partner, the compound of the present invention can be administered with high local concentrations at or near a target site and thus treats the disorder at the target site more effectively.

The antibody targeting agents include antibodies or antigen-binding fragments thereof, that bind to a targetable or accessible component of a tumor cell, tumor vasculature, or tumor stroma. The "targetable or accessible component" of a tumor cell, tumor vasculature or tumor stroma, is preferably a surface-expressed, surface-accessible or surface-localized component. The antibody targeting agents also include antibodies or antigen-binding fragments thereof, that bind to an intracellular component that is released from a necrotic tumor cell. Preferably such antibodies are monoclonal antibodies, or antigen-binding fragments thereof, that bind to insoluble intracellular antigen(s) present in cells that may be induced to be permeable, or in cell ghosts of substantially all neoplastic and normal cells, but are not present or accessible on the exterior of normal living cells of a mammal.

As used herein, the term "antibody" is intended to refer broadly to any immunologic binding agent such as IgG, IgM, IgA, IgE, F(ab')2, a univalent fragment such as Fab', Fab, Dab, as well as engineered antibodies such as recombinant antibodies, humanized antibodies, bispecific antibodies, and the like. The antibody can be either the polyclonal or the monoclonal, although the monoclonal is preferred. There is a very broad array of antibodies known in the art that have immunological specificity for the cell surface of virtually any solid tumor type (see, Summary Table on monoclonal antibodies for solid tumors in U.S. Pat. No. 5,855,866 to Thorpe et al). Methods are known to those skilled in the art to produce and isolate antibodies against tumor (see, U.S. Pat. No. 5,855, 866 to Thorpe et al., and U.S. Pat. No. 6,342,219 to Thorpe et al.).

Techniques for conjugating therapeutic moiety to antibodies are well known. (See, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985)). Similar techniques can also be applied to attach compounds of the invention to non-antibody targeting agents. Those skilled in the art will know, or be able to determine, methods of forming conjugates with non-antibody targeting agents, such as small molecules, oligopeptides, polysaccharides, or other polyanionic compounds.

Although any linking moiety that is reasonably stable in blood, can be used to link the compounds of the present invention to the targeting agent, biologically-releasable bonds and/or selectively cleavable spacers or linkers are preferred. "Biologically-releasable bonds" and "selectively cleavable spacers or linkers" still have reasonable stability in the circulation, but are releasable, cleavable or hydrolyzable only or preferentially under certain conditions, i.e., within a certain environment, or in contact with a particular agent. Such bonds include, for example, disulfide and trisulfide bonds and acid-labile bonds, as described in U.S. Pat. Nos. 5,474,765 and 5,762,918 and enzyme-sensitive bonds, including peptide bonds, esters, amides, phosphodiesters and glycosides as described in U.S. Pat. Nos. 5,474,765 and 5,762,918. Such selective-release design features facilitate sustained release of the compounds from the conjugates at the intended target site.

The present invention further provides a method of treating of a disorder related to FLT3, particularly a tumor, comprising administering to a subject a therapeutically effective amount of a compound of the present invention conjugated to a targeting agent.

When proteins such as antibodies or growth factors, or polysaccharides are used as targeting agents, they are preferably administered in the form of injectable compositions. The injectable antibody solution will be administered into a vein, artery or into the spinal fluid over the course of from 2 minutes to about 45 minutes, preferably from 10 to 20 minutes. In certain cases, intradermal and intracavitary administration are advantageous for tumors restricted to areas close to particular regions of the skin and/or to particular body cavities. In addition, intrathecal administrations may be used for tumors located in the brain.

A therapeutically effective dose of a compound of the present invention conjugated to a targeting agent depends on the individual, the disease type, the disease state, the method of administration and other clinical variables. The effective dosages are readily determinable using data from animal models, including those presented herein.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A method for treating leukemia comprising administering to a subject in need thereof a compound:

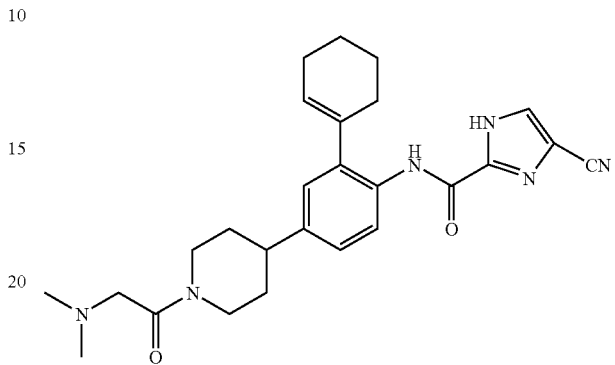

or a pharmaceutically acceptable salt thereof.

2. A method of treating leukemia in a subject in need thereof comprising administering to the subject a therapeutically effective amount of a pharmaceutical composition comprising a compound:

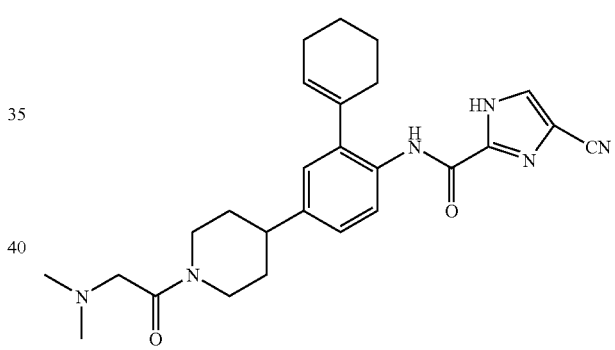

or a pharmaceutically acceptable salt thereof, and a pharmaceutically acceptable carrier.

* * * * *